(12) United States Patent
Koyama et al.

(10) Patent No.: US 7,504,437 B2
(45) Date of Patent: Mar. 17, 2009

(54) BENZYLAMINE ANALOGUES

(75) Inventors: Kazuo Koyama, Kawaguchi (JP); Shinji Marumoto, Tokyo (JP); Narihiro Toda, Tokyo (JP); Keiko Suzuki, Tokyo (JP)

(73) Assignee: BTG International Limited, London (GB)

(*) Notice: Subject to any disclaimer, the term of this patent is extended or adjusted under 35 U.S.C. 154(b) by 58 days.

(21) Appl. No.: 10/629,108

(22) Filed: Jul. 28, 2003

(65) Prior Publication Data
US 2004/0067981 A1 Apr. 8, 2004

Related U.S. Application Data

(63) Continuation-in-part of application No. PCT/JP02/00400, filed on Jan. 22, 2002.

(30) Foreign Application Priority Data

Jan. 26, 2001 (JP) ............... 2001-018386
Oct. 1, 2001 (JP) ............... 2001-305182

(51) Int. Cl.
*A61K 31/136* (2006.01)
*C07C 211/03* (2006.01)

(52) U.S. Cl. ............... 514/651; 560/156
(58) Field of Classification Search ............... 514/651; 560/156
See application file for complete search history.

(56) References Cited

U.S. PATENT DOCUMENTS

| | | | |
|---|---|---|---|
| 3,217,007 A | 11/1965 | Brossi et al. |
| 3,557,122 A | 1/1971 | Shavel, Jr. et al. |
| 3,647,799 A | 3/1972 | Watanabe et al. |
| 4,207,343 A | 6/1980 | Lavagnino et al. |
| 4,292,320 A | 9/1981 | Kishimoto et al. |
| 4,851,537 A | 7/1989 | Noyori et al. |
| 5,135,947 A | 8/1992 | Robertson et al. |
| 5,292,962 A | 3/1994 | Alt et al. |
| 5,578,627 A | 11/1996 | Takeda et al. |
| 5,681,940 A | 10/1997 | Wang et al. |
| 5,712,378 A | 1/1998 | Wang |
| 6,049,000 A | 4/2000 | Strohriegl et al. |
| 6,191,266 B1 | 2/2001 | Wang |
| 6,313,326 B1 | 11/2001 | Strohriegl et al. |
| 6,355,799 B1 | 3/2002 | Gupta et al. |
| 6,423,865 B1 | 7/2002 | Strohriegl et al. |
| 6,743,902 B1 | 6/2004 | Wang |
| 2004/0006235 A1 | 1/2004 | Pauluth et al. |

FOREIGN PATENT DOCUMENTS

| | | |
|---|---|---|
| CA | 2 271 937 A1 | 6/1998 |
| CA | 2 397 018 A1 | 7/2001 |
| CN | 990725 A | 6/1976 |
| EP | 1 253 142 A1 | 10/2002 |
| GB | 1 487 457 | 9/1997 |
| JP | 50-35175 | 4/1975 |
| JP | 50-35175 A | 4/1975 |
| JP | 52-102281 | 8/1977 |
| JP | 57-139066 | 8/1982 |
| JP | 57-139066 A | 8/1982 |
| JP | 8-41008 A | 2/1996 |
| WO | WO89/04305 A1 | 5/1989 |
| WO | WO89-08170 A1 | 4/1993 |
| WO | WO93/17994 A1 | 9/1993 |
| WO | WO94/10158 A1 | 5/1994 |
| WO | WO94/12461 A1 | 6/1994 |
| WO | WO95/16682 A1 | 6/1995 |
| WO | WO 96/14329 A1 | 5/1996 |
| WO | WO 96/22276 A1 | 7/1996 |
| WO | WO96/22276 A1 | 7/1996 |
| WO | WO96/26196 A2 | 8/1996 |
| WO | WO98/26127 A1 | 6/1998 |
| WO | WO98/27972 A2 | 7/1998 |
| WO | WO99/21837 A1 | 5/1999 |
| WO | WO 01/32624 A1 | 5/2001 |
| WO | WO 01/53267 A1 | 7/2001 |

(Continued)

OTHER PUBLICATIONS

F. Kallay et al., "The Reaction of Flavanone with Hydrazine", *Tetrahedron*, 1965, vol. 21, pp. 19 to 24.

(Continued)

*Primary Examiner*—Taofiq A Solola
(74) *Attorney, Agent, or Firm*—Frishauf, Holtz, Goodman & Chick, P.C.

(57) ABSTRACT

A compound of the formula (I):

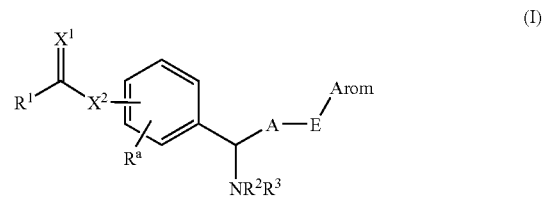

(I)

wherein $R^1$ represents $C_1-C_6$ alkyl, amino($C_1-C_6$ alkyl)amino, di($C_1-C_6$ alkyl)amino or a nitrogen-containing saturated heterocyclic; $R^2$ and $R^3$ are the same or different and represent hydrogen or $C_1-C_6$ alkyl; $R^a$ represents $C_1-C_6$ alkyl or $C_2-C_6$ alkenyl or together with $R^2$ represents a $C_1-C_3$ alkylene; Arom represents aryl or heteroaryl; A represents a $C_1-C_6$ alkylene; E represents a single bond, oxygen, sulfur or $R^4NR^4$—, wherein $R^4$ is hydrogen or $C_1-C_7$ alkenoyl; $X^1$ and $X^2$ are the same or different and represent oxygen or sulfur; or a pharmacologically acceptable salt or ester thereof. The compound has superior acetylcholinesterase inhibitory action and selective serotonin reuptake inhibitory action, and is useful for treating or preventing Alzheimer's disease, depression, Huntington's chorea, Pick's disease, tardive dyskinesia, compulsive disorders or panic disorders.

70 Claims, No Drawings

FOREIGN PATENT DOCUMENTS

WO  WO 02/090361 A1  11/2002

OTHER PUBLICATIONS

Richard J. Harvey et al., "The Clinical Efficacy of Tacrine", *Rev. Contemp. Pharmacother.*, 6, pp. 335-348, (1995).

S.L. Rogers, Ph.D. et al., "A 24-Week, Double-Blind, Placebo-Controlled Trial of Donepezil in Patients with Alzheimer's Disease", *Neurology*, 50, pp. 136-145, Jan. 1998.

Gal Richter-Levin et al., "Age-Related Cognitive Deficits in Rats Are Associated with a Combined Loss of Cholinergic and Serotonergic Functions", *Annals New York Academy of Sciences*, 695, pp. 254-257, (1993).

Paul Benfield et al., "Fluoxetine, A Review of Its Pharmacodynamic and Pharmacokinetic Properties, and Therapeutic Efficacy in Depressive Illness", *Drugs*, 32, pp. 481-508, (1986).

Minezo Otsuka et al., "The Whole Body Autoradiographic Studies on the Distribution of Radioisotopes. XXVIII," Feb. 1972, pp. 102 to 109.

Adeboye Adejare et al., "Syntheses and β-Adrenergic Agonist and Antiaggregatory Properties of N-Substituted Trimetoquinol Analogues," *J. Med. Chem.*, 29, pp. 1603 to 1609, (1986).

Juko Sugihara et al., "Studies on Intestinal Lymphatic Absorption of Drugs. I. Lymphatic Absorption of Alkyl Ester Derivatives and α-Monoglyceride Derivatives of Drugs," *Journal of Pharmacobiodynamics*, 11, pp. 369 to 376, (1988).

Koichiro Yamada et al., "Studies on 1, 2, 3, 4-Tetrahydroisoquinoline Derivatives. I. Syntheses and β-Adrenoceptor Activities of Positional Isomers of Trimetoquinol with Respect to Its 6, 7-Dihydroxyl Groups," *Chem. Pharm. Bull.*, 29(3), pp. 744 to 753, (1981).

Manyam B.V., Giacobini E. & Colliver J.A., Cerebrospinal fluid acetylcholinesterase and choline measurements in Huntington's disease, *J. Neurol.*, 237, (5) 281-284 (1990).

Rot U., Kobal J., Server A., Pirtosek Z., Mesec A., Rivastigmine in the treatment of Huntington's disease, *European Journal of Neurology: The Official Journal of the European Federation of Neurological Societies*, 9, 689-690 (2002).

Marina De Tommaso, M.D., Nicola Specchio, N.D., Vittorio Sciruicchio, M.D., Olimpia Difruscolo, M.D., Luigi Maria Specchio, M.D., Effects of rivastigmine on motor and cognitive impairment in Huntington's disease, *Movement Disorders*, 19 (12), 1516-1518 (2004).

Duan W., Guo Z., Jiang H., Adenheim B., Xu X., Cadet J.L. & Mattson M.P., Paroxetine retards disease onset and progression in Huntington's mutant mice, *Ann. Neurol.*, 55, 5900594, (2004).

Paulsen J. et al., Depression and Stages of Huntington's Disease, *J. Neuropsychiatry Clin. Neurosci.*, 17: 496-502 (2005).

Sparks D.L., Danner F.W., Davis. D.G., Hackney C., Landers T. & Coyne C.M., "Neurochemical and histopathologic characteristic of Pick's disease in a non demented individual", *J. Neuropathol. Exp. Neurol.*, 53 (1), 37-42, (1994).

Perry, R.J. and Miller B.L., Behavior and Treatment in frontotemporal dementia, *Neurology*, 56 (Supplement 4) S46-S61, (2001).

Swartz, J.R., Miller B.L., Lesser I.M. Carby Al.L, "Frontoteporal dementia: treatment response to serotonin selective reuptake inhibitors", *J. Clin. Psychiatry*, 58, 212-216, (1997).

Ingram N.A.W. and Newgreen D.B., The use of tacrine for tardive dyskinesia, *Am. J. Psychiatry*, 140, 1629-1631, (1983).

Caroff S.N. et al., Treatment of tardive dyskinesia with donepezil, *J. Clin. Psychiatry*, 62, 128-129, (2001).

Winblad et al., Donezepil in patients with severe Alzheimer's disease: double blind, parallel group, placebo controlled study, *Lancet*, e-pub., Mar. 23, 2006.

Fallon B.A. and Mathew S.J., Biological Therapies for Obsessive-Compulsive Disorders, *Journal of Psychiatric Practice*, 113-128, May 2000.

Sheehan, D.V., "The Management of Panic Disorder", *J. Clin. Psychiatry*, 2002, 63 (suppl. 14), 17-21.

Fernandez H. and Friedman J., "Donezepil for Huntington's Disease", *Movement Disorders*, 15, 173-176, 2000.

Hiroshi Kogen et al., "Design and Synthesis of Dual Inhibitors of Acetylcholinesterase and Serotonin Transporter Targeting Potential Agents for Alzheimer's Disease," *Organic Letters*, (2002), vol. 4, No. 20, pp. 3359-3362.

Narihiro Toda et al., "Design, Synthesis and Structure-Activity Relationships of Dual Inhibitors of Acetylcholinesterase and Serotonin Transporter as Potential Agents for Alzheimer's Disease," *Bioorganic & Medicinal Chemistry*, (2003), 11, pp. 1935-1955.

Narihiro Toda et al., "A Conformational Restriction Approach to the Development of Dual Inhibitors of Acetylcholinesterase and Serotonin Transporter as Potential Agents for Alzheimer's Disease," *Bioorganic & Medicinal Chemistry*, (2003), 11, pp. 4389-4415.

BENZYLAMINE ANALOGUES

CROSS REFERENCE TO RELATED APPLICATION

This application is a continuation-in-part application of International Application PCT/JP02/00400 filed Jan. 22, 2002, the entire contents of which are hereby incorporated by reference herein.

BACKGROUND OF THE INVENTION

1. Technical Field

The present invention relates to benzylamine analogues, pharmacologically acceptable salts or esters thereof and pharmaceutical compositions containing the same that have superior acetylcholinesterase inhibitory action and selective serotonin reuptake inhibitory action, and which are useful as therapeutic or prophylactic drugs for Alzheimer's disease, depression, Huntington's chorea, Pick's disease, tardive dyskinesia, compulsive disorders or panic disorders.

2. Background Art

Given the rapid growth of the elderly population, there is an urgent desire for the establishment of a treatment method for senile dementia as typified by Alzheimer's disease, and research and development is being conducted on therapeutic drugs for Alzheimer's disease from various perspectives. Since decreased acetylcholine concentration in the brain and decreased cholinergic function are observed in Alzheimer's disease patients, studies have been conducted on the treatment of Alzheimer's disease using acetylcholine precursor compounds, acetylcholinesterase inhibitors and acetylcholine agonists for the purpose of activating cholinergic function. Activation of the central cholinergic nervous system has been demonstrated to be effective for the treatment of mild to moderate cases of Alzheimer's disease by clinical application of acetylcholinesterase inhibitors (Rev. Contemp. Pharmacother., 6, 335 (1995)). Serious adverse side effects, namely liver toxicity, which were observed with early acetylcholinesterase inhibitors, have been improved considerably by ensuring inhibitory action specificity of the compounds to acetylcholinesterase and butylcholinesterase, and second generation acetylcholinesterase inhibitors are currently being developed (Neurology, 50, 136 (1998)).

Depression is frequently reported as a peripheral symptom in early Alzheimer's disease patients. Treatment using antidepressants has been tried, based on the idea that while impairment of cognitive function is still mild, core symptoms such as cognitive function can be expected to be improved by alleviating the depression (Ann. N.Y. Acad. Sci., 695, 254 (1993)). At present, the brain's serotonin system is widely recognized to be involved in depression. Research is being conducted on drugs that act on serotonin receptors or serotonin reuptake inhibitors, and selective serotonin reuptake inhibitors have been reported to be antidepressants having minimal adverse side effects (Drugs, 32, 481 (1986)). Drugs that are provided with both acetylcholinesterase inhibitory action and selective serotonin reuptake inhibitor action are expected to be able to alleviate depression and improve cognitive function, which are the core symptoms of Alzheimer's disease, and are thought to be more effective therapeutic drugs for Alzheimer's disease than compounds only having acetylcholinesterase inhibitory action. However, compounds having a similar chemical structure to the compounds of the present invention that also have both acetylcholinesterase inhibitory action and selective serotonin reuptake inhibitory action have heretofore not been known.

SUMMARY OF THE INVENTION

As a result of seeking to develop compounds having both superior acetylcholinesterase inhibitory action and selective serotonin reuptake inhibitory action, and conducting earnest research over an extended period of time on the synthesis of various benzene derivatives and their pharmacological activity, the inventors of the present invention found that benzylamine analogues having an amine at the benzyl position have both superior acetylcholinesterase inhibitory action and selective serotonin reuptake inhibitory action, and are useful as therapeutic or prophylactic drugs (particularly therapeutic drugs) for Alzheimer's disease, depression, Huntington's chorea, Pick's disease, tardive dyskinesia, compulsive disorders or panic disorders (and particularly Alzheimer's disease), thereby leading to completion of the present invention.

The novel benzylamine analogues of the present invention are compounds of formula (I):

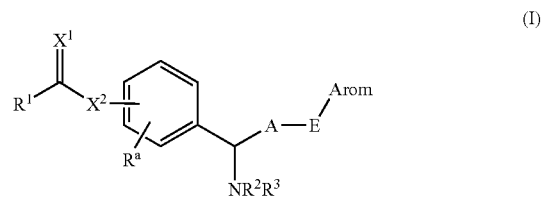

[wherein $R^1$ represents a $C_1$–$C_6$ alkyl group, an amino group, a ($C_1$–$C_6$ alkyl)amino group, a di($C_1$–$C_6$ alkyl)amino group or a nitrogen-containing saturated heterocyclic group;

$R^2$ and $R^3$ are the same or different and represent a hydrogen atom or a $C_1$–$C_6$ alkyl group;

Arom represents an aryl group, an aryl group substituted at from 1 to 5 positions by substituent(s) which are the same or different selected from the substituent group α, a heteroaryl group, or a heteroaryl group substituted at from 1 to 3 positions by substituent(s) which are the same or different selected from the substituent group α;

A represents a $C_1$–$C_6$ alkylene group;

$R^a$ represents a hydrogen atom, a $C_1$–$C_6$ alkyl group or a $C_2$–$C_6$ alkenyl group or, together with $R^2$, represents a $C_1$–$C_3$ alkylene group (in the case of $C_2$–$C_3$, it may contain a double bond);

E represents a single bond, an oxygen atom, a sulfur atom or a group of the formula: —$NR^4$— (wherein $R^4$ represents a hydrogen atom or a $C_1$–$C_7$ alkanoyl group);

$X^1$ and $X^2$ are the same or different and represent an oxygen atom or a sulfur atom]

or a pharmacologically acceptable salt or ester thereof.

<Substituent Group α> halogen atom, $C_1$–$C_6$ alkyl group, halogeno $C_1$–$C_6$ alkyl group, $C_1$–$C_6$ alkoxy group, $C_1$–$C_6$ alkylthio group, $C_1$–$C_3$ alkylenedioxy group, $C_1$–$C_7$ alkanoyl group, $C_2$–$C_7$ alkyloxycarbonyl group, amino group, $C_1$–$C_7$ alkanoylamino group, hydroxyl group, mercapto group, cyano group, nitro group and carboxyl group.

DETAILED DESCRIPTION OF THE INVENTION

The compound of the above formula (I) or the pharmacologically acceptable salt or ester is preferably (1) a compound or pharmacologically acceptable salt or ester thereof in which the group of formula: $R^1$—C(=$X^1$)— is a carbamoyl group, a $(C_1-C_4$ alkyl)carbamoyl group, a di($C_1-C_4$ alkyl)carbamoyl group, a thiocarbamoyl group, a $(C_1-C_4$ alkyl)thiocarbamoyl group or a di($C_1-C_4$ alkyl)thiocarbamoyl group, (2) a compound or pharmacologically acceptable salt or ester thereof in which the group of formula: $R^1$—C(=$X^1$)— is a $(C_1-C_4$ alkyl)carbamoyl group, a di($C_1-C_4$ alkyl)carbamoyl group, a $(C_1-C_4$ alkyl)thiocarbamoyl group or a di($C_1-C_4$ alkyl)thiocarbamoyl group, (3) a compound or pharmacologically acceptable salt or ester thereof in which the group of formula: $R^1$—C(=$X^1$)— is a $(C_1-C_4$ alkyl)carbamoyl group or a di($C_1-C_4$ alkyl)carbamoyl group, (4) a compound or pharmacologically acceptable salt or ester thereof in which the group of formula: $R^1$—C(=$X^1$)— is a di($C_1-C_4$ alkyl)carbamoyl group, (5) a compound or pharmacologically acceptable salt or ester thereof in which the group of formula: $R^1$—C(=$X^1$)— is a dimethylcarbamoyl group or an ethylmethylcarbamoyl group, (6) a compound or pharmacologically acceptable salt or ester thereof in which the group of formula: $R^1$—C(=$X^1$)— is a dimethylcarbamoyl group, (7) a compound or pharmacologically acceptable salt or ester thereof in which $R^3$ is a $C_1-C_6$ alkyl group, (8) a compound or pharmacologically acceptable salt or ester thereof in which $R^3$ is a methyl group or an ethyl group, (9) a compound or pharmacologically acceptable salt or ester thereof in which $R^3$ is a methyl group,

(10) a compound or pharmacologically acceptable salt or ester thereof in which $R^2$ is a hydrogen atom or a $C_1-C_6$ alkyl group,

(11) a compound or pharmacologically acceptable salt or ester thereof in which $R^2$ is a hydrogen atom, a methyl group or an ethyl group,

(12) a compound or pharmacologically acceptable salt or ester thereof in which $R^2$ is a hydrogen atom or a methyl group,

(13) a compound or pharmacologically acceptable salt or ester thereof in which $R^a$, together with $R^2$, is a $C_1-C_3$ alkylene group which may contain a double bond,

(14) a compound or pharmacologically acceptable salt or ester thereof in which $R^a$, together with $R^2$, is a $C_2-C_3$ alkylene group which may contain a double bond,

(15) a compound or pharmacologically acceptable salt or ester thereof in which $R^a$, together with $R^2$, is a $C_3$ alkylene group which contains a double bond,

(16) a compound or pharmacologically acceptable salt or ester thereof in which $R^a$ is a hydrogen atom or a methyl group,

(17) a compound or pharmacologically acceptable salt or ester thereof in which $R^a$ is a hydrogen atom,

(18) a compound or pharmacologically acceptable salt or ester thereof in which Arom is a phenyl group, a phenyl group substituted at from 1 to 3 positions by substituent(s) which may be the same or different selected from the substituent group α, a pyridyl group, or a pyridyl group substituted at one position by a substituent selected from the substituent group α,

(19) a compound or pharmacologically acceptable salt or ester thereof in which Arom is a phenyl group or a phenyl group substituted at from 1 to 3 positions by substituent(s) which may be the same or different selected from the substituent group α,

(20) a compound or pharmacologically acceptable salt thereof in which Arom is a phenyl group substituted at one or two positions by substituent(s) which may be the same or different selected from the substituent group α1, or a phenyl group substituted at three positions by halogen atoms,

(21) a compound or pharmacologically acceptable salt thereof in which Arom is a phenyl group substituted at one or two positions by substituent(s) which may be the same or different selected from the substituent group α2, or a phenyl group substituted at three positions by fluorine atoms or chlorine atoms,

(22) a compound or pharmacologically acceptable salt thereof in which Arom is a phenyl group substituted at one or two positions by substituent(s) which may be the same or different selected from the substituent group α3, or a phenyl group substituted at three positions by fluorine atoms,

(23) a compound or pharmacologically acceptable salt thereof in which Arom is a phenyl group substituted at one or two positions by substituent(s) which may be the same or different selected from the substituent group α4, or a phenyl group substituted at three positions by fluorine atoms,

(24) a compound or pharmacologically acceptable salt thereof in which Arom is a phenyl group substituted at one position by a fluorine atom, a chlorine atom or a nitro group, or a phenyl group substituted at two positions by fluorine atoms,

(25) a compound or pharmacologically acceptable salt thereof in which Arom is a 4-fluorophenyl group, a 4-chlorophenyl group, a 4-nitrophenyl group or a 3,4-difluorophenyl group,

(26) a compound or pharmacologically acceptable salt or ester thereof in which A is a $C_1-C_4$ alkylene group,

(27) a compound or pharmacologically acceptable salt or ester thereof in which A is a methylene group or an ethylene group,

(28) a compound or pharmacologically acceptable salt or ester thereof in which A is an ethylene group,

(29) a compound or pharmacologically acceptable salt or ester thereof in which E is an oxygen atom or a single bond,

(30) a compound or pharmacologically acceptable salt or ester thereof in which E is an oxygen atom,

(31) a compound or pharmacologically acceptable salt or ester thereof in which $X^2$ is an oxygen atom,

(32) a compound or pharmacologically acceptable salt or ester thereof in which the group of formula: $R^1$—C(=$X^1$)—$X^2$— is attached at the para-position,

(33) a compound or pharmacologically acceptable salt or ester thereof in which $R^1$ is an amino group, a $(C_1-C_6$ alkyl)amino group or a di($C_1-C_6$ alkyl)amino group,

(34) a compound or pharmacologically acceptable salt or ester thereof in which $R^1$ is an amino group, a $(C_1-C_4$ alkyl)amino group or a di($C_1-C_4$ alkyl)amino group,

(35) a compound or pharmacologically acceptable salt or ester thereof in which $R^1$ is a $(C_1-C_4$ alkyl)amino group or a di($C_1-C_4$ alkyl)amino group,

(36) a compound or pharmacologically acceptable salt or ester thereof in which $X^1$ is an oxygen atom, <Substituent Group α1> halogen atom, $C_1-C_4$ alkyl group, $C_1-C_4$ alkyl group substituted by from 1 to 3 fluorine atoms, $C_1-C_4$ alkoxy group, $C_1-C_4$ alkylthio group, methylenedioxy group, ethylenedioxy group, $C_1-C_4$ alkanoyl group, cyano group and nitro group, <Substituent Group α2> fluorine atom, chlorine atom, methyl group, trifluoromethyl group, methoxy group, methylthio group, acetyl group, cyano group and nitro group, <Substituent Group α3> fluorine atom, chlorine atom, methylthio group, acetyl group, cyano group and nitro group, <Substituent Group α4> fluorine atom, chlorine atom, methylthio group and nitro group.

The pharmaceutical compositions of the present invention contain a compound of the above formula (I) or a pharmacologically acceptable salt or ester thereof as an active ingredient.

The inhibitors of acetylcholineesterase and selective serotonin reuptake of the present invention contain a compound of the above formula (I) or a pharmacologically acceptable salt or ester thereof.

The therapeutic or prophylactic drugs for Alzheimer's disease, depression, Huntington's chorea, Pick's disease, tardive dyskinesia, compulsive disorders or panic disorders (preferably Alzheimer's disease) of the present invention contain a compound of the above formula (I) or a pharmacologically acceptable salt or ester thereof.

The "$C_1$–$C_6$ alkyl group" in $R^1$ to $R^3$ and <substituent group α> in formula (I) may be a straight or branched chain alkyl group having from 1 to 6 carbon atoms such as methyl, ethyl, propyl, isopropyl, butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl, and is preferably a straight or branched chain alkyl group having from 1 to 4 carbon atoms, more preferably a methyl group.

The "($C_1$–$C_6$ alkyl)amino group" in $R^1$ in formula (I) may be a straight or branched chain alkylamino group having from 1 to 6 carbon atoms such as methylamino, ethylamino, propylamino, isopropylamino, butylamino, isobutylamino, s-butylamino, t-butylamino, pentylamino, isopentylamino, 2-methylbutylamino, neopentylamino, 1-ethylpropylamino, hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino and 2-ethylbutylamino, and is preferably a methylamino group.

The "di($C_1$–$C_6$ alkyl)amino group" in $R^1$ in the above formula (I) may be a straight or branched chain dialkylamino group having from 2 to 12 carbon atoms such as dimethylamino, diethylamino, ethylmethylamino, dipropylamino, diisopropylamino, dibutylamino, diisobutylamino, di-s-butylamino, di-tert-butylamino, dipentylamino, diisopentylamino, dineopentylamino, di-1-ethylpropylamino, dihexylamino and diisohexylamino, and is preferably dimethylamino or ethylmethylamino, more preferably a dimethylamino group.

The "nitrogen-containing saturated heterocyclic group" in $R^1$ in the above formula (I) may be a 5 to 7-membered saturated heterocyclic group containing one nitrogen atom and from 0 to 3 sulfur atoms, oxygen atoms or/and nitrogen atoms such as morpholinyl, thiomorpholinyl, pyrrolidinyl, imidazolidinyl, pyrazolidinyl, piperidinyl and piperazinyl, and is preferably a morpholinyl group.

Preferred groups for $R^1$ in the above formula (I) are ($C_1$–$C_6$ alkyl)amino groups or di($C_1$–$C_6$ alkyl)amino groups, more preferably di($C_1$–$C_6$ alkyl)amino groups.

The "aryl group" and the "aryl group" of the "aryl group substituted at from 1 to 5 positions by substituent(s) which are the same or different selected from the substituent group a" in Arom in the above formula (I) may be an aromatic hydrocarbon group having from 5 to 14 carbon atoms such as phenyl, indenyl, naphthyl, phenanthrenyl and anthracenyl, and is preferably a phenyl group.

The "heteroaryl group" and the "heteroaryl group" of the "heteroaryl group substituted at from 1 to 3 positions by substituent(s) selected from the substituent group a" in Arom in the above formula (I) may be a 5 to 10-membered aromatic heterocyclic group containing from 1 to 3 sulfur atoms, oxygen atoms and/or nitrogen atoms such as furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, thiadiazolyl, pyranyl, pyridyl, pyridazinyl, pyrimidinyl, pyrazinyl and quinolyl, and is preferably a pyridyl group.

The "$C_1$–$C_6$ alkylene group" in A in the above formula (I) may be a straight alkylene group having from 1 to 6 carbon atoms such as methylene, ethylene, propylene, trimethylene, tetramethylene, pentamethylene and hexamethylene, and is preferably a straight alkylene group having from 1 to 4 carbon atoms, more preferably a methylene or ethylene, further more preferably an ethylene group.

The "$C_1$–$C_7$ alkanoyl group" in $R^4$ and <substituent group α> in the above formula (I) may be an alkylcarbonyl group having from 1 to 7 carbon atoms such as formyl, acetyl, propionyl, butyryl, isobutyryl, pentanoyl and hexanoyl, and is preferably an acetyl group.

The preferred group for $X^1$ in the above formula (I) is an oxygen atom.

The "halogen atom" in <substituent group α> in the above formula (I) is a fluorine atom, a chlorine atom, a bromine atom or an iodine atom, and is preferably a fluorine atom or a chlorine atom.

The "halogeno $C_1$–$C_6$ alkyl group" in <substituent group α> in the above formula (I) means a group in which the "$C_1$–$C_6$ alkyl group" is substituted by halogen atom(s) and may be a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl or 2,2-dibromoethyl, and is preferably a trifluoromethyl group.

The "$C_1$–$C_6$ alkoxy group" in <substituent group α> in the above formula (I) indicates a group in which the above "$C_1$–$C_6$ alkyl group" is bonded to an oxygen atom and is a straight or branched chain alkoxy group having from 1 to 6 carbon atoms such as methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy, and is preferably a methoxy group.

The "$C_1$–$C_6$ alkylthio group" in $R^a$ and <substituent group α> in the above formula (I) indicates a group in which the above "$C_1$–$C_6$ alkyl group" is bonded to a sulfur atom and is a straight or branched chain alkylthio group having from 1 to 6 carbon atoms such as methylthio, ethylthio, n-propylthio, isopropylthio, n-butylthio, isobutylthio, s-butylthio, tert-butylthio, n-pentylthio, isopentylthio, 2-methylbutylthio, neopentylthio, 1-ethylpropylthio, n-hexylthio, isohexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio and 2-ethylbutylthio, and is preferably a methylthio group.

The "$C_1$–$C_3$ alkylene group which may contain a double bond" for $R^a$ and $R^2$ in the above formula (I) indicates a straight or branched chain alkylene group having from 1 to 3 carbon atoms which may contain a double bond such as methylene, methylmethylene, ethylene, propylene, trimethylene, vinylene or propynylene, and is preferably a straight or branched chain alkylene group having 2 or 3 carbon atoms which may contain a double bond, more preferably a propynylene group.

The "$C_1$–$C_3$ alkylenedioxy group" in <substituent group α> in the above formula (I) indicates methylenedioxy, ethylenedioxy or propylenedioxy, and is preferably a methylenedioxy group.

The "$C_2$–$C_7$ alkyloxycarbonyl group" in <substituent group α> in the above formula (I) may be an alkyloxycarbonyl group having from 2 to 7 carbon atoms such as methoxycarbonyl, ethoxycarbonyl, tert-butoxycarbonyl and isobutoxycarbonyl, and is preferably a methoxycarbonyl group.

The "$C_1$–$C_7$ alkanoylamino group" in <substituent group α> in the above formula (I) indicates a group in which the "$C_1$–$C_7$ alkanoyl group" is substituted by an amino group and may be an alkylcarbonylamino group having from 1 to 7 carbon atoms such as formylamino, acetylamino, propionylamino, butyrylamino, isobutyrylamino and pentanoylamino, and is preferably an acetylamino group.

In the above, the "ester thereof" indicates an ester, since the compounds of the present invention can be made into esters, and this ester indicates an "ester of a hydroxyl group" and an "ester of a carboxyl group" and means an ester in which the ester residue is a "general protecting group" or a "protecting group which is cleavable by chemical or enzymatic hydrolysis in vivo".

The "general protecting group" is a protecting group which is cleavable by a chemical process such as hydrogenolysis, hydrolysis, electrolysis and photolysis. The "general protecting group" relating to the "ester of a hydroxyl group" may be an "aliphatic acyl group" such as an alkylcarbonyl group, e.g., formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl; a carboxylated alkylcarbonyl group, e.g., succinoyl, glutaroyl and adipoyl; a lower alkylcarbonyl group substituted by one or more halogen atoms, e.g., chloroacetyl, dichloroacetyl, trichloroacetyl and trifluoroacetyl; a saturated cyclic hydrocarbon-carbonyl group, e.g., cyclopropylcarbonyl, cyclobutylcarbonyl, cyclopentylcarbonyl, cyclohexylcarbonyl, cycloheptylcarbonyl and cyclooctylcarbonyl; a lower alkoxy lower alkylcarbonyl group, e.g., methoxyacetyl; or an unsaturated alkylcarbonyl group, e.g., (E)-2-methyl-2-butenoyl; an "aromatic acyl group" such as an arylcarbonyl group e.g., benzoyl, naphthoyl, pyridoyl, thienoyl and furoyl; an arylcarbonyl group substituted by one or more halogen atoms, e.g., 2-bromobenzoyl and 4-chlorobenzoyl; a lower alkylated arylcarbonyl group, e.g., 2,4,6-trimethylbenzoyl and 4-toluoyl; a lower alkoxylated arylcarbonyl group, e.g., 4-anisoyl; a carboxylated arylcarbonyl group, e.g., 2-carboxybenzoyl, 3-carboxybenzoyl and 4-carboxybenzoyl; a nitrated arylcarbonyl group, e.g., 4-nitrobenzoyl and 2-nitrobenzoyl; a lower alkoxycarbonylated arylcarbonyl group, e.g., 2-(methoxycarbonyl)benzoyl; or an arylated arylcarbonyl group, e.g., 4-phenylbenzoyl; an "aralkylcarbonyl group" such as a lower alkylcarbonyl group substituted with from 1 to 3 aryl groups, e.g., phenylacetyl, α-naphthylpropionyl, β-naphthylbutyryl, diphenylisobutyryl, triphenylacetyl, α-naphthyldiphenylisobutyryl and 9-anthrylpentanoyl; or a lower alkylcarbonyl group which is substituted with from 1 to 3 aryl groups in which said aryl moiety is substituted with lower alkyl group(s), lower alkoxy group(s), nitro group(s), halogen atom(s) and/or cyano group(s), e.g., 4-methylphenylacetyl, 2,4,6-trimethylphenylformyl, 3,4,5-trimethylphenylbutyryl, 4-methoxyphenylisobutyryl, 4-methoxyphenyldiphenylpivaloyl, 2-nitrophenylacetyl, 4-nitrophenylpropionyl, 4-chlorophenylbutyryl, 4-bromophenylacetyl and 4-cyanophenylpentanoyl; a "tetrahydropyranyl or tetrahydrothiopyranyl group" such as tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl; a "tetrahydrofuranyl or tetrahydrothiofuranyl group" such as tetrahydrofuran-2-yl and tetrahydrothiofuran-2-yl; a "silyl group" such as a tri(lower alkyl)silyl group e.g., trimethylsilyl, triethylsilyl, isopropyldimethylsilyl, t-butyldimethylsilyl, methyldiisopropylsilyl, methyl di-t-butylsilyl and triisopropylsilyl; or a tri(lower alkyl)silyl group which is substituted with one or two aryl groups, e.g., diphenylmethylsilyl, diphenylbutylsilyl, diphenylisopropylsilyl and phenyldiisopropylsilyl; an "alkoxymethyl group" such as a lower alkoxymethyl group, e.g., methoxymethyl, 1,1-dimethyl-1-methoxymethyl, ethoxymethyl, propoxymethyl, isopropoxymethyl, butoxymethyl and t-butoxymethyl; a lower alkoxylated lower alkoxymethyl group, e.g., 2-methoxyethoxymethyl; or a lower alkoxymethyl group which is substituted with one or more halogen atoms, e.g., 2,2,2-trichloroethoxymethyl and bis(2-chloroethoxy)methyl; a "substituted ethyl group" such as a lower alkoxylated ethyl group, e.g., 1-ethoxyethyl-1-(isopropoxy)ethyl; or a halogenated ethyl group, e.g., 2,2,2-trichloroethyl; an "aralkyl group" such as a lower alkyl group which is substituted with from 1 to 3 aryl groups, e.g., benzyl, α-naphthylmethyl, β-naphthylmethyl, diphenylmethyl, triphenylmethyl, α-naphthyldiphenylmethyl and 9-anthrylmethyl; or a lower alkyl group which is substituted with from 1 to 3 aryl groups in which said aryl moiety is substituted with lower alkyl group(s), lower alkoxy group(s), nitro group(s), halogen atom(s) and/or cyano group(s), e.g., 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl; an "alkoxycarbonyl group" such as a lower alkoxycarbonyl group, e.g., methoxycarbonyl, ethoxycarbonyl, t-butoxycarbonyl and isobutoxycarbonyl; or a lower alkoxycarbonyl group which is substituted with halogen atom(s) and/or tri (lower alkyl)silyl group(s), e.g., 2,2,2-trichloroethoxycarbonyl and 2-trimethylsilylethoxycarbonyl; an "alkenyloxycarbonyl group" such as vinyloxycarbonylallyloxycarbonyl; or an "aralkyloxycarbonyl group" in which the aryl moiety may be substituted with one or two lower alkoxy groups and/or nitro groups such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl.

On the other hand, the "general protecting group" relating to the "ester of a carboxyl group" may preferably be a "lower alkyl group" such as methyl, ethyl, propyl, isopropyl, butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl; an "alkenyl group" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl; an "alkynyl group" such as ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl; a "lower alkyl group which is substituted with one or more halogen atoms" such as trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl and 2,2-dibromoethyl; a "hydroxy lower alkyl group" such as 2-hydroxyethyl, 2,3-dihydroxypropyl, 3-hydroxypropyl, 3,4-dihydroxybutyl and 4-hydroxybutyl; an "aliphatic acyl"—"lower alkyl group" such as acetylmethyl; an "aralkyl group" such as a lower alkyl group which is substituted with from 1 to 3 aryl groups e.g., benzyl, phenethyl, 3-phenylpropyl, α-naphthylmethyl, β-naphthylmethyl, diphenylmethyl, triphenylmethyl, 6-phenylhexyl, α-naphthyldiphenylmethyl and 9-anthrylmethyl; or a lower alkyl group which is substituted with from 1 to 3 aryl groups in which said aryl moiety is substituted with lower alkyl group(s), lower alkoxy group(s), nitro group(s), halogen atom(s), cyano group(s) and/or alkoxycarbonyl group(s), e.g., 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl, piperonyl and 4-methoxycarbonylbenzyl; or a "silyl group" such as trimethylsilyl, triethylsilyl, isopropyldimethylsilyl, t-butyldimethylsilyl, methyldiisopropylsilyl, methyl di-t-butylsilyl, triisopropylsilyl, methyldiphenylsilyl, isopropyldiphenylsilyl, butyldiphenylsilyl and phenyldiisopropylsilyl.

The "protecting group which is cleavable by chemical or enzymatic hydrolysis in vivo" means a protecting group which is cleavable by a biological method such as hydrolysis in the human body to produce a free acid or a salt thereof. The suitability of such a derivative can be determined by administering it to an experimental animal such as a rat or a mouse by an intravenous injection, measuring a body fluid of the animal thereafter and detecting the original compound or a pharmacologically acceptable salt thereof.

The "protecting group which is cleavable by chemical or enzymatic hydrolysis in vivo" relating to the "ester of a hydroxyl group" may be a 1-(acyloxy) "lower alkyl group" such as a 1-("aliphatic acyl"oxy) "lower alkyl group", e.g., formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl; a 1-("aliphatic acyl"thio) "lower alkyl group", e.g., formylthiomethyl, acetylthiomethyl, dimethylaminoacetylthiomethyl, propionylthiomethyl, butyrylthiomethyl, pivaloylthiomethyl, valerylthiomethyl, isovalerylthiomethyl, hexanoylthiomethyl, 1-formylthioethyl, 1-acetylthioethyl, 1-propionylthioethyl, 1-butyrylthioethyl, 1-pivaloylthioethyl, 1-valerylthioethyl, 1-isovalerylthioethyl, 1-hexanoylthioethyl, 1-formylthiopropyl, 1-acetylthiopropyl, 1-propionylthiopropyl, 1-butyrylthiopropyl, 1-pivaloylthiopropyl, 1-valerylthiopropyl, 1-isovalerylthiopropyl, 1-hexanoylthiopropyl, 1-acetylthiobutyl, 1-propionylthiobutyl, 1-butyrylthiobutyl, 1-pivaloylthiobutyl, 1-acetylthiopentyl, 1-propionylthiopentyl, 1-butyrylthiopentyl, 1-pivaloylthiopentyl and 1-pivaloylthiohexyl; a 1-("cycloalkyl"carbonyloxy) "lower alkyl group", e.g., cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl; or a 1-("aromatic acyl"oxy) "lower alkyl group" such as benzoyloxymethyl; an (alkoxycarbonyloxy)alkyl group such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(t-butoxycarbonyloxy)ethyl), 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 2-(methoxycarbonyloxy)ethyl, 2-(ethoxycarbonyloxy)ethyl, 2-(propoxycarbonyloxy)ethyl, 2-(isopropoxycarbonyloxy)ethyl, 2-(butoxycarbonyloxy)ethyl, 2-(isobutoxycarbonyloxy)ethyl, 2-(pentyloxycarbonyloxy)ethyl, 2-(hexyloxycarbonyloxy)ethyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl; a "phthalidyl group" such as phthalidyl, dimethylphthalidyl and dimethoxyphthalidyl; a "carbonyloxyalkyl group" such as an oxodioxolenylmethyl group, e.g., (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl-2-oxo-1,3-dioxolen-4-yl)methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl; the above "aliphatic acyl group"; the above "aromatic acyl group" a "half ester salt residual group of succinic acid"; a "phosphoric acid ester salt residual group"; an "ester forming residual group such as an amino acid"; a carbamoyl group; a carbamoyl group substituted by one or two lower alkyl groups; a carboxy "lower alkyl" dithioethyl group such as 2-carboxyethyldithioethyl, 3-carboxypropyldithioethyl, 4-carboxybutyldithioethyl, 5-carboxypentyldithioethyl and 6-carboxyhexyldithioethyl; or a "lower alkyl group" dithioethyl group such as methyldithioethyl, ethyldithioethyl, propyldithioethyl, butyldithioethyl, pentyldithioethyl and hexyldithioethyl.

On the other hand, the "protecting group which is cleavable by chemical or enzymatic hydrolysis in vivo" relating to the "ester of a carboxyl group" may specifically be an "alkoxy lower alkyl group" such as a lower alkoxy lower alkyl group, e.g., methoxymethyl, 1-ethoxyethyl, 1-methyl-1-methoxyethyl, 1-(isopropoxy)ethyl, 2-methoxyethyl, 2-ethoxyethyl, 1,1-dimethyl-1-methoxyethyl, ethoxymethyl, propoxymethyl, isopropoxymethyl, butoxymethyl and t-butoxymethyl; a lower alkoxylated lower alkoxy lower alkyl group, e.g. 2-methoxyethoxymethyl; an "aryl group" oxy "lower alkyl group", e.g., phenoxymethyl; or a halogenated lower alkoxy lower alkyl group, e.g., 2,2,2-trichloroethoxymethyl and bis (2-chloroethoxy)methyl; a "lower alkoxy" carbonyl "lower alkyl group" such as methoxycarbonylmethyl; a cyano "lower alkyl group" such as cyanomethyl and 2-cyanoethyl; a "lower alkyl group" thiomethyl group such as methylthiomethyl and ethylthiomethyl; an "aryl group" thiomethyl group such as phenylthiomethyl and naphthylthiomethyl; a "lower alkyl group" sulfonyl "lower alkyl group" which may be substituted by halogen atom(s) such as 2-methanesulfonylethyl and 2-trifluoromethanesulfonylethyl; an "aryl group" sulfonyl "lower alkyl group" such as 2-benzenesulfonylethyl and 2-toluenesulfonylethyl; an acyloxy "lower alkyl group" such as an "aliphatic acyl" oxy "lower alkyl group", e.g., formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl; a "cycloalkyl" carbonyloxy "lower alkyl group", e.g., cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl; or an "aromatic acyl" oxy "lower alkyl group", e.g., benzoyloxymethyl; an (alkoxycarbonyloxy)alkyl group such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy) ethyl, 1-(isobutoxycarbonyloxy)ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 2-(methoxycarbonyloxy)ethyl, 2-(ethoxycarbonyloxy)ethyl, 2-(propoxycarbonyloxy)ethyl, 2-(isopropoxycarbonyloxy)ethyl, 2-(butoxycarbonyloxy)ethyl, 2-(isobutoxycarbonyloxy) ethyl, 2-(pentyloxycarbonyloxy)ethyl, 2-(hexyloxycarbonyloxy)ethyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy) propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy) butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)pentyl, 1-(ethoxycarbonyloxy)pentyl, 1-(methoxycarbonyloxy) hexyl and 1-(ethoxycarbonyloxy)hexyl; a "carbonyloxyalkyl group" such as an oxodioxolenylmethyl group, e.g., (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1, 3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl; a "phthalidyl group" such as phthalidyl, dimethylphthalidyl and dimethoxyphthalidyl; an "aryl group" such as phenyl and indanyl; the above "lower alkyl group"; the above "alkylthio group"; a "carboxy group alkyl group" such as carboxyl group methyl; or an "amide forming residual group of an amino acid" such as phenylalanine.

In the compound (I) of the present invention, while optical isomers (including diastereomers) based on asymmetrical carbon atom(s) in the molecule exist, and geometric isomers based on a ring structure sometimes exist, these respective isomers are included in the present invention.

The "pharmacologically acceptable salt thereof" means a salt since the compound (I) of the present invention can be converted into salts, and these salts may preferably be a metal salt such as an alkali metal salt, e.g., a sodium salt, a potassium salt and a lithium salt; a alkaline earth metal salt, e.g., a calcium salt and a magnesium salt; an aluminum salt; an iron salt; a zinc salt; a copper salt; a nickel salt; or a cobalt salt; an amine salt such as an inorganic salt, e.g., an ammonium salt; or an organic salt, e.g., a t-octylamine salt, a dibenzylamine salt, a morpholine salt, a glucosamine salt, a phenylglycinealkyl ester salt, an ethylenediamine salt, a N-methylglucamine salt, a guanidine salt, a diethylamine salt, a triethylamine salt, a dicyclohexylamine salt, a N,N'-dibenzylethylenediamine salt, a chloroprocaine salt, a procaine salt, a diethanolamine salt, a N-benzyl-phenethylamine salt, a piperazine salt, a tetramethylammonium salt and a tris(hydroxymethyl)aminomethane salt; an inorganic acid salt such as a hydrogen halide salt, e.g., hydrofluoride, hydrochloride, hydrobromide and hydroiodide; nitrate; perchlorate; sulfate; or phosphate; an organic acid salt such as a lower alkanesulfonate, e.g., methanesulfonate, trifluoromethanesulfonate and ethanesulfonate; a arylsulfonate, e.g., benzenesulfonate and p-toluenesulfonate; acetate; malate; fumarate; succinate; citrate; tartrate; oxalate; or maleate; an amino acid salt such as glycine salt, lysine salt, arginine salt, ornithine salt, glutamate and aspartate; and are more preferably an inorganic acid salt.

The compound (I) of the present invention can also exist as a hydrate. Compounds shown in the following Table 1 to Table 5 are specifically illustrated as preferred compounds of formula (I). However, the compound of the present invention is not limited to these.

The meaning of the abbreviations in the following Table 1 to Table 5 is shown below. That is, Ac represents an acetyl group, tBu represents a t-butyl group, Car represents a carbamoyl group, diMeCar represents a N,N-dimethylcarbamoyl group,
diMeTcr represents a N,N-dimethylthiocarbamoyl group,
diEtCar represents a N,N-diethylcarbamoyl group,
diPrCar represents a N,N-diisopropylcarbamoyl group,
MeEtCar represents a N-methyl-N-ethylcarbamoyl group,
Et represents an ethyl group,
Me represents a methyl group,
diMeN represents a dimethylamino group,
MeEtN represents a methylethylamino group,
MeOCO represents a methoxycarbonyl group,
Mor represents a morpholino group,
Mtdo represents a methylenedioxy group,
pentaFPH represents a pentafluorophenyl group,
Ph represents a phenyl group,
Pr represets a propyl group,
iPr represents an isopropyl group,
Py-2-yl represents a pyridin-2-yl group,
Py-3-yl represents a pyridin-3-yl group,
Py-4-yl represents a pyridin-4-yl group, and
Thi-3-yl represents a thiophen-3-yl group.

TABLE 1

(Ia)

| Compound No. | $R^1$—(C=$X^1$) | $R^2R^3N$ | A | E | Arom |
|---|---|---|---|---|---|
| 1-1 | diMeCar | MeNH | (CH$_2$)$_2$ | — | 4-F—Ph |
| 1-2 | EtCar | MeNH | (CH$_2$)$_2$ | — | 4-F—Ph |
| 1-3 | EtCar | MeNH | (CH$_2$)$_2$ | — | 4-MeO—Ph |
| 1-4 | Ac | MeNH | (CH$_2$)$_2$ | — | 4-F—Ph |
| 1-5 | tBu-(C=O) | MeNH | (CH$_2$)$_2$ | — | 4-F—Ph |
| 1-6 | diEtCar | MeNH | (CH$_2$)$_2$ | — | 4-F—Ph |
| 1-7 | diEtCar | MeNH | (CH$_2$)$_2$ | O | 4-Cl—Ph |
| 1-8 | diEtCar | MeNH | (CH$_2$)$_2$ | O | 3-Cl—Ph |
| 1-9 | diPrCar | MeNH | (CH$_2$)$_2$ | — | 4-F—Ph |
| 1-10 | MeEtCar | MeNH | (CH$_2$)$_2$ | O | 4-Cl—Ph |
| 1-11 | Mor-(C=O) | MeNH | (CH$_2$)$_2$ | — | 4-F—Ph |
| 1-12 | diMeTcr | MeNH | (CH$_2$)$_2$ | — | 4-F—Ph |
| 1-13 | diMeCar | MeNH | (CH$_2$)$_2$ | — | 4-Cl—Ph |
| 1-14 | diMeCar | MeNH | (CH$_2$)$_2$ | — | 4-CF$_3$—Ph |
| 1-15 | diMeCar | MeNH | (CH$_2$)$_2$ | — | 4-MeO—Ph |
| 1-16 | diMeCar | diMeN | (CH$_2$)$_2$ | — | 4-MeO—Ph |
| 1-17 | diMeCar | MeNH | (CH$_2$)$_2$ | — | 3-MeO-4-MeO—Ph |
| 1-18 | diMeCar | MeNH | (CH$_2$)$_2$ | — | 3,4-Mtdo-Ph |
| 1-19 | diMeCar | MeNH | (CH$_2$)$_2$ | — | 4-NO$_2$—Ph |
| 1-20 | diMeCar | MeNH | (CH$_2$)$_2$ | — | 3-F-4-F—Ph |
| 1-21 | diMeCar | diMeN | (CH$_2$)$_2$ | — | 4-F—Ph |
| 1-22 | diMeCar | diMeN | (CH$_2$)$_2$ | — | 4-Cl—Ph |
| 1-23 | diMeCar | diMeN | (CH$_2$)$_2$ | — | 4-NO$_2$—Ph |
| 1-24 | diMeCar | diMeN | (CH$_2$)$_2$ | — | 3-F-4-F—Ph |
| 1-25 | diMeCar | MeNH | (CH$_2$)$_3$ | — | 4-F—Ph |
| 1-26 | diMeCar | MeNH | (CH$_2$)$_3$ | — | 4-Cl—Ph |
| 1-27 | diMeCar | MeNH | (CH$_2$)$_3$ | — | 4-NO$_2$—Ph |
| 1-28 | diMeCar | MeNH | (CH$_2$)$_3$ | — | 3-F-4-F—Ph |
| 1-29 | diMeCar | diMeN | (CH$_2$)$_3$ | — | 4-F—Ph |
| 1-30 | diMeCar | diMeN | (CH$_2$)$_3$ | — | 4-Cl—Ph |
| 1-31 | diMeCar | diMeN | (CH$_2$)$_3$ | — | 4-NO$_2$—Ph |
| 1-32 | diMeCar | diMeN | (CH$_2$)$_3$ | — | 3-F-4-F—Ph |
| 1-33 | diMeCar | MeNH | CH$_2$ | O | 4-F—Ph |
| 1-34 | diMeCar | MeNH | CH$_2$ | O | 4-Cl—Ph |
| 1-35 | diMeCar | MeNH | CH$_2$ | O | 4-NO$_2$—Ph |
| 1-36 | diMeCar | MeNH | CH$_2$ | O | 3-F-4-F—Ph |
| 1-37 | diMeCar | diMeN | CH$_2$ | O | 4-F—Ph |
| 1-38 | diMeCar | diMeN | CH$_2$ | O | 4-Cl—Ph |
| 1-39 | diMeCar | diMeN | CH$_2$ | O | 4-NO$_2$—Ph |
| 1-40 | diMeCar | diMeN | CH$_2$ | O | 3-F-4-F—Ph |
| 1-41 | diMeCar | MeNH | (CH$_2$)$_2$ | S | 4-F—Ph |
| 1-42 | diMeCar | MeNH | (CH$_2$)$_2$ | S | 4-Cl—Ph |
| 1-43 | diMeCar | MeNH | (CH$_2$)$_2$ | S | 4-NO$_2$—Ph |
| 1-44 | diMeCar | MeNH | (CH$_2$)$_2$ | S | 3-F-4-F—Ph |
| 1-45 | diMeCar | diMeN | (CH$_2$)$_2$ | S | 4-F—Ph |
| 1-46 | diMeCar | diMeN | (CH$_2$)$_2$ | S | 4-Cl—Ph |
| 1-47 | diMeCar | diMeN | (CH$_2$)$_2$ | S | 4-NO$_2$—Ph |
| 1-48 | diMeCar | diMeN | (CH$_2$)$_2$ | S | 3-F-4-F—Ph |
| 1-49 | diMeCar | MeNH | (CH$_2$)$_2$ | NH | 4-F—Ph |
| 1-50 | diMeCar | MeNH | (CH$_2$)$_2$ | NH | 4-Cl—Ph |
| 1-51 | diMeCar | MeNH | (CH$_2$)$_2$ | NH | 3-F—Ph |
| 1-52 | diMeCar | MeNH | (CH$_2$)$_2$ | NH | 3-Cl—Ph |
| 1-53 | diMeCar | MeNH | (CH$_2$)$_2$ | NH | 4-NO$_2$—Ph |
| 1-54 | diMeCar | MeNH | (CH$_2$)$_2$ | NH | 3-F-4-F—Ph |
| 1-55 | diMeCar | diMeN | (CH$_2$)$_2$ | NH | 4-F—Ph |
| 1-56 | diMeCar | diMeN | (CH$_2$)$_2$ | NH | 4-Cl—Ph |
| 1-57 | diMeCar | diMeN | (CH$_2$)$_2$ | NH | 4-NO$_2$—Ph |
| 1-58 | diMeCar | diMeN | (CH$_2$)$_2$ | NH | 3-F-4-F—Ph |
| 1-59 | diMeCar | MeNH | (CH$_2$)$_2$ | NAc | 4-Cl—Ph |
| 1-60 | diMeCar | MeNH | (CH$_2$)$_2$ | NAc | 3-F—Ph |
| 1-61 | diMeCar | MeNH | (CH$_2$)$_2$ | NAc | 4-NO$_2$—Ph |
| 1-62 | diMeCar | diMeN | (CH$_2$)$_2$ | NAc | 4-Cl—Ph |
| 1-63 | diMeCar | diMeN | (CH$_2$)$_2$ | NAc | 3-F—Ph |
| 1-64 | diMeCar | diMeN | (CH$_2$)$_2$ | NAc | 4-NO$_2$—Ph |
| 1-65 | diMeCar | NH$_2$ | (CH$_2$)$_2$ | O | 4-F—Ph |
| 1-66 | diMeCar | NH$_2$ | (CH$_2$)$_2$ | O | 4-NO$_2$—Ph |
| 1-67 | diMeCar | EtNH | (CH$_2$)$_2$ | O | 4-F—Ph |
| 1-68 | diMeCar | EtNH | (CH$_2$)$_2$ | O | 3-F—Ph |
| 1-69 | diMeCar | EtNH | (CH$_2$)$_2$ | O | 4-Cl—Ph |
| 1-70 | diMeCar | EtNH | (CH$_2$)$_2$ | O | 3-NO$_2$—Ph |
| 1-71 | diMeCar | EtNH | (CH$_2$)$_2$ | O | 4-NO$_2$—Ph |
| 1-72 | diMeCar | EtNH | (CH$_2$)$_2$ | O | 3-F-4-F—Ph |
| 1-73 | diMeCar | PrNH | (CH$_2$)$_2$ | O | 4-F—Ph |
| 1-74 | diMeCar | MeNH | (CH$_2$)$_2$ | O | Ph |
| 1-75 | diMeCar | MeNH | (CH$_2$)$_2$ | O | 4-F—Ph |
| 1-76 | diMeCar | MeNH | (CH$_2$)$_2$ | O | 3-F—Ph |
| 1-77 | diMeCar | MeNH | (CH$_2$)$_2$ | O | 2-F—Ph |
| 1-78 | diMeCar | MeNH | (CH$_2$)$_2$ | O | 4-Cl—Ph |
| 1-79 | diMeCar | MeNH | (CH$_2$)$_2$ | O | 3-Cl—Ph |
| 1-80 | diMeCar | MeNH | (CH$_2$)$_2$ | O | 2-Cl—Ph |
| 1-81 | diMeCar | MeNH | (CH$_2$)$_2$ | O | 4-Br—Ph |
| 1-82 | diMeCar | MeNH | (CH$_2$)$_2$ | O | 4-Me—Ph |
| 1-83 | diMeCar | MeNH | (CH$_2$)$_2$ | O | 3-Me—Ph |
| 1-84 | diMeCar | MeNH | (CH$_2$)$_2$ | O | 2-Me—Ph |
| 1-85 | diMeCar | MeNH | (CH$_2$)$_2$ | O | 4-CF$_3$—Ph |
| 1-86 | diMeCar | MeNH | (CH$_2$)$_2$ | O | 4-MeO—Ph |
| 1-87 | diMeCar | MeNH | (CH$_2$)$_2$ | O | 3-MeO—Ph |
| 1-88 | diMeCar | MeNH | (CH$_2$)$_2$ | O | 2-MeO—Ph |
| 1-89 | diMeCar | MeNH | (CH$_2$)$_2$ | O | 4-Ac—Ph |
| 1-90 | diMeCar | MeNH | (CH$_2$)$_2$ | O | 3-Ac—Ph |
| 1-91 | diMeCar | MeNH | (CH$_2$)$_2$ | O | 4-CN—Ph |
| 1-92 | diMeCar | MeNH | (CH$_2$)$_2$ | O | 4-NO$_2$—Ph |
| 1-93 | diMeCar | MeNH | (CH$_2$)$_2$ | O | 2-NO$_2$—Ph |
| 1-94 | diMeCar | MeNH | (CH$_2$)$_2$ | O | 3-NO$_2$—Ph |
| 1-95 | diMeCar | MeNH | (CH$_2$)$_2$ | O | 4-NH$_2$—Ph |
| 1-96 | diMeCar | MeNH | (CH$_2$)$_2$ | O | 3-NH$_2$—Ph |
| 1-97 | diMeCar | MeNH | (CH$_2$)$_2$ | O | 4-AcNH—Ph |
| 1-98 | diMeCar | MeNH | (CH$_2$)$_2$ | O | 3-AcNH—Ph |
| 1-99 | diMeCar | MeNH | (CH$_2$)$_2$ | O | 4-COOH—Ph |
| 1-100 | diMeCar | MeNH | (CH$_2$)$_2$ | O | 3,4-Mtdo-Ph |
| 1-101 | diMeCar | MeNH | (CH$_2$)$_2$ | O | 2-F-4-F—Ph |
| 1-102 | diMeCar | MeNH | (CH$_2$)$_2$ | O | 3-F-4-F—Ph |
| 1-103 | diMeCar | MeNH | (CH$_2$)$_2$ | O | 3-F-5-F—Ph |
| 1-104 | diMeCar | MeNH | (CH$_2$)$_2$ | O | 3-F-4-Cl—Ph |
| 1-105 | diMeCar | MeNH | (CH$_2$)$_2$ | O | 2-F-4-NO$_2$—Ph |

TABLE 1-continued (Ia)

| Compound No. | R¹—(C=X¹) | R²R³N | A | E | Arom |
|---|---|---|---|---|---|
| 1-106 | diMeCar | MeNH | (CH$_2$)$_2$ | O | 2-Cl-4-F—Ph |
| 1-107 | diMeCar | MeNH | (CH$_2$)$_2$ | O | 2-Cl-4-Cl—Ph |
| 1-108 | diMeCar | MeNH | (CH$_2$)$_2$ | O | 2-Cl-4-NO$_2$—Ph |
| 1-109 | diMeCar | MeNH | (CH$_2$)$_2$ | O | 3-Cl-4-F—Ph |
| 1-110 | diMeCar | MeNH | (CH$_2$)$_2$ | O | 3-Cl-4-Cl—Ph |
| 1-111 | diMeCar | MeNH | (CH$_2$)$_2$ | O | 2-Me-4-F—Ph |
| 1-112 | diMeCar | MeNH | (CH$_2$)$_2$ | O | 2-Me-4-Cl—Ph |
| 1-113 | diMeCar | MeNH | (CH$_2$)$_2$ | O | 3-Me-4-Cl—Ph |
| 1-114 | diMeCar | MeNH | (CH$_2$)$_2$ | O | 3-Me-4-Me—Ph |
| 1-115 | diMeCar | MeNH | (CH$_2$)$_2$ | O | 3-Me-4-NO$_2$—Ph |
| 1-116 | diMeCar | MeNH | (CH$_2$)$_2$ | O | 3-NO$_2$-4-Cl—Ph |
| 1-117 | diMeCar | MeNH | (CH$_2$)$_2$ | O | 3-F-4-F-5-F—Ph |
| 1-118 | diMeCar | MeNH | (CH$_2$)$_2$ | O | 2-F-3-F-5-F—Ph |
| 1-119 | diMeCar | MeNH | (CH$_2$)$_2$ | O | Py-3-yl |
| 1-120 | diMeCar | MeNH | (CH$_2$)$_2$ | O | 5-Cl—Py-3-yl |
| 1-121 | diMeCar | MeNH | (CH$_2$)$_2$ | O | 2-Me—Py-3-yl |
| 1-122 | diMeCar | MeNH | (CH$_2$)$_2$ | O | 6-Me—Py-3-yl |
| 1-123 | diMeCar | MeNH | (CH$_2$)$_2$ | O | Py-2-yl |
| 1-124 | diMeCar | MeNH | (CH$_2$)$_2$ | O | 6-Cl—Py-2-yl |
| 1-125 | diMeCar | MeNH | (CH$_2$)$_2$ | O | 6-CF$_3$—Py-2-yl |
| 1-126 | diMeCar | MeNH | (CH$_2$)$_2$ | O | 6-NO$_2$—Py-2-yl |
| 1-127 | diMeCar | MeNH | (CH$_2$)$_2$ | O | Py-4-yl |
| 1-128 | diMeCar | MeNH | (CH$_2$)$_2$ | O | 2-NO$_2$—Py-4-yl |
| 1-129 | diMeCar | MeNH | (CH$_2$)$_2$ | O | Thi-3-yl |
| 1-130 | diMeCar | MeNH | (CH$_2$)$_2$ | O | 2-MeOCO-Thi-3-yl |
| 1-131 | diMeCar | diMeN | (CH$_2$)$_2$ | O | Ph |
| 1-132 | diMeCar | diMeN | (CH$_2$)$_2$ | O | 4-F—Ph |
| 1-133 | diMeCar | diMeN | (CH$_2$)$_2$ | O | 3-F—Ph |
| 1-134 | diMeCar | diMeN | (CH$_2$)$_2$ | O | 2-F—Ph |
| 1-135 | diMeCar | diMeN | (CH$_2$)$_2$ | O | 4-Cl—Ph |
| 1-136 | diMeCar | diMeN | (CH$_2$)$_2$ | O | 3-Cl—Ph |
| 1-137 | diMeCar | diMeN | (CH$_2$)$_2$ | O | 2-Cl—Ph |
| 1-138 | diMeCar | diMeN | (CH$_2$)$_2$ | O | 4-Br—Ph |
| 1-139 | diMeCar | diMeN | (CH$_2$)$_2$ | O | 4-Me—Ph |
| 1-140 | diMeCar | diMeN | (CH$_2$)$_2$ | O | 3-Me—Ph |
| 1-141 | diMeCar | diMeN | (CH$_2$)$_2$ | O | 2-Me—Ph |
| 1-142 | diMeCar | diMeN | (CH$_2$)$_2$ | O | 4-CF$_3$—Ph |
| 1-143 | diMeCar | diMeN | (CH$_2$)$_2$ | O | 4-MeO—Ph |
| 1-144 | diMeCar | diMeN | (CH$_2$)$_2$ | O | 3-MeO—Ph |
| 1-145 | diMeCar | diMeN | (CH$_2$)$_2$ | O | 2-MeO—Ph |
| 1-146 | diMeCar | diMeN | (CH$_2$)$_2$ | O | 4-Ac—Ph |
| 1-147 | diMeCar | diMeN | (CH$_2$)$_2$ | O | 3-Ac—Ph |
| 1-148 | diMeCar | diMeN | (CH$_2$)$_2$ | O | 4-CN—Ph |
| 1-149 | diMeCar | diMeN | (CH$_2$)$_2$ | O | 4-NO$_2$—Ph |
| 1-150 | diMeCar | diMeN | (CH$_2$)$_2$ | O | 2-NO$_2$—Ph |
| 1-151 | diMeCar | diMeN | (CH$_2$)$_2$ | O | 3-NO$_2$—Ph |
| 1-152 | diMeCar | diMeN | (CH$_2$)$_2$ | O | 4-NH$_2$—Ph |
| 1-153 | diMeCar | diMeN | (CH$_2$)$_2$ | O | 3-NH$_2$—Ph |
| 1-154 | diMeCar | diMeN | (CH$_2$)$_2$ | O | 4-AcNH—Ph |
| 1-155 | diMeCar | diMeN | (CH$_2$)$_2$ | O | 3-AcNH—Ph |
| 1-156 | diMeCar | diMeN | (CH$_2$)$_2$ | O | 4-COOH—Ph |
| 1-157 | diMeCar | diMeN | (CH$_2$)$_2$ | O | 3,4-Mtdo-Ph |
| 1-158 | diMeCar | diMeN | (CH$_2$)$_2$ | O | 2-F-4-F—Ph |
| 1-159 | diMeCar | diMeN | (CH$_2$)$_2$ | O | 3-F-4-F—Ph |
| 1-160 | diMeCar | diMeN | (CH$_2$)$_2$ | O | 3-F-5-F—Ph |
| 1-161 | diMeCar | diMeN | (CH$_2$)$_2$ | O | 3-F-4-Cl—Ph |
| 1-162 | diMeCar | diMeN | (CH$_2$)$_2$ | O | 2-F-4-NO$_2$—Ph |
| 1-163 | diMeCar | diMeN | (CH$_2$)$_2$ | O | 2-Cl-4-F—Ph |
| 1-164 | diMeCar | diMeN | (CH$_2$)$_2$ | O | 2-Cl-4-Cl—Ph |
| 1-165 | diMeCar | diMeN | (CH$_2$)$_2$ | O | 2-Cl-4-NO$_2$—Ph |
| 1-166 | diMeCar | diMeN | (CH$_2$)$_2$ | O | 3-Cl-4-F—Ph |
| 1-167 | diMeCar | diMeN | (CH$_2$)$_2$ | O | 3-Cl-4-Cl—Ph |
| 1-168 | diMeCar | diMeN | (CH$_2$)$_2$ | O | 2-Me-4-F—Ph |
| 1-169 | diMeCar | diMeN | (CH$_2$)$_2$ | O | 2-Me-4-Cl—Ph |
| 1-170 | diMeCar | diMeN | (CH$_2$)$_2$ | O | 3-Me-4-Cl—Ph |
| 1-171 | diMeCar | diMeN | (CH$_2$)$_2$ | O | 3-Me-4-Me—Ph |
| 1-172 | diMeCar | diMeN | (CH$_2$)$_2$ | O | 3-Me-4-NO$_2$—Ph |
| 1-173 | diMeCar | diMeN | (CH$_2$)$_2$ | O | 3-NO$_2$-4-Cl—Ph |
| 1-174 | diMeCar | diMeN | (CH$_2$)$_2$ | O | 3-F-4-F-5-F—Ph |
| 1-175 | diMeCar | diMeN | (CH$_2$)$_2$ | O | 2-F-3-F-5-F—Ph |
| 1-176 | diMeCar | diMeN | (CH$_2$)$_2$ | O | Py-3-yl |
| 1-177 | diMeCar | diMeN | (CH$_2$)$_2$ | O | 5-Cl—Py-3-yl |
| 1-178 | diMeCar | diMeN | (CH$_2$)$_2$ | O | 2-Me—Py-3-yl |
| 1-179 | diMeCar | diMeN | (CH$_2$)$_2$ | O | 6-Me—Py-3-yl |
| 1-180 | diMeCar | diMeN | (CH$_2$)$_2$ | O | Py-2-yl |
| 1-181 | diMeCar | diMeN | (CH$_2$)$_2$ | O | 6-Cl—Py-2-yl |
| 1-182 | diMeCar | diMeN | (CH$_2$)$_2$ | O | 6-CF$_3$—Py-2-yl |
| 1-183 | diMeCar | diMeN | (CH$_2$)$_2$ | O | 6-NO$_2$—Py-2-yl |
| 1-184 | diMeCar | diMeN | (CH$_2$)$_2$ | O | Py-4-yl |
| 1-185 | diMeCar | diMeN | (CH$_2$)$_2$ | O | 2-NO$_2$—Py-4-yl |
| 1-186 | diMeCar | diMeN | (CH$_2$)$_2$ | O | Thi-3-yl |
| 1-187 | diMeCar | diMeN | (CH$_2$)$_2$ | O | 2-MeOCO-Thi-3-yl |
| 1-188 | diMeCar | MeEtN | (CH$_2$)$_2$ | O | 4-F—Ph |
| 1-189 | diMeCar | MeEtN | (CH$_2$)$_2$ | O | 4-NO$_2$—Ph |
| 1-190 | diMeCar | MeEtN | (CH$_2$)$_2$ | O | 4-Cl—Ph |
| 1-191 | diMeCar | MeEtN | (CH$_2$)$_2$ | O | 3-F-4-F—Ph |
| 1-192 | diMeCar | MeHN | (CH$_2$)$_3$ | O | 4-F—Ph |
| 1-193 | diMeCar | MeHN | (CH$_2$)$_3$ | O | 4-Cl—Ph |
| 1-194 | diMeCar | MeHN | (CH$_2$)$_3$ | O | 4-NO$_2$—Ph |
| 1-195 | diMeCar | MeHN | (CH$_2$)$_2$ | O | 2-F-4-NO$_2$—Ph |
| 1-196 | diMeCar | diMeN | (CH$_2$)$_2$ | O | 2-F-4-NO$_2$—Ph |
| 1-197 | diMeCar | MeHN | (CH$_2$)$_2$ | S | 2-F-4-NO$_2$—Ph |
| 1-198 | diMeCar | diMeN | (CH$_2$)$_2$ | S | 2-F-4-NO$_2$—Ph |
| 1-199 | diMeCar | MeHN | (CH$_2$)$_2$ | O | 4-MeS—Ph |
| 1-200 | diMeCar | diMeN | (CH$_2$)$_2$ | O | 4-MeS—Ph |
| 1-201 | diMeCar | MeHN | (CH$_2$)$_2$ | S | 4-MeS—Ph |
| 1-202 | diMeCar | diMeN | (CH$_2$)$_2$ | S | 4-MeS—Ph |
| 1-203 | diMeCar | MeHN | (CH$_2$)$_2$ | O | pentaFPh |
| 1-204 | diMeCar | diMeN | (CH$_2$)$_2$ | O | pentaFPh |
| 1-205 | diMeCar | MeHN | (CH$_2$)$_2$ | O | naphtalene-1-yl |
| 1-206 | diMeCar | MeHN | (CH$_2$)$_2$ | O | quinoline-6-yl |
| 1-207 | diMeCar | MeHN | (CH$_2$)$_2$ | O | naphtalene-2-yl |

TABLE 2

(Ib)

| Compound No. | R¹—(C=X¹) | R²R³N | A | E | Arom |
|---|---|---|---|---|---|
| 2-1 | diMeCar | MeNH | (CH$_2$)$_2$ | — | 4-F—Ph |
| 2-2 | EtCar | MeNH | (CH$_2$)$_2$ | O | 4-F—Ph |
| 2-3 | EtCar | MeNH | (CH$_2$)$_2$ | — | 4-MeO—Ph |
| 2-4 | Ac | MeNH | (CH$_2$)$_2$ | O | 4-F—Ph |
| 2-5 | tBu-(C=O) | MeNH | (CH$_2$)$_2$ | O | 4-F—Ph |
| 2-6 | diEtCar | MeNH | (CH$_2$)$_2$ | O | 4-F—Ph |
| 2-7 | diEtCar | MeNH | (CH$_2$)$_2$ | — | 4-Cl—Ph |
| 2-8 | diEtCar | MeNH | (CH$_2$)$_2$ | — | 3-Cl—Ph |
| 2-9 | diPrCar | MeNH | (CH$_2$)$_2$ | O | 4-F—Ph |
| 2-10 | MeEtCar | MeNH | (CH$_2$)$_2$ | — | 4-Cl—Ph |

TABLE 2-continued (Ib)

$$R^1-\overset{X^1}{\underset{}{C}}-O-\underset{}{\text{Ph}}-\underset{NR^2R^3}{\overset{}{CH}}-A-E-\text{Arom}$$

| Compound No. | R¹—(C=X¹) | R²R³N | A | E | Arom |
|---|---|---|---|---|---|
| 2-11 | Mor-(C=O) | MeNH | (CH₂)₂ | O | 4-F—Ph |
| 2-12 | diMeTcr | MeNH | (CH₂)₂ | O | 4-F—Ph |
| 2-13 | diMeCar | MeNH | (CH₂)₂ | — | 4-Cl—Ph |
| 2-14 | diMeCar | MeNH | (CH₂)₂ | — | 4-CF₃—Ph |
| 2-15 | diMeCar | MeNH | (CH₂)₂ | — | 4-MeO—Ph |
| 2-16 | diMeCar | diMeN | (CH₂)₂ | — | 4-MeO—Ph |
| 2-17 | diMeCar | MeNH | (CH₂)₂ | — | 3-MeO-4-MeO—Ph |
| 2-18 | diMeCar | MeNH | (CH₂)₂ | — | 3,4-Mtdo-Ph |
| 2-19 | diMeCar | MeNH | (CH₂)₂ | — | 4-NO₂—Ph |
| 2-20 | diMeCar | MeNH | (CH₂)₂ | — | 3-F-4-F—Ph |
| 2-21 | diMeCar | diMeN | (CH₂)₂ | — | 4-F—Ph |
| 2-22 | diMeCar | diMeN | (CH₂)₂ | — | 4-Cl—Ph |
| 2-23 | diMeCar | diMeN | (CH₂)₂ | — | 4-NO₂—Ph |
| 2-24 | diMeCar | diMeN | (CH₂)₂ | — | 3-F-4-F—Ph |
| 2-25 | diMeCar | MeNH | (CH₂)₃ | — | 4-F—Ph |
| 2-26 | diMeCar | MeNH | (CH₂)₃ | — | 4-Cl—Ph |
| 2-27 | diMeCar | MeNH | (CH₂)₃ | — | 4-NO₂—Ph |
| 2-28 | diMeCar | MeNH | (CH₂)₃ | — | 3-F-4-F—Ph |
| 2-29 | diMeCar | diMeN | (CH₂)₃ | — | 4-F—Ph |
| 2-30 | diMeCar | diMeN | (CH₂)₃ | — | 4-Cl—Ph |
| 2-31 | diMeCar | diMeN | (CH₂)₃ | — | 4-NO₂—Ph |
| 2-32 | diMeCar | diMeN | (CH₂)₃ | — | 3-F-4-F—Ph |
| 2-33 | diMeCar | MeNH | CH₂ | O | 4-F—Ph |
| 2-34 | diMeCar | MeNH | CH₂ | O | 4-Cl—Ph |
| 2-35 | diMeCar | MeNH | CH₂ | O | 4-NO₂—Ph |
| 2-36 | diMeCar | MeNH | CH₂ | O | 3-F-4-F—Ph |
| 2-37 | diMeCar | diMeN | CH₂ | O | 4-F—Ph |
| 2-38 | diMeCar | diMeN | CH₂ | O | 4-Cl—Ph |
| 2-39 | diMeCar | diMeN | CH₂ | O | 4-NO₂—Ph |
| 2-40 | diMeCar | diMeN | CH₂ | O | 3-F-4-F—Ph |
| 2-41 | diMeCar | MeNH | (CH₂)₂ | S | 4-F—Ph |
| 2-42 | diMeCar | MeNH | (CH₂)₂ | S | 4-Cl—Ph |
| 2-43 | diMeCar | MeNH | (CH₂)₂ | S | 4-NO₂—Ph |
| 2-44 | diMeCar | MeNH | (CH₂)₂ | S | 3-F-4-F—Ph |
| 2-45 | diMeCar | diMeN | (CH₂)₂ | S | 4-F—Ph |
| 2-46 | diMeCar | diMeN | (CH₂)₂ | S | 4-Cl—Ph |
| 2-47 | diMeCar | diMeN | (CH₂)₂ | S | 4-NO₂—Ph |
| 2-48 | diMeCar | diMeN | (CH₂)₂ | S | 3-F-4-F—Ph |
| 2-49 | diMeCar | MeNH | (CH₂)₂ | NH | 4-F—Ph |
| 2-50 | diMeCar | MeNH | (CH₂)₂ | NH | 4-Cl—Ph |
| 2-51 | diMeCar | MeNH | (CH₂)₂ | NH | 3-F—Ph |
| 2-52 | diMeCar | MeNH | (CH₂)₂ | NH | 3-Cl—Ph |
| 2-53 | diMeCar | MeNH | (CH₂)₂ | NH | 4-NO₂—Ph |
| 2-54 | diMeCar | MeNH | (CH₂)₂ | NH | 3-F-4-F—Ph |
| 2-55 | diMeCar | diMeN | (CH₂)₂ | NH | 4-F—Ph |
| 2-56 | diMeCar | diMeN | (CH₂)₂ | NH | 4-Cl—Ph |
| 2-57 | diMeCar | diMeN | (CH₂)₂ | NH | 4-NO₂—Ph |
| 2-58 | diMeCar | diMeN | (CH₂)₂ | NH | 3-F-4-F—Ph |
| 2-59 | diMeCar | MeNH | (CH₂)₂ | NAc | 4-Cl—Ph |
| 2-60 | diMeCar | MeNH | (CH₂)₂ | NAc | 3-F—Ph |
| 2-61 | diMeCar | MeNH | (CH₂)₂ | NAc | 4-NO₂—Ph |
| 2-62 | diMeCar | diMeN | (CH₂)₂ | NAc | 4-Cl—Ph |
| 2-63 | diMeCar | diMeN | (CH₂)₂ | NAc | 3-F—Ph |
| 2-64 | diMeCar | diMeN | (CH₂)₂ | NAc | 4-NO₂—Ph |
| 2-65 | diMeCar | NH₂ | (CH₂)₂ | O | 4-F—Ph |
| 2-66 | diMeCar | NH₂ | (CH₂)₂ | O | 4-NO₂—Ph |
| 2-67 | diMeCar | EtNH | (CH₂)₂ | O | 4-F—Ph |
| 2-68 | diMeCar | EtNH | (CH₂)₂ | O | 3-F—Ph |
| 2-69 | diMeCar | EtNH | (CH₂)₂ | O | 4-Cl—Ph |
| 2-70 | diMeCar | EtNH | (CH₂)₂ | O | 3-NO₂—Ph |
| 2-71 | diMeCar | EtNH | (CH₂)₂ | O | 4-NO₂—Ph |
| 2-72 | diMeCar | EtNH | (CH₂)₂ | O | 3-F-4-F—Ph |
| 2-73 | diMeCar | PrNH | (CH₂)₂ | O | 4-F—Ph |
| 2-74 | diMeCar | MeNH | (CH₂)₂ | O | Ph |
| 2-75 | diMeCar | MeNH | (CH₂)₂ | O | 4-F—Ph |
| 2-76 | diMeCar | MeNH | (CH₂)₂ | O | 3-F—Ph |
| 2-77 | diMeCar | MeNH | (CH₂)₂ | O | 2-F—Ph |
| 2-78 | diMeCar | MeNH | (CH₂)₂ | O | 4-Cl—Ph |
| 2-79 | diMeCar | MeNH | (CH₂)₂ | O | 3-Cl—Ph |
| 2-80 | diMeCar | MeNH | (CH₂)₂ | O | 2-Cl—Ph |
| 2-81 | diMeCar | MeNH | (CH₂)₂ | O | 4-Br—Ph |
| 2-82 | diMeCar | MeNH | (CH₂)₂ | O | 4-Me—Ph |
| 2-83 | diMeCar | MeNH | (CH₂)₂ | O | 3-Me—Ph |
| 2-84 | diMeCar | MeNH | (CH₂)₂ | O | 2-Me—Ph |
| 2-85 | diMeCar | MeNH | (CH₂)₂ | O | 4-CF₃—Ph |
| 2-86 | diMeCar | MeNH | (CH₂)₂ | O | 4-MeO—Ph |
| 2-87 | diMeCar | MeNH | (CH₂)₂ | O | 3-MeO—Ph |
| 2-88 | diMeCar | MeNH | (CH₂)₂ | O | 2-MeO—Ph |
| 2-89 | diMeCar | MeNH | (CH₂)₂ | O | 4-Ac—Ph |
| 2-90 | diMeCar | MeNH | (CH₂)₂ | O | 3-Ac—Ph |
| 2-91 | diMeCar | MeNH | (CH₂)₂ | O | 4-CN—Ph |
| 2-92 | diMeCar | MeNH | (CH₂)₂ | O | 4-NO₂—Ph |
| 2-93 | diMeCar | MeNH | (CH₂)₂ | O | 2-NO₂—Ph |
| 2-94 | diMeCar | MeNH | (CH₂)₂ | O | 3-NO₂—Ph |
| 2-95 | diMeCar | MeNH | (CH₂)₂ | O | 4-NH₂—Ph |
| 2-96 | diMeCar | MeNH | (CH₂)₂ | O | 3-NH₂—Ph |
| 2-97 | diMeCar | MeNH | (CH₂)₂ | O | 4-AcNH—Ph |
| 2-98 | diMeCar | MeNH | (CH₂)₂ | O | 3-AcNH—Ph |
| 2-99 | diMeCar | MeNH | (CH₂)₂ | O | 4-COOH—Ph |
| 2-100 | diMeCar | MeNH | (CH₂)₂ | O | 3,4-Mtdo-Ph |
| 2-101 | diMeCar | MeNH | (CH₂)₂ | O | 2-F-4-F—Ph |
| 2-102 | diMeCar | MeNH | (CH₂)₂ | O | 3-F-4-F—Ph |
| 2-103 | diMeCar | MeNH | (CH₂)₂ | O | 3-F-5-F—Ph |
| 2-104 | diMeCar | MeNH | (CH₂)₂ | O | 3-F-4-Cl—Ph |
| 2-105 | diMeCar | MeNH | (CH₂)₂ | O | 2-F-4-NO₂—Ph |
| 2-106 | diMeCar | MeNH | (CH₂)₂ | O | 2-Cl-4-F—Ph |
| 2-107 | diMeCar | MeNH | (CH₂)₂ | O | 2-Cl-4-Cl—Ph |
| 2-108 | diMeCar | MeNH | (CH₂)₂ | O | 2-Cl-4-NO₂—Ph |
| 2-109 | diMeCar | MeNH | (CH₂)₂ | O | 3-Cl-4-F—Ph |
| 2-110 | diMeCar | MeNH | (CH₂)₂ | O | 3-Cl-4-Cl—Ph |
| 2-111 | diMeCar | MeNH | (CH₂)₂ | O | 2-Me-4-F—Ph |
| 2-112 | diMeCar | MeNH | (CH₂)₂ | O | 2-Me-4-Cl—Ph |
| 2-113 | diMeCar | MeNH | (CH₂)₂ | O | 3-Me-4-Cl—Ph |
| 2-114 | diMeCar | MeNH | (CH₂)₂ | O | 3-Me-4-Me—Ph |
| 2-115 | diMeCar | MeNH | (CH₂)₂ | O | 3-Me-4-NO₂—Ph |
| 2-116 | diMeCar | MeNH | (CH₂)₂ | O | 3-NO₂-4-Cl—Ph |
| 2-117 | diMeCar | MeNH | (CH₂)₂ | O | 3-F-4-F-5-F—Ph |
| 2-118 | diMeCar | MeNH | (CH₂)₂ | O | 2-F-3-F-5-F—Ph |
| 2-119 | diMeCar | MeNH | (CH₂)₂ | O | Py-3-yl |
| 2-120 | diMeCar | MeNH | (CH₂)₂ | O | 5-Cl—Py-3-yl |
| 2-121 | diMeCar | MeNH | (CH₂)₂ | O | 2-Me—Py-3-yl |
| 2-122 | diMeCar | MeNH | (CH₂)₂ | O | 6-Me—Py-3-yl |
| 2-123 | diMeCar | MeNH | (CH₂)₂ | O | Py-2-yl |
| 2-124 | diMeCar | MeNH | (CH₂)₂ | O | 6-Cl—Py-2-yl |
| 2-125 | diMeCar | MeNH | (CH₂)₂ | O | 6-CF₃—Py-2-yl |
| 2-126 | diMeCar | MeNH | (CH₂)₂ | O | 6-NO₂—Py-2-yl |
| 2-127 | diMeCar | MeNH | (CH₂)₂ | O | Py-4-yl |
| 2-128 | diMeCar | MeNH | (CH₂)₂ | O | 2-NO₂—Py-4-yl |
| 2-129 | diMeCar | MeNH | (CH₂)₂ | O | Thi-3-yl |
| 2-130 | diMeCar | MeNH | (CH₂)₂ | O | 2-MeOCO-Thi-3-yl |
| 2-131 | diMeCar | diMeN | (CH₂)₂ | O | Ph |
| 2-132 | diMeCar | diMeN | (CH₂)₂ | O | 4-F—Ph |
| 2-133 | diMeCar | diMeN | (CH₂)₂ | O | 3-F—Ph |
| 2-134 | diMeCar | diMeN | (CH₂)₂ | O | 2-F—Ph |
| 2-135 | diMeCar | diMeN | (CH₂)₂ | O | 4-Cl—Ph |
| 2-136 | diMeCar | diMeN | (CH₂)₂ | O | 3-Cl—Ph |
| 2-137 | diMeCar | diMeN | (CH₂)₂ | O | 2-Cl—Ph |
| 2-138 | diMeCar | diMeN | (CH₂)₂ | O | 4-Br—Ph |
| 2-139 | diMeCar | diMeN | (CH₂)₂ | O | 4-Me—Ph |
| 2-140 | diMeCar | diMeN | (CH₂)₂ | O | 3-Me—Ph |
| 2-141 | diMeCar | diMeN | (CH₂)₂ | O | 2-Me—Ph |
| 2-142 | diMeCar | diMeN | (CH₂)₂ | O | 4-CF₃—Ph |

TABLE 2-continued (Ib)

Structure: R¹—(C(=X¹))—O—[phenyl(1,3-disubstituted)]—CH(NR²R³)—A—E—Arom

| Compound No. | R¹—(C=X¹) | R²R³N | A | E | Arom |
|---|---|---|---|---|---|
| 2-143 | diMeCar | diMeN | (CH₂)₂ | O | 4-MeO—Ph |
| 2-144 | diMeCar | diMeN | (CH₂)₂ | O | 3-MeO—Ph |
| 2-145 | diMeCar | diMeN | (CH₂)₂ | O | 2-MeO—Ph |
| 2-146 | diMeCar | diMeN | (CH₂)₂ | O | 4-Ac—Ph |
| 2-147 | diMeCar | diMeN | (CH₂)₂ | O | 3-Ac—Ph |
| 2-148 | diMeCar | diMeN | (CH₂)₂ | O | 4-CN—Ph |
| 2-149 | diMeCar | diMeN | (CH₂)₂ | O | 4-NO₂—Ph |
| 2-150 | diMeCar | diMeN | (CH₂)₂ | O | 2-NO₂—Ph |
| 2-151 | diMeCar | diMeN | (CH₂)₂ | O | 3-NO₂—Ph |
| 2-152 | diMeCar | diMeN | (CH₂)₂ | O | 4-NH₂—Ph |
| 2-153 | diMeCar | diMeN | (CH₂)₂ | O | 3-NH₂—Ph |
| 2-154 | diMeCar | diMeN | (CH₂)₂ | O | 4-AcNH—Ph |
| 2-155 | diMeCar | diMeN | (CH₂)₂ | O | 3-AcNH—Ph |
| 2-156 | diMeCar | diMeN | (CH₂)₂ | O | 4-COOH—Ph |
| 2-157 | diMeCar | diMeN | (CH₂)₂ | O | 3,4-Mtdo-Ph |
| 2-158 | diMeCar | diMeN | (CH₂)₂ | O | 2-F-4-F—Ph |
| 2-159 | diMeCar | diMeN | (CH₂)₂ | O | 3-F-4-F—Ph |
| 2-160 | diMeCar | diMeN | (CH₂)₂ | O | 3-F-5-F—Ph |
| 2-161 | diMeCar | diMeN | (CH₂)₂ | O | 3-F-4-Cl—Ph |
| 2-162 | diMeCar | diMeN | (CH₂)₂ | O | 2-F-4-NO₂—Ph |
| 2-163 | diMeCar | diMeN | (CH₂)₂ | O | 2-Cl-4-F—Ph |
| 2-164 | diMeCar | diMeN | (CH₂)₂ | O | 2-Cl-4-Cl—Ph |
| 2-165 | diMeCar | diMeN | (CH₂)₂ | O | 2-Cl-4-NO₂—Ph |
| 2-166 | diMeCar | diMeN | (CH₂)₂ | O | 3-Cl-4-F—Ph |
| 2-167 | diMeCar | diMeN | (CH₂)₂ | O | 3-Cl-4-Cl—Ph |
| 2-168 | diMeCar | diMeN | (CH₂)₂ | O | 2-Me-4-F—Ph |
| 2-169 | diMeCar | diMeN | (CH₂)₂ | O | 2-Me-4-Cl—Ph |
| 2-170 | diMeCar | diMeN | (CH₂)₂ | O | 3-Me-4-Cl—Ph |
| 2-171 | diMeCar | diMeN | (CH₂)₂ | O | 3-Me-4-Me—Ph |
| 2-172 | diMeCar | diMeN | (CH₂)₂ | O | 3-Me-4-NO₂—Ph |
| 2-173 | diMeCar | diMeN | (CH₂)₂ | O | 3-NO₂-4-Cl—Ph |
| 2-174 | diMeCar | diMeN | (CH₂)₂ | O | 3-F-4-F-5-F—Ph |
| 2-175 | diMeCar | diMeN | (CH₂)₂ | O | 2-F-3-F-5-F—Ph |
| 2-176 | diMeCar | diMeN | (CH₂)₂ | O | Py-3-yl |
| 2-177 | diMeCar | diMeN | (CH₂)₂ | O | 5-Cl—Py-3-yl |
| 2-178 | diMeCar | diMeN | (CH₂)₂ | O | 2-Me—Py-3-yl |
| 2-179 | diMeCar | diMeN | (CH₂)₂ | O | 6-Me—Py-3-yl |
| 2-180 | diMeCar | diMeN | (CH₂)₂ | O | Py-2-yl |
| 2-181 | diMeCar | diMeN | (CH₂)₂ | O | 6-Cl—Py-2-yl |
| 2-182 | diMeCar | diMeN | (CH₂)₂ | O | 6-CF₃—Py-2-yl |
| 2-183 | diMeCar | diMeN | (CH₂)₂ | O | 6-NO₂—Py-2-yl |
| 2-184 | diMeCar | diMeN | (CH₂)₂ | O | Py-4-yl |
| 2-185 | diMeCar | diMeN | (CH₂)₂ | O | 2-NO₂—Py-4-yl |
| 2-186 | diMeCar | diMeN | (CH₂)₂ | O | Thi-3-yl |
| 2-187 | diMeCar | diMeN | (CH₂)₂ | O | 2-MeOCO-Thi-3-yl |
| 2-188 | diMeCar | MeEtN | (CH₂)₂ | O | 4-F—Ph |
| 2-189 | diMeCar | MeEtN | (CH₂)₂ | O | 4-NO₂—Ph |
| 2-190 | diMeCar | MeEtN | (CH₂)₂ | O | 4-Cl—Ph |
| 2-191 | diMeCar | MeEtN | (CH₂)₂ | O | 3-F-4-F—Ph |
| 2-192 | diMeCar | MeHN | (CH₂)₃ | O | 4-F—Ph |
| 2-193 | diMeCar | MeHN | (CH₂)₃ | O | 4-Cl—Ph |
| 2-194 | diMeCar | MeHN | (CH₂)₃ | O | 4-NO₂—Ph |
| 2-195 | diMeCar | diMeN | (CH₂)₂ | O | 2-F-4-NO₂—Ph |
| 2-196 | diMeCar | diMeN | (CH₂)₂ | O | 2-F-4-NO₂—Ph |
| 2-197 | diMeCar | diMeN | (CH₂)₂ | S | 2-F-4-NO₂—Ph |
| 2-198 | diMeCar | diMeN | (CH₂)₂ | S | 2-F-4-NO₂—Ph |
| 2-199 | diMeCar | MeHN | (CH₂)₂ | S | 4-MeS—Ph |
| 2-200 | diMeCar | diMeN | (CH₂)₂ | S | 4-MeS—Ph |
| 2-201 | diMeCar | MeHN | (CH₂)₂ | S | 4-MeS—Ph |
| 2-202 | diMeCar | diMeN | (CH₂)₂ | S | 4-MeS—Ph |
| 2-203 | diMeCar | diMeN | (CH₂)₂ | O | pentaFPh |
| 2-204 | diMeCar | diMeN | (CH₂)₂ | O | pentaFPh |
| 2-205 | diMeCar | MeHN | (CH₂)₂ | O | naphtalene-1-yl |
| 2-206 | diMeCar | MeHN | (CH₂)₂ | O | quinoline-6-yl |
| 2-207 | diMeCar | MeHN | (CH₂)₂ | O | naphtalene-2-yl |

TABLE 3

(Ic)

Structure: R¹—(C(=X¹))—O—[phenyl(1,2-disubstituted)]—CH(NR²R³)—A—E—Arom

| Compound No. | R¹—(C=X¹) | R²R³N | A | E | Arom |
|---|---|---|---|---|---|
| 3-1 | diMeCar | NH₂ | (CH₂)₂ | O | 4-F—Ph |
| 3-2 | diMeCar | NH₂ | (CH₂)₂ | O | 4-NO₂—Ph |
| 3-3 | diMeCar | EtNH | (CH₂)₂ | O | 4-F—Ph |
| 3-4 | diMeCar | EtNH | (CH₂)₂ | O | 3-F—Ph |
| 3-5 | diMeCar | EtNH | (CH₂)₂ | O | 4-Cl—Ph |
| 3-6 | diMeCar | EtNH | (CH₂)₂ | O | 3-NO₂—Ph |
| 3-7 | diMeCar | EtNH | (CH₂)₂ | O | 4-NO₂—Ph |
| 3-8 | diMeCar | EtNH | (CH₂)₂ | O | 3-F-4-F—Ph |
| 3-9 | diMeCar | PrNH | (CH₂)₂ | O | 4-F—Ph |
| 3-10 | diMeCar | MeNH | (CH₂)₂ | O | Ph |
| 3-11 | diMeCar | MeNH | (CH₂)₂ | O | 4-F—Ph |
| 3-12 | diMeCar | MeNH | (CH₂)₂ | O | 3-F—Ph |
| 3-13 | diMeCar | MeNH | (CH₂)₂ | O | 2-F—Ph |
| 3-14 | diMeCar | MeNH | (CH₂)₂ | O | 4-Cl—Ph |
| 3-15 | diMeCar | MeNH | (CH₂)₂ | O | 3-Cl—Ph |
| 3-16 | diMeCar | MeNH | (CH₂)₂ | O | 2-Cl—Ph |
| 3-17 | diMeCar | MeNH | (CH₂)₂ | O | 4-Br—Ph |
| 3-18 | diMeCar | MeNH | (CH₂)₂ | O | 4-Me—Ph |
| 3-19 | diMeCar | MeNH | (CH₂)₂ | O | 3-Me—Ph |
| 3-20 | diMeCar | MeNH | (CH₂)₂ | O | 2-Me—Ph |
| 3-21 | diMeCar | MeNH | (CH₂)₂ | O | 4-CF₃—Ph |
| 3-22 | diMeCar | MeNH | (CH₂)₂ | O | 4-MeO—Ph |
| 3-23 | diMeCar | MeNH | (CH₂)₂ | O | 3-MeO—Ph |
| 3-24 | diMeCar | MeNH | (CH₂)₂ | O | 2-MeO—Ph |
| 3-25 | diMeCar | MeNH | (CH₂)₂ | O | 4-Ac—Ph |
| 3-26 | diMeCar | MeNH | (CH₂)₂ | O | 3-Ac—Ph |
| 3-27 | diMeCar | MeNH | (CH₂)₂ | O | 4-CN—Ph |
| 3-28 | diMeCar | MeNH | (CH₂)₂ | O | 4-NO₂—Ph |
| 3-29 | diMeCar | MeNH | (CH₂)₂ | O | 2-NO₂—Ph |
| 3-30 | diMeCar | MeNH | (CH₂)₂ | O | 3-NO₂—Ph |
| 3-31 | diMeCar | MeNH | (CH₂)₂ | O | 4-NH₂—Ph |
| 3-32 | diMeCar | MeNH | (CH₂)₂ | O | 3-NH₂—Ph |
| 3-33 | diMeCar | MeNH | (CH₂)₂ | O | 4-AcNH—Ph |
| 3-34 | diMeCar | MeNH | (CH₂)₂ | O | 3-AcNH—Ph |
| 3-35 | diMeCar | MeNH | (CH₂)₂ | O | 4-COOH—Ph |
| 3-36 | diMeCar | MeNH | (CH₂)₂ | O | 3,4-Mtdo-Ph |
| 3-37 | diMeCar | MeNH | (CH₂)₂ | O | 2-F-4-F—Ph |
| 3-38 | diMeCar | MeNH | (CH₂)₂ | O | 3-F-4-F—Ph |
| 3-39 | diMeCar | MeNH | (CH₂)₂ | O | 3-F-5-F—Ph |
| 3-40 | diMeCar | MeNH | (CH₂)₂ | O | 3-F-4-Cl—Ph |
| 3-41 | diMeCar | MeNH | (CH₂)₂ | O | 2-F-4-NO₂—Ph |
| 3-42 | diMeCar | MeNH | (CH₂)₂ | O | 2-Cl-4-F—Ph |
| 3-43 | diMeCar | MeNH | (CH₂)₂ | O | 2-Cl-4-Cl—Ph |
| 3-44 | diMeCar | MeNH | (CH₂)₂ | O | 2-Cl-4-NO₂—Ph |
| 3-45 | diMeCar | MeNH | (CH₂)₂ | O | 3-Cl-4-F—Ph |
| 3-46 | diMeCar | MeNH | (CH₂)₂ | O | 3-Cl-4-Cl—Ph |
| 3-47 | diMeCar | MeNH | (CH₂)₂ | O | 2-Me-4-F—Ph |
| 3-48 | diMeCar | MeNH | (CH₂)₂ | O | 2-Me-4-Cl—Ph |
| 3-49 | diMeCar | MeNH | (CH₂)₂ | O | 3-Me-4-Cl—Ph |
| 3-50 | diMeCar | MeNH | (CH₂)₂ | O | 3-Me-4-Me—Ph |
| 3-51 | diMeCar | MeNH | (CH₂)₂ | O | 3-Me-4-NO₂—Ph |
| 3-52 | diMeCar | MeNH | (CH₂)₂ | O | 3-NO₂-4-Cl—Ph |
| 3-53 | diMeCar | MeNH | (CH₂)₂ | O | 3-F-4-F-5-F—Ph |
| 3-54 | diMeCar | MeNH | (CH₂)₂ | O | 2-F-3-F-5-F—Ph |
| 3-55 | diMeCar | MeNH | (CH₂)₂ | O | Py-3-yl |
| 3-56 | diMeCar | MeNH | (CH₂)₂ | O | 5-Cl—Py-3-yl |
| 3-57 | diMeCar | MeNH | (CH₂)₂ | O | 2-Me—Py-3-yl |
| 3-58 | diMeCar | MeNH | (CH₂)₂ | O | 6-Me—Py-3-yl |
| 3-59 | diMeCar | MeNH | (CH₂)₂ | O | Py-2-yl |
| 3-60 | diMeCar | MeNH | (CH₂)₂ | O | 6-Cl—Py-2-yl |
| 3-61 | diMeCar | MeNH | (CH₂)₂ | O | 6-CF₃—Py-2-yl |
| 3-62 | diMeCar | MeNH | (CH₂)₂ | O | 6-NO₂—Py-2-yl |

TABLE 3-continued (Ic)

| Compound No. | R¹—(C═X¹) | R²R³N | A | E | Arom |
|---|---|---|---|---|---|
| 3-63 | diMeCar | MeNH | (CH$_2$)$_2$ | O | Py-4-yl |
| 3-64 | diMeCar | MeNH | (CH$_2$)$_2$ | O | 2-NO$_2$—Py-4-yl |
| 3-65 | diMeCar | MeNH | (CH$_2$)$_2$ | O | Thi-3-yl |
| 3-66 | diMeCar | MeNH | (CH$_2$)$_2$ | O | 2-MeOCO-Thi-3-yl |
| 3-67 | diMeCar | diMeN | (CH$_2$)$_2$ | O | Ph |
| 3-68 | diMeCar | diMeN | (CH$_2$)$_2$ | O | 4-F—Ph |
| 3-69 | diMeCar | diMeN | (CH$_2$)$_2$ | O | 3-F—Ph |
| 3-70 | diMeCar | diMeN | (CH$_2$)$_2$ | O | 2-F—Ph |
| 3-71 | diMeCar | diMeN | (CH$_2$)$_2$ | O | 4-Cl—Ph |
| 3-72 | diMeCar | diMeN | (CH$_2$)$_2$ | O | 3-Cl—Ph |
| 3-73 | diMeCar | diMeN | (CH$_2$)$_2$ | O | 2-Cl—Ph |
| 3-74 | diMeCar | diMeN | (CH$_2$)$_2$ | O | 4-Br—Ph |
| 3-75 | diMeCar | diMeN | (CH$_2$)$_2$ | O | 4-Me—Ph |
| 3-76 | diMeCar | diMeN | (CH$_2$)$_2$ | O | 3-Me—Ph |
| 3-77 | diMeCar | diMeN | (CH$_2$)$_2$ | O | 2-Me—Ph |
| 3-78 | diMeCar | diMeN | (CH$_2$)$_2$ | O | 4-CF$_3$—Ph |
| 3-79 | diMeCar | diMeN | (CH$_2$)$_2$ | O | 4-MeO—Ph |
| 3-80 | diMeCar | diMeN | (CH$_2$)$_2$ | O | 3-MeO—Ph |
| 3-81 | diMeCar | diMeN | (CH$_2$)$_2$ | O | 2-MeO—Ph |
| 3-82 | diMeCar | diMeN | (CH$_2$)$_2$ | O | 4-Ac—Ph |
| 3-83 | diMeCar | diMeN | (CH$_2$)$_2$ | O | 3-Ac—Ph |
| 3-84 | diMeCar | diMeN | (CH$_2$)$_2$ | O | 4-CN—Ph |
| 3-85 | diMeCar | diMeN | (CH$_2$)$_2$ | O | 4-NO$_2$—Ph |
| 3-86 | diMeCar | diMeN | (CH$_2$)$_2$ | O | 2-NO$_2$—Ph |
| 3-87 | diMeCar | diMeN | (CH$_2$)$_2$ | O | 3-NO$_2$—Ph |
| 3-88 | diMeCar | diMeN | (CH$_2$)$_2$ | O | 4-NH$_2$—Ph |
| 3-89 | diMeCar | diMeN | (CH$_2$)$_2$ | O | 3-NH$_2$—Ph |
| 3-90 | diMeCar | diMeN | (CH$_2$)$_2$ | O | 4-AcNH—Ph |
| 3-91 | diMeCar | diMeN | (CH$_2$)$_2$ | O | 3-AcNH—Ph |
| 3-92 | diMeCar | diMeN | (CH$_2$)$_2$ | O | 4-COOH—Ph |
| 3-93 | diMeCar | diMeN | (CH$_2$)$_2$ | O | 3,4-Mtdo-Ph |
| 3-94 | diMeCar | diMeN | (CH$_2$)$_2$ | O | 2-F-4-F—Ph |
| 3-95 | diMeCar | diMeN | (CH$_2$)$_2$ | O | 3-F-4-F—Ph |
| 3-96 | diMeCar | diMeN | (CH$_2$)$_2$ | O | 3-F-5-F—Ph |
| 3-97 | diMeCar | diMeN | (CH$_2$)$_2$ | O | 3-F-4-Cl—Ph |
| 3-98 | diMeCar | diMeN | (CH$_2$)$_2$ | O | 2-F-4-NO$_2$—Ph |
| 3-99 | diMeCar | diMeN | (CH$_2$)$_2$ | O | 2-Cl-4-F—Ph |
| 3-100 | diMeCar | diMeN | (CH$_2$)$_2$ | O | 2-Cl-4-Cl—Ph |
| 3-101 | diMeCar | diMeN | (CH$_2$)$_2$ | O | 2-Cl-4-NO$_2$—Ph |
| 3-102 | diMeCar | diMeN | (CH$_2$)$_2$ | O | 3-Cl-4-F—Ph |
| 3-103 | diMeCar | diMeN | (CH$_2$)$_2$ | O | 3-Cl-4-Cl—Ph |
| 3-104 | diMeCar | diMeN | (CH$_2$)$_2$ | O | 2-Me-4-F—Ph |
| 3-105 | diMeCar | diMeN | (CH$_2$)$_2$ | O | 2-Me-4-Cl—Ph |
| 3-106 | diMeCar | diMeN | (CH$_2$)$_2$ | O | 3-Me-4-Cl—Ph |
| 3-107 | diMeCar | diMeN | (CH$_2$)$_2$ | O | 3-Me-4-Me—Ph |
| 3-108 | diMeCar | diMeN | (CH$_2$)$_2$ | O | 3-Me-4-NO$_2$—Ph |
| 3-109 | diMeCar | diMeN | (CH$_2$)$_2$ | O | 3-NO$_2$-4-Cl—Ph |
| 3-110 | diMeCar | diMeN | (CH$_2$)$_2$ | O | 3-F-4-F-5-F—Ph |
| 3-111 | diMeCar | diMeN | (CH$_2$)$_2$ | O | 2-F-3-F-5-F—Ph |
| 3-112 | diMeCar | diMeN | (CH$_2$)$_2$ | O | Py-3-yl |
| 3-113 | diMeCar | diMeN | (CH$_2$)$_2$ | O | 5-Cl—Py-3-yl |
| 3-114 | diMeCar | diMeN | (CH$_2$)$_2$ | O | 2-Me—Py-3-yl |
| 3-115 | diMeCar | diMeN | (CH$_2$)$_2$ | O | 6-Me—Py-3-yl |
| 3-116 | diMeCar | diMeN | (CH$_2$)$_2$ | O | Py-2-yl |
| 3-117 | diMeCar | diMeN | (CH$_2$)$_2$ | O | 6-Cl—Py-2-yl |
| 3-118 | diMeCar | diMeN | (CH$_2$)$_2$ | O | 6-CF$_3$—Py-2-yl |
| 3-119 | diMeCar | diMeN | (CH$_2$)$_2$ | O | 6-NO$_2$—Py-2-yl |
| 3-120 | diMeCar | diMeN | (CH$_2$)$_2$ | O | Py-4-yl |
| 3-121 | diMeCar | diMeN | (CH$_2$)$_2$ | O | 2-NO$_2$—Py-4-yl |
| 3-122 | diMeCar | diMeN | (CH$_2$)$_2$ | O | Thi-3-yl |
| 3-123 | diMeCar | diMeN | (CH$_2$)$_2$ | O | 2-MeOCO-Thi-3-yl |

TABLE 4

(Id)

| Compound No. | R$^a$ | R² | R³ | A | E | Arom |
|---|---|---|---|---|---|---|
| 4-1 | α-Me | H | Me | (CH$_2$)$_2$ | O | 4-F—Ph |
| 4-2 | α-Me | H | Me | (CH$_2$)$_2$ | O | 4-NO$_2$—Ph |
| 4-3 | α-Me | H | Me | (CH$_2$)$_2$ | O | 4-Cl—Ph |
| 4-4 | α-Me | H | Me | (CH$_2$)$_2$ | O | 3-F—Ph |
| 4-5 | α-Me | H | Me | (CH$_2$)$_2$ | O | 3-Cl—Ph |
| 4-6 | α-Me | H | Me | (CH$_2$)$_2$ | O | 4-SMe—Ph |
| 4-7 | α-Me | H | Me | (CH$_2$)$_2$ | O | 2-Cl-3-Me—Ph |
| 4-8 | α-Me | H | Me | (CH$_2$)$_2$ | O | 2-Cl-4-NO$_2$—Ph |
| 4-9 | α-Me | H | Me | (CH$_2$)$_2$ | O | 2-Cl-4-F—Ph |
| 4-10 | α-Me | H | Me | (CH$_2$)$_2$ | O | 3-Me-4-Cl—Ph |
| 4-11 | β-Me | H | Me | (CH$_2$)$_2$ | O | 4-F—Ph |
| 4-12 | β-Me | H | Me | (CH$_2$)$_2$ | O | 4-NO$_2$—Ph |

TABLE 4-continued (Id)

| Compound No. | $R^a$ | $R^2$ | $R^3$ | A | E | Arom |
|---|---|---|---|---|---|---|
| 4-13 | β-Me | H | Me | $(CH_2)_2$ | O | 4-Cl—Ph |
| 4-14 | β-Me | H | Me | $(CH_2)_2$ | O | 3-F—Ph |
| 4-15 | β-Me | H | Me | $(CH_2)_2$ | O | 3-Cl—Ph |
| 4-16 | β-Me | H | Me | $(CH_2)_2$ | O | 4-SMe—Ph |
| 4-17 | β-Me | H | Me | $(CH_2)_2$ | O | 2-Cl-3-Me—Ph |
| 4-18 | β-Me | H | Me | $(CH_2)_2$ | O | 2-Cl-4-$NO_2$—Ph |
| 4-19 | β-Me | H | Me | $(CH_2)_2$ | O | 2-Cl-4-F—Ph |
| 4-20 | β-Me | H | Me | $(CH_2)_2$ | O | 3-Me-4-Cl—Ph |
| 4-21 | α-$(CH_2)$— |  | H | $(CH_2)_2$ | O | 4-F—Ph |
| 4-22 | α-$(CH_2)$— |  | H | $(CH_2)_2$ | O | 4-$NO_2$—Ph |
| 4-23 | α-$(CH_2)$— |  | H | $(CH_2)_2$ | O | 4-Cl—Ph |
| 4-24 | α-$(CH_2)$— |  | H | $(CH_2)_2$ | O | 3-F—Ph |
| 4-25 | α-$(CH_2)$— |  | H | $(CH_2)_2$ | O | 3-Cl—Ph |
| 4-26 | α-$(CH_2)$— |  | H | $(CH_2)_2$ | O | 4-SMe—Ph |
| 4-27 | α-$(CH_2)$— |  | H | $(CH_2)_2$ | O | 2-Cl-3-Me—Ph |
| 4-28 | α-$(CH_2)$— |  | H | $(CH_2)_2$ | O | 2-Cl-4-$NO_2$—Ph |
| 4-29 | α-$(CH_2)$— |  | H | $(CH_2)_2$ | O | 2-Cl-4-F—Ph |
| 4-30 | α-$(CH_2)$— |  | H | $(CH_2)_2$ | O | 3-Me-4-Cl—Ph |
| 4-31 | α-$(CH_2)$— |  | Me | $(CH_2)_2$ | O | 4-F—Ph |
| 4-32 | α-$(CH_2)$— |  | Me | $(CH_2)_2$ | O | 4-$NO_2$—Ph |
| 4-33 | α-$(CH_2)$— |  | Me | $(CH_2)_2$ | O | 4-Cl—Ph |
| 4-34 | α-$(CH_2)$— |  | Me | $(CH_2)_2$ | O | 3-F—Ph |
| 4-35 | α-$(CH_2)$— |  | Me | $(CH_2)_2$ | O | 3-Cl—Ph |
| 4-36 | α-$(CH_2)$— |  | Me | $(CH_2)_2$ | O | 4-SMe—Ph |
| 4-37 | α-$(CH_2)$— |  | Me | $(CH_2)_2$ | O | 2-Cl-3-Me—Ph |
| 4-38 | α-$(CH_2)$— |  | Me | $(CH_2)_2$ | O | 2-Cl-4-$NO_2$—Ph |
| 4-39 | α-$(CH_2)$— |  | Me | $(CH_2)_2$ | O | 2-Cl-4-F—Ph |
| 4-40 | α-$(CH_2)$— |  | Me | $(CH_2)_2$ | O | 3-Me-4-Cl—Ph |
| 4-41 | α-$(CH_2)_2$— |  | H | $(CH_2)_2$ | O | 4-F—Ph |
| 4-42 | α-$(CH_2)_2$— |  | H | $(CH_2)_2$ | O | 4-$NO_2$—Ph |
| 4-43 | α-$(CH_2)_2$— |  | H | $(CH_2)_2$ | O | 4-Cl—Ph |
| 4-44 | α-$(CH_2)_2$— |  | H | $(CH_2)_2$ | O | 3-F—Ph |
| 4-45 | α-$(CH_2)_2$— |  | H | $(CH_2)_2$ | O | 3-Cl—Ph |
| 4-46 | α-$(CH_2)_2$— |  | H | $(CH_2)_2$ | O | 4-SMe—Ph |
| 4-47 | α-$(CH_2)_2$— |  | H | $(CH_2)_2$ | O | 2-Cl-3-Me—Ph |
| 4-48 | α-$(CH_2)_2$— |  | H | $(CH_2)_2$ | O | 2-Cl-4-$NO_2$—Ph |
| 4-49 | α-$(CH_2)_2$— |  | H | $(CH_2)_2$ | O | 2-Cl-4-F—Ph |
| 4-50 | α-$(CH_2)_2$— |  | H | $(CH_2)_2$ | O | 3-Me-4-Cl—Ph |
| 4-51 | α-$(CH_2)_2$— |  | Me | $(CH_2)_2$ | O | 4-F—Ph |
| 4-52 | α-$(CH_2)_2$— |  | Me | $(CH_2)_2$ | O | 4-$NO_2$—Ph |
| 4-53 | α-$(CH_2)_2$— |  | Me | $(CH_2)_2$ | O | 4-Cl—Ph |
| 4-54 | α-$(CH_2)_2$— |  | Me | $(CH_2)_2$ | O | 3-F—Ph |
| 4-55 | α-$(CH_2)_2$— |  | Me | $(CH_2)_2$ | O | 3-Cl—Ph |
| 4-56 | α-$(CH_2)_2$— |  | Me | $(CH_2)_2$ | O | 4-SMe—Ph |
| 4-57 | α-$(CH_2)_2$— |  | Me | $(CH_2)_2$ | O | 2-Cl-3-Me—Ph |
| 4-58 | α-$(CH_2)_2$— |  | Me | $(CH_2)_2$ | O | 2-Cl-4-$NO_2$—Ph |
| 4-59 | α-$(CH_2)_2$— |  | Me | $(CH_2)_2$ | O | 2-Cl-4-F—Ph |
| 4-60 | α-$(CH_2)_2$— |  | Me | $(CH_2)_2$ | O | 3-Me-4-Cl—Ph |
| 4-61 | α-$(CH_2)_2$— |  | Me | $(CH_2)_2$ | S | 4-F—Ph |
| 4-62 | α-$(CH_2)_2$— |  | Me | $(CH_2)_2$ | S | 4-$NO_2$—Ph |
| 4-63 | α-$(CH_2)_2$— |  | Me | $(CH_2)_2$ | S | 4-Cl—Ph |
| 4-64 | α-$(CH_2)_2$— |  | Me | $(CH_2)_2$ | S | 3-F—Ph |
| 4-65 | α-$(CH_2)_2$— |  | Me | $(CH_2)_2$ | S | 3-Cl—Ph |
| 4-66 | α-$(CH_2)_2$— |  | Me | $(CH_2)_2$ | S | 4-SMe—Ph |
| 4-67 | α-$(CH_2)_2$— |  | Me | $(CH_2)_2$ | S | 2-Cl-3-Me—Ph |
| 4-68 | α-$(CH_2)_2$— |  | Me | $(CH_2)_2$ | S | 2-Cl-4-$NO_2$—Ph |
| 4-69 | α-$(CH_2)_2$— |  | Me | $(CH_2)_2$ | S | 2-Cl-4-F—Ph |
| 4-70 | α-$(CH_2)_2$— |  | Me | $(CH_2)_2$ | S | 3-Me-4-Cl—Ph |
| 4-71 | α-$(CH_2)_2$— |  | Me | $(CH_2)_3$ | O | 4-F—Ph |
| 4-72 | α-$(CH_2)_2$— |  | Me | $(CH_2)_3$ | O | 4-$NO_2$—Ph |
| 4-73 | α-$(CH_2)_2$— |  | Me | $(CH_2)_3$ | O | 4-Cl—Ph |
| 4-74 | α-$(CH_2)_2$— |  | Me | $(CH_2)_3$ | O | 3-F—Ph |
| 4-75 | α-$(CH_2)_2$— |  | Me | $(CH_2)_3$ | O | 3-Cl—Ph |
| 4-76 | α-$(CH_2)_2$— |  | Me | $(CH_2)_3$ | O | 4-SMe—Ph |

TABLE 4-continued (Id)

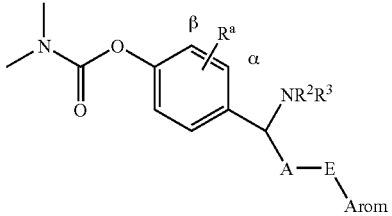

| Compound No. | $R^a$ | $R^2$ | $R^3$ | A | E | Arom |
|---|---|---|---|---|---|---|
| 4-77 | α-(CH$_2$)$_2$— | | Me | (CH$_2$)$_3$ | O | 2-Cl-3-Me—Ph |
| 4-78 | α-(CH$_2$)$_2$— | | Me | (CH$_2$)$_3$ | O | 2-Cl-4-NO$_2$—Ph |
| 4-79 | α-(CH$_2$)$_2$— | | Me | (CH$_2$)$_3$ | O | 2-Cl-4-F—Ph |
| 4-80 | α-(CH$_2$)$_2$— | | Me | (CH$_2$)$_3$ | O | 3-Me-4-Cl—Ph |
| 4-81 | α-(CH$_2$)$_3$— | | H | (CH$_2$)$_2$ | O | 4-F—Ph |
| 4-82 | α-(CH$_2$)$_3$— | | H | (CH$_2$)$_2$ | O | 4-NO$_2$—Ph |
| 4-83 | α-(CH$_2$)$_3$— | | H | (CH$_2$)$_2$ | O | 4-Cl—Ph |
| 4-84 | α-(CH$_2$)$_3$— | | H | (CH$_2$)$_2$ | O | 3-F—Ph |
| 4-85 | α-(CH$_2$)$_3$— | | H | (CH$_2$)$_2$ | O | 3-Cl—Ph |
| 4-86 | α-(CH$_2$)$_3$— | | H | (CH$_2$)$_2$ | O | 4-SMe—Ph |
| 4-87 | α-(CH$_2$)$_3$— | | H | (CH$_2$)$_2$ | O | 2-Cl-3-Me—Ph |
| 4-88 | α-(CH$_2$)$_3$— | | H | (CH$_2$)$_2$ | O | 2-Cl-4-NO$_2$—Ph |
| 4-89 | α-(CH$_2$)$_3$— | | H | (CH$_2$)$_2$ | O | 2-Cl-4-F—Ph |
| 4-90 | α-(CH$_2$)$_3$— | | H | (CH$_2$)$_2$ | O | 3-Me-4-Cl—Ph |
| 4-91 | α-(CH$_2$)$_3$— | | Me | (CH$_2$)$_2$ | O | 4-F—Ph |
| 4-92 | α-(CH$_2$)$_3$— | | Me | (CH$_2$)$_2$ | O | 4-NO$_2$—Ph |
| 4-93 | α-(CH$_2$)$_3$— | | Me | (CH$_2$)$_2$ | O | 4-Cl—Ph |
| 4-94 | α-(CH$_2$)$_3$— | | Me | (CH$_2$)$_2$ | O | 3-F—Ph |
| 4-95 | α-(CH$_2$)$_3$— | | Me | (CH$_2$)$_2$ | O | 3-Cl—Ph |
| 4-96 | α-(CH$_2$)$_3$— | | Me | (CH$_2$)$_2$ | O | 4-SMe—Ph |
| 4-97 | α-(CH$_2$)$_3$— | | Me | (CH$_2$)$_2$ | O | 2-Cl-3-Me—Ph |
| 4-98 | α-(CH$_2$)$_3$— | | Me | (CH$_2$)$_2$ | O | 2-Cl-4-NO$_2$—Ph |
| 4-99 | α-(CH$_2$)$_3$— | | Me | (CH$_2$)$_2$ | O | 2-Cl-4-F—Ph |
| 4-100 | α-(CH$_2$)$_3$— | | Me | (CH$_2$)$_2$ | O | 3-Me-4-Cl—Ph |
| 4-101 | α-(CH$_2$)$_3$— | | Me | (CH$_2$)$_2$ | S | 4-F—Ph |
| 4-102 | α-(CH$_2$)$_3$— | | Me | (CH$_2$)$_2$ | S | 4-NO$_2$—Ph |
| 4-103 | α-(CH$_2$)$_3$— | | Me | (CH$_2$)$_2$ | S | 4-Cl—Ph |
| 4-104 | α-(CH$_2$)$_3$— | | Me | (CH$_2$)$_2$ | S | 3-F—Ph |
| 4-105 | α-(CH$_2$)$_3$— | | Me | (CH$_2$)$_2$ | S | 3-Cl—Ph |
| 4-106 | α-(CH$_2$)$_3$— | | Me | (CH$_2$)$_2$ | S | 4-SMe—Ph |
| 4-107 | α-(CH$_2$)$_3$— | | Me | (CH$_2$)$_2$ | S | 2-Cl-3-Me—Ph |
| 4-108 | α-(CH$_2$)$_3$— | | Me | (CH$_2$)$_2$ | S | 2-Cl-4-NO$_2$—Ph |
| 4-109 | α-(CH$_3$)$_3$— | | Me | (CH$_2$)$_2$ | S | 2-Cl-4-F—Ph |
| 4-110 | α-(CH$_2$)$_3$— | | Me | (CH$_2$)$_2$ | S | 3-Me-4-Cl—Ph |
| 4-111 | α-(CH$_2$)$_3$— | | Me | (CH$_2$)$_3$ | O | 4-F—Ph |
| 4-112 | α-(CH$_2$)$_3$— | | Me | (CH$_2$)$_3$ | O | 4-NO$_2$—Ph |
| 4-113 | α-(CH$_2$)$_3$— | | Me | (CH$_2$)$_3$ | O | 4-Cl—Ph |
| 4-114 | α-(CH$_2$)$_3$— | | Me | (CH$_2$)$_3$ | O | 3-F—Ph |
| 4-115 | α-(CH$_2$)$_3$— | | Me | (CH$_2$)$_3$ | O | 3-Cl—Ph |
| 4-116 | α-(CH$_2$)$_3$— | | Me | (CH$_2$)$_3$ | O | 4-SMe—Ph |
| 4-117 | α-(CH$_2$)$_3$— | | Me | (CH$_2$)$_3$ | O | 2-Cl-3-Me—Ph |
| 4-118 | α-(CH$_2$)$_3$— | | Me | (CH$_2$)$_3$ | O | 2-Cl-4-NO$_2$—Ph |
| 4-119 | α-(CH$_2$)$_3$— | | Me | (CH$_2$)$_3$ | O | 2-Cl-4-F—Ph |
| 4-120 | α-(CH$_2$)$_3$— | | Me | (CH$_2$)$_3$ | O | 3-Me-4-Cl—Ph |
| 4-121 | α-CH=CH—CH$_2$— | | H | (CH$_2$)$_2$ | O | 4-F—Ph |
| 4-122 | α-CH=CH—CH$_2$— | | H | (CH$_2$)$_2$ | O | 4-NO$_2$—Ph |
| 4-123 | α-CH=CH—CH$_2$— | | H | (CH$_2$)$_2$ | O | 4-Cl—Ph |
| 4-124 | α-CH=CH—CH$_2$— | | H | (CH$_2$)$_2$ | O | 3-F—Ph |
| 4-125 | α-CH=CH—CH$_2$— | | H | (CH$_2$)$_2$ | O | 3-Cl—Ph |
| 4-126 | α-CH=CH—CH$_2$— | | H | (CH$_2$)$_2$ | O | 4-SMe—Ph |
| 4-127 | α-CH=CH—CH$_2$— | | H | (CH$_2$)$_2$ | O | 2-Cl-3-Me—Ph |
| 4-128 | α-CH=CH—CH$_2$— | | H | (CH$_2$)$_2$ | O | 2-Cl-4-NO$_2$—Ph |
| 4-129 | α-CH=CH—CH$_2$— | | H | (CH$_2$)$_2$ | O | 2-Cl-4-F—Ph |
| 4-130 | α-CH=CH—CH$_2$— | | H | (CH$_2$)$_2$ | O | 3-Me-4-Cl—Ph |
| 4-131 | α-CH=CH—CH$_2$— | | Me | (CH$_2$)$_2$ | O | 4-F—Ph |
| 4-132 | α-CH=CH—CH$_2$— | | Me | (CH$_2$)$_2$ | O | 4-NO$_2$—Ph |
| 4-133 | α-CH=CH—CH$_2$— | | Me | (CH$_2$)$_2$ | O | 4-Cl—Ph |
| 4-134 | α-CH=CH—CH$_2$— | | Me | (CH$_2$)$_2$ | O | 3-F—Ph |
| 4-135 | α-CH=CH—CH$_2$— | | Me | (CH$_2$)$_2$ | O | 3-Cl—Ph |
| 4-136 | α-CH=CH—CH$_2$— | | Me | (CH$_2$)$_2$ | O | 4-SMe—Ph |
| 4-137 | α-CH=CH—CH$_2$— | | Me | (CH$_2$)$_2$ | O | 2-Cl-3-Me—Ph |
| 4-138 | α-CH=CH—CH$_2$— | | Me | (CH$_2$)$_2$ | O | 2-Cl-4-NO$_2$—Ph |
| 4-139 | α-CH=CH—CH$_2$— | | Me | (CH$_2$)$_2$ | O | 2-Cl-4-F—Ph |
| 4-140 | α-CH=CH—CH$_2$— | | Me | (CH$_2$)$_2$ | O | 3-Me-4-Cl—Ph |

TABLE 4-continued

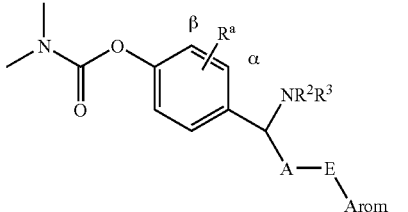

(Id)

| Compound No. | $R^a$ | $R^2$ | $R^3$ | A | E | Arom |
|---|---|---|---|---|---|---|
| 4-141 | α-CH=CH—CH₂— | Me | (CH₂)₂ | S | 4-F—Ph |
| 4-142 | α-CH=CH—CH₂— | Me | (CH₂)₂ | S | 4-NO₂—Ph |
| 4-143 | α-CH=CH—CH₂— | Me | (CH₂)₂ | S | 4-Cl—Ph |
| 4-144 | α-CH=CH—CH₂— | Me | (CH₂)₂ | S | 3-F—Ph |
| 4-145 | α-CH=CH—CH₂— | Me | (CH₂)₂ | S | 3-Cl—Ph |
| 4-146 | α-CH=CH—CH₂— | Me | (CH₂)₂ | S | 4-SMe—Ph |
| 4-147 | α-CH=CH—CH₂— | Me | (CH₂)₂ | S | 2-Cl-3-Me—Ph |
| 4-148 | α-CH=CH—CH₂— | Me | (CH₂)₂ | S | 2-Cl-4-NO₂—Ph |
| 4-149 | α-CH=CH—CH₂— | Me | (CH₂)₂ | S | 2-Cl-4-F—Ph |
| 4-150 | α-CH=CH—CH₂— | Me | (CH₂)₂ | S | 3-Me-4-Cl—Ph |
| 4-151 | α-CH=CH—CH₂— | Me | (CH₂)₃ | O | 4-F—Ph |
| 4-152 | α-CH=CH—CH₂— | Me | (CH₂)₃ | O | 4-NO₂—Ph |
| 4-153 | α-CH=CH—CH₂— | Me | (CH₂)₃ | O | 4-Cl—Ph |
| 4-154 | α-CH=CH—CH₂— | Me | (CH₂)₃ | O | 3-F—Ph |
| 4-155 | α-CH=CH—CH₂— | Me | (CH₂)₃ | O | 3-Cl—Ph |
| 4-156 | α-CH=CH—CH₂— | Me | (CH₂)₃ | O | 4-SMe—Ph |
| 4-157 | α-CH=CH—CH₂— | Me | (CH₂)₃ | O | 2-Cl-3-Me—Ph |
| 4-158 | α-CH=CH—CH₂— | Me | (CH₂)₃ | O | 2-Cl-4-NO₂—Ph |
| 4-159 | α-CH=CH—CH₂— | Me | (CH₂)₃ | O | 2-Cl-4-F—Ph |
| 4-160 | α-CH=CH—CH₂— | Me | (CH₂)₃ | O | 3-Me-4-Cl—Ph |

TABLE 5

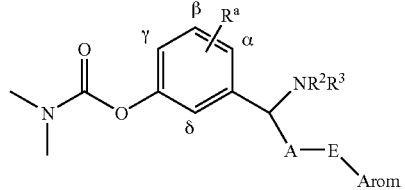

(Ie)

| Compound No. | $R^a$ | $R^2$ | $R^3$ | A | E | Arom |
|---|---|---|---|---|---|---|
| 5-1 | α-Me | H | Me | (CH₂)₂ | O | 4-F—Ph |
| 5-2 | α-Me | H | Me | (CH₂)₂ | O | 4-NO₂—Ph |
| 5-3 | α-Me | H | Me | (CH₂)₂ | O | 4-Cl—Ph |
| 5-4 | α-Me | H | Me | (CH₂)₂ | O | 3-F—Ph |
| 5-5 | α-Me | H | Me | (CH₂)₂ | O | 3-Cl—Ph |
| 5-6 | α-Me | H | Me | (CH₂)₂ | O | 4-SMe—Ph |
| 5-7 | α-Me | H | Me | (CH₂)₂ | O | 2-Cl-3-Me—Ph |
| 5-8 | α-Me | H | Me | (CH₂)₂ | O | 2-Cl-4-NO₂—Ph |
| 5-9 | α-Me | H | Me | (CH₂)₂ | O | 2-Cl-4-F—Ph |
| 5-10 | α-Me | H | Me | (CH₂)₂ | O | 3-Me-4-Cl—Ph |
| 5-11 | β-Me | H | Me | (CH₂)₂ | O | 4-F—Ph |
| 5-12 | β-Me | H | Me | (CH₂)₂ | O | 4-NO₂—Ph |
| 5-13 | β-Me | H | Me | (CH₂)₂ | O | 4-Cl—Ph |
| 5-14 | β-Me | H | Me | (CH₂)₂ | O | 3-F—Ph |
| 5-15 | β-Me | H | Me | (CH₂)₂ | O | 3-Cl—Ph |
| 5-16 | β-Me | H | Me | (CH₂)₂ | O | 4-SMe—Ph |
| 5-17 | β-Me | H | Me | (CH₂)₂ | O | 2-Cl-3-Me—Ph |
| 5-18 | β-Me | H | Me | (CH₂)₂ | O | 2-Cl-4-NO₂—Ph |
| 5-19 | β-Me | H | Me | (CH₂)₂ | O | 2-Cl-4-F—Ph |
| 5-20 | β-Me | H | Me | (CH₂)₂ | O | 3-Me-4-Cl—Ph |
| 5-21 | γ-Me | H | Me | (CH₂)₂ | O | 4-F—Ph |
| 5-22 | γ-Me | H | Me | (CH₂)₂ | O | 4-NO₂—Ph |
| 5-23 | γ-Me | H | Me | (CH₂)₂ | O | 4-Cl—Ph |
| 5-24 | γ-Me | H | Me | (CH₂)₂ | O | 3-F—Ph |
| 5-25 | γ-Me | H | Me | (CH₂)₂ | O | 3-Cl—Ph |
| 5-26 | γ-Me | H | Me | (CH₂)₂ | O | 4-SMe—Ph |
| 5-27 | γ-Me | H | Me | (CH₂)₂ | O | 2-Cl-3-Me—Ph |
| 5-28 | γ-Me | H | Me | (CH₂)₂ | O | 2-Cl-4-NO₂—Ph |
| 5-29 | γ-Me | H | Me | (CH₂)₂ | O | 2-Cl-4-F—Ph |
| 5-30 | γ-Me | H | Me | (CH₂)₂ | O | 3-Me-4-Cl—Ph |
| 5-31 | δ-Me | H | Me | (CH₂)₂ | O | 4-F—Ph |
| 5-32 | δ-Me | H | Me | (CH₂)₂ | O | 4-NO₂—Ph |
| 5-33 | δ-Me | H | Me | (CH₂)₂ | O | 4-Cl—Ph |
| 5-34 | δ-Me | H | Me | (CH₂)₂ | O | 3-F—Ph |
| 5-35 | δ-Me | H | Me | (CH₂)₂ | O | 3-Cl—Ph |
| 5-36 | δ-Me | H | Me | (CH₂)₂ | O | 4-SMe—Ph |
| 5-37 | δ-Me | H | Me | (CH₂)₂ | O | 2-Cl-3-Me—Ph |
| 5-38 | δ-Me | H | Me | (CH₂)₂ | O | 2-Cl-4-NO₂—Ph |
| 5-39 | δ-Me | H | Me | (CH₂)₂ | O | 2-Cl-4-F—Ph |
| 5-40 | δ-Me | H | Me | (CH₂)₂ | O | 3-Me-4-Cl—Ph |
| 5-41 | α-(CH₂)— | H | (CH₂)₂ | O | 4-F—Ph |
| 5-42 | α-(CH₂)— | H | (CH₂)₂ | O | 4-NO₂—Ph |
| 5-43 | α-(CH₂)— | H | (CH₂)₂ | O | 4-Cl—Ph |
| 5-44 | α-(CH₂)— | H | (CH₂)₂ | O | 3-F—Ph |
| 5-45 | α-(CH₂)— | H | (CH₂)₂ | O | 3-Cl—Ph |
| 5-46 | α-(CH₂)— | H | (CH₂)₂ | O | 4-SMe—Ph |
| 5-47 | α-(CH₂)— | H | (CH₂)₂ | O | 2-Cl-3-Me—Ph |
| 5-48 | α-(CH₂)— | H | (CH₂)₂ | O | 2-Cl-4-NO₂—Ph |
| 5-49 | α-(CH₂)— | H | (CH₂)₂ | O | 2-Cl-4-F—Ph |
| 5-50 | α-(CH₂)— | H | (CH₂)₂ | O | 3-Me-4-Cl—Ph |
| 5-51 | α-(CH₂)— | Me | (CH₂)₂ | O | 4-F—Ph |
| 5-52 | α-(CH₂)— | Me | (CH₂)₂ | O | 4-NO₂—Ph |
| 5-53 | α-(CH₂)— | Me | (CH₂)₂ | O | 4-Cl—Ph |
| 5-54 | α-(CH₂)— | Me | (CH₂)₂ | O | 3-F—Ph |
| 5-55 | α-(CH₂)— | Me | (CH₂)₂ | O | 3-Cl—Ph |
| 5-56 | α-(CH₂)— | Me | (CH₂)₂ | O | 4-SMe—Ph |
| 5-57 | α-(CH₂)— | Me | (CH₂)₂ | O | 2-Cl-3-Me—Ph |
| 5-58 | α-(CH₂)— | Me | (CH₂)₂ | O | 2-Cl-4-NO₂—Ph |
| 5-59 | α-(CH₂)— | Me | (CH₂)₂ | O | 2-Cl-4-F—Ph |
| 5-60 | α-(CH₂)— | Me | (CH₂)₂ | O | 3-Me-4-Cl—Ph |
| 5-61 | α-(CH₂)₂— | H | (CH₂)₂ | O | 4-F—Ph |
| 5-62 | α-(CH₂)₂— | H | (CH₂)₂ | O | 4-NO₂—Ph |

TABLE 5-continued

| | | | | | |
|---|---|---|---|---|---|
| 5-63 | α-(CH$_2$)$_2$— | H | (CH$_2$)$_2$ | O | 4-Cl—Ph |
| 5-64 | α-(CH$_2$)$_2$— | H | (CH$_2$)$_2$ | O | 3-F—Ph |
| 5-65 | α-(CH$_2$)$_2$— | H | (CH$_2$)$_2$ | O | 3-Cl—Ph |
| 5-66 | α-(CH$_2$)$_2$— | H | (CH$_2$)$_2$ | O | 4-SMe—Ph |
| 5-67 | α-(CH$_2$)$_2$— | H | (CH$_2$)$_2$ | O | 2-Cl-3-Me—Ph |
| 5-68 | α-(CH$_2$)$_2$— | H | (CH$_2$)$_2$ | O | 2-Cl-4-NO$_2$—Ph |
| 5-69 | α-(CH$_2$)$_2$— | H | (CH$_2$)$_2$ | O | 2-Cl-4-F—Ph |
| 5-70 | α-(CH$_2$)$_2$— | H | (CH$_2$)$_2$ | O | 3-Me-4-Cl—Ph |
| 5-71 | α-(CH$_2$)$_2$— | Me | (CH$_2$)$_2$ | O | 4-F—Ph |
| 5-72 | α-(CH$_2$)$_2$— | Me | (CH$_2$)$_2$ | O | 4-NO$_2$—Ph |
| 5-73 | α-(CH$_2$)$_2$— | Me | (CH$_2$)$_2$ | O | 4-Cl—Ph |
| 5-74 | α-(CH$_2$)$_2$— | Me | (CH$_2$)$_2$ | O | 3-F—Ph |
| 5-75 | α-(CH$_2$)$_2$— | Me | (CH$_2$)$_2$ | O | 3-Cl—Ph |
| 5-76 | α-(CH$_2$)$_2$— | Me | (CH$_2$)$_2$ | O | 4-SMe—Ph |
| 5-77 | α-(CH$_2$)$_2$— | Me | (CH$_2$)$_2$ | O | 2-Cl-3-Me—Ph |
| 5-78 | α-(CH$_2$)$_2$— | Me | (CH$_2$)$_2$ | O | 2-Cl-4-NO$_2$—Ph |
| 5-79 | α-(CH$_2$)$_2$— | Me | (CH$_2$)$_2$ | O | 2-Cl-4-F—Ph |
| 5-80 | α-(CH$_2$)$_2$— | Me | (CH$_2$)$_2$ | O | 3-Me-4-Cl—Ph |
| 5-81 | α-(CH$_2$)$_2$— | Me | (CH$_2$)$_2$ | S | 4-F—Ph |
| 5-82 | α-(CH$_2$)$_2$— | Me | (CH$_2$)$_2$ | S | 4-NO$_2$—Ph |
| 5-83 | α-(CH$_2$)$_2$— | Me | (CH$_2$)$_2$ | S | 4-Cl—Ph |
| 5-84 | α-(CH$_2$)$_2$— | Me | (CH$_2$)$_2$ | S | 3-F—Ph |
| 5-85 | α-(CH$_2$)$_2$— | Me | (CH$_2$)$_2$ | S | 3-Cl—Ph |
| 5-86 | α-(CH$_2$)$_2$— | Me | (CH$_2$)$_2$ | S | 4-SMe—Ph |
| 5-87 | α-(CH$_2$)$_2$— | Me | (CH$_2$)$_2$ | S | 2-Cl-3-Me—Ph |
| 5-88 | α-(CH$_2$)$_2$— | Me | (CH$_2$)$_2$ | S | 2-Cl-4-NO$_2$—Ph |
| 5-89 | α-(CH$_2$)$_2$— | Me | (CH$_2$)$_2$ | S | 2-Cl-4-F—Ph |
| 5-90 | α-(CH$_2$)$_2$— | Me | (CH$_2$)$_2$ | S | 3-Me-4-Cl—Ph |
| 5-91 | α-(CH$_2$)$_2$— | Me | (CH$_2$)$_3$ | O | 4-F—Ph |
| 5-92 | α-(CH$_2$)$_2$— | Me | (CH$_2$)$_3$ | O | 4-NO$_2$—Ph |
| 5-93 | α-(CH$_2$)$_2$— | Me | (CH$_2$)$_3$ | O | 4-Cl—Ph |
| 5-94 | α-(CH$_2$)$_2$— | Me | (CH$_2$)$_3$ | O | 3-F—Ph |
| 5-95 | α-(CH$_2$)$_2$— | Me | (CH$_2$)$_3$ | O | 3-Cl—Ph |
| 5-96 | α-(CH$_2$)$_2$— | Me | (CH$_2$)$_3$ | O | 4-SMe—Ph |
| 5-97 | α-(CH$_2$)$_2$— | Me | (CH$_2$)$_3$ | O | 2-Cl-3-Me—Ph |
| 5-98 | α-(CH$_2$)$_2$— | Me | (CH$_2$)$_3$ | O | 2-Cl-4-NO$_2$—Ph |
| 5-99 | α-(CH$_2$)$_2$— | Me | (CH$_2$)$_3$ | O | 2-Cl-4-F—Ph |
| 5-100 | α-(CH$_2$)$_2$— | Me | (CH$_2$)$_3$ | O | 3-Me-4-Cl—Ph |
| 5-101 | α-(CH$_2$)$_3$— | H | (CH$_2$)$_2$ | O | 4-F—Ph |
| 5-102 | α-(CH$_2$)$_3$— | H | (CH$_2$)$_2$ | O | 4-NO$_2$—Ph |
| 5-103 | α-(CH$_2$)$_3$— | H | (CH$_2$)$_2$ | O | 4-Cl—Ph |
| 5-104 | α-(CH$_2$)$_3$— | H | (CH$_2$)$_2$ | O | 3-F—Ph |
| 5-105 | α-(CH$_2$)$_3$— | H | (CH$_2$)$_2$ | O | 3-Cl—Ph |
| 5-106 | α-(CH$_2$)$_3$— | H | (CH$_2$)$_2$ | O | 4-SMe—Ph |
| 5-107 | α-(CH$_2$)$_3$— | H | (CH$_2$)$_2$ | O | 2-Cl-3-Me—Ph |
| 5-108 | α-(CH$_2$)$_3$— | H | (CH$_2$)$_2$ | O | 2-Cl-4-NO$_2$—Ph |
| 5-109 | α-(CH$_2$)$_3$— | H | (CH$_2$)$_2$ | O | 2-Cl-4-F—Ph |
| 5-110 | α-(CH$_2$)$_3$— | H | (CH$_2$)$_2$ | O | 3-Me-4-Cl—Ph |
| 5-111 | α-(CH$_2$)$_3$— | Me | (CH$_2$)$_2$ | O | 4-F—Ph |
| 5-112 | α-(CH$_2$)$_3$— | Me | (CH$_2$)$_2$ | O | 4-NO$_2$—Ph |
| 5-113 | α-(CH$_2$)$_3$— | Me | (CH$_2$)$_2$ | O | 4-Cl—Ph |
| 5-114 | α-(CH$_2$)$_3$— | Me | (CH$_2$)$_2$ | O | 3-F—Ph |
| 5-115 | α-(CH$_2$)$_3$— | Me | (CH$_2$)$_2$ | O | 3-Cl—Ph |
| 5-116 | α-(CH$_2$)$_3$— | Me | (CH$_2$)$_2$ | O | 4-SMe—Ph |
| 5-117 | α-(CH$_2$)$_3$— | Me | (CH$_2$)$_2$ | O | 2-Cl-3-Me—Ph |
| 5-118 | α-(CH$_2$)$_3$— | Me | (CH$_2$)$_2$ | O | 2-Cl-4-NO$_2$—Ph |
| 5-119 | α-(CH$_2$)$_3$— | Me | (CH$_2$)$_2$ | O | 2-Cl-4-F—Ph |
| 5-120 | α-(CH$_2$)$_3$— | Me | (CH$_2$)$_2$ | O | 3-Me-4-Cl—Ph |
| 5-121 | α-(CH$_2$)$_3$— | Me | (CH$_2$)$_2$ | S | 4-F—Ph |
| 5-122 | α-(CH$_2$)$_3$— | Me | (CH$_2$)$_2$ | S | 4-NO$_2$—Ph |
| 5-123 | α-(CH$_2$)$_3$— | Me | (CH$_2$)$_2$ | S | 4-Cl—Ph |
| 5-124 | α-(CH$_2$)$_3$— | Me | (CH$_2$)$_2$ | S | 3-F—Ph |
| 5-125 | α-(CH$_2$)$_3$— | Me | (CH$_2$)$_2$ | S | 3-Cl—Ph |
| 5-126 | α-(CH$_2$)$_3$— | Me | (CH$_2$)$_2$ | S | 4-SMe—Ph |
| 5-127 | α-(CH$_2$)$_3$— | Me | (CH$_2$)$_2$ | S | 2-Cl-3-Me—Ph |
| 5-128 | α-(CH$_2$)$_3$— | Me | (CH$_2$)$_2$ | S | 2-Cl-4-NO$_2$—Ph |
| 5-129 | α-(CH$_2$)$_3$— | Me | (CH$_2$)$_2$ | S | 2-Cl-4-F—Ph |
| 5-130 | α-(CH$_2$)$_3$— | Me | (CH$_2$)$_2$ | S | 3-Me-4-Cl—Ph |
| 5-131 | α-(CH$_2$)$_3$— | Me | (CH$_2$)$_3$ | O | 4-F—Ph |
| 5-132 | α-(CH$_2$)$_3$— | Me | (CH$_2$)$_3$ | O | 4-NO$_2$—Ph |
| 5-133 | α-(CH$_2$)$_3$— | Me | (CH$_2$)$_3$ | O | 4-Cl—Ph |
| 5-134 | α-(CH$_2$)$_3$— | Me | (CH$_2$)$_3$ | O | 3-F—Ph |
| 5-135 | α-(CH$_2$)$_3$— | Me | (CH$_2$)$_3$ | O | 3-Cl—Ph |
| 5-136 | α-(CH$_2$)$_3$— | Me | (CH$_2$)$_3$ | O | 4-SMe—Ph |
| 5-137 | α-(CH$_2$)$_3$— | Me | (CH$_2$)$_3$ | O | 2-Cl-3-Me—Ph |
| 5-138 | α-(CH$_2$)$_3$— | Me | (CH$_2$)$_3$ | O | 2-Cl-4-NO$_2$—Ph |
| 5-139 | α-(CH$_2$)$_3$— | Me | (CH$_2$)$_3$ | O | 2-Cl-4-F—Ph |
| 5-140 | α-(CH$_2$)$_3$— | Me | (CH$_2$)$_3$ | O | 3-Me-4-Cl—Ph |
| 5-141 | α-CH=CH—CH$_2$— | H | (CH$_2$)$_2$ | O | 4-F—Ph |
| 5-142 | α-CH=CH—CH$_2$— | H | (CH$_2$)$_2$ | O | 4-NO$_2$—Ph |
| 5-143 | α-CH=CH—CH$_2$— | H | (CH$_2$)$_2$ | O | 4-Cl—Ph |
| 5-144 | α-CH=CH—CH$_2$— | H | (CH$_2$)$_2$ | O | 3-F—Ph |
| 5-145 | α-CH=CH—CH$_2$— | H | (CH$_2$)$_2$ | O | 3-Cl—Ph |
| 5-146 | α-CH=CH—CH$_2$— | H | (CH$_2$)$_2$ | O | 4-SMe—Ph |
| 5-147 | α-CH=CH—CH$_2$— | H | (CH$_2$)$_2$ | O | 2-Cl-3-Me—Ph |
| 5-148 | α-CH=CH—CH$_2$— | H | (CH$_2$)$_2$ | O | 2-Cl-4-NO$_2$—Ph |
| 5-149 | α-CH=CH—CH$_2$— | H | (CH$_2$)$_2$ | O | 2-Cl-4-F—Ph |
| 5-150 | α-CH=CH—CH$_2$— | H | (CH$_2$)$_2$ | O | 3-Me-4-Cl—Ph |
| 5-151 | α-CH=CH—CH$_2$— | Me | (CH$_2$)$_2$ | O | 4-F—Ph |
| 5-152 | α-CH=CH—CH$_2$— | Me | (CH$_2$)$_2$ | O | 4-NO$_2$—Ph |
| 5-153 | α-CH=CH—CH$_2$— | Me | (CH$_2$)$_2$ | O | 4-Cl—Ph |
| 5-154 | α-CH=CH—CH$_2$— | Me | (CH$_2$)$_2$ | O | 3-F—Ph |
| 5-155 | α-CH=CH—CH$_2$— | Me | (CH$_2$)$_2$ | O | 3-Cl—Ph |
| 5-156 | α-CH=CH—CH$_2$— | Me | (CH$_2$)$_2$ | O | 4-SMe—Ph |
| 5-157 | α-CH=CH—CH$_2$— | Me | (CH$_2$)$_2$ | O | 2-Cl-3-Me—Ph |
| 5-158 | α-CH=CH—CH$_2$— | Me | (CH$_2$)$_2$ | O | 2-Cl-4-NO$_2$—Ph |
| 5-159 | α-CH=CH—CH$_2$— | Me | (CH$_2$)$_2$ | O | 2-Cl-4-F—Ph |
| 5-160 | α-CH=CH—CH$_2$— | Me | (CH$_2$)$_2$ | O | 3-Me-4-Cl—Ph |
| 5-161 | α-CH=CH—CH$_2$— | Me | (CH$_2$)$_2$ | S | 4-F—Ph |
| 5-162 | α-CH=CH—CH$_2$— | Me | (CH$_2$)$_2$ | S | 4-NO$_2$—Ph |
| 5-163 | α-CH=CH—CH$_2$— | Me | (CH$_2$)$_2$ | S | 4-Cl—Ph |
| 5-164 | α-CH=CH—CH$_2$— | Me | (CH$_2$)$_2$ | S | 3-F—Ph |
| 5-165 | α-CH=CH—CH$_2$— | Me | (CH$_2$)$_2$ | S | 3-Cl—Ph |
| 5-166 | α-CH=CH—CH$_2$— | Me | (CH$_2$)$_2$ | S | 4-SMe—Ph |
| 5-167 | α-CH=CH—CH$_2$— | Me | (CH$_2$)$_2$ | S | 2-Cl-3-Me—Ph |
| 5-168 | α-CH=CH—CH$_2$— | Me | (CH$_2$)$_2$ | S | 2-Cl-4-NO$_2$—Ph |
| 5-169 | α-CH=CH—CH$_2$— | Me | (CH$_2$)$_2$ | S | 2-Cl-4-F—Ph |
| 5-170 | α-CH=CH—CH$_2$— | Me | (CH$_2$)$_2$ | S | 3-Me-4-Cl—Ph |
| 5-171 | α-CH=CH—CH$_2$— | Me | (CH$_2$)$_3$ | O | 4-F—Ph |
| 5-172 | α-CH=CH—CH$_2$— | Me | (CH$_2$)$_3$ | O | 4-NO$_2$—Ph |
| 5-173 | α-CH=CH—CH$_2$— | Me | (CH$_2$)$_3$ | O | 4-Cl—Ph |
| 5-174 | α-CH=CH—CH$_2$— | Me | (CH$_2$)$_3$ | O | 3-F—Ph |
| 5-175 | α-CH=CH—CH$_2$— | Me | (CH$_2$)$_3$ | O | 3-Cl—Ph |
| 5-176 | α-CH=CH—CH$_2$— | Me | (CH$_2$)$_3$ | O | 4-SMe—Ph |
| 5-177 | α-CH=CH—CH$_2$— | Me | (CH$_2$)$_3$ | O | 2-Cl-3-Me—Ph |
| 5-178 | α-CH=CH—CH$_2$— | Me | (CH$_2$)$_3$ | O | 2-Cl-4-NO$_2$—Ph |
| 5-179 | α-CH=CH—CH$_2$— | Me | (CH$_2$)$_3$ | O | 2-Cl-4-F—Ph |
| 5-180 | α-CH=CH—CH$_2$— | Me | (CH$_2$)$_3$ | O | 3-Me-4-Cl—Ph |
| 5-181 | δ-(CH$_2$)— | H | (CH$_2$)$_2$ | O | 4-F—Ph |
| 5-182 | δ-(CH$_2$)— | H | (CH$_2$)$_2$ | O | 4-NO$_2$—Ph |
| 5-183 | δ-(CH$_2$)— | H | (CH$_2$)$_2$ | O | 4-Cl—Ph |
| 5-184 | δ-(CH$_2$)— | H | (CH$_2$)$_2$ | O | 3-F—Ph |
| 5-185 | δ-(CH$_2$)— | H | (CH$_2$)$_2$ | O | 3-Cl—Ph |
| 5-186 | δ-(CH$_2$)— | H | (CH$_2$)$_2$ | O | 4-SMe—Ph |
| 5-187 | δ-(CH$_2$)— | H | (CH$_2$)$_2$ | O | 2-Cl-3-Me—Ph |
| 5-188 | δ-(CH$_2$)— | H | (CH$_2$)$_2$ | O | 2-Cl-4-NO$_2$—Ph |
| 5-189 | δ-(CH$_2$)— | H | (CH$_2$)$_2$ | O | 2-Cl-4-F—Ph |
| 5-190 | δ-(CH$_2$)— | H | (CH$_2$)$_2$ | O | 3-Me-4-Cl—Ph |
| 5-191 | δ-(CH$_2$)— | Me | (CH$_2$)$_2$ | O | 4-F—Ph |
| 5-192 | δ-(CH$_2$)— | Me | (CH$_2$)$_2$ | O | 4-NO$_2$—Ph |
| 5-193 | δ-(CH$_2$)— | Me | (CH$_2$)$_2$ | O | 4-Cl—Ph |
| 5-194 | δ-(CH$_2$)— | Me | (CH$_2$)$_2$ | O | 3-F—Ph |
| 5-195 | δ-(CH$_2$)— | Me | (CH$_2$)$_2$ | O | 3-Cl—Ph |
| 5-196 | δ-(CH$_2$)— | Me | (CH$_2$)$_2$ | O | 4-SMe—Ph |
| 5-197 | δ-(CH$_2$)— | Me | (CH$_2$)$_2$ | O | 2-Cl-3-Me—Ph |
| 5-198 | δ-(CH$_2$)— | Me | (CH$_2$)$_2$ | O | 2-Cl-4-NO$_2$—Ph |
| 5-199 | δ-(CH$_2$)— | Me | (CH$_2$)$_2$ | O | 2-Cl-4-F—Ph |
| 5-200 | δ-(CH$_2$)— | Me | (CH$_2$)$_2$ | O | 3-Me-4-Cl—Ph |
| 5-201 | δ-(CH$_2$)$_2$— | H | (CH$_2$)$_2$ | O | 4-F—Ph |
| 5-202 | δ-(CH$_2$)$_2$— | H | (CH$_2$)$_2$ | O | 4-NO$_2$—Ph |
| 5-203 | δ-(CH$_2$)$_2$— | H | (CH$_2$)$_2$ | O | 4-Cl—Ph |
| 5-204 | δ-(CH$_2$)$_2$— | H | (CH$_2$)$_2$ | O | 3-F—Ph |
| 5-205 | δ-(CH$_2$)$_2$— | H | (CH$_2$)$_2$ | O | 3-Cl—Ph |
| 5-206 | δ-(CH$_2$)$_2$— | H | (CH$_2$)$_2$ | O | 4-SMe—Ph |
| 5-207 | δ-(CH$_2$)$_2$— | H | (CH$_2$)$_2$ | O | 2-Cl-3-Me—Ph |
| 5-208 | δ-(CH$_2$)$_2$— | H | (CH$_2$)$_2$ | O | 2-Cl-4-NO$_2$—Ph |
| 5-209 | δ-(CH$_2$)$_2$— | H | (CH$_2$)$_2$ | O | 2-Cl-4-F—Ph |
| 5-210 | δ-(CH$_2$)$_2$— | H | (CH$_2$)$_2$ | O | 3-Me-4-Cl—Ph |
| 5-211 | δ-(CH$_2$)$_2$— | Me | (CH$_2$)$_2$ | O | 4-F—Ph |
| 5-212 | δ-(CH$_2$)$_2$— | Me | (CH$_2$)$_2$ | O | 4-NO$_2$—Ph |
| 5-213 | δ-(CH$_2$)$_2$— | Me | (CH$_2$)$_2$ | O | 4-Cl—Ph |
| 5-214 | δ-(CH$_2$)$_2$— | Me | (CH$_2$)$_2$ | O | 3-F—Ph |
| 5-215 | δ-(CH$_2$)$_2$— | Me | (CH$_2$)$_2$ | O | 3-Cl—Ph |
| 5-216 | δ-(CH$_2$)$_2$— | Me | (CH$_2$)$_2$ | O | 4-SMe—Ph |
| 5-217 | δ-(CH$_2$)$_2$— | Me | (CH$_2$)$_2$ | O | 2-Cl-3-Me—Ph |
| 5-218 | δ-(CH$_2$)$_2$— | Me | (CH$_2$)$_2$ | O | 2-Cl-4-NO$_2$—Ph |
| 5-219 | δ-(CH$_2$)$_2$— | Me | (CH$_2$)$_2$ | O | 2-Cl-4-F—Ph |
| 5-220 | δ-(CH$_2$)$_2$— | Me | (CH$_2$)$_2$ | O | 3-Me-4-Cl—Ph |

TABLE 5-continued

| | | | | | |
|---|---|---|---|---|---|
| 5-221 | δ-(CH₂)₂— | Me | (CH₂)₂ | S | 4-F—Ph |
| 5-222 | δ-(CH₂)₂— | Me | (CH₂)₂ | S | 4-NO₂—Ph |
| 5-223 | δ-(CH₂)₂— | Me | (CH₂)₂ | S | 4-Cl—Ph |
| 5-224 | δ-(CH₂)₂— | Me | (CH₂)₂ | S | 3-F—Ph |
| 5-225 | δ-(CH₂)₂— | Me | (CH₂)₂ | S | 3-Cl—Ph |
| 5-226 | δ-(CH₂)₂— | Me | (CH₂)₂ | S | 4-SMe—Ph |
| 5-227 | δ-(CH₂)₂— | Me | (CH₂)₂ | S | 2-Cl-3-Me—Ph |
| 5-228 | δ-(CH₂)₂— | Me | (CH₂)₂ | S | 2-Cl-4-NO₂—Ph |
| 5-229 | δ-(CH₂)₂— | Me | (CH₂)₂ | S | 2-Cl-4-F—Ph |
| 5-230 | δ-(CH₂)₂— | Me | (CH₂)₂ | S | 3-Me-4-Cl—Ph |
| 5-231 | δ-(CH₂)₂— | Me | (CH₂)₃ | O | 4-F—Ph |
| 5-232 | δ-(CH₂)₂— | Me | (CH₂)₃ | O | 4-NO₂—Ph |
| 5-233 | δ-(CH₂)₂— | Me | (CH₂)₃ | O | 4-Cl—Ph |
| 5-234 | δ-(CH₂)₂— | Me | (CH₂)₃ | O | 3-F—Ph |
| 5-235 | δ-(CH₂)₂— | Me | (CH₂)₃ | O | 3-Cl—Ph |
| 5-236 | δ-(CH₂)₂— | Me | (CH₂)₃ | O | 4-SMe—Ph |
| 5-237 | δ-(CH₂)₂— | Me | (CH₂)₃ | O | 2-Cl-3-Me—Ph |
| 5-238 | δ-(CH₂)₂— | Me | (CH₂)₃ | O | 2-Cl-4-NO₂—Ph |
| 5-239 | δ-(CH₂)₂— | Me | (CH₂)₃ | O | 2-Cl-4-F—Ph |
| 5-240 | δ-(CH₂)₂— | Me | (CH₂)₃ | O | 3-Me-4-Cl—Ph |
| 5-241 | δ-(CH₂)₃— | H | (CH₂)₂ | O | 4-F—Ph |
| 5-242 | δ-(CH₂)₃— | H | (CH₂)₂ | O | 4-NO₂—Ph |
| 5-243 | δ-(CH₂)₃— | H | (CH₂)₂ | O | 4-Cl—Ph |
| 5-244 | δ-(CH₂)₃— | H | (CH₂)₂ | O | 3-F—Ph |
| 5-245 | δ-(CH₂)₃— | H | (CH₂)₂ | O | 3-Cl—Ph |
| 5-246 | δ-(CH₂)₃— | H | (CH₂)₂ | O | 4-SMe—Ph |
| 5-247 | δ-(CH₂)₃— | H | (CH₂)₂ | O | 2-Cl-3-Me—Ph |
| 5-248 | δ-(CH₂)₃— | H | (CH₂)₂ | O | 2-Cl-4-NO₂—Ph |
| 5-249 | δ-(CH₂)₃— | H | (CH₂)₂ | O | 2-Cl-4-F—Ph |
| 5-250 | δ-(CH₂)₃— | H | (CH₂)₂ | O | 3-Me-4-Cl—Ph |
| 5-251 | δ-(CH₂)₃— | Me | (CH₂)₂ | O | 4-F—Ph |
| 5-252 | δ-(CH₂)₃— | Me | (CH₂)₂ | O | 4-NO₂—Ph |
| 5-253 | δ-(CH₂)₃— | Me | (CH₂)₂ | O | 4-Cl—Ph |
| 5-254 | δ-(CH₂)₃— | Me | (CH₂)₂ | O | 3-F—Ph |
| 5-255 | δ-(CH₂)₃— | Me | (CH₂)₂ | O | 3-Cl—Ph |
| 5-256 | δ-(CH₂)₃— | Me | (CH₂)₂ | O | 4-SMe—Ph |
| 5-257 | δ-(CH₂)₃— | Me | (CH₂)₂ | O | 2-Cl-3-Me—Ph |
| 5-258 | δ-(CH₂)₃— | Me | (CH₂)₂ | O | 2-Cl-4-NO₂—Ph |
| 5-259 | δ-(CH₂)₃— | Me | (CH₂)₂ | O | 2-Cl-4-F—Ph |
| 5-260 | δ-(CH₂)₃— | Me | (CH₂)₂ | O | 3-Me-4-Cl—Ph |
| 5-261 | δ-(CH₂)₃— | Me | (CH₂)₂ | S | 4-F—Ph |
| 5-262 | δ-(CH₂)₃— | Me | (CH₂)₂ | S | 4-NO₂—Ph |
| 5-263 | δ-(CH₂)₃— | Me | (CH₂)₂ | S | 4-Cl—Ph |
| 5-264 | δ-(CH₂)₃— | Me | (CH₂)₂ | S | 3-F—Ph |
| 5-265 | δ-(CH₂)₃— | Me | (CH₂)₂ | S | 3-Cl—Ph |
| 5-266 | δ-(CH₂)₃— | Me | (CH₂)₂ | S | 4-SMe—Ph |
| 5-267 | δ-(CH₂)₃— | Me | (CH₂)₂ | S | 2-Cl-3-Me—Ph |
| 5-268 | δ-(CH₂)₃— | Me | (CH₂)₂ | S | 2-Cl-4-NO₂—Ph |
| 5-269 | δ-(CH₂)₃— | Me | (CH₂)₂ | S | 2-Cl-4-F—Ph |
| 5-270 | δ-(CH₂)₃— | Me | (CH₂)₂ | S | 3-Me-4-Cl—Ph |
| 5-271 | δ-(CH₂)₃— | Me | (CH₂)₃ | O | 4-F—Ph |
| 5-272 | δ-(CH₂)₃— | Me | (CH₂)₃ | O | 4-NO₂—Ph |
| 5-273 | δ-(CH₂)₃— | Me | (CH₂)₃ | O | 4-Cl—Ph |
| 5-274 | δ-(CH₂)₃— | Me | (CH₂)₃ | O | 3-F—Ph |
| 5-275 | δ-(CH₂)₃— | Me | (CH₂)₃ | O | 3-Cl—Ph |
| 5-276 | δ-(CH₂)₃— | Me | (CH₂)₃ | O | 4-SMe—Ph |
| 5-277 | δ-(CH₂)₃— | Me | (CH₂)₃ | O | 2-Cl-3-Me—Ph |
| 5-278 | δ-(CH₂)₃— | Me | (CH₂)₃ | O | 2-Cl-4-NO₂—Ph |
| 5-279 | δ-(CH₂)₃— | Me | (CH₂)₃ | O | 2-Cl-4-F—Ph |
| 5-280 | δ-(CH₂)₃— | Me | (CH₂)₃ | O | 3-Me-4-Cl—Ph |
| 5-281 | δ-CH=CH—CH₂— | H | (CH₂)₂ | O | 4-F—Ph |
| 5-282 | δ-CH=CH—CH₂— | H | (CH₂)₂ | O | 4-NO₂—Ph |
| 5-283 | δ-CH=CH—CH₂— | H | (CH₂)₂ | O | 4-Cl—Ph |
| 5-284 | δ-CH=CH—CH₂— | H | (CH₂)₂ | O | 3-F—Ph |
| 5-285 | δ-CH=CH—CH₂— | H | (CH₂)₂ | O | 3-Cl—Ph |
| 5-286 | δ-CH=CH—CH₂— | H | (CH₂)₂ | O | 4-SMe—Ph |
| 5-287 | δ-CH=CH—CH₂— | H | (CH₂)₂ | O | 2-Cl-3-Me—Ph |
| 5-288 | δ-CH=CH—CH₂— | H | (CH₂)₂ | O | 2-Cl-4-NO₂—Ph |
| 5-289 | δ-CH=CH—CH₂— | H | (CH₂)₂ | O | 2-Cl-4-F—Ph |
| 5-290 | δ-CH=CH—CH₂— | H | (CH₂)₂ | O | 3-Me-4-Cl—Ph |
| 5-291 | δ-CH=CH—CH₂— | Me | (CH₂)₂ | O | 4-F—Ph |
| 5-292 | δ-CH=CH—CH₂— | Me | (CH₂)₂ | O | 4-NO₂—Ph |
| 5-293 | δ-CH=CH—CH₂— | Me | (CH₂)₂ | O | 4-Cl—Ph |
| 5-294 | δ-CH=CH—CH₂— | Me | (CH₂)₂ | O | 3-F—Ph |
| 5-295 | δ-CH=CH—CH₂— | Me | (CH₂)₂ | O | 3-Cl—Ph |
| 5-296 | δ-CH=CH—CH₂— | Me | (CH₂)₂ | O | 4-SMe—Ph |
| 5-297 | δ-CH=CH—CH₂— | Me | (CH₂)₂ | O | 2-Cl-3-Me—Ph |
| 5-298 | δ-CH=CH—CH₂— | Me | (CH₂)₂ | O | 2-Cl-4-NO₂—Ph |
| 5-299 | δ-CH=CH—CH₂— | Me | (CH₂)₂ | O | 2-Cl-4-F—Ph |
| 5-300 | δ-CH=CH—CH₂— | Me | (CH₂)₂ | O | 3-Me-4-Cl—Ph |
| 5-301 | δ-CH=CH—CH₂— | Me | (CH₂)₂ | S | 4-F—Ph |
| 5-302 | δ-CH=CH—CH₂— | Me | (CH₂)₂ | S | 4-NO₂—Ph |
| 5-303 | δ-CH=CH—CH₂— | Me | (CH₂)₂ | S | 4-Cl—Ph |
| 5-304 | δ-CH=CH—CH₂— | Me | (CH₂)₂ | S | 3-F—Ph |
| 5-305 | δ-CH=CH—CH₂— | Me | (CH₂)₂ | S | 3-Cl—Ph |
| 5-306 | δ-CH=CH—CH₂— | Me | (CH₂)₂ | S | 4-Sme—Ph |
| 5-307 | δ-CH=CH—CH₂— | Me | (CH₂)₂ | S | 2-Cl-3-Me—Ph |
| 5-308 | δ-CH=CH—CH₂— | Me | (CH₂)₂ | S | 2-Cl-4-NO₂—Ph |
| 5-309 | δ-CH=CH—CH₂— | Me | (CH₂)₂ | S | 2-Cl-4-F—Ph |
| 5-310 | δ-CH=CH—CH₂— | Me | (CH₂)₂ | S | 3-Me-4-Cl—Ph |
| 5-311 | δ-CH=CH—CH₂— | Me | (CH₂)₃ | O | 4-F—Ph |
| 5-312 | δ-CH=CH—CH₂— | Me | (CH₂)₃ | O | 4-NO₂—Ph |
| 5-313 | δ-CH=CH—CH₂— | Me | (CH₂)₃ | O | 4-Cl—Ph |
| 5-314 | δ-CH=CH—CH₂— | Me | (CH₂)₃ | O | 3-F—Ph |
| 5-315 | δ-CH=CH—CH₂— | Me | (CH₂)₃ | O | 3-Cl—Ph |
| 5-316 | δ-CH=CH—CH₂— | Me | (CH₂)₃ | O | 4-Sme—Ph |
| 5-317 | δ-CH=CH—CH₂— | Me | (CH₂)₃ | O | 2-Cl-3-Me—Ph |
| 5-318 | δ-CH=CH—CH₂— | Me | (CH₂)₃ | O | 2-Cl-4-NO₂—Ph |
| 5-319 | δ-CH=CH—CH₂— | Me | (CH₂)₃ | O | 2-Cl-4-F—Ph |
| 5-320 | δ-CH=CH—CH₂— | Me | (CH₂)₃ | O | 3-Me-4-Cl—Ph |

Among the exemplary compounds, preferred are Compound No. 1-1, 1-7, 1-8, 1-10, 1-13, 1-19, 1-23, 1-26, 1-33, 1-34, 1-35, 1-36, 1-37, 1-38, 1-39, 1-40, 1-41, 1-42, 1-43, 1-45, 1-46, 1-47, 1-48, 1-49, 1-50, 1-51, 1-52, 1-53, 1-54, 1-55, 1-56, 1-57, 1-58, 1-59, 1-60, 1-61, 1-65, 1-66, 1-67, 1-68, 1-70, 1-71, 1-72, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-128, 1-129, 1-132, 1-133, 1-134, 1-135, 1-136, 1-137, 1-138, 1-142, 1-143, 1-144, 1-145, 1-146, 1-148, 1-149, 1-150, 1-151, 1-152, 1-153, 1-154, 1-155, 1-156, 1-157, 1-158, 1-160, 1-161, 1-162, 1-163, 1-165, 1-174, 1-180, 1-181, 1-182, 1-183, 1-187, 1-188, 1-189, 1-190, 1-191, 1-192, 1-193, 1-194, 1-195, 1-196, 1-199, 1-200, 1-203, 1-204, 1-205, 1-206, 2-1, 2-2, 2-3, 2-4, 2-5, 2-6, 2-9, 2-11, 2-12, 2-13, 2-14, 2-15, 2-16, 2-17, 2-18, 2-19, 2-22, 2-24, 2-25, 2-26, 2-27, 2-41, 2-42, 2-43, 2-49, 2-51, 2-53, 2-65, 2-67, 2-73, 2-75, 2-76, 2-77, 2-78, 2-79, 2-80, 2-81, 2-82, 2-85, 2-86, 2-87, 2-88, 2-89, 2-90, 2-91, 2-92, 2-93, 2-94, 2-95, 2-96, 2-97, 2-98, 2-100, 2-101, 2-102, 2-103, 2-104, 2-105, 2-106, 2-107, 2-108, 2-109, 2-132, 2-133, 2-134, 2-135, 2-136, 2-137, 2-138, 2-142, 2-143, 2-144, 2-145, 2-146, 2-147, 2-148, 2-149, 2-150, 2-151, 2-152, 2-154, 2-155, 2-157, 2-158, 2-159, 2-160, 2-161, 2-167, 2-173, 2-192, 2-193, 2-194, 2-199, 2-200, 3-11, 3-12, 3-14, 3-15, 3-17, 3-21, 3-25, 3-26, 3-27, 3-28, 3-29, 3-30, 3-68, 3-69, 3-71, 3-72, 3-74, 3-78, 3-82, 3-83, 3-84, 3-85, 3-87, 3-88, 3-89, 3-90, 3-91, 4-2, 4-3, 4-6, 4-12, 4-13, 4-16, 4-52, 4-58, 4-60, 4-98, 4-132, 4-136, 4-139, 4-140, 5-73, 5-160 and 5-300, more preferred are Compound No. 1-1, 1-7, 1-8, 1-10, 1-13, 1-19, 1-23, 1-26, 1-34, 1-39, 1-41, 1-42, 1-43, 1-45, 1-46, 1-47, 1-49, 1-50, 1-51, 1-52, 1-53, 1-59, 1-60, 1-61, 1-66, 1-67, 1-68, 1-70, 1-71, 1-72, 1-74, 1-75, 1-76, 1-77, 1-78, 1-79, 1-80, 1-81, 1-82, 1-84, 1-85, 1-86, 1-87, 1-88, 1-89, 1-90, 1-91, 1-92, 1-93, 1-94, 1-95, 1-96, 1-97, 1-98, 1-99, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-128, 1-129, 1-132, 1-133, 1-134, 1-135, 1-136, 1-137, 1-142, 1-144, 1-146, 1-149, 1-151, 1-156, 1-158, 1-159, 1-160, 1-165, 1-174, 1-180, 1-181, 1-182, 1-183, 1-187, 1-188, 1-189, 1-190, 1-191, 1-192, 1-193, 1-194, 1-195, 1-199, 1-200, 2-1, 2-2, 2-3, 2-4, 2-5, 2-6, 2-9, 2-11, 2-12, 2-13, 2-14, 2-15, 2-16, 2-17, 2-18, 2-22, 2-25, 2-26, 2-65, 2-67, 2-73, 2-75, 2-78, 2-79, 2-82, 2-86, 2-88, 2-92, 2-94, 2-104, 2-109, 2-132, 2-135, 2-136, 2-142, 2-149, 2-161, 2-167, 2-194, 2-199, 2-200, 4-2, 4-12, 4-60, 4-132 and 4-139, further more preferred are the compounds given below; Compound No. 1-75: 4-[3-(4-fluorophenoxy)-1-methylaminopropyl]phenyl dimethylcarbamate Compound No. 1-76: 4-[3-(3-fluorophenoxy)-1-methylaminopropyl]phenyl dimethylcarbamate Compound No. 1-78: 4-[3-(4-chlorophenoxy)-1-methylaminopropyl]phenyl dimethylcarbamate Compound No. 1-79: 4-[3-(3-chlorophenoxy)-1-methylaminopropyl]phenyl dimethylcarbamate Compound No. 1-92: 4-[3-(4-nitrophenoxy)-1-methylaminopropyl]phenyl dimethylcarbamate Compound No. 1-102: 4-[3-(3,4-difluorophenoxy)-1-methylaminopropyl]phenyl dimethylcarbamate Compound No. 1-104: 4-[3-(4-chloro-3-fluorophenoxy)-1-methylaminopropyl]phenyl dimethylcarbamate Compound No. 1-108: 4-[3-(2-chloro-4-nitrophenoxy)-1-methylaminopropyl]phenyl dimethylcarbamate Compound No. 1-132: 4-[1-dimethylamino-3-(4-fluorophenoxy)propyl]phenyl dimethylcarbamate Compound No. 1-133: 4-[1-dimethylamino-3-(3-fluorophenoxy)propyl]phenyl dimethylcarbamate Compound No. 1-135: 4-[3-(4-chlorophenoxy)-1-dimethylaminopropyl]phenyl dimethylcarbamate Compound No. 1-136: 4-[3-(3-chlorophenoxy)-1-dimethylaminopropyl]phenyl dimethylcarbamate Compound No. 1-149: 4-[1-dimethylamino-3-(4-nitrophenoxy)propyl]phenyl dimethylcarbamate Compound No. 1-159: 4-[3-(3,4-difluorophenoxy)-1-dimethylaminopropyl]phenyl dimethylcarbamate Compound No. 1-165: 4-[3-(2-chloro-4-nitrophenoxy)-1-dimethylaminopropyl]phenyl dimethylcarbamate Compound No. 2-92: 3-[1-methylamino-3-(4-nitrophenoxy)propyl]phenyl dimethylcarbamate Compound No. 2-149: 3-[1-dimethylamino-3-(4-nitrophenoxy)propyl]phenyl dimethylcarbamate and Compound No. 4-132: 2-methyl-1-[2-(4-nitrophenoxy)-ethyl]-2,3-dihydro-1H-benzo[c]azepin-7-yl dimethylcarbamate

[Mode for Carrying Out the Invention]

The compound (I) of the present invention can be obtained by Process A to Process C described below.

Process A

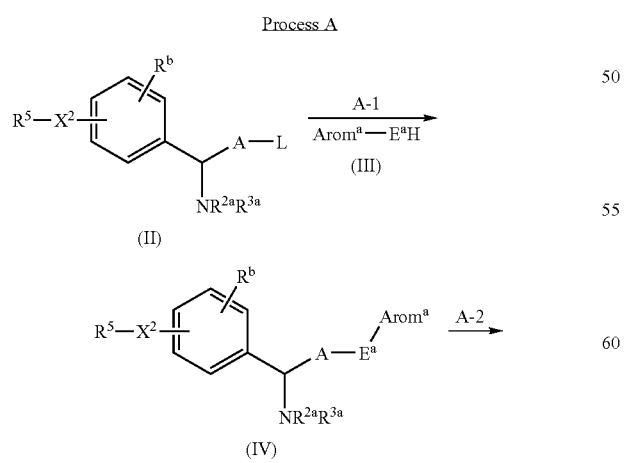

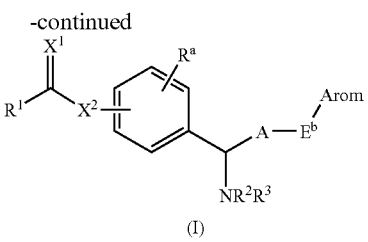

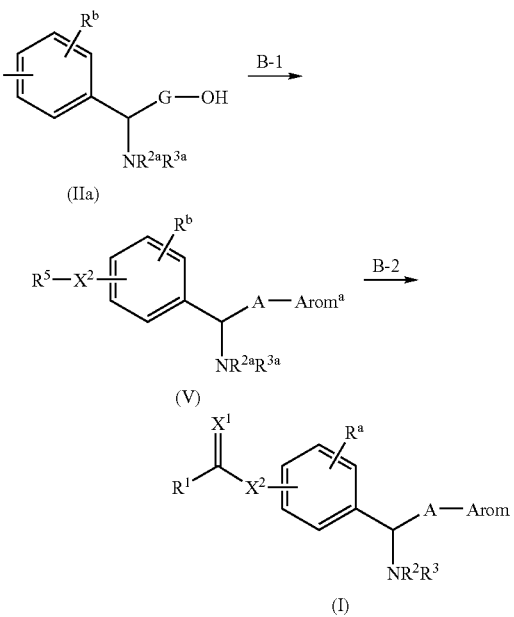

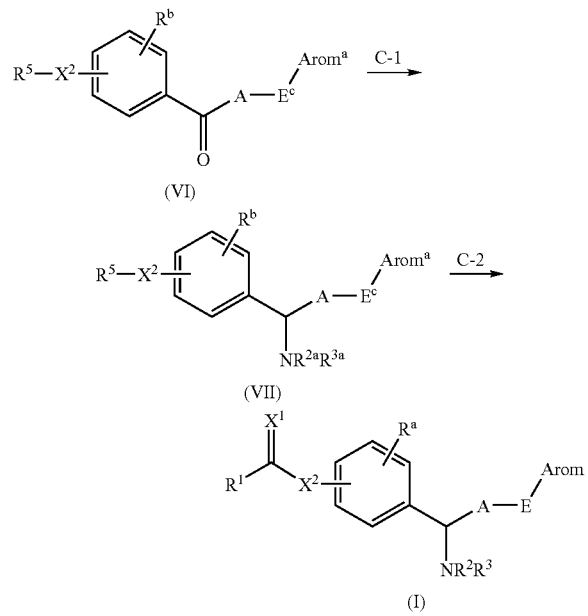

In the above, $R^1$ to $R^3$, $R^a$, A, Arom, E, $X^1$ and $X^2$ have the same meanings as defined above; $R^{2a}$ has the same meaning as the above $R^2$, or represents an allyl group or a protecting group for an amino group; $R^{3a}$ has the same meaning as the above $R^1$ or represents a protecting group for an amino group; $R^5$ represents a hydrogen atom, a protecting group for a hydroxyl group or a group of the formula: $R^1$—C(=$X^1$)— (wherein $R^1$ and $X^1$ have the same meanings as defined above); $R^b$ has the same meaning as the above $R^a$, or represents a hydroxyl group, a hydroxyl group substituted by a leaving group or a vinyl group; Arom$^a$ has the same meaning as the above Arom or represents a group in which a carboxyl group, a hydroxyl group or an amino group on Arom is protected, if necessary, by a protecting group for the respective functional group(s); $E^a$ represents an oxygen atom, a sulfur atom, an —NH— group or an -NQ- group (wherein Q represents a protecting group for an amino group); $E^b$ has the same meaning as the above E, except that it cannot represent a single bond; $E^c$ represents a single bond, an oxygen atom, a sulfur atom, an —NH— group or an -NQ- group (wherein Q represents a protecting group for an amino group); G represents a $C_1$–$C_5$ alkylene group; and L represents a hydroxyl group or a leaving group.

The protecting group for the hydroxyl group in $R^5$ and Arom$^a$ is not particularly limited so long as it can stably protect the hydroxyl group during the reaction, and specifically means a protecting group which is cleavable by a chemical method such as hydrogenolysis, hydrolysis, electrolysis and photolysis, and may include the above "aliphatic acyl group"; the above "aromatic acyl group"; the above "tetrahydropyranyl or tetrahydrothiopyranyl group"; the above "silyl group"; the above "alkoxymethyl group"; the above "substituted ethyl group"; the above "aralkyl group"; the above "alkoxycarbonyl group"; the above "alkenyloxycarbonyl group"; the above "aralkyloxycarbonyl group".

The protecting group for the amino group in $R^{2a}$, $R^{3a}$, Arom$^a$ and Q is not particularly limited so long as it can stably protect the amino group during the reaction, and specifically means a protecting group which is cleavable by a chemical method such as hydrogenolysis, hydrolysis, electrolysis and photolysis, and may include the above "aliphatic acyl group"; the above "aromatic acyl group"; the above "alkoxycarbonyl group"; the above "aralkyloxycarbonyl group"; the above "silyl group"; the above "aralkyl group"; a "substituted methylene group" forming a Schiff base such as N,N-dimethylaminomethylene, benzylidene, 4-methoxybenzylidene, 4-nitrobenzylidene, salicylidene, 5-chlorosalicylidene, diphenylmethylene or (5-chloro-2-hydroxyphenyl)phenylmethylene; an "aromatic sulfonyl group" such as an arylsulfonyl group, e.g., benzenesulfonyl, or an arylsulfonyl group substituted by lower alkyl or lower alkoxy, e.g., p-toluenesulfonyl, pentamethylbenzenesulfonyl, p-methoxybenzenesulfonyl, 2,4,6-trimethoxybenzenesulfonyl or 3-methoxy-4-t-butylbenzenesulfonyl; or an "aliphatic sulfonyl group" such as an alkylsulfonyl group, e.g., methanesulfonyl or t-butylsulfonyl, or an alkylsulfonyl group substituted by a halogen atom, a silyl group or an aryl group, e.g., trifluoromethylsulfonyl, trisilylethanesulfonyl or benzylsulfonyl.

The protecting group in Arom$^a$ is not particularly limited so long as it can stably protect the carboxyl group during the reaction, and specifically means a protecting group which is cleavable by a chemical method such as hydrogenolysis, hydrolysis, electrolysis and photolysis, and may include the above "lower alkyl group"; the above "alkenyl group"; the above "alkynyl group"; the above "lower alkyl group"; an "aliphatic acyl"-"lower alkyl group" such as acetylmethyl; the above "aralkyl group"; or the above "silyl group".

The leaving group in $R^b$ and L is not particularly limited so long as it is a functional group which can react with a nucleophilic reagent to carry out a substitution reaction, and the group may include the above "halogen atom"; a "lower alkylsulfonyloxy group" such as methanesulfonyloxy or ethanesulfonyloxy; a "halogen-substituted lower alkylsulfonyloxy group" such as trifluoromethanesulfonyloxy; an "aromatic sulfonyloxy group" such as an arylsulfonyloxy group, e.g., benzenesulfonyloxy; a lower alkylated arylsulfonyloxy group, e.g., p-toluenesulfonyloxy; or a halogen-substituted arylsulfonyloxy group, e.g., para-chlorobenzenesulfonyloxy.

In the following, the respective steps of Process A to Process C are described in detail.

(Process A)

(Step A-1)

This step is to prepare a compound (IV) by reacting a compound (II) which is obtained by Process D, Process E, Process H, Process I or Process J described later, or publicly known, or easily obtainable from publicly known compounds, with a compound (III) which is publicly known, or easily obtainable from publicly known compounds, in the presence of a base.

This step is carried out by a reaction (reaction A-1a) in which the compound (II) and the compound (III) form an ether in the case where $E^a$ is an oxygen or sulfur atom, or a reaction (reaction A-1b) in which the compound (II) and the compound (III) form an amine in the case where Ea is an amino group.

(Reaction A-1a)

This reaction is accomplished by <Method 1> in which after (α) an alkyl or arylsulfonyl halide (preferably methanesulfonyl chloride) is reacted with the hydroxyl group of the compound (III), (β) it is condensed with the compound (II) in the presence of a base; or <Method 2> in which the compound (III) and the compound (II) are condensed by a Mitsunobu reaction described in Bull. Chem. Soc. Jap., 40, 2380 (1967).

<Method 1>

(α) Reaction of Hydroxyl Group and Sulfonyl Halide

The solvent to be employed here is not particularly limited so long as it does not inhibit the reaction and dissolves the starting material to some extent, and may preferably be an aromatic hydrocarbon such as benzene; or an ether such as diethyl ether, tetrahydrofuran, dioxane or dimethoxyethane, and is preferably an ether (particularly tetrahydrofuran).

The base to be employed here may be an organic base such as triethylamine, diisopropylamine, isopropylethylamine, N-methylmorpholine, pyridine, 4-(N,N-dimethylamino)pyridine, N,N-dimethylaniline or N,N-diethylaniline, and is preferably triethylamine.

The reaction temperature varies depending on the solvent, starting material, reagent, etc., but it is usually from −20 to 50° C., preferably from 0 to 25° C.

The reaction time varies depending on the solvent, starting material, reagent, reaction temperature, etc., but it is usually from 5 minutes to 10 hours, preferably from 10 minutes to 3 hours.

After the reaction, the desired compound of the present step is collected from the reaction mixture by conventional methods. For example, after the reaction, the desired compound is extracted by adding water to the reaction mixture and adding a solvent immiscible with water (for example, benzene, ether, ethyl acetate, etc.), the extracted organic layer is washed with water and is then dried using anhydrous magnesium sulfate, etc. Thereafter, the solvent is evaporated to obtain the desired compound. The thus obtained desired compound can be further purified, if necessary, by conventional methods, for example, recrystallization, reprecipitation and chromatography. The desired compound of the present step can be used for the subsequent step without purifying it.

(β) Condensation with the Compound (II)

The solvent to be employed here is not particularly limited so long as it does not inhibit the reaction and dissolves the starting materials to some extent, and may preferably be an ether such as tetrahydrofuran, dioxane or dimethoxyethane; a nitrile such as acetonitrile or isobutyronitrile; an amide such as formamide, dimethylformamide, dimethylacetamide or hexamethylphosphoric triamide; or a sulfoxide such as dimethyl sulfoxide or sulfolane, and is preferably an amide (particularly dimethylformamide).

The base to be empoyed here may be an alkali metal hydroxide such as lithium hydroxide, sodium hydroxide or potassium hydroxide; an alkali metal hydride such as lithium hydride, sodium hydride or potassium hydride; an alkyl lithium such as methyl lithium, ethyl lithium or butyl lithium; or a lithium alkylamide such as lithium diisopropylamide, lithium dicyclohexylamide or lithium bis(trimethylsilyl) amide, and is preferably a metal hydride (particularly sodium hydride).

The reaction temperature varies depending on the solvent, starting material, reagent, etc. but it is usually from 0 to 180° C., preferably from 0 to 500° C.

The reaction time varies depending on the solvent, starting material, reagent, reaction temperature, etc., but it is usually from 1 to 24 hours, preferably from 2 to 12 hours.

After the reaction, the desired compound of the present step is collected from the reaction mixture by conventional methods. For example, after completion of the reaction, the desired compound is extracted by adding water to the reaction mixture and adding a solvent immiscible with water (for example, benzene, ether, ethyl acetate, etc.), the extracted organic layer is washed with water and is dried using anhydrous magnesium sulfate, etc. and thereafter the solvent is evaporated to obtain the desired compound. The thus obtained desired compound can be further purified, if necessary, by conventional methods, for example, recrystallization, reprecipitation and chromatography.

<Method 2>

The solvent to be employed here is not particularly limited so long as it does not inhibit the reaction and dissolves the starting materials to some extent, and may be an aliphatic hydrocarbon such as hexane, heptane, ligroin or petroleum ether; an aromatic hydrocarbon such as benzene, toluene or xylene; a halogenated hydrocarbon such as dichloromethane, chloroform, carbon tetrachloride, dichloroethane, chlorobenzene or dichlorobenzene; or an ether such as diethyl ether, diisopropyl ether, tetrahydrofuran, dioxane, dimethoxyethane or diethylene glycol dimethyl ether, and is preferably an aliphatic hydrocarbon, aromatic hydrocarbon or ether, more preferably an ether (particularly tetrahydrofuran).

The phosphine to be employed here may be a tri-$C_1$–$C_6$ alkylphosphine such as trimethylphosphine, triethylphosphine, tripropylphosphine, tributylphosphine, tripentylphosphine or trihexylphosphine; a tri-$C_6$–$C_{10}$ arylphosphine such as triphenylphosphine, triindenylphosphine or trinaphthylphosphine; or a tri-$C_6$–$C_{10}$ arylphosphine which may have $C_1$–$C_4$ alkyl as a substituent group such as tolyldiphenylphosphine, tritolylphosphine, trimesitylphosphine, tributylphenylphosphine or tri-6-ethyl-2-naphthylphosphine, and is preferably a tri-$C_1$–$C_6$ alkylphosphin (particularly trimethylphosphine, triethylphosphine, tripropylphosphine or tributylphosphine) or a tri-$C_6$–$C_{10}$arylphosphine (particularly triphenylphosphine, triindenylphosphine or trinaphthylphosphine), more preferably a tri-$C_6$–$C_{10}$ arylphosphine (particularly triphenylphosphine).

The azo compound to be employed here may be a di-$C_1$–$C_4$ alkyl azodicarboxylate such as dimethyl azodicarboxylate, diethyl azodicarboxylate, dipropyl azodicarboxylate or dibutyl azodicarboxylate, and is preferably diethyl azodicarboxylate.

The reaction temperature varies depending on the starting compound, reagent, etc., but it is usually from −10° C. to 100° C., preferably from 0° C. to 50° C.

The reaction time varies depending on the starting compound, reagent and reaction temperature, but it is usually from 5 minutes to 24 hours, preferably from 10 minutes to 12 hours.

After the reaction, the desired compound of the present step is collected from the reaction mixture according to conventional methods. For example, the desired compound is obtained by removing insolubles by filtration in the case where they exist and evaporating the solvent. The obtained desired compound can be further purified, if necessary, by conventional methods, for example, recrystallization, reprecipitation or chromatography.

(Reaction A-1b)

This reaction is carried out similarly to <Method 1> of the (Reaction A-1a).

(Step A-2)

This step is to prepare the compound (I), if necessary, by carrying out a deprotection reaction (Reaction A-2a) of a protecting group, an N-alkylation reaction (Reaction A-2b) of the amine, a carbamoylation reaction (Reaction A-2c) of the hydroxyl group and a cyclization reaction (Reaction A-2d) on the compound (IV) obtained in step A-1.

(Reaction A-2a)

The removal of the protecting group of the amino group varies depending on the kind thereof but it is generally carried out according to well known methods in the technology of synthetic organic chemistry as follows.

In the case where the protecting group of the amino group is a t-butoxycarbonyl group, a 2-trimethylsilylethoxycarbonyl group or a p-methoxybenzyloxycarbonyl group, it can be eliminated by treating it with an acid in an inert solvent or an aqueous solvent. At that time, the desired compound can be also obtained as a salt.

The acid to be employed here can be, for example, hydrochloric acid, sulfuric acid, phosphoric acid, hydrobromic acid or trifluoroacetic acid, and is preferably hydrochloric acid, sulfuric acid, hydrobromic acid or trifluoroacetic acid.

The solvent to be employed here is not particularly limited so long as it does not inhibit the reaction and dissolves the starting materials to some extent, and may be an aliphatic hydrocarbon such as hexane, heptane, ligroin or petroleum ether; an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; an ester such as methyl acetate or ethyl acetate; an alcohol such as methanol, ethanol, propanol, isopropanol or butanol; an amide such as formamide, N,N-dimethylformamide, N,N-dimethylacetamide or hexamethylphosphoric triamide; a sulfoxide such as dimethyl sulfoxide or sulfolane; an aliphatic acid such as formic acid or acetic acid; or water or a mixture of water and the above solvents, and is preferably a halogenated hydrocarbon, ether, alcohol, aliphatic acid or a mixture of water and the above solvents, more preferably an ester (particularly ethyl acetate), or an ether (particularly tetrahydrofuran or dioxane).

The reaction temperature varies depending on the starting compound, solvent and acid used, but it is usually from −20° C. to 100° C., preferably from 0° C. to 80° C.

The reaction time varies depending on the starting compound, solvent and acid used, but it is usually from 5 minutes to 20 hours, preferably from one hour to 10 hours.

After the reaction, the desired compound of the present reaction is collected from the reaction mixture according to conventional methods. For example, the desired compound is obtained by collecting the desired compound precipitated in the reaction solution or appropriately neutralizing the reaction solution, evaporating the solvent, pouring water into the reaction mixture, adding a solvent immiscible with water (for example, benzene, ether, ethyl acetate, etc.) to perform an extraction and washing the organic layer containing the desired compound with water, followed by drying with anhydrous magnesium sulfate, etc. and evaporating off the solvent. The thus obtained desired compound can be further purified, if necessary, by conventional methods, for example, recrystallization, reprecipitation or chromatography.

In the case where the protecting group of the amino group is a t-butoxycarbonyl group, it can also be eliminated by treating it with a silyl compound or Lewis acid, particularly in an inert solvent.

The silyl compound to be employed here is, for example, trimethylsilyl chloride, trimethylsilyl iodide or trimethylsilyl trifluoromethanesulfonate, and the Lewis acid to be employed here is, for example, aluminum chloride.

The solvent to be employed here is not particularly limited so long as it does not inhibit the reaction and dissolves the starting material to some extent, and may be a halogenated hydrocarbon such as dichloromethane, chloroform or carbon tetrachloride; an ether such as diethyl ether, tetrahydrofuran or dioxane; or a nitrile such as acetonitrile, and is preferably a halogenated hydrocarbon (particularly dichloromethane or chloroform) or a nitrile (particularly acetonitrile).

The reaction temperature varies depending on the starting compound, reagent and solvent, but it is usually from −20° to 100° C., preferably from 0° C. to 50° C.

The reaction time varies depending on the starting compound, reagent, solvent and reaction temperature, but it is usually from 10 minutes to 10 hours, preferably from 30 minutes to 3 hours.

After the reaction, the desired compound of the present step is collected from the reaction mixture according to conventional methods. For example, the desired compound is obtained by evaporating the solvent, adding water to the reaction mixture and making the aqueous layer alkaline to collect the precipitated substance by filtration, or adding a solvent immiscible with water (for example, benzene, ether, ethyl acetate, etc.) to perform an extraction and washing the organic layer containing the desired compound with water, followed by drying with anhydrous magnesium sulfate, etc. and evaporating off the solvent. The thus obtained desired compound can be further purified, if necessary, by conventional methods, for example, recrystallization, reprecipitation and chromatography.

In the case where the protecting group of the amino group is an allyloxycarbonyl group, it can be usually eliminated by reacting it with tetrakis(triphenylphosphine)palladium or bis(triphenylphosphine)palladium chloride in the presence of from 1 to 3 equivalents of potassium 2-ethylhexanoate, methyl malonate, dimedone or tributyl tin hydride in an inert solvent.

The solvent to be employed here is not particularly limited so long as it does not affect the present reaction, and may be a halogenated hydrocarbon such as dichloromethane, chloroform or carbon tetrachloride; an ether such as diethyl ether, tetrahydrofuran or dioxane; or an ester such as ethyl acetate or propyl acetate, and is preferably a halogenated hydrocarbon (particularly dichloromethane), an ether (particularly tetrahydrofuran) or an ester (particularly ethyl acetate).

The reaction temperature varies depending on the starting compound, solvent and reducing agent used, but it is usually from −10° to 80° C., preferably from 0° C. to 500° C.

The reaction time varies depending on the starting compound, solvent, reducing agent used, and the reaction temperature, but it is usually from 30 minutes to 24 hours, preferably from one hour to 8 hours.

After the reaction, the desired compound of the present step is collected from the reaction mixture according to conventional methods. For example, the desired compound is obtained by removing the palladium catalyst by filtration and then evaporating the solvent, pouring water into the reaction mixture and making the aqueous layer alkaline to collect the precipitated substance by filtration, or adding a solvent immiscible with water (for example, benzene, ether, ethyl acetate, etc.) to perform an extraction and washing the organic layer containing the desired compound with water, followed by drying with anhydrous magnesium sulfate, etc. and evaporating off the solvent. The obtained desired compound can be further purified, if necessary, by conventional methods, for example, recrystallization, reprecipitation or chromatography.

The removal of the protecting group of the hydroxyl group varies depending on the kind thereof but it is generally carried out according to well known methods in the technology of synthetic organic chemistry as follows.

The solvent to be employed here is not particularly limited so long as it does not inhibit the reaction and dissolves the starting material to some extent, and may be an aliphatic hydrocarbon such as hexane, cyclohexane, heptane, ligroin or petroleum ether; an aromatic hydrocarbon such as benzene, toluene or xylene; an ether such as diethyl ether, diisopropyl ether, tetrahydrofuran, dioxane, dimethoxyethane or diethylene glycol dimethyl ether; an ester such as methyl acetate or ethyl acetate; an alcohol such as methanol, ethanol, propanol, isopropanol, butanol or isobutanol; or a mixture obtained by arbitrarily mixing the above solvents and water, and is preferably an alcohol (particularly methanol) or a mixture of an alcohol and water.

The catalyst to be employed here is not particularly limited so long as it is usually used for catalytic reduction reactions, and may be palladium black, palladium-carbon, palladium hydroxide, palladium hydroxide-carbon, Raney nickel, rhodium-aluminum oxide, palladium-barium sulfate, platinum oxide or platinum black, and is preferably palladium-carbon or palladium hydroxide-carbon.

An acid can be added to effectively carry out the reaction in the present step. The acid to be employed here may be a mineral acid such as hydrochloric acid or hydrobromic acid; or an organic acid such as picric acid, formic acid, acetic acid, propionic acid, trifluoroacetic acid, benzenesulfonic acid, 4-toluenesulfonic acid or camphorsulfonic acid, and is preferably acetic acid.

The reaction temperature varies depending on the starting compound, reagent, etc., but it is usually from −10° to 100° C., preferably from 0° C. to 50° C.

The reaction time varies depending on the starting compound, reagent and reaction temperature, but it is usually from 10 minutes to 48 hours, preferably from 30 minutes to 24 hours.

After the reaction, the desired compound is collected from the reaction mixture according to conventional methods. For example, after the reaction, the desired compound is obtained by removing the catalyst by filtration and evaporating the filtrate. The obtained desired compound can be further purified, if necessary, by conventional methods, for example, recrystallization, reprecipitation or chromatography.

The removal of the protecting group of the carboxyl group varies depending on the kind thereof but it is generally carried out according to well known methods in the technology of synthetic organic chemistry as follows.

In the case where a lower alkyl group or an aryl group is used as the protecting group of the carboxyl group, it can be removed by treatment with an acid or a base.

As the acid, hydrochloric acid, sulfuric acid, phosphoric acid or hydrobromic acid are used, and the base is not particularly limited so long as it does not affect other portions of the compound, and may preferably be an alkali metal carbonate such as sodium carbonate or potassium carbonate; an alkali metal hydroxide such as sodium hydroxide or potassium hydroxide; or a concentrated ammonia-methanol solution.

Isomerization sometimes occurs during hydrolysis by a base.

The solvent to be employed here is not particularly limited so long as it is usually used for hydrolysis reactions and does not inhibit the reaction, and may preferably be water; or a mixture of an organic solvent such as an alcohol, e.g., methanol, ethanol and n-propanol or an ether, e.g., tetrahydrofuran and dioxane, and water.

The reaction temperature and the reaction time vary depending on the starting material, solvent, reagent used, etc. and are not particularly limited, but the reaction is usually carried out at from 0° to 150° C. for from 1 to 10 hours.

In the case where the protecting group of the carboxyl group is a diaryl-substituted methyl group such as diphenylmethyl, it is usually eliminated by treating it with an acid in an inert solvent.

The solvent to be employed here is preferably an aromatic hydrocarbon such as anisole, and as the acid, a fluorinated organic acid such as trifluoroacetic acid is used.

The reaction temperature and the reaction time vary depending on the starting material, solvent, acid used, etc., but the reaction is usually carried out at room temperature for 30 minutes to 10 hours.

In the case where the protecting group of the carboxyl group is an aralkyl group or a halogeno-lower alkyl group, it is usually eliminated by reduction in a solvent.

As the reduction method, in the case where the protecting group of the carboxyl group is a halogeno-lower alkyl group, a method employing chemical reduction such as zinc-acetic acid is preferably used, and in the case where it is an aralkyl group, a method employing catalytic reduction using a catalyst such as palladium-carbon or platinum is carried out, or a method employing chemical reduction using an alkali metal sulfide such as potassium sulfide or sodium sulfide is carried out.

The solvent to be employed here is not particularly limited so long as it does not affect the present reaction, and may preferably be an alcohol such as methanol or ethanol; an ether such as tetrahydrofuran or dioxane; an aliphatic acid such as acetic acid; or a mixture of these organic solvents and water.

The reaction temperature and the reaction time vary depending on the starting material, solvent and reduction method, but the reaction is usually carried out at from 0° C. to approximately room temperature for from 5 minutes to 12 hours.

In the case where the protecting group of the carboxyl group is an alkoxymethyl group, it is usually eliminated by treating it with an acid in a solvent.

The acid to be employed here is not particularly limited so long as it is usually used as Bronsted acid, and may preferably be an inorganic acid such as hydrochloric acid or sulfuric acid, or an organic acid such as acetic acid or para-toluenesulfonic acid.

The solvent to be employed here is not particularly limited so long as it does not affect the present reaction, and may preferably be an alcohol such as methanol or ethanol; an ether such as tetrahydrofuran or dioxane; or a mixture of these organic solvents and water.

The reaction temperature and the reaction time vary depending on the starting material, solvent and acid used, but the reaction is usually carried out at from 0° C. to 50° C. for from 10 minutes to 18 hours.

If the elimination of the protecting group of the carboxyl group is carried out by treatment with ammonia according to conventional methods, the carboxyl group can be also amidated.

An alkali metal salt can be prepared, if desired, by dissolving the thus produced carboxylic acid in a mixture of water and an organic solvent immiscible with water such as ethyl acetate, adding an aqueous solution of an alkali metal carbonate or hydrogencarbonate such as aqueous sodium hydrogencarbonate solution or aqueous potassium carbonate solution at from 0° C. to room temperature, followed by adjusting the pH of the mixture to approximately 7 and collecting the precipitate by filtration.

The thus prepared salt or the above carboxylic acid can be reacted with 2 equivalents of base (preferably an organic base such as triethylamine or dicyclohexylamine; an alkali metal salt hydride such as sodium hydride; or an alkali metal carbonate or hydrogencarbonate such as sodium hydrogencarbonate, sodium carbonate or potassium carbonate) in a solvent (preferably an ether such as tetrahydrofuran; or a polar solvent such as N,N-dimethylformamide, dimethyl sulfoxide, hexamethylphosphoric triamide or triethylphosphate), followed by reaction with an aliphatic acyloxymethyl halide such as acetoxymethyl chloride or propionyloxymethyl bromide, a 1-lower alkoxycarbonyloxyethyl halide such as 1-methoxycarbonyloxyethyl chloride or 1-ethoxycarbonyloxyethyl iodide, a phthalidyl halide, or a (2-oxo-5-methyl-1,3-dioxolen-4-yl)methyl halide, to prepare an ester product protected by a protecting group of the carboxyl group which is easily hydrolized in a living body.

The reaction temperature and the reaction time vary depending on the starting material, solvent and the kind of reaction reagent, but the reaction is usually carried out at from 0° C. to 100° C. for from 0.5 to 10 hours.

(Reaction A-2b)

The N-alkylation of the amine is accomplished by <Method 1>: a combination of an alkylcarbonyl compound and a reducing agent or <Method 2>: reaction with an alkyl halide in the presence of a base.

<Method 1>

The solvent to be employed here is not particularly limited so long as it does not inhibit the reaction and dissolves the starting material to some extent, and may be water; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; a nitrile such as acetonitrile or isobutyronitrile; an amide such as formamide, N,N-dimethylformamide, N,N-dimethylacetamide, N-methyl-2-pyrrolidone, N-methylpyrrolidinone or hexamethylphosphoric triamide; a sulfoxide such as dimethyl sulfoxide or sulfolane; or an organic base such as N-methylmorpholine, triethylamine, tripropylamine, tributylamine, diisopropylethylamine dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline or N,N-diethylaniline; and is preferably an alcohol. The reaction can be also carried out, if necessary, without using a solvent.

The reducing agent to be employed here may be a metal borohydride such as sodium borohydride or sodium cyanoborohydride; a combination of hydrogen gas and a catalyst such as palladium-carbon, platinum or Raney nickel; or a combination of zinc and hydrochloric acid, and is preferably a metal borohydride. In the case where the alkylating agent is formaldehyde, formic acid can be also used.

The reaction temperature varies depending on the starting compound, reagent and solvent, but it is usually from −20° C. to 200° C., preferably from 0° C. to 100° C.

The reaction time varies depending mainly on the reaction temperature, starting compound, and the kind of solvent used, but it is usually from 10 minutes to 24 hours, preferably from one hour to 12 hours.

After the reaction, the desired compound of the present reaction is obtained, for example, by concentrating the reaction mixture, adding an organic solvent immiscible with water such as ethyl acetate, washing with water, separating the organic layer containing the desired compound, drying with anhydrous magnesium sulfate and evaporating the solvent.

<Method 2>

The solvent to be employed here is not particularly limited so long as it does not inhibit the reaction and dissolves the starting material to some extent, and may be an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; a nitrile such as acetonitrile or isobutyronitrile; an amide such as formamide, N,N-dimethylformamide, N,N-dimethylacetamide, N-methyl-2-pyrrolidone, N-methylpyrrolidone or hexamethylphosphoric triamide; a sulfoxide such as dimethyl sulfoxide or sulfolane; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline or N,N-diethylaniline, and is preferably an amide, particularly preferably N,N-dimethylacetamide.

The base to be employed here may be an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably an alkali metal carbonate, particularly preferably potassium carbonate.

Sodium iodide may be also added in order to effectively carry out the reaction.

The reaction temperature varies depending on the starting compound, reagent and solvent, but it is usually from 0° C. to 200° C., preferably from 20° C. to 100° C.

The reaction time varies mainly depending on the reaction temperature, starting compound, and the kind of solvent used, but it is usually from 10 minutes to 24 hours, preferably from one hour to 12 hours.

After the reaction, the desired compound of the present reaction is obtained, for example, by concentrating the reaction mixture, adding an organic solvent immiscible with water such as ethyl acetate, washing with water, separating the organic layer containing the desired compound, drying with anhydrous magnesium sulfate and evaporating the solvent.

(Reaction A-2c)

The solvent to be employed here is not particularly limited so long as it does not inhibit the reaction and dissolves the starting material to some extent, and may be an aliphatic hydrocarbon such as hexane or heptane; an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or diethylene glycol dimethyl ether; a nitrile such as acetonitrile or isobutyronitrile; or an amide such as formamide, N,N-dimethylformamide, N,N-dimethylacetamide, N-methyl-2-pyrrolidone, N-methylpyrrolidinone or hexamethylphosphoric triamide, and is preferably a halogenated hydrocarbon (particularly dichloromethane), an ether (particularly tetrahydrofuran) or an amide (particularly N,N-dimethylformamide).

The base to be employed here may be an alkali metal carbonate such as sodium carbonate, potassium carbonate or lithium carbonate; an alkali metal hydride such as lithium hydride, sodium hydride or potassium hydride; or an organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU), and is preferably an alkali metal carbonate (particularly potassium carbonate) or an organic amine (particularly triethylamine).

The reaction temperature varies depending on the starting compound, solvent and base used, but it is usually from −20° C. to 100° C., preferably from 0° C. to 50° C.

The reaction time varies depending on the starting compound, solvent and base used, but it is usually from 5 minutes to 48 hours, preferably from one hour to 10 hours.

After the reaction, the desired compound of the present reaction is collected from the reaction mixture according to conventional methods. For example, the desired compound precipitated in the reaction solution is obtained by collecting through filtration, or appropriately neutralizing the reaction solution, evaporating the solvent, pouring water into the reaction mixture and adding a solvent immiscible with water (for example, benzene, ether, ethyl acetate, etc.) to perform an extraction, washing the organic layer containing the desired compound with water, drying with anhydrous magnesium sulfate and evaporating the solvent. The thus obtained desired compound can be further purified, if necessary, by conventional methods, for example, recrystallization, reprecipitation or chromatography.

(Reaction A-2d)

This reaction is accomplished by vinylating the phenyl group (α) and allylating the amino group (β), followed by cyclization of the vinyl group and the allyl group by olefin metathesis (γ) Either the vinylation (α) or the allylation (β) may be carried out first.

(α)

The solvent to be employed here is not particularly limited so long as it does not inhibit the reaction and dissolves the starting material to some extent, and may be an aliphatic hydrocarbon such as hexane or heptane; an aromatic hydrocarbon such as benzene, toluene or xylene; an ether such as diethyl ether, diisopropyl ether, tetrahydrofuran, dioxane, dimethoxyethane or diethylene glycol dimethyl ether; a nitrile such as acetonitrile or isobutyronitrile; or an amide such as formamide, N,N-dimethylformamide, N,N-dimethylacetamide, N-methyl-2-pyrrolidone, N-methylpyrrolidinone or hexamethylphosphoric triamide, and is preferably an ether (particularly tetrahydrofuran or dioxane) or an amide (particularly N,N-dimethylformamide).

Lithium chloride can be added for the purpose of promoting the reaction.

The catalyst to be employed here is not particularly limited so long as it can vinylate the hydroxyl group of the phenol, and is preferably a palladium catalyst, that is, a catalyst containing 0 valent- or 2 valent-palladium metal which is used in organic synthesis, and may be palladium metal, palladium-carbon, palladium hydroxide, palladium chloride, palladium (II) acetate, tris(dibenzylideneacetone)dipalladium-chloroform, allyl palladium chloride, [1,2-bis(diphenylphosphino)ethane]palladium dichloride, bis(tri-o-toluylphosphine)palladium dichloride, bis(triphenylphosphine)palladium dichloride, tetrakis(triphenylphosphine)palladium, dichloro[1,1'-bis(diphenylphosphino)ferrocene]palladium, or a catalyst produced in solution by adding a ligand into the reaction solution of these. The ligand added into the reaction solution may be a phosphoric ligand such as 1,1'-bis(diphenylphosphino)ferrocene, bis(2-diphenylphosphinophenyl) ether, 2,2'-bis(diphenylphosphino)-1,1'-binaphthol, 1,3-bis(diphenylphosphino)propane, 1,4-bis(diphenylphosphino)butane, tri-o-toluylphosphine, 2-diphenylphosphino-2'-methoxy-1,1'-binaphthyl or 2,2-bis(diphenylphosphino)-1,1'-binaphthyl. The above palladium catalyst is preferably palladium acetate, tris(dibenzylideneacetone)dipalladium-chloroform, a combination of palladium acetate and the ligand bis(2-diphenylphosphinophenyl) ether, or a combination of tris(dibenzylideneacetone)dipalladium-chloroform and the ligand 1,1'-bis(diphenylphosphino)ferrocene, more preferably a combination of palladium acetate and the ligand bis(2-diphenylphosphinophenyl) ether, or a combination of tris(dibenzylideneacetone)dipalladium-chloroform and the ligand 1,1'-bis(diphenylphosphino)ferrocene.

The reagent to be employed in the present reaction is not particularly limited so long as it is used for Stille coupling and produces a vinyl group, and is preferably tributylvinyl tin.

The reaction temperature varies depending on the starting compound, solvent and base used, but it is usually from −20° C. to 50° C., preferably from 0° C. to 25° C.

The reaction time varies depending on the starting compound, solvent and base used, but it is usually from 5 minutes to 24 hours, preferably from 30 minutes to 12 hours.

After the reaction, the desired compound of the present reaction is collected from the reaction mixture according to conventional methods. For example, the desired compound is obtained by collecting the desired compound precipitated in the reaction solution by filtration, or adding a saturated aqueous potassium fluoride solution, filtering the solvent to evaporate the solvent in the filtrate, adding water and a solvent immiscible with water (for example, benzene, ether, ethyl acetate, etc.) to perform an extraction, washing the organic layer containing the desired compound with water, drying with anhydrous magnesium sulfate and evaporating the solvent. The obtained desired compound can be further purified, if necessary, by conventional methods, for example, recrystallization, reprecipitation or chromatography.

(β)

The solvent to be employed here is not particularly limited so long as it does not inhibit the reaction and dissolves the starting material to some extent, and may be an aliphatic hydrocarbon such as hexane or heptane; an aromatic hydrocarbon such as benzene, toluene or xylene; an ether such as diethyl ether, diisopropyl ether, tetrahydrofuran, dioxane, dimethoxyethane or diethylene glycol dimethyl ether; a nitrile such as acetonitrile or isobutyronitrile; or an amide such as formamide, N,N-dimethylformamide, N,N-dimethylacetamide, N-methyl-2-pyrrolidone, N-methylpyrrolidinone or hexamethylphosphoric triamide, and is preferably an amide (particularly N,N-dimethylformamide).

The allylating reagent to be employed here is on allyl halide, preferably allyl bromide or allyl iodide, more preferably allyl bromide.

The base to be employed here may be an alkali metal carbonate such as sodium carbonate, potassium carbonate or lithium carbonate; an alkali metal hydride such as lithium hydride, sodium hydride or potassium hydride; an alkali metal alkoxide such as sodium methoxide, sodium ethoxide, potassium methoxide, potassium ethoxide, potassium t-butoxide or lithium methoxide; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably an alkali metal hydride (particularly sodium hydride).

The reaction temperature varies depending on the starting compound, solvent and base used, but it is usually from 0° C. to 200° C., preferably from 20° C. to 100° C.

The reaction time varies depending on the starting compound, solvent and base used, but it is usually from 5 minutes to 48 hours, preferably from 1 hour to 12 hours.

After the reaction, the desired compound of the present reaction is collected from the reaction mixture according to conventional methods. For example, the desired compound is obtained by collecting the desired compound precipitated in the reaction solution, or neutralizing appropriately the reaction mixture, pouring water into the reaction mixture, adding a solvent immiscible with water (for example, benzene, ether, ethyl acetate, etc.) to perform an extraction, washing the organic layer containing the desired compound with water, followed by drying with anhydrous magnesium sulfate, and evaporating the solvent. The thus obtained desired compound can be further purified, if necessary, by conventional methods, for example, recrystallization, reprecipitation or chromatography.

(γ)

The solvent to be employed here is not particularly limited so long as it does not inhibit the reaction and dissolves the starting material to some extent, and may be an aromatic hydrocarbon such as benzene, toluene or xylene; a halogenated hydrocarbon such as dichloromethane, chloroform, carbon tetrachloride, dichloroethane, chlorobenzene or dichlorobenzene; or an ether such as diethyl ether, diisopropyl ether, tetrahydrofuran, dioxane, dimethoxyethane or diethylene glycol dimethyl ether, and is preferably an aromatic hydrocarbon or a halogenated hydrocarbon, more preferably toluene or dichloromethane.

The catalyst to be employed here is not particularly limited so long as it can be used for olefin metathesis, and is preferably Grubbs catalyst in which two phosphine ligands are coordinated to benzylidene dihalogenated ruthenium, and this catalyst may be benzylidenebis(tricyclohexylphosphine)dichlororuthenium, benzylidenebis(triphenylphosphine)dichlororuthenium, or benzylidenedichloro(1,3-dimesityl-2-imidazolidinylidene)(tricyclohexylphosphine)ruthenium.

The reaction temperature varies depending on the starting compound, solvent and base used, but it is usually from 0° C. to 120° C., preferably from 25° C. to 40° C.

The reaction time varies depending on the starting compound, solvent and base used, but it is usually from 1 hour to 24 hours, preferably from 2 hours to 12 hours.

After completion of the reaction, the desired compound of the present reaction is collected from the reaction mixture according to conventional methods. For example, the desired compound is obtained by collecting the desired compound precipitated in the reaction solution, or evaporating the solvent. The thus obtained desired compound can be further purified, if necessary, by conventional methods, for example, recrystallization, reprecipitation or chromatography.

In the present step, any of the deprotection reactions of the protecting groups, the N-alkylation reaction of the amine, the carbonylation reaction of the hydroxyl group, and the cyclization reaction, may be carried out first depending on the structure of the desired compound. In the case where the conditions are common to them, the reactions may be carried out consecutively without purification.

(Process B)

(Step B-1)

This step is to prepare a compound (V) by oxidizing the hydroxyl group of the compound (IIa) obtained by Process D, Process E, Process H, Process I or Process J described later, or which is publicly known or easily obtainable from known compounds, to a formyl group (Reaction B-1a), carrying out a Wittig reaction on the formyl group (Reaction B-1b), and reducing the obtained compound (Reaction B-1c).

(Reaction B-1a)

The oxidizing agent to be employed here is not particularly limited so long as it is usually used for oxidation reactions and may preferably be a manganese oxide such as manganese dioxide; a chromic acid compound such as chromic anhydride-pyridine complex; a reagent used for Swern oxidation (a combination of dimethyl sulfoxide and an activating agent (dicyclohexylcarbodiimide, dicyclohexylcarbodiimide and pyridine-trifluoroacetic acid, oxalyl chloride, acetic anhydride, phosphorus pentoxide, pyridine-sulfuric anhydride, sulfur trioxide-pyridine, mercury acetate, chlorine or N-chlorosuccinimide)); a transition metal oxidizing agent such as tetrapropylammonium perruthenate; or a high valence iodine oxidizing agent such as 1,1,1-triacetoxy-1,1-dihydro-1,2-benziodoxol-3(1H)-one, and is more preferably a chromic acid compound.

The solvent to be employed here is not particularly limited so long as it does not inhibit the reaction and dissolves the starting material to some extent, and may preferably be an aromatic hydrocarbon such as benzene, toluene or xylene; a halogenated hydrocarbon such as dichloromethane, chloroform or dichloroethane; an ester such as ethyl acetate; an ether such as tetrahydrofuran, dioxane or dimethoxyethane; a ketone such as acetone or methyl ethyl ketone; or a nitrile such as acetonitrile or isobutyronitrile, and is more preferably a halogenated hydrocarbon (particularly dichloromethane).

The reaction temperature varies depending on the solvent, starting material, reagent, etc., but it is usually from −60° C. to 50° C.

The reaction time varies depending on the solvent, starting material, reagent, reaction temperature, etc. but it is usually from one to 16 hours.

After the reaction, the desired compound of the present reaction is collected from the reaction mixture according to conventional methods. For example, the desired compound is obtained by appropriately neutralizing the reaction mixture, or in the case where insolubles exist, removing them by filtration, adding an organic solvent immiscible with water such as ethyl acetate, washing with water, separating the organic layer containing the desired compound, drying with anhydrous magnesium sulfate and evaporating the solvent. The thus obtained desired compound can be further purified, if necessary, by conventional methods, for example, recrystallization, reprecipitation or chromatography.

(Reaction B-1b)

The reaction is carried out in the presence of a base. The base to be employed here may be an alkyl lithium such as methyl lithium or butyl lithium; an alkali metal hydride such as sodium hydride or potassium hydride; an alkali metal amide such as lithium amide, sodium amide or potassium amide; an alkali metal alkoxide such as sodium methoxide, sodium ethoxide, potassium propoxide, sodium butoxide, potassium-t-butoxide or sodium-t-pentoxide; or an alkali metal disilazide such as lithium hexamethyldisilazide, sodium hexamethyldisilazide or potassium hexamethyldisilazide; and is preferably an alkali metal hydride, alkali metal alkoxide or alkali metal disilazide, more preferably sodium hydride, potassium hydride, potassium-t-butoxide, sodium hexamethyldisilazide, potassium hexamethyldisilazide or lithium hexamethyldisilazide, particularly preferably sodium hydride or potassium hydride.

The Wittig reagent to be employed here is preferably a combination of a triphenylphosphorane such as benzylidenetriphenylphosphorane, and the corresponding benzyl halide compound, or a phosphonium salt obtained by the combination.

The solvent to be employed here is preferably an ether such as diethyl ether, diisopropyl ether, tetrahydrofuran, dioxane, dimethoxyethane or diethylene glycol dimethyl ether (particularly tetrahydrofuran).

The present reaction is preferably carried out under an inert gas stream such as nitrogen, helium or argon.

The reaction temperature varies depending on the solvent, starting compound, reagent, etc., but it is preferably from −78° C. to room temperature.

The reaction time varies depending on the solvent, starting compound, reagent, reaction temperature, etc., but it is preferably from 10 minutes to 5 hours.

After the reaction, the desired compound of the present reaction is collected from the reaction mixture according to conventional methods. For example, after completion of the reaction, the desired compound is obtained by pouring the reaction mixture into an aqueous ammonium chloride solution, extracting the mixture with a solvent immiscible with water, for example, benzene, ether or ethyl acetate, and evaporating the solvent from the extract. The thus obtained desired compound can be further purified, if necessary, by conventional methods, for example, recrystallization, reprecipitation or chromatography.

(Reaction B-1c)

The solvent to be employed here is not particularly limited so long as it does not inhibit the reaction and dissolves the starting material to some extent, and may be an aliphatic hydrocarbon such as hexane, cyclohexane, heptane, ligroin or petroleum ether; an aromatic hydrocarbon such as benzene, toluene or xylene; an ether such as diethyl ether, diisopropyl ether, tetrahydrofuran, dioxane, dimethoxyethane or diethylene glycol dimethyl ether; an ester such as methyl acetate or ethyl acetate; or an alcohol such as methanol, ethanol, propanol, isopropanol, butanol or isobutanol, and is preferably an ester (particularly ethyl acetate) or an alcohol (particularly methanol).

The catalytic reduction catalyst to be employed here is not particularly limited so long as it is used for usual catalytic reduction reactions, and may be palladium black, palladium-carbon, palladium hydroxide, palladium hydroxide-carbon, Raney nickel, rhodium-aluminum oxide, palladium-barium sulfate, platinum oxide or platinum black, and is preferably palladium-carbon.

The reaction temperature varies depending on the starting compound, reagent, etc., but it is usually from −10° C. to 100° C., preferably from 0° C. to 50° C.

The reaction time varies depending on the starting compound, reagent and reaction temperature, but it is usually from 10 minutes to 48 hours, preferably from 30 minutes to 24 hours.

After the reaction, the desired compound is collected from the reaction mixture according to conventional methods. For example, after completion of the reaction, the desired compound is obtained by removing the catalyst by filtration and evaporating the filtrate. The thus obtained desired compound can be further purified, if necessary, by conventional methods, for example, recrystallization, reprecipitation or chromatography.

(Step B-2)

This step is to prepare the compound (I) by carrying out, if necessary, a deprotection reaction of the protecting group, an N-alkylation reaction of the amine, and a carbamoylation reaction of the hydroxyl group of the compound (V) obtained in Step B-1.

The present step is carried out similarly to Step A-2.

(Process C)

(Step C-1)

This step is to prepare the compound (VII) by reducing the carbonyl group of the compound (VI) obtained by Process F or Process G described later (Reaction C-1a), further halogenating the obtained hydroxyl group (Reaction C-1b) and thereafter aminating it (Reaction C-1c).

(Reaction C-1a)

The reducing agent to be employed here is preferably a hydride compound such as lithium aluminum hydride, sodium borohydride or diisobutyl aluminum hydride, more preferably sodium borohydride.

The solvent to be employed here is not particularly limited so long as it does not inhibit the reaction and dissolves the starting material to some extent, and may preferably be an ether such as diethyl ether, tetrahydrofuran, dioxane or dimethoxyethane; or an alcohol such as methanol or ethanol, and is preferably an ether (particularly tetrahydrofuran) or an alcohol (particularly methanol).

The reaction temperature varies depending on the solvent, starting material, reagent, etc., but it is usually from −78° C. to 100° C., preferably from −78° C. to room temperature.

The reaction time varies depending on the solvent, starting material, reagent, reaction temperature, etc., but it is usually from 10 minutes to 24 hours, preferably from one to 10 hours.

After the reaction, the desired compound of the present reaction is collected from the reaction mixture according to conventional methods. For example, the desired compound is obtained by appropriately neutralizing the reaction mixture, or, in the case where insolubles exist, removing them by filtration, adding an organic solvent immiscible with water such as ethyl acetate, washing with water, separating the organic layer containing the desired compound, drying with anhydrous magnesium sulfate, and evaporating the solvent. The thus obtained desired compound can be further purified, if necessary, by conventional methods, for example, recrystallization, reprecipitation or chromatography.

(Reaction C-1b)

The phosphine to be employed here may be a tri-$C_1$–$C_6$ alkylphosphine such as trimethylphosphine, triethylphosphine, tripropylphosphine, tributylphosphine, tripentylphosphine or trihexylphosphine; a tri-$C_6$–$C_{10}$arylphosphine such as triphenylphosphine, triindenylphosphine or trinaphthylphosphine; or a tri-$C_6$–$C_{10}$ arylphosphine which may have a $C_1$–$C_4$ alkyl substituent, such as tolyldiphenylphosphine, tritolylphosphine, trimesitylphosphine, tributylphenylphosphine or tri-6-ethyl-2-naphthylphosphine, and is preferably a tri-$C_1$–$C_6$ alkylphosphine (particularly trimethylphosphine, triethylphosphine, tripropylphosphine or tributylphosphine) or a tri-$C_6$–$C_{10}$arylphosphine (particularly triphenylphosphine, triindenylphosphine or trinaphthylphosphine), more preferably a tri-$C_6$–$C_{10}$ arylphosphine (particularly triphenylphosphine).

The halogenating agent to be employed is a carbon tetrahalide such as carbon tetrabromide.

The solvent to be employed here is not particularly limited so long as it does not inhibit the reaction and dissolves the starting material to some extent, and may be an aliphatic hydrocarbon such as hexane, heptane, ligroin or petroleum ether; an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; a nitrile such as acetonitrile; an amide such as formamide, dimethylformamide dimethylacetamide, hexamethylphosphoramide (HMPA) or hexamethylphosphorus triamide (HMPT); or a sulfoxide such as dimethyl sulfoxide or sulfolane, and is preferably a halogenated hydrocarbon.

The reaction temperature varies depending on the starting compound, reagent, etc., but it is usually from −10° C. to 100° C., preferably from 0° C. to 50° C.

The reaction time varies depending on the starting compound, reagent and reaction temperature, but it is usually from 5 minutes to 10 hours, preferably from 10 minutes to 3 hours.

After the reaction, the desired compound of the present reaction is collected from the reaction mixture according to conventional methods. For example, the desired compound is obtained by appropriately neutralizing the reaction mixture, and, in the case where insolubles exist, removing them by filtration, adding an organic solvent immiscible with water such as ethyl acetate, washing with water, separating the organic layer containing the desired compound, drying with anhydrous magnesium sulfate or the like and evaporating the solvent. The thus obtained desired compound can be further purified, if necessary, by conventional methods, for example, recrystallization, reprecipitation or chromatography.

(Reaction C-1c)

The solvent to be employed here is not particularly limited so long as it does not inhibit the reaction and dissolves the starting material to some extent, and may be an aliphatic hydrocarbon such as hexane, heptane, ligroin or petroleum ether; an aromatic hydrocarbon such as benzene, toluene or xylene; an ether such as diethyl ether, diisopropyl ether, tetrahydrofuran, dioxane, dimethoxyethane or diethylene glycol dimethyl ether; an alcohol such as methanol or ethanol; a nitrile such as acetonitrile; an amide such as formamide, dimethylformamide, dimethylacetamide, hexamethylphosphoramide (HMPA) or hexamethylphosphorus triamide (HMPT); or a sulfoxide such as dimethyl sulfoxide or sulfolane, and is preferably an alcohol.

The reaction temperature varies depending on the starting compound, reagent, etc., but it is usually from 0° C. to 150° C., preferably from 0° C. to 50° C.

The reaction time varies depending on the starting compound, reagent and reaction temperature, but it is usually from 5 minutes to 24 hours, preferably from one hour to 24 hours.

After the reaction, the desired compound of the present step is collected from the reaction mixture according to conventional methods. For example, the desired compound is obtained by adding water to the reaction mixture, adding a solvent immiscible with water (for example, benzene, ether, ethyl acetate, etc.) to extract the desired compound, washing the extracted organic layer with water, drying with anhydrous magnesium sulfate or the like and evaporating the solvent. The thus obtained desired compound can be further purified, if necessary, by conventional methods, for example, recrystallization, reprecipitation or chromatography.

(Step C-2)

This step is to prepare the compound (I) by carrying out, if necessary, a deprotection reaction of the protecting group, an N-alkylation reaction of the amine, and a carbamoylation reaction of the hydroxyl group of the compound (VII) obtained in Step C-1.

The present step is carried out similarly to Step A-2.

The compound (II) used in the above Process A and Process B can be obtained by the following Process D, Process E, Process H, Process I or Process J, and the compound (VI) used in Process C can be obtained by the following Process F or Process G.

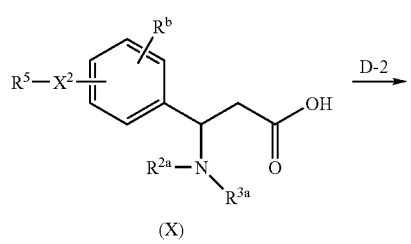

-continued

Process F

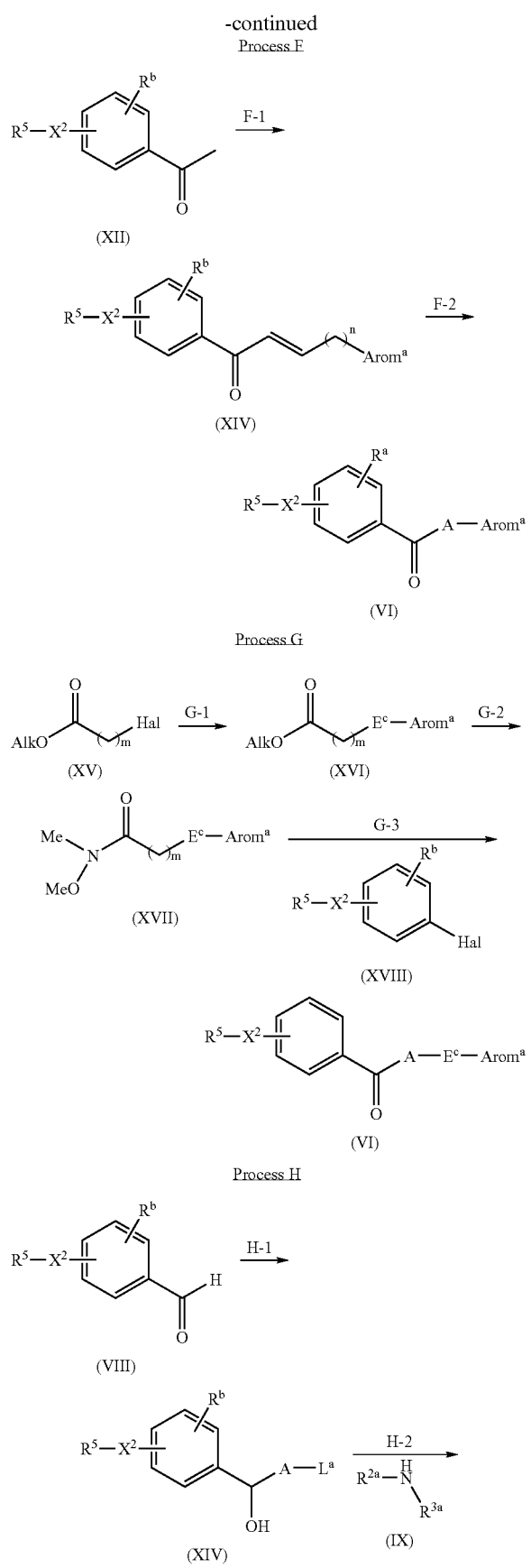

Process G

Process H

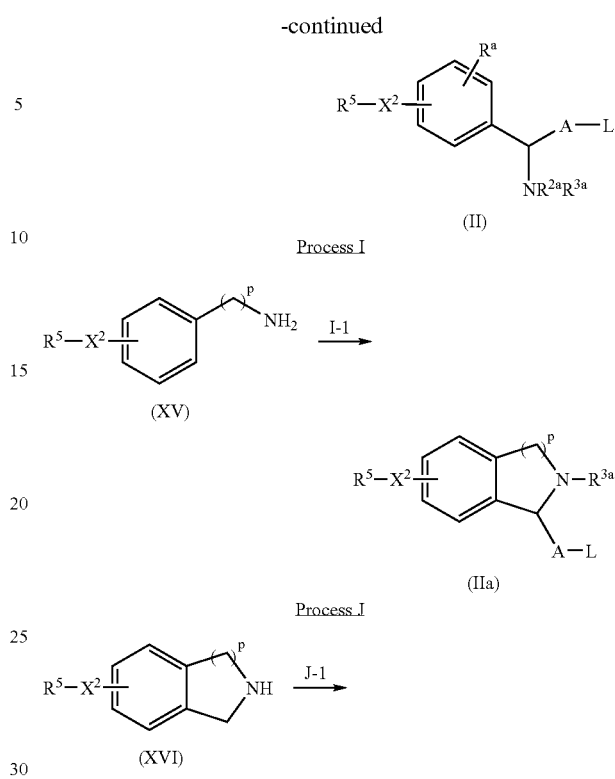

Process I

Process J

In the above schemes, $R^5$, $R^{2a}$, $R^{3a}$, $R^b$, A, $Arom^a$, $E^c$, L and $X^2$ have the same meanings as defined above, Alk represents a $C_1$–$C_6$ alkyl group, Hal represents a halogen atom, $L^a$ indicates the above L or a protected hydroxyl group, n represents an integer of from 0 to 4, m represents an integer of from 1 to 6 and p represents an integer of from 1 to 3.

The protecting group for the hydroxyl group in $L^a$ is not particularly limited so long as it can stably protect the hydroxyl group during the reaction, and specifically means a protecting group which is cleavable by a chemical method such as hydrogenolysis, hydrolysis, electrolysis and photolysis, and may include the above "aliphatic acyl group"; the above "aromatic acyl group"; the above "tetrahydropyranyl or tetrahydrothiopyranyl group"; the above "silyl group" the above "alkoxymethyl group"; the above "substituted ethyl group"; the above "aralkyl group"; the above "alkoxycarbonyl group"; the above "alkenyloxycarbonyl group"; and the above "aralkyloxycarbonyl group".

In the following, Process D to Process J are described in detail.

(Process D)

(Step D-1)

This step is to prepare the compound (X) by reacting the compound (VIII) which is publicly known or easily obtainable from publicly known compounds, the compound (IX) and malonic acid.

The present step is accomplished by reacting the compounds according to the method described in Helv. Chim. Acta, 68, 403 (1985).

The solvent to be employed here is not particularly limited so long as it does not inhibit the reaction and dissolves the starting material to some extent, and may be an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or diethylene glycol dimethyl ether; an ester such as methyl acetate or ethyl acetate; or an alcohol such as methanol, ethanol, propanol, isopropanol, butanol or isobutanol, and is preferably an alcohol (particularly ethanol or propanol).

The reaction temperature varies depending on the starting compound, reagent, etc., but it is usually from 0° C. to 150° C., preferably from 50° C. to 100° C.

The reaction time varies depending on the starting compound, reagent and reaction temperature, but it is usually from 30 minutes to 24 hours, preferably from one hour to 12 hours.

After the reaction, the desired compound is collected from the reaction mixture according to conventional methods. For example, after completion of the reaction, the desired compound is obtained by collecting by filtration. The desired compound of the present step can be used for the subsequent step without purification.

In the desired compound of the present reaction, if necessary, a protecting group can be introduced onto the hydroxyl group and the amino group according to known methods (for example, the methods described in "Protective Groups in Organic Synthesis" (written by Theodora W. Geene, Peter G. M. Wuts, 1999 published by A Wiley-Interscience Publication)). The reaction for introducing the protecting group may be carried out in an arbitrary step other than the present step, and a person skilled in the art, when introducing the protecting group, can easily select an appropriate step depending on the desired compound.

Namely, in the case where a protecting group is introduced onto the hydroxyl group, for example, the step is carried out as follows.

The compound employed for protecting the hydroxyl group may be an aralkyl halide compound such as benzyl chloride, benzyl bromide, 4-nitrobenzyl bromide or 4-methoxybenzyl bromide; an alkoxy-, alkylthio- or aralkyloxy-substituted alkyl halide compound such as methoxymethyl chloride, methylthiomethyl chloride, ethoxyethyl chloride or benzyloxymethyl chloride; an unsaturated ether such as methylvinyl ether or ethylvinyl ether; or a silyl compound such as hexamethyldisilazane, trimethylsilyl chloride, tri-n-propylsilyl chloride, t-butyldimethylsilyl chloride or diphenyl-t-butylsilyl chloride, as the preferred compounds.

The reagent employed here may be an organic base such as triethylamine, pyridine, 4-N,N-dimethylaminopyridine, imidazole or 1,8-diazabicyclo[5.4.0]undec-7-ene (DBU); or an inorganic base such as sodium hydroxide, potassium hydroxide or potassium carbonate. In the case where an unsaturated ether is used, the reaction is carried out in the presence of a small amount of an acid, for example, a mineral acid such as hydrochloric acid or hydrobromic acid, or an organic acid such as picric acid, trifluoroacetic acid, benzenesulfonic acid, 4-toluenesulfonic acid or camphorsulfonic acid in the presence or absence of an inert solvent. The solvent to be employed here is not particularly limited so long as it does not inhibit the reaction and dissolves the starting material to some extent, and may be an ether such as ether, tetrahydrofuran or dioxane; an amide such as formamide, dimethylformamide or dimethylacetamide; a halogenated hydrocarbon such as dichloromethane, chloroform or carbon tetrachloride; or an aromatic hydrocarbon such as benzene, toluene or xylene, and is preferably an amide (particularly dimethylformamide) or a halogenated hydrocarbon. The reaction can also be carried out by using an excess amount of vinyl ether compound to act also as the solvent in the absence of an inert solvent.

The reaction temperature varies depending on the solvent, starting material, reagent, reaction temperature, etc., but it is usually from 0° C. to 500° C.

The reaction time varies depending on the solvent, starting material, reagent, reaction temperature, etc. but it is usually from 30 minutes to 3 hours.

After the reaction, the desired compound of the present reaction is collected from the reaction mixture according to conventional methods. For example, the desired compound is obtained by appropriately neutralizing the reaction mixture, and, in the case where insolubles exist, removing them by filtration, adding an organic solvent immiscible with water such as ethyl acetate, washing with water, separating the organic layer containing the desired compound, drying with anhydrous magnesium sulfate or the like and evaporating the solvent. The thus obtained desired compound can be further purified, if necessary, by conventional methods, for example, recrystallization, reprecipitation or chromatography.

In the case where a protecting group is introduced onto the amino group, the step is, for example, carried out as follows.

The introduction of the protecting group is accomplished by <Method 1> in which the compound is reacted with from 1 to 4 equivalents (preferably from 2 to 3 equivalents) of a compound of formula: $P^1$-LG or a compound of formula: $P^1$—O—$P^1$ (in the case where $P^1$ is an acyl group) in the presence or absence of a base (preferably in the absence of a base) in an inert solvent; or <Method 2> in which the compound is reacted with a compound of formula: $P^1$—OH (in the case where $P^1$ is an acyl group) in the presence of a condensing agent and in the presence or absence of a catalytic amount of base (preferably in the presence of both) in an inert solvent; or <Method 3> in which the compound is reacted with a compound of formula: $P^1$—OH (in the case where $P^1$ is an acyl group) in the presence of a halogenated phosphoric acid dialkyl ester (preferably diethyl chlorophosphate) and a base in an inert solvent.

In the above, the leaving group LG may be a group similar to those described above.

The compound of formula: $P^1$-LG used in the above <Method 1> may be t-butoxycarbonyl chloride, t-butoxycarbonyl bromide, 2-trimethylsilylethoxycarbonyl chloride, 2-trimethylsilylethoxycarbonyl bromide, p-methoxybenzyloxycarbonyl chloride, p-methoxybenzyloxycarbonyl bromide, allyloxycarbonyl chloride or allyloxycarbonyl bromide, and is preferably t-butoxycarbonyl chloride.

The compound of formula: $P^1$—O—$P^1$ used in <Method 1> may be di-t-butyl dicarbonate, 2-trimethylsilylethoxycarboxylic anhydride, p-methoxybenzyloxycarboxylic acid or allyloxycarboxylic anhydride, and is preferably di-t-butyl dicarbonate.

The solvent employed in <Method 1> is not particularly limited so long as it does not inhibit the reaction and dissolves the starting material to some extent, and may be an aliphatic hydrocarbon such as hexane or heptane; an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or diethylene glycol dimethyl ether; a nitrile such as acetonitrile or isobutyronitrile; or an amide such as formamide, N,N-dimethylformamide, N,N-dimethylacetamide, N-methyl-2-pyrrolidone, N-methylpyrrolidinone or hexamethylphosphoric triamide, and is preferably an ether (particularly diethyl ether or tetrahydrofuran) or a halogenated hydrocarbon (particularly dichloromethane).

The base employed in <Method 1> may be an organic amine such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, imidazole, quinoline, N,N-dimethylaniline or N,N-diethylaniline, and is preferably triethylamine or 4-(N,N-dimethylamino)pyridine.

A catalytic amount of 4-(N,N-dimethylamino)pyridine or 4-pyrrolidinopyridine can be also used in combination with other bases, and a quaternary ammonium salt such as benzyltriethylammonium chloride or tetrabutylammonium chloride or a crown ether such as dibenzo-18-crown-6 can be also added in order to effectively carry out the reaction.

The reaction temperature in <Method 1> is usually from −20° C. to 100° C., preferably from −10° C. to 50° C.

The reaction time in <Method 1> mainly varies depending on the reaction temperature, starting compound, base used and kind of solvent used, but it is usually from 10 minutes to one day, preferably from 30 minutes to 12 hours.

The compound of formula: $P^1$—OH employed in the above <Method 2> and <Method 3> may be t-butoxycarboxylic acid, 2-trimethylsilylethoxycarboxylic acid, p-methoxybenzyloxycarboxylic acid or allyloxycarboxylic acid, and is preferably pivalic acid.

The solvent employed in the above <Method 2> is not particularly limited so long as it does not inhibit the reaction and dissolves the starting material to some extent, and may be an aliphatic hydrocarbon such as hexane or heptane; an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or diethylene glycol dimethyl ether; a nitrile such as acetonitrile or isobutyronitrile; or an amide such as formamide, N,N-dimethylformamide, N,N-dimethylacetamide, N-methyl-2-pyrrolidone, N-methylpyrrolidinone or hexamethylphosphoric triamide, and is preferably a halogenated hydrocarbon (dichloromethane or carbon tetrachloride) or an ether (particularly diethyl ether, tetrahydrofuran or dioxane).

The condensing agent employed in <Method 2> may be dicyclohexylcarbodiimide, carbonyldimidazole or 1-methyl-2-chloro-pyridinium iodide-triethylamine, and is preferably dicyclohexylcarbodiimide.

The base employed in <Method 2> can be one which is similar to the base employed in the above <Method 1>, preferably triethylamine or 4-(N,N-dimethylamino)pyridine.

The reaction temperature in <Method 2> is usually from −20° C. to 80° C., preferably from 0° C. to 30° C.

The reaction time in <Method 2> varies depending mainly on the reaction temperature, starting compound, reaction reagent and kind of solvent used, but it is usually from 10 minutes to 3 days, preferably from 30 minutes to one day.

The solvent employed in the above <Method 3> is not particularly limited so long as it does not inhibit the reaction and dissolves the starting material to some extent, and may be an aliphatic hydrocarbon such as hexane or heptane; an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or diethylene glycol dimethyl ether; a nitrile such as acetonitrile or isobutyronitrile; or an amide such as formamide, N,N-dimethylformamide, N,N-dimethylacetamide, N-methyl-2-pyrrolidone, N-methylpyrrolidinone or hexamethylphosphoric triamide, and is preferably an ether (diethyl ether or tetrahydrofuran) or an amide (N,N-dimethylformamide or N,N-dimethylacetamide).

The base employed in <Method 3> can be, for example, one which is similar to the base employed in the above <Method 1>, preferably triethylamine or 4-(N,N-dimethylamino)pyridine.

The reaction temperature in <Method 3> is from 0° C. to the reflux temperature of the solvent used, preferably from 20° C. to 50° C.

The reaction time in <Method 3> varies depending mainly on the reaction temperature, starting compound, reaction reagent and kind of solvent used, but it is usually from 10 minutes to 3 days, preferably from 30 minutes to one day.

After the reaction, the desired compound obtained by the above method is collected from the reaction mixture according to conventional methods. For example, after completion of the reaction, the desired compound is obtained by evaporating the solvent or by pouring water onto the residue after the solvent is evaporated, adding a solvent immiscible with water (for example, benzene, ether, ethyl acetate, etc.) to extract the desired compound, washing the extracted organic layer with water, followed by drying with anhydrous magnesium sulfate or the like and evaporating the solvent. The thus obtained desired compound can be further purified, if necessary, according to conventional methods, for example, recrystallization, reprecipitation or chromatography.

(Step D-2)

This step is to prepare the compound (XI) by esterifying the carboxyl group of the compound (X) obtained in Step D-1.

The solvent to be employed here is not particularly limited so long as it does not inhibit the reaction and dissolves the starting material to some extent, and may be water; an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or diethylene glycol dimethyl ether; a nitro compound such as nitroethane or nitrobenzene; a nitrile such as acetonitrile or isobutyronitrile; an amide such as formamide, dimethylformamide, dimethylacetamide or hexamethylphosphoric triamide; or a sulfoxide such as dimethyl sulfoxide or sulfolane. In the present reaction, an esterifying agent such as ethanol can be used as the solvent.

The esterifying reagent to be employed here may be a combination of an alcohol such as methanol or ethanol and an inorganic acid such as sulfuric acid; an alkylated inorganic acid such as dimethylsulfuric acid; or an alkyldiazo compound such as diazomethane.

The reaction temperature varies depending on the starting compound, reagent, etc., but it is usually from 0° C. to 150° C., preferably from 20° C. to 100° C.

The reaction time varies depending on the starting compound, reagent and reaction temperature, but it is usually from 30 minutes to 24 hours, preferably from one hour to 12 hours.

After the reaction, the desired compound is collected from the reaction mixture according to conventional methods. For example, after completion of the reaction, the desired compound is obtained by collecting through filtration. Or, for example, after completion of the reaction, the desired compound is obtained by adding water to the reaction solution, adding a solvent immiscible with water (for example, benzene, ether, ethyl acetate, etc.) to extract the desired compound, washing the extracted organic layer with water, drying with anhydrous magnesium sulfate or the like and evaporating the solvent. The thus obtained desired compound can be further purified, if necessary, by conventional methods, for example, recrystallization, reprecipitation or chromatography.

(Step D-3)

This step is to prepare the compound (II) by reducing the ester of the compound (XI) obtained in Step D-2.

The reducing agent to be employed here is preferably a hydride compound such as lithium aluminum hydride, sodium borohydride, lithium borohydride or diisobutyl aluminum hydride, more preferably lithium aluminum hydride.

The solvent to be employed here is not particularly limited so long as it does not inhibit the reaction and dissolves the starting material to some extent, and may be an ether such as diethyl ether, tetrahydrofuran, dioxane or dimethoxyethane, and is preferably an ether (particularly tetrahydrofuran).

The reaction temperature varies depending on the solvent, starting material, reagent, etc., but it is usually from −78° C. to 100° C., preferably from −78° C. to room temperature.

The reaction time varies depending on the solvent, starting material, reagent, reaction temperature, etc., but it is usually from 10 minutes to 24 hours, preferably from one hour to 10 hours.

After the reaction, the desired compound of the present reaction is collected from the reaction mixture according to conventional methods. For example, the desired compound is obtained by appropriately neutralizing the reaction mixture and, in the case where insolubles exist, removing them by filtration, adding an organic solvent immiscible with water such ethyl acetate, washing with water, separating the organic layer containing the desired compound, drying with anhydrous magnesium sulfate or the like and evaporating the solvent. The thus obtained desired compound can be further purified, if necessary, by conventional methods, for example, recrystallization, reprecipitation or chromatography.

In the case where A of the desired compound is a group other than a methylene group, after the hydroxyl group moiety is further substituted for a cyano group (Reaction D-3a) and converted into a formyl group by reduction (Reaction D-3b), it is further reduced to a hydroxyl group (Reaction D-3c). Thereby, it can be converted into an ethylene group in which the number of carbons is increased by one, and the desired compound (II) can be prepared by repeating this step a plurality of times.

Further, in the case where the desired compound is cyclized, the desired compound (II) can be prepared by carrying out a cyclization reaction (D-3d).

(Reaction D-3a)

The present reaction is accomplished by (α) reacting an alkyl or arylsulfonyl halide (preferably methanesulfonyl chloride) with the hydroxyl group of the compound and (β) reacting the product with an alkyl metal cyanide (preferably sodium cyanide or potassium cyanide).

(α) Reaction of Hydroxyl Group with a Sulfonyl Halide

The solvent to be employed here is not particularly limited so long as it does not inhibit the reaction and dissolves the starting material to some extent, and may preferably be an aromatic hydrocarbon such as benzene; a halogenated hydrocarbon such as dichloromethane or chloroform; or an ether such as diethyl ether, tetrahydrofuran, dioxane or dimethoxyethane, and is preferably an ether (particularly tetrahydrofuran).

The base to be employed here may be an organic base such as triethylamine, diisopropylamine, isopropylethylamine, N-methylmorpholine, pyridine, 4-(N,N-dimethylamino)pyridine, N,N-dimethylaniline or N,N-diethylaniline, and is preferably triethylamine.

The reaction temperature varies depending on the solvent, starting material, reagent, etc., but it is usually from −20 to 50° C., preferably from 0 to 25° C.

The reaction time varies depending on the solvent, starting material, reagent, reaction temperature, etc., but it is usually from 5 minutes to 10 hours, preferably from 10 minutes to 3 hours.

After the reaction, the desired compound of the present step is collected from the reaction mixture according to conventional methods. For example, after completion of the reaction, the desired compound is obtained by adding water to the reaction solution, adding a solvent immiscible with water (for example, benzene, ether, ethyl acetate, etc.) to extract the desired compound, washing the extracted organic layer with water, drying with anhydrous magnesium sulfate or the like and evaporating the solvent. The thus obtained desired compound can be further purified, if necessary, by conventional methods, for example, recrystallization, reprecipitation or chromatography. The desired compound of the present step can be used for the subsequent step without purification.

(β) Reaction with Cyanide

The solvent to be employed here is not particularly limited so long as it does not inhibit the reaction and dissolves the starting material to some extent, and may be an ether such as tetrahydrofuran, dioxane or dimethoxyethane; a nitrile such as acetonitrile or isobutyronitrile; an amide such as formamide, dimethylformamide, dimethylacetamide and hexamethylphosphoric triamide; or a sulfoxide such as dimethyl sulfoxide or sulfolane, and is preferably an amide (particularly dimethylformamide).

In the present reaction, crown ether compound can be added. The crown ether compound employed here may be 12-crown-4, 15-crown-5,18-crown-6,1-aza-12-crown-4,1-aza-15-crown-5, 1-aza-18-crown-6, benzo-15-crown-5,4'-nitrobenzo-15-crown-5, benzo-18-crown-6, dibenzo-18-crown-6, dibenzo-24-crown-8, dicyclohexano-18-crown-6 or dicyclohexano-24-crown-8, and is preferably 15-crown-5, 18-crown-6,1-aza-15-crown-5,1-aza-18-crown-6, benzo-15-crown-5,4'-nitrobenzo-15-crown-5, benzo-18-crown-6, dibenzo-18-crown-6 or dicyclohexano-18-crown-6, more preferably 15-crown-5,18-crown-6,1-aza-18-crown-6, benzo-18-crown-6, dibenzo-18-crown-6 or dicyclohexano-18-crown-6, particularly preferably 15-crown-5 or 18-crown-6.

The reaction temperature varies depending on the solvent, starting material, reagent, etc., but it is usually from 0 to 180° C., preferably from 0 to 500° C.

The reaction time varies depending on the solvent, starting material, reagent, reaction temperature, etc. but it is usually from 1 to 24 hours, preferably from 2 to 12 hours.

After the reaction, the desired compound of the present step is collected from the reaction mixture according to conventional methods. For example, after completion of the reaction, the desired compound is obtained by adding water to the reaction solution, adding a solvent immiscible with water (for example, benzene, ether, ethyl acetate, etc.) to extract the desired compound, washing the extracted organic layer with water, drying with anhydrous magnesium sulfate or the like and evaporating the solvent. The thus obtained desired compound can be further purified, if necessary, by conventional methods, for example, recrystallization, reprecipitation or chromatography.

(Reaction D-3b)

The reducing agent employed here is preferably diisobutyl aluminum hydride.

The solvent to be employed here is not particularly limited so long as it does not inhibit the reaction and dissolves the starting material to some extent, and may preferably be an ether such as diethyl ether, tetrahydrofuran, dioxane or dimethoxyethane; a halogenated hydrocarbon such as dichloromethane, chloroform or dichloroethane; an aromatic hydrocarbon such as benzene, toluene or xylene; or an aliphatic hydrocarbon such as pentane or hexane, and is more preferably a halogenated hydrocarbon such as dichloromethane.

The present step is preferably carried out under an inert gas stream such as nitrogen, helium or argon.

The reaction temperature varies depending on the solvent, starting material, reagent, etc., but it is usually from −78° C. to 50° C., preferably from −20° C. to room temperature.

The reaction time varies depending on the solvent, starting material, reagent, reaction temperature, etc., but it is usually from 10 minutes to 24 hours, preferably from one to 5 hours.

After the reaction, the desired compound of the present reaction is collected from the reaction mixture according to conventional methods. For example, the desired compound is obtained by appropriately neutralizing the reaction mixture and, in the case where insolubles exist, removing them by filtration, adding a solvent immiscible with water such as ethyl acetate, washing with water, separating the organic layer containing the desired compound, drying with anhydrous magnesium sulfate or the like and evaporating the solvent. The thus obtained desired compound can be further purified, if necessary, by conventional methods, for example, recrystallization, reprecipitation or chromatography. The desired compound of the present step can be used for the subsequent step without purification.

(Reaction D-3c)

The reducing agent to be employed here is preferably a hydride compound such as lithium aluminum hydride, sodium borohydride or diisobutyl aluminum hydride, more preferably sodium borohydride.

The solvent to be employed here is not particularly limited so long as it does not inhibit the reaction and dissolves the starting material to some extent, and may preferably be an ether such as diethyl ether, tetrahydrofuran, dioxane or dimethoxyethane; or an alcohol such as methanol or ethanol, and is preferably an ether (particularly tetrahydrofuran) or an alcohol (particularly methanol).

The reaction temperature varies depending on the solvent, starting material, reagent, etc., but it is usually from −78° C. to 100° C., preferably from −78° C. to room temperature.

The reaction time varies depending on the solvent, starting material, reagent, reaction temperature, etc., but it is usually from 10 minutes to 24 hours, preferably from one to 10 hours.

After completion of the reaction, the desired compound of the present reaction is collected from the reaction mixture according to conventional methods. For example, the desired compound is obtained by appropriately neutralizing the reaction mixture and, in the case where insolubles exist, removing them by filtration, adding an organic solvent immiscible with water such as ethyl acetate, washing with water, separating the organic layer containing the desired compound, drying with anhydrous magnesium sulfate or the like and evaporating the solvent. The thus obtained desired compound can be further purified, if necessary, by conventional methods, for example, recrystallization, reprecipitation or chromatography.

A leaving group can be introduced, if necessary, to the desired compound of the present reaction by known methods.

Namely, in the case where the leaving group is a halogen atom, the desired compound can be obtained according to the process of (Reaction C-1b), and in the case where the leaving group is a sulfonyloxy group, the desired compound can be obtained according to the method of (Reaction D-3a) (α).

(Reaction D-3d)

This reaction is carried out similarly to (Reaction A-2d).

The present reaction may be carried out at any stage of the reduction reaction of the ester or (Reaction D-3a) to (Reaction D-3c), depending on the desired compound.

(Process E)

(Step E-1)

This step is to prepare the compound (XII) by enolating an acetate derivative with a base, followed by reacting with the compound (VIII), which is publicly known or easily obtainable from known compounds.

The solvent to be employed here is not particularly limited so long as it does not inhibit the reaction and dissolves the starting material to some extent, and may be an aliphatic hydrocarbon such as hexane, cyclohexane, heptane, ligroin or petroleum ether; an aromatic hydrocarbon such as benzene, toluene or xylene; an ether such as diethyl ether, diisopropyl ether, tetrahydrofuran, dioxane, dimethoxyethane or diethylene glycol dimethyl ether; an amide such as formamide, N,N-dimethylformamide, N,N-dimethylacetamide or N-methyl-2-pyrrolidinone; or a sulfoxide such as dimethyl sulfoxide or sulfolane, and is preferably an alcohol (particularly methanol or ethanol).

The base may be an alkali metal hydroxide such as lithium hydroxide, sodium hydroxide or potassium hydroxide; an alkali metal hydride such as lithium hydride, sodium hydride or potassium hydride; an alkyl lithium such as methyl lithium, ethyl lithium or butyl lithium; or a lithium alkylamide such as lithium diisopropylamide, lithium dicyclohexylamide or lithium bis(trimethylsilyl)amide, and is preferably an alkali metal hydroxide (particularly potassium hydroxide).

The reaction temperature varies depending on the starting compound, reagent, etc., but it is usually from −100° C. to 50° C., preferably from 0° C. to room temperature.

The reaction time varies depending on the starting compound, reagent and reaction temperature, but it is usually from 5 minutes to 24 hours, preferably from one hour to 12 hours.

After the reaction, the desired compound is collected from the reaction mixture according to conventional methods. For example, after completion of the reaction, the desired compound is obtained by adding water to the reaction solution, adding a solvent immiscible with water (for example, benzene, ether, ethyl acetate, etc.) to extract the desired compound, washing the extracted organic layer with water, drying with anhydrous magnesium sulfate or the like and evaporating the solvent. The thus obtained desired compound can be further purified, if necessary, by conventional methods, for example, recrystallization, reprecipitation or chromatography. A plurality of compounds can sometimes be obtained in the present step but it can be easily judged by a person skilled in the art which compound is the desired compound by using the usual means (for example, measurement of a coupling constant in NMR spectrum, etc.) and the desired compound can be obtained.

(E-2)

The present step is to prepare the compound (XI) by carrying out a Michael addition using a metal amide on the compound (XII).

The present step can be accomplished by the addition reaction of the metal amide derived from benzylphenylethylamine described in Tetrahedron; Asymmetry, 2, 183 (1991).

The solvent to be employed here is not particularly limited so long as it does not inhibit the reaction and dissolves the starting material to some extent, and may be an aliphatic hydrocarbon such as hexane, cyclohexane, heptane, ligroin or petroleum ether; an aromatic hydrocarbon such as benzene, toluene or xylene; an ether such as diethyl ether, diisopropyl ether, tetrahydrofuran, dioxane, dimethoxyethane or diethylene glycol dimethyl ether; or an amide such as formamide, N,N-dimethylformamide, N,N-dimethylacetamide, N-methyl-2-pyrrolidone, N-methylpyrrolidinone or hexamethylphosphoric triamide, and is preferably an ether (particularly tetrahydrofuran).

The reaction is carried out in the presence of a base. The base to be employed here may be an alkyl lithium such as methyl lithium or butyl lithium; an alkali metal disilazide such as lithium hexamethyldisilazide, sodium hexamethyldisilazide or potassium hexamethyldisilazide; or a lithium amide such as lithium diisopropylamide or lithium dicyclohexylamide, and is preferably an alkyl lithium (particularly butyl lithium).

The reaction temperature varies depending on the starting compound, reagent, etc., but it is usually from −78° C. to 40° C., preferably from −78° C. to 0° C.

The reaction time varies depending on the starting compound, reagent, and reaction temperature, but it is usually from 10 minutes to 24 hours, preferably from 10 minutes to 4 hours.

After the reaction, the desired compound is collected from the reaction mixture according to conventional methods. For example, after completion of the reaction, the desired compound is obtained by removing the catalyst by filtration and evaporating the filtrate. The thus obtained desired compound can be further purified, if necessary, by conventional methods, for example, recrystallization, reprecipitation or chromatography.

(Step E-3)

This step is to prepare the compound (II) by reducing the ester of the compound (XI) obtained in Step E-2.

The present step is carried out similarly to Step D-3

(Process F)

(Step F-1)

This step is to prepare the compound (XIV) by enolating the compound (XII), which is publicly known or easily obtainable from publicly known compounds, with a base, followed by reacting with an aldehyde.

The present reaction is carried out similarly to Step E-1.

(Step F-2)

This step is to prepare the compound (VI) by reducing the compound (XIV) obtained in Step F-1.

The present step is carried out similarly to (Reaction B-1c).

(Process G)

(Step G-1)

This step is to prepare the compound (XIV) by reacting the compound (XV), which is publicly known or easily obtainable from publicly known compounds, with a compound of the formula: $R^3$-$E^c$-H (wherein $R^3$ and $E^c$ have the same meanings as defined above) in the presence of a base.

The present step is carried out similarly to Step A-1.

(Step G-2)

This step is a step in which the ester of the compound (XVI) obtained in G-1 is hydrolized (Reaction G-2a) and is then amidated (Reaction G-2b).

(Reaction G-2a)

The base may preferably be an alkali metal carbonate such as sodium carbonate or potassium carbonate; an alkali metal hydroxide such as sodium hydroxide or potassium hydroxide; or a concentrated ammonia-methanol solution.

The solvent to be employed here may preferably be water; or a mixture of an organic solvent such as an alcohol, e.g., methanol, ethanol or n-propanol, or an ether, e.g., tetrahydrofuran or dioxane, and water.

The reaction temperature and the reaction time vary depending on the starting material, solvent and reagent used, but the reaction is usually carried out at from 0° C. to 150° C. for from one to 10 hours in order to inhibit side reactions.

After the reaction, the desired compound is collected from the reaction mixture according to conventional methods. For example, after completion of the reaction, the desired compound is obtained by evaporating the filtrate. The thus obtained desired compound can be further purified, if necessary, by conventional methods, for example, recrystallization, reprecipitation or chromatography.

(Reaction G-2b)

The reaction is carried out according to conventional methods in peptide synthesis, for example, by an activated ester method, a mixed acid anhydride method, or a condensation method.

1) The activated ester method is carried out by reacting the compound with an active esterifying agent in an inert solvent to prepare an active ester and reacting it with N,O-dimethylhydroxylamine in an inert solvent.

The active esterifying agent employed here may be an N-hydroxy compound such as N-hydroxysuccinimide, 1-hydroxybenzotriazole or N-hydroxy-5-norbornene-2,3-dicarboximide; or a disulfide compound such as dipyridyl disulfide. Furthermore, the active esterification reaction is preferably carried out in the presence of a condensing agent such as dicyclohexylcarbodiimide, carbonyldiimidazole or triphenylphosphine.

The solvent to be employed in both reactions is not particularly limited so long as it does not inhibit the reaction and dissolves the starting material to some extent, and may be a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; a nitrile such as acetonitrile or isobutyronitrile; or an amide such as formamide, dimethylformamide, dimethylacetamide, hexamethylphosphoramide (HMPA) or hexamethylphosphorus triamide (HMPT), and is preferably an ether (particularly tetrahydrofuran), a nitrile (particularly acetonitrile) or an amide (particularly dimethylformamide).

The reaction temperature varies depending on the starting compound, reagent, etc., but it is usually from −20° C. to 100° C. for the active esterification reaction, preferably from 0° C. to 50° C. For the reaction with the active ester compound, it is from −20° C. to 100° C., preferably from 0° C. to 50° C.

The reaction time varies depending on the starting compound, reagent and reaction temperature, but it is usually from 30 minutes to 24 hours in both reactions, preferably from 1 to 12 hours.

After the reaction, the desired compound of the present reaction is collected from the reaction mixture according to conventional methods. For example, after completion of the reaction, the desired compound is obtained by evaporating the solvent, or pouring water onto the residue from which the solvent has been evaporated, adding a solvent immiscible with water (for example, benzene, ether, ethyl acetate, etc.) to extract the desired compound, washing the extracted organic layer with water, drying with anhydrous magnesium sulfate or the like and evaporating the solvent. The thus obtained desired compound can be further purified, if necessary, by conventional methods, for example, recrystallization, reprecipitation or chromatography.

2) Next, the mixed acid anhydride method is carried out by reacting the compound with a mixed acid anhydride forming agent in the presence or absence of a base (preferably in the presence of a base) in an inert solvent to prepare a mixed acid anhydride, and reacting the mixed acid anhydride with N,O-dimethylhydroxylamine in an inert solvent.

The mixed acid anhydride forming agent employed here may be an oxalyl halide such as oxalyl chloride; a chloroformic acid C1–C5 ester such as ethyl chloroformate or isobutyl chloroformate; a C1–C5 alkanoyl halide such as pivaloyl chloride; or a C1–C4 alkyl or di-C6–C14 arylcyanophosphoric acid such as diethylcyanophosphoric acid or diphenylcyanophosphoric acid, and is preferably an oxalyl halide (particularly oxalyl chloride).

The reaction is carried out in the presence or absence of a base, but it is preferably carried out in the presence of a base. The base employed here may be an alkali metal carbonate such as sodium carbonate, potassium carbonate or lithium carbonate; or an organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO), or 1,8-diazabicyclo[5.4.0]undec-7-ene (DBU), and is preferably an organic amine (particularly triethylamine).

The reaction to prepare the mixed acid anhydride is preferably carried out in the presence of a solvent. The solvent to be employed here is not particularly limited so long as it dissolves the starting material to some extent, and may be a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; or an amide such as formamide, dimethylformamide, dimethylacetamide, hexamethylphosphoramide (HMPA), or hexamethylphosphorus triamide (HMPT), and is preferably a halogenated hydrocarbon (particularly dichloromethane).

The reaction temperature for the reaction to prepare the mixed acid anhydride varies depending on the starting compound, reagent, etc., but it is usually from −50° C. to 100° C., preferably from −10° C. to 50° C.

The reaction time for the reaction to prepare the mixed acid anhydride varies depending on the starting compound, reagent and reaction temperature, but it is usually from 5 minutes to 20 hours, preferably from 10 minutes to 10 hours.

Next, the solvent to be employed for the reaction of the mixed acid anhydride and N,O-dimethylhydroxylamine is not particularly limited so long as it does not inhibit the reaction and dissolves the starting material to some extent, and may be an ether such as diethyl ether, diisopropyl ether, tetrahydrofuran, dioxane, dimethoxyethane or diethylene glycol dimethyl ether; or an amide such as formamide, dimethylformamide, dimethylacetamide, hexamethylphosphoramide (HMPA) or hexamethylphosphorus triamide (HMPT), and is preferably an amide (particularly dimethylformamide).

The reaction temperature for the reaction with the mixed acid anhydride varies depending on the starting compound, reagent, etc., but it is usually from −30° C. to 100° C., preferably from 0° C. to 80° C.

The reaction time for the reaction with the mixed acid anhydride varies depending on the starting compound, reagent and reaction temperature, but it is usually from 5 minutes to 24 hours, preferably from 10 minutes to 12 hours.

After the reaction, the desired compound of the present reaction is collected from the reaction mixture according to conventional methods. For example, after completion of the reaction, the desired compound is obtained by evaporating the solvent, or pouring water onto the residue from which the solvent has been evaporated, adding a solvent immiscible with water (for example, benzene, ether, ethyl acetate, etc.) to extract the desired compound, washing the extracted organic layer with water, drying with anhydrous magnesium sulfate or the like and evaporating the solvent. The thus obtained desired compound can be further purified, if necessary, by conventional methods, for example, recrystallization, reprecipitation or chromatography.

3) Next, the condensation method is carried out by reacting the compound with N,O-dimethylhydroxylamine in an inert solvent using a condensing agent and a base.

The condensing agent employed here may be an azodicarboxylic acid di-lower alkyl ester-triphenylphosphine such as diethyl azodicarboxylate-triphenylphosphine; an N,N'-dicycloalkylcarbodiimide such as N,N'-dicyclohexylcarbodiimide (DCC); a 2-halo-1-lower alkyl pyridinium halide such as 2-chloro-1-methylpyridinium iodide; a diarylphosphorylazide such as diphenylphosphorylazide (DPPA); a chloroformate such as ethyl chloroformate or isobutyl chloroformate; a phosphoryl chloride such as diethyl phosphoryl chloride; an imidazole derivative such as N,N'-carbodiimidazole (CDI); a carbodiimide derivative such as 1-ethyl-3-(3-diethylaminopropyl)carbodiimide hydrochloride (EDAPC); or a sulfonyl chloride derivative such as 2,4,6-triisopropylbenzenesulfonyl chloride, and is preferably DDC, CDI, 2-chloro-1-methylpyridinium iodide, isobutyl chloroformate or diethylphosphoryl chloride.

The base employed here may be an organic base such as triethylamine, tributylamine, diisopropylethylamine, N-methylmorpholine, pyridine, 4-(N,N-dimethylamino)pyridine, 4-pyrrolidinopyridine, N,N-dimethylaniline, N,N-diethylaniline, 1,5-diazabicyclo[4.3.0]non-5-ene, 1,4-diazabicyclo[2.2.2]octane (DABCO), or 1,8-diazabicyclo[5.4.0]undec-7-ene (DBU), and is preferably triethylamine, diisopropylethylamine, pyridine or 4-pyrrolidinopyridine.

The solvent to be employed here is not particularly limited so long as it does not inhibit the reaction and dissolves the starting material to some extent, and may preferably be an aromatic hydrocarbon such as benzene, toluene or xylene; a halogenated hydrocarbon such as dichloromethane, chloroform or dichloroethane; an ester such as ethyl acetate or propyl acetate; an ether such as diethyl ether, tetrahydrofuran, dioxane, dimethoxyethane or diethylene glycol dimethyl ether; a ketone such as acetone or methyl ethyl ketone; a nitro compound such as nitromethane; a nitrile such as acetonitrile or isobutyronitrile; or an amide such as dimethylformamide, dimethylacetamide or hexamethylphosphoric triamide, and is more preferably a nitrile (particularly acetonitrile), an aromatic hydrocarbon (particularly benzene), a halogenated hydrocarbon (particularly dichloromethane), or an ether (particularly tetrahydrofuran).

The reaction temperature varies depending on the solvent, starting material, reagent, etc., but it is usually from 0° C. to 150° C., preferably from 25° C. to 120° C.

The reaction time varies depending on the solvent, starting material, reagent, reaction temperature, etc., but it is usually from 10 minutes to 48 hours, preferably from one to 24 hours.

After the reaction, the desired compound of the present reaction is collected from the reaction mixture according to conventional methods. For example, the desired compound is obtained by adding an organic solvent immiscible with water such as ethyl acetate to the reaction mixture, washing with water, separating the organic layer containing the desired compound, drying with anhydrous magnesium sulfate or the like and evaporating the solvent. The thus obtained desired compound can be further purified, if necessary, according to conventional methods, for example, recrystallization, reprecipitation or chromatography.

(Step G-3)

This step is to prepare the compound (VI) by reacting the carbanion obtained by treatment of the compound (XVIII) with a base, with the compound (XVII) obtained in step G-2.

When the compound (XVIII) is treated with a base, the base employed may be an alkyl lithium such as methyl lithium, butyl lithium, s-butyl lithium or t-butyl lithium, and is preferably butyl lithium, s-butyl lithium or t-butyl lithium, more preferably butyl lithium.

The solvent to be employed here is not particularly limited so long as it does not inhibit the reaction and dissolves the starting material to some extent, and may be an aliphatic or alicyclic hydrocarbon such as hexane or cyclohexane; an aromatic hydrocarbon such as benzene, toluene or xylene; or an ether such as diethyl ether, tetrahydrofuran or dioxane, and is preferably an aromatic hydrocarbon or an ether, more preferably an ether (particularly tetrahydrofuran).

The reaction temperature varies depending on the solvent, starting compound, reagent, etc., but it is usually from −78° C. to 0° C., preferably from −78° C. to −20° C.

The reaction time varies depending on the solvent, starting compound, reagent, reaction temperature, etc. but it is usually from 10 minutes to 24 hours, preferably from 10 minutes to 6 hours.

After the reaction, the desired compound of the present reaction is collected from the reaction mixture according to conventional methods. For example, after completion of the reaction, the desired compound is obtained by pouring the reaction mixture into an aqueous solution such as a cooled saturated aqueous ammonium chloride solution, adding a solvent immiscible with water (for example, benzene, ether, ethyl acetate, etc.) to extract the desired compound, washing the extracted organic layer with water, drying with anhydrous magnesium sulfate or the like and evaporating the solvent. The thus obtained desired compound can be further purified, if necessary, by conventional methods, for example, recrystallization, reprecipitation or chromatography.

(Process H)

(Step H-1)

This step is one in which after an aldol condensation reaction is carried out on the compound (VIII), which is publicly known or easily obtainable from publicly known compounds (Reaction H-1a), the ester is reduced (Reaction H-1b) and the produced primary alcohol is protected, if necessary (Reaction H-1c).

(Reaction H-1a)

The present reaction is carried out by firstly treating the reagent with a base to prepare an organic anionic reagent and adding the compound (VIII) thereto.

The solvent to be employed here may be an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; or an ether such as diethyl ether, diisopropyl ether, tetrahydrofuran, dioxane, dimethoxyethane or diethylene glycol dimethyl ether, and is preferably an ether (particularly tetrahydrofuran).

The reagent employed in the present reaction is not particularly limited so long as it can be used for aldol condensations, but it is preferably ethyl acetate.

The base employed here may be an alkali metal hydride such as lithium hydride, sodium hydride or potassium hydride; an alkali metal hydroxide such as sodium hydroxide, potassium hydroxide, barium hydroxide or lithium hydroxide; or an organometal base such as butyl lithium, lithium diisopropylamide or lithium bis(trimethylsilyl)amide, and is preferably an organometal base (particularly lithium bis(trimethylsilyl)amide).

The reaction temperature varies depending on the solvent, starting compound, reagent, etc., but it is usually from −100° C. to 50° C., preferably from −78° C. to 0° C.

The reaction time varies depending on the solvent, starting compound, reagent, reaction temperature, etc. but it is usually from 5 minutes to 12 hours, preferably from 30 minutes to 10 hours.

After the reaction, the desired compound of the present reaction is collected from the reaction mixture according to conventional methods. For example, the desired compound is obtained by collecting the desired compound precipitated in the reaction solution by filtration, or appropriately neutralizing the reaction solution, evaporating the solvent, pouring water into the reaction solution, adding a solvent immiscible with water (for example, benzene, ether, ethyl acetate, etc.) to carry out an extraction, washing the organic layer containing the desired compound with water, drying with anhydrous magnesium sulfate or the like and evaporating the solvent. The thus obtained desired compound can be further purified, if necessary, according to conventional methods, for example, recrystallization, reprecipitation or chromatography.

(Reaction H-1b)

This reaction is carried out similarly to the reduction reaction of the ester in Step D-3.

(Reaction H-1c)

This reaction is carried out similarly to the protection reaction of the hydroxyl group in Step D-2.

In the present step, the desired $R^b$ can be obtained by carrying out a similar reaction to (α) in (Reaction A-2d), if necessary.

(Step H-2)

This step is to prepare the compound (II) by reacting the compound (IX) with the compound (XIV) obtained in Step H-1 (Reaction H-2a); and then carrying out similar reactions (Reaction H-2b) to those in (Reaction D-3a) to (Reaction D-3d).

(Reaction H-2a)

This step is accomplished by carrying a reaction similar to <Method 1> of (Reaction A-1a), or carrying out a reaction similar to (β) of <Method 1> of (Reaction A-1a), after carrying out a reaction similar to (Reaction C-1b).

(Reaction H-2b)

This reaction is carried out similarly to (Reaction D-3a) to (Reaction D-3d).

(Process I)

(Step I-1)

This step is to prepare the compound (IIa) by carrying out an acylation reaction (Reaction I-1a) on the compound (XV), which is publicly known or easily obtainable from publicly known compounds, followed by carrying out a Bischler-Napieralski reaction (Reaction I-1b), and by reducing the thus obtained compound (Reaction I-1c).

(Reaction I-1a)

The solvent to be employed here may be an aliphatic hydrocarbon such as hexane, heptane, ligroin or petroleum ether; an aromatic hydrocarbon such as benzene, toluene or xylene; a halogenated hydrocarbon such as methylene chloride, chloroform, carbon tetrachloride, dichloroethane, chlorobenzene or dichlorobenzene; an ether such as diethyl ether, diisopropyl ether, tetrahydrofuran, dioxane, dimethoxy ethane or diethylene glycol dimethyl ether; an amide such as formamide, N,N-dimethylformamide, N,N-dimethylacetamide, N-methyl-2-pyrrolidone, N-methylpyrrolidinone or hexamethylphosphoric triamide; or a sulfoxide such as dimethyl sulfoxide or sulfolane, and is preferably an amide (particularly dimethylformamide) or a halogenated hydrocarbon (particularly dichloromethane).

The acylating agent employed here is not particularly limited so long as the produced amide becomes an amide appropriate for the Bischler-Napieralski reaction, and is preferably ethylmalonyl chloride.

The base employed here may be an alkali metal carbonate such as sodium carbonate, potassium carbonate or lithium carbonate; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene(DBN), 1,4-diazabicylo[2.2.2]octane (DABCO) or 1,8-diazabicyclo[5.4.0]undec-7-ene (DBU), and is preferably potassium carbonate or triethylamine.

The reaction temperature varies depending on the solvent, starting compound, reagent, etc., but it is usually from −100° C. to 50° C., preferably from −78° C. to 0° C.

The reaction time varies depending on the solvent, starting compound, reagent, the reaction temperature, etc., but it is usually from 5 minutes to 12 hours, preferably from 30 minutes to 10 hours.

After the reaction, the desired compound of the present reaction is collected from the reaction mixture according to conventional methods. For example, the desired compound is obtained by collecting the desired compound precipitated in the reaction solution by filtration, or appropriately neutralizing the reaction solution, evaporating the solvent, pouring water into the reaction solution, adding a solvent immiscible with water (for example, benzene, ether, ethyl acetate, etc.) to perform an extraction, washing the organic layer containing the desired compound with water, drying with anhydrous magnesium sulfate or the like and evaporating the solvent. The thus obtained desired compound can be further purified, if necessary, according to conventional methods, for example, recrystallization, reprecipitation or chromatography.

(Reaction I-1b)

This reaction is carried out in phosphorus oxychloride.

The reaction temperature varies depending on the solvent, starting compound, reagent, etc., but it is usually from 25° C. to 120° C., preferably from 50° C. to 100° C.

The reaction time varies depending on the solvent, starting compound, reagent, reaction temperature, etc., but it is usually from 5 minutes to 48 hours, preferably from one hour to 12 hours.

After the reaction, the desired compound of the present reaction is collected from the reaction mixture according to conventional methods. For example the desired compound may be obtained by filtration of the desired compound precipitated in the reaction solution or by evaporation of the resulting organic layer after appropriately neutralizing the reaction solution, filtering, evaporating the solvent, pouring water into the reaction solution, adding a solvent immiscible with water (for example, benzene, ether, ethyl acetate, etc.) to perform an extraction, washing the organic layer containing the desired compound with water and then drying with anhydrous magnesium sulfate or the like. The thus obtained desired compound can be further purified, if necessary, by conventional methods, for example, recrystallization, reprecipitation or chromatography.

(Reaction I-1c)

In this reaction, after a similar reaction to the catalytic reduction in (Reaction A-2a) is carried out, a reaction is carried out similar to (Step D-3).

(Process J)

(Step J-1)

This step is to prepare the compound (IIa) in optically active form by introducing a chiral auxiliary group to the compound (XVI), which is publicly known or easily obtainable from publicly known compounds (Reaction J-1a), introducing a side chain thereto (Reaction J-1b), and removing the chiral auxiliary group (Reaction J-1c).

(Reaction J-1a)

The solvent to be employed here may be an aromatic hydrocarbon such as benzene, toluene or xylene; or an ether such as diethyl ether, diisopropyl ether, tetrahydrofuran, dioxane, dimethoxyethane or diethylene glycol dimethyl ether, and is preferably an aromatic hydrocarbon (particularly toluene).

The group to introduce the chiral auxiliary group employed here is not particularly limited so long as it is usually used, and may be N,N-dimethyl-N'-[(S/R)-2-(3,3-dimethyl-1- methoxybutyl)]formamidine, N,N-dimethyl-N'-[(S/R)-2-(3-methyl-1-methoxybutyl)]formamidine or N,N-dimethyl-N'-[(S/R)-2-(3-methyl-1-methoxypentyl)]formamidine, and is preferably N,N-dimethyl-N'-[(S)-2-(3,3-dimethyl-1-methoxybutyl)]formamidine or N,N-dimethyl-N'-[(R)-2-(3,3-dimethyl-1-methoxybutyl)]formamidine.

The reaction temperature varies depending on the solvent, starting compound, reagent, etc., but it is usually from 50° C. to 200° C., preferably from 100° C. to 150° C.

The reaction time varies depending on the solvent, starting compound, reagent, reaction temperature, etc., but it is usually from one hour to 72 hours, preferably from 12 hours to 48 hours.

After the reaction, the desired compound of the present reaction is collected from the reaction mixture according to conventional methods. For example, after completion of the reaction, the desired compound is obtained by pouring the reaction mixture into an aqueous solution such as a cooled saturated aqueous ammonium chloride solution, adding a solvent immiscible with water (for example, benzene, ether, ethyl acetate, etc.) to extract the desired compound, washing the extracted organic layer with water, drying with anhydrous magnesium sulfate or the like, and evaporating the solvent. The thus obtained desired compound can be further purified, if necessary, according to conventional methods, for example, recrystallization, reprecipitation or chromatography.

(Reaction J-1b)

The solvent to be employed here may be an aliphatic hydrocarbon such as hexane, heptane, ligroin or petroleum ether; an aromatic hydrocarbon such as benzene, toluene or xylene; or an ether such as diethyl ether, diisopropyl ether, tetrahydrofuran, dioxane, dimethoxyethane or diethylene glycol dimethyl ether, and is preferably an ether (particularly the tetrahydrofuran).

The reagent employed here is a 2-halogeno-1-hydroxyethyl silyl ether, preferably 2-bromo-1-hydroxyethyl-t-butyldimethylsilyl ether.

The base employed here may be an organometal base such as butyl lithium, lithium diisopropylamide or lithium bis(trimethylsilyl)amide, and is preferably butyl lithium.

The reaction temperature varies depending on the solvent, starting compound, reagent, etc., but it is usually from −90° C. to 0° C., preferably from −78° C. to −20° C.

The reaction time varies depending on the solvent, starting compound, reagent, reaction temperature, etc., but it is usually from 5 minutes to 12 hours, preferably from 30 minutes to 3 hours.

After the reaction, the desired compound of the present reaction is collected from the reaction mixture according to conventional methods. For example, the desired compound is obtained by adding methanol and then evaporating the solvent. The thus obtained desired compound can be further purified, if necessary, according to conventional methods, for example, recrystallization, reprecipitation or chromatography.

(Reaction J-1c)

The solvent to be employed here may be an ether such as diethyl ether, diisopropyl ether, tetrahydrofuran, dioxane, dimethoxyethane or diethylene glycol dimethyl ether; or an alcohol such as methanol, ethanol, n-propanol, isopropanol, n-butanol, isobutanol, t-butanol, isoamyl alcohol, diethylene glycol, glycerine, octanol, cyclohexanol or methyl cellosolve, and is preferably an alcohol (particularly ethanol).

The acid to be employed here is not particularly limited so long as it is used in usual reactions as an acid catalyst, and may preferably be an organic acid such as acetic acid, formic acid, oxalic acid, methanesulfonic acid, p-toluenesulfonic acid, camphorsulfonic acid, trifluoroacetic acid or trifluoromethanesulfonic acid, and is preferably acetic acid.

The reagent employed here is hydrazine, preferably hydrazine monohydrate.

The reaction temperature varies depending on the solvent, starting compound, reagent, etc., but it is usually from −20° C. to 50° C., preferably from 0° C. to 25° C.

The reaction time varies depending on the solvent, starting compound, reagent, reaction temperature, etc., but it is usually from 30 minutes to 24 hours, preferably from one hour to 12 hours.

After the reaction, the desired compound of the present reaction is collected from the reaction mixture according to conventional methods. For example, after completion of the reaction, the desired compound is obtained by pouring the reaction mixture into an aqueous solution such as a cooled saturated aqueous ammonium chloride solution, adding a solvent immiscible with water (for example, benzene, ether, ethyl acetate, etc.) to extract the desired compound, washing the extracted organic layer with water, drying with anhydrous magnesium sulfate or the like and evaporating the solvent. The thus obtained desired compound can be further purified, if necessary, according to conventional methods, for example, recrystallization, reprecipitation or chromatography.

The optical purity of the desired compound can be measured by conventional methods, for example, analysis by chiral HPLC or the like.

The compounds of the present invention (I) or pharmacologically acceptable salts thereof exert both acetylcholinesterase inhibitory activity and serotonin re-uptake inhibitory activity. In addition, the compounds of the present invention (I) exhibit excellent pharmacodynamics, such as absorption, distribution, and elimination half-life from the blood stream, and their toxicity to organs such as the liver and kidney are low. Thus the compounds of the present invention (I) are useful as remedies and particularly they are useful as prophylactic or therapeutic agents for various neurological disorders.

In cases where the compounds of the present invention are used as prophylactic or therapeutic agents for the disorders described above, the compounds expressed by the general formula (I) described above or pharmacologically acceptable salts or esters thereof may be orally administered in formulations such as tablets, capsules, granules, powders, or syrups, or non-orally administered in formulations such as injections, suppositories, patches, or formulations for external application, by optionally mixing with a pharmacologically acceptable diluent and excipient, i.e., carrier, etc.

Preparations are prepared by conventionally known methods using additives such as excipients (for instance, organic excipients including sugar derivatives such as lactose, sucrose, glucose, mannitol and sorbitol; starch derivatives such as corn starch, potato starch, a-starch and dextrin; cellulose derivatives such as crystalline cellulose; gum Arabic; dextran; pullulan; and inorganic excipients including silicate derivatives such as light anhydrous silicic acid, synthetic aluminum silicate, calcium silicate and magnesium aluminometasilicate; phosphates such as calcium hydrogenphosphate; carbonates such as calcium carbonate; and sulfates such as calcium sulfate), lubricants (for instance, stearic acid, metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL-leucine; laurylsulphates such as sodium lauryl sulfate and magnesium lauryl sulfate; silicates such as silicic anhydride and silicic hydrate; and starch derivatives described above can be listed), binders (for instance, hydroxypropylcellulose, hydroxypropylmethylcellulose, polyvinylpyrrolidone, Macrogol and similar excipients, described above), disintegrants (for instance, cellulose derivatives such as low-substituted hydroxypropylcellulose, carboxymethylcellulose, calcium carboxymethylcellulose and internally crosslinked-sodium carboxymethylcellulose; chemically modified starch/cellulose derivatives such as carboxymethylstarch, sodium carboxymethylstarch, crosslinked polyvinylpyrrolidone;), emulsifiers (for instance, colloidal clay such as bentonite and veegum; metal hydrates such as magnesium hydroxide and aluminum hydroxide; anionic surfactants such as sodium lauryl sulfate and calcium stearate; cationic surfactants such as benzalkonium chloride; and non-ionic surfactants such as polyoxyethylenealkyl ethers, polyoxyethylene sorbitan fatty acid esters, and sucrose esters of fatty acids), stabilizers (for instance, para-oxy benzoates such as methylparaben and propylparaben; alcohols such as chlorobutanol, benzylalcohol and phenylethylalcohol; benzalkonium chloride; phenols such as phenol and cresol; thimerosal; dehydroacetic acid; and sorbic acid), flavors (for instance, conventionally employed sweeteners, acidifiers and flavors), and diluents, etc.

The dosage varies depending on the symptoms, age, etc. of the patient (human). For example, in the case of oral administration, it is desirable to administer 1 mg (preferably 30 mg) as a lower limit and 2000 mg (preferably 1500 mg) as an upper limit per one time for an adult (human) and one to six times a day depending on the symptoms. In the case of intravenous administration, it is desirable to administer 0.5 mg (preferably 5 mg) as a lower limit and 500 mg (preferably 250 mg) as an upper limit per one time for an adult (human) and one to six times a day depending on the symptoms.

The above dosage ranges are based on a human adult. The dosage range for mammals who differ in weight from a human adult would be proportional to the respective average weight of a human adult and a non-human mammal.

BEST MODE FOR CARRYING OUT THE INVENTION

EXAMPLE 1

3-[1-Methylamino-3-[(4-trifluoromethyl)phenyl] propyl]phenyl dimethylcarbamate hydrochloride (Exemplification compound number 2-14)

(a) 3-Acetylphenyl dimethylcarbamate

Tetrahydrofuran (100 ml) was added to sodium hydride (1.94 g, 45 mmol) under an atmosphere of nitrogen. To the suspension was added a tetrahydrofuran solution of 1-(3-hydroxyphenyl)ethanone (5.05 g, 37 mmol) in an ice bath. After stirring the mixture for 15 minutes dimethylcarbamyl chloride (1.7 ml, 19 mmol) was added dropwise into the mixture and the resulting mixture was stirred at room temperature for 4 hours. Saturated aqueous sodium chloride solution was added to the reaction mixture. The resulting mixture was extracted with ethyl acetate. The organic layer was washed with water and saturated sodium chloride solution, dried over anhydrous magnesium sulfate and concentrated under reduced pressure. The residue was purified by chromatography on a silica gel column to afford the desired compound (6.54 g).

$^1$H-NMR(400 MHz,CDCl$_3$) δ ppm: 2.60 (3H,s), 3.03 (3H, s), 3.12 (3H,s), 7.34 (1H,d,J=7.9 Hz), 7.46 (1H,t,J=7.9 Hz), 7.70 (1H,s), 7.79 (1H,d,J=7.9 Hz).

(b) 3-[3-(4-Trifluoromethyl)phenyl]acryloyl]phenyl dimethylcarbamate

3-Acetylphenyl dimethylcarbamate (1.30 g, 6.3 mmol) obtained from Example 1a and 4-(trifluoromethyl)benzaldehyde (1.25 g, 6.9 mmol) were dissolved in ethanol (35 ml). To the ethanol solution was added potassium hydroxide (42 mg, 0.63 mmol) and the resulting mixture was stirred at room temperature for 3 hours. Water was added to the reaction mixture and the aqueous layer was extracted with ether. The organic layer was dried over anhydrous magnesium sulfate and concentrated under reduced pressure. The residue was purified by chromatography on a silica gel column to afford the desired compound (1.74 g).

$^1$H-NMR(400 MHz,CDCl$_3$) δ: 3.04 (3H,s), 3.14 (3H,s) 7.38 (1H,dd,J=8.1 Hz,1.4 Hz), 7.49–7.57 (2H,m), 7.68 (2H, d,J=8.5 Hz), 7.73–7.77 (3H,m), 7.82 (1H,d,J=13.8 Hz), 7.86 (1H,d,J=7.2 Hz).

(c) 3-[3-[(4-Trifluoromethyl)phenyl]propionyl]phenyl dimethylcarbamate

3-[3-(4-Trifluoromethyl)phenyl]acryloyl]phenyl dimethylcarbamate (1.71 g, 5.2 mmol) obtained from Example 1b was dissolved in ethyl acetate (50 ml). To the solution was added 5% palladium on charcoal (40 mg) and the resulting mixture was stirred under an atmosphere of hydrogen at room temperature for 2 hours. The catalyst was removed by filtration and the filtrate was concentrated under reduced pressure to afford the crude desired product which was used in next step reaction without purification.

(d) 3-[1-Hydroxy-3-[(4-trifluoromethyl)phenyl]propyl]phenyl dimethylcarbamate

The crude product of 3-[3-[(4-trifluoromethyl)phenyl]propionyl]phenyl dimethylcarbamate obtained from Example 1c was dissolved in methanol (60 ml). To the solution was slowly added sodium borohydride (216 mg, 5.7 mmol) in an ice bath and the resulting mixture was stirred for 1 hour. Water was added to the reaction mixture and the methanol was evaporated under reduced pressure and the aqueous residue was extracted with ethyl acetate. The organic layer was washed with water and saturated aqueous sodium chloride solution, dried over anhydrous magnesium sulfate and concentrated under reduced pressure. The residue was purified by chromatography on a silica gel column to afford the desired compound (1.63 g).

$^1$H-NMR(400 MHz,CDCl$_3$) δ ppm: 1.96–2.15 (2H,m), 2.62–2.84 (2H,m), 3.00 (3H,s), 3.10 (3H,s), 4.65 (1H,dd, J=7.5 Hz,5.4 Hz), 7.02 (1H,d,J=8.4 Hz), 7.11 (1H,s), 7.15 (1H,d,J=7.7 Hz), 7.26–7.35 (3H,m), 7.52 (1H,d,J=8.1 Hz).

(e) 3-[1-Bromo-3-[(4-trifluoromethyl)phenyl]propyl]phenyl dimethylcarbamate

3-[1-Hydroxy-3-[(4-trifluoromethyl)phenyl]propyl]phenyl dimethylcarbamate (372 mg, 1.1 mmol) obtained from Example 1d and triphenylphosphine (349 mg, 1.3 mmol) were dissolved in dichloromethane under an atmosphere of nitrogen. To the solution was added carbon tetrabromide (441 mg, 1.3 mmol) in an ice bath and the mixture was stirred for 20 minutes. The reaction mixture was concentrated under reduced pressure to afford the crude desired product which was used in next step reaction without purification.

(f) 3-[1-Methylamino-3-[(4-trifluoromethyl)phenyl]propyl] phenyl dimethylcarbamate hydrochloride A 40% ethylamine solution in methanol (5 ml) was added to the crude product of 3-[1-bromo-3-[(4-trifluoromethyl) phenyl]propyl]phenyl dimethylcarbamate obtained from Example 1d and the mixture was stirred overnight. The reaction mixture was concentrated under reduced pressure and the residue was partitioned between saturated aqueous sodium hydrogencarbonate solution and ethyl acetate. The organic layer was washed with water and saturated aqueous sodium chloride solution, dried over anhydrous magnesium sulfate and concentrated under reduced pressure. The residue was purified by chromatography on a silica gel column to give 3-[1-methylamino-3-[(4-trifluoromethyl)phenyl]propyl] phenyl dimethylcarbamate (209 mg). The product was treated with 1N hydrogen chloride/ethyl acetate solution to afford the title compound as an amorphous solid.

$^1$H-NMR(500 MHz,CDCl$_3$) δ ppm: 2.39 (3H,s), 2.51–2.61 (3H,m), 2.78–2.81 (1H,m), 3.02 (3H,s), 3.12 (3H,s), 3.85 (1H,br s), 7.19–7.24 (4H,m), 7.45–7.49 (4H,m), 9.90 (1H,br s), 10.30 (1H,br s).

EXAMPLE 2

3-[3-(4-Methoxyphenyl)-1-methylaminopropyl]phenyl dimethylcarbamate hydrochloride (Exemplification compound number 2-15)

4-Methoxybenzaldehyde was treated using similar procedures to those described in Example 1 to afford the title compound as an amorphous solid.

$^1$H-NMR(400 MHz,CDCl$_3$) δ ppm: 2.39 (3H,s), 2.34–2.52 (3H,m), 2.70–2.76 (1H,m), 3.02 (3H,s), 3.12 (3H,s), 3.74 (3H,s), 3.84 (1H,br s), 6.77 (2H,d,J=8.6 Hz), 7.03 (2H,d, J=8.6 Hz), 7.21 (1H,dd,J=6.4 Hz,2.5 Hz), 7.23 (1H,s), 7.43–7.48 (2H,m), 9.83 (1H,br s), 10.20 (1H,br s).

EXAMPLE 3

3-[1-Dimethylamino-3-(4-methoxyphenyl)propyl] phenyl dimethylcarbamate hydrochloride (Exemplification compound number 2-16)

Formic acid (10 ml) and 35% aqueous formaldehyde solution (10 ml) were added to 3-[3-(4-methoxyphenyl)-1-methylaminopropyl]phenyl dimethylcarbamate (500 mg, 1.4 mmol) obtained from Example 2 and the mixture was stirred at 90° C. for 2 hours. After cooling the reaction mixture to room temperature the mixture was neutralized with 1N aqueous sodium hydroxide solution. The neutralized mixture was extracted with ether and the organic layer was dried over anhydrous sodium sulfate and concentrated under reduced pressure. The residue was purified by chromatography on a silica gel column using ethyl acetate:methanol=80:20 as the eluent to give 3-[1-dimethylamino-3-(4-methoxyphenyl)propyl]phenyl dimethylcarbamate. The product was treated with 1N hydrogen chloride/ethyl acetate solution to afford the title compound as an amorphous solid.

$^1$H-NMR(400 MHz,CDCl$_3$) δ ppm: 2.33–2.39 (1H,m), 2.44–2.57 (2H,m), 2.60 (3H,br s), 2.66 (3H,br s), 2.74–2.81 (1H,m), 3.03 (3H,s), 3.14 (3H,s), 3.78 (3H,s), 3.95–3.99 (1H, m), 6.81 (2H,d,J=8.6 Hz), 7.02 (2H,d,J=8.6 Hz), 7.21 (1H,s), 7.25–7.31 (2H,m), 7.50 (2H,t,J=7.9 Hz).

EXAMPLE 4

3-[3-(3,4-Dimethoxyphenyl)-1-methylaminopropyl] phenyl dimethylcarbamate hydrochloride (Exemplification compound number 2-17)

3,4-Dimethoxybenzaldehyde was treated using similar procedures to those described in Example 1 to afford the title compound as an amorphous solid.

$^1$H-NMR(400 MHz,CDCl$_3$) δ ppm: 2.39 (3H,s), 2.33–2.60 (3H,m), 2.78–2.83 (1H,m), 3.01 (3H,s), 3.11 (3H,s), 3.82 (3H,s), 3.83 (1H,br s), 3.85 (3H,s), 6.65–6.76 (3H,m), 7.20–7.22 (2H,m), 7.45–7.47 (2H,m), 9.88 (1H,br s), 10.20 (1H,br s)

EXAMPLE 5

3-(3-Benzo[1,3]dioxol-5-yl-1-methylaminopropyl) phenyl dimethylcarbamate hydrochloride (Exemplification compound number 2-18)

Benzo[1,3]dioxol-5-carboaldehyde was treated using similar procedures to those described in Example 1 to afford the title compound as an amorphous solid.

$^1$H-NMR(400 MHz,CDCl$_3$) δ ppm: 2.40 (3H,s), 2.32–2.50 (3H,m), 2.67–2.71 (1H,m), 3.06 (3H,s), 3.12 (3H,s), 3.87 (1H,br s), 5.87 (2H,s), 6.55 (1H,d,J=7.9 Hz), 6.61 (1H,s), 6.66 (1H,d,J=7.9 Hz), 7.19–7.25 (1H,m), 7.29 (1H,s), 7.44–7.48 (2H,m), 9.84 (1H,br s), 10.18 (1H,br s).

EXAMPLE 6

3-[3-(4-Methoxyphenyl)-1-methylaminopropyl]phenyl ethylcarbamate hydrochloride (Exemplification compound number 2-3)

(a) t-Butyl N-[1-[(3-dimethylcarbamoyloxy)phenyl]-3-(4-methoxyphenyl)propyl]-N-methylcarbamate 3-[3-(4-Methoxyphenyl)-1-methylaminopropyl]phenyl dimethylcarbamate (342 mg, 1.0 mmol) obtained from Example 2 was dissolved in tetrahydrofuran (5 ml) under an atmosphere of nitrogen and di-tert-butyl dicarbonate (262 mg, 1.2 mmol) was added to the solution. The mixture was stirred at room temperature overnight. After evaporation of the solvent of the reaction mixture under reduced pressure, the residue was purified by chromatography on a silica gel column using hexane:ethyl acetate=80:20 as the eluent to afford the desired compound (420 mg).

$^1$H-NMR(400 MHz,CDCl$_3$) δ ppm: 1.54 (9H,s), 2.11–2.26 (2H,m), 2.66 (5H,br s), 3.05 (3H,s), 3.14 (3H,s), 3.85 (3H,s), 5.26 (0.5H,br s), 5.55 (0.5H,br s), 6.89 (2H,d,J=8.6 Hz), 7.06–7.15 (2H,m), 7.18 (2H,d,J=8.6 Hz), 7.36 (1H,t,J=8.1 Hz).

(b) t-Butyl N-[1-(3-hydroxyphenyl)-3-(4-methoxyphenyl) propyl]-N-methylcarbamate t-Butyl N-[1-[(3-dimethylcarbamoyloxy)phenyl]-3-(4-methoxyphenyl)propyl]-N-methylcarbamate (300 mg, 0.68 mmol) obtained from Example 2a was dissolved in methanol (3 ml) and 1N aqueous lithium hydroxide solution (3 ml) was added to the solution. The mixture was stirred at room temperature for 3 hours. The reaction mixture was partitioned between water and ethyl acetate. The organic layer was washed with water and saturated aqueous sodium chloride solution, dried over magnesium sulfate and concentrated under reduced pressure. The residue was purified by chromatography on a silica gel column using hexane:ethyl acetate=80:20 as the eluent to afford the desired compound (245 mg).

$^1$H-NMR(400 MHz,CDCl$_3$) δ ppm: 1.50 (9H,s), 2.10–2.22 (2H,m), 2.64 (5H,br s), 3.80 (3H,s), 5.23 (0.5H,br s), 5.50 (0.5H,br s), 6.83 (2H,d,J=8.6 Hz), 7.01–7.12 (2H,m), 7.15 (2H,d,J=8.6 Hz), 7.31 (1H,t,J=8.0 Hz).

(c) t-Butyl N-[1-[(3-ethylcarbamoyloxy)phenyl]-3-(4-methoxyphenyl)propyl]-N-methylcarbamate t-Butyl N-[1-(3-hydroxyphenyl)-3-(4-methoxyphenyl)propyl]-N-methylcarbamate (250 mg, 0.67 mmol) obtained from Example 6b was dissolved in tetrahydrofuran (2 ml) under an atmosphere of nitrogen, and triethylamine (0.16 ml, 1.3 mmol) and ethyl isocyanate (0.11 ml, 1.3 mmol) were sequentially added to the solution. The resulting mixture was stirred at room temperature for 1 hour and concentrated under reduced pressure. The residue was purified by chromatography on a silica gel column using hexane:ethyl acetate=90:10 as the eluent to give the desired compound (198 mg).

$^1$H-NMR(400 MHz,CDCl$_3$) δ ppm: 1.21 (3H,t,J=7.3 Hz), 1.48 (9H,s), 2.06–2.19 (2H,m), 2.60 (5H,br s), 3.27–3.38 (2H,m), 3.79 (3H,s), 5.00 (1H,br s), 5.20 (0.5H,br s), 5.45 (0.5H,br s), 6.84 (2H,d,J=8.6 Hz), 7.02–7.11 (2H,m), 7.13 (2H,d,J=8.6 Hz), 7.30 (1H,t,J=8.0 Hz).

(d) 3-[3-(4-Methoxyphenyl)-1-methylaminopropyl]phenyl ethylcarbamate hydrochloride t-Butyl N-[1-[(3-ethylcarbamoyloxy)phenyl]-3-(4-methoxyphenyl)propyl]-N-methylcarbamate (198 mg, 0.45 mmol) obtained from Example 6c was dissolved in ethyl acetate (3 ml) and 4N hydrogen chloride/ethyl acetate solution (1 ml) was added to the solution. The mixture was stirred at room temperature overnight and concentrated under reduced pressure. The residue was partitioned between saturated aqueous sodium hydrogencarbonate solution and ethyl acetate. The organic layer was dried over anhydrous sodium sulfate and concentrated under reduced pressure. The residue was purified by chromatography on a silica gel column using ethyl acetate methanol=80:20 as the eluent to give 3-[3-(4-methoxyphenyl)-1-methylaminopropyl]phenyl ethylcarbamate (133 mg). The product was treated with 1N hydrogen chloride/ethyl acetate solution to afford the title compound as an amorphous solid.

$^1$H-NMR(400 MHz,CDCl$_3$) δ ppm: 1.23 (3H,t,J=7.3 Hz), 2.38 (3H,s), 2.33–2.52 (3H,m), 2.70–2.75 (1H,m), 3.28–3.36 (2H,m), 3.74 (3H,s), 3.84. (1H,br s), 5.16 (1H,t,J=5.7 Hz), 6.77 (2H,d,J=8.6 Hz), 7.02 (2H,d,J=8.6 Hz), 7.23 (1H,d, J=8.1 Hz), 7.26 (1H,s), 7.39–7.47 (2H,m), 9.80 (1H,br s), 10.17 (1H,br s).

EXAMPLE 7

3-[1-Methylamino-3-[(4-trifluoromethyl)phenoxy]propyl]phenyl dimethylcarbamate hydrochloride
(Exemplification compound number 2-85)

(a) 3-(3-Hydroxyphenyl)-3-methylaminopropionic acid

3-Hydroxybenzaldehyde (25.7 g, 210 mmol) was dissolved in ethanol (70 ml), and malonic acid (25.7 g) and the acetic acid salt of methylamine (38.6 g) were added to the solution. The resulting mixture was heated under reflux for 3 hours. Crystals which precipitated in the reaction mixture were collected by filtration to afford the desired compound (24.1 g).

$^1$H-NMR (400 MHz,DMSO-d$_6$) δ: 2.23(3H,s), 2.30(1H, dd,J=15.5,4.1 Hz), 2.42–2.48(1H,m), 3.89–3.92(1H,m), 6.70 (1H,dd,J=7.8,1.7 Hz), 6.78–6.81(2H,m), 7.15(1H,t,J=7.8 Hz), 9.50(1H,brs).

(b) Ethyl 3-(3-hydroxyphenyl)-3-methylaminopropionate 3-(3-Hydroxyphenyl)-3-methylaminopropionic acid (24.1 g) obtained from Example 7a was dissolved in ethanol (200 ml), and concentrated sulfuric acid (10 ml) was added dropwise to the solution. The resulting mixture was heated under reflux for 8 hours. The reaction mixture was neutralized with saturated aqueous sodium hydrogencarbonate solution and the solvent was removed under reduced pressure. The residual aqueous solution was extracted with ethyl acetate. The organic layer was dried over anhydrous magnesium sulfate and concentrated under reduced pressure to afford the desired compound which was used in next step reaction without further purification.

(c) Ethyl 3-[N-(t-butoxycarbonyl)-N-methylamino]-3-(3-hydroxyphenyl)propionate

The crude product of ethyl 3-(3-hydroxyphenyl)-3-methylaminopropionate obtained from Example 7b was dissolved in tetrahydrofuran (200 ml) under an atmosphere of nitrogen and di-tert-butyl dicarbonate (32 g, 150 mmol) was added to the solution. The mixture was stirred at room temperature overnight. The reaction mixture was concentrated under reduced pressure and purified by chromatography on a silica gel column using hexane:ethyl acetate=70:30 as the eluent to afford the desired compound (37 g).

$^1$H-NMR (400 MHz,CDCl$_3$) δ: 1.24(3H,t,J=7.1 HZ), 1.47 (9H,s), 2.64(3H,brs), 2.84–2.96(2H,m), 4.10–4.16(2H,m), 5.64(1/2H,brs), 5.82(1/2H,brs), 6.74–6.76 (2H,m), 6.8(1H,d, J=7.7 Hz), 7.20(1H,t,J=8.1 Hz).

(d) Ethyl 3-[N-(t-butoxycarbonyl)-N-methylamino]-3-[(3-dimethylcarbamoyloxy)phenyl]propionate Tetrahydrofuran (100 ml) was added to sodium hydride (1.01 g, 23 mmol) under an atmosphere of nitrogen and to the mixture was added a solution of ethyl 3-[N-(t-butoxycarbonyl)-N-methylamino]-3-(3-hydroxyphenyl)propionate (5.00 g, 16 mmol) obtained from Example 7c in tetrahydrofuran in an ice bath. After stirring the resulting mixture for 20 minutes, dimethylcarbamyl chloride (1.7 ml, 19 mmol) was added dropwise and the resulting mixture was stirred at room temperature for 1 hour. The reaction mixture was partitioned between saturated aqueous sodium chloride solution and ethyl acetate. The organic layer was washed with water and saturated aqueous sodium chloride solution, dried over anhydrous magnesium sulfate and concentrated under reduced pressure. The residue was purified by chromatography on a silica gel column using hexane:ethyl acetate=60:40 to afford the desired compound (4.85 g).

$^1$H-NMR (400 MHz,CDCl$_3$) δ: 1.24(3H,t,J=7.1 Hz), 1.47 (9H,s), 2.67(3H,brs), 2.90–2.93(2H,m), 3.01(3H,s), 3.10(3H, s), 4.11–4.15(2H,m), 5.67(1/2H,brs), 5.85(1/2H,brs), 6.99(1H,s), 7.05(1H,dd,J=7.9, 2.0 Hz), 7.10(1H,brs), 7.32 (1H, t, d=7.9 Hz).

(e) t-Butyl N-[1-[(3-dimethylcarbamoyloxy)phenyl]-3-hydroxypropyl]-N-methylcarbamate Tetrahydrofuran (100 ml) was added to lithium aluminum hydride (770 mg, 20 mmol) under an atmosphere of nitrogen, and to the mixture was added a tetrahydrofuran solution of ethyl 3-[N-(t-butoxycarbonyl)-N-methylamino]-3-[(3-dimethylcarbamoyloxy)phenyl]propionate (4.01 g 10 mmol) obtained from Example 7d at –78° C. After stirring the mixture for 20 minutes, the mixture was slowly warmed to 0° C. and then stirred for 30 minutes. To the reaction mixture was added sequentially water (0.8 ml), 15% aqueous sodium hydroxide solution (0.8 ml) and water (0.8 ml). The resulting mixture was stirred at room temperature for 30 minutes. After addition of anhydrous magnesium sulfate to the mixture, the resulting mixture was filtered and the filtrate was concentrated under reduced pressure. The residue was purified by chromatography on a silica gel column using hexane:ethyl acetate=20:80 as the eluent to afford the desired compound (2.40 g).

¹H-NMR (400 MHz,CDCl₃) δ ppm: 1.51 (9H,s), 1.92–1.97 (1H,m), 2.14–2.21 (1H,m), 2.46 (3H,s), 3.02 (3H,s), 3.11 (3H,s), 3.48–3.54 (1H,m), 3.58–3.62 (1H,m), 3.75 (1H,brs), 5.57–5.60 (1H,m), 7.04–7.06 (2H,m), 7.13–7.15 (1H,m), 7.34 (1H,t,J=8.2 Hz).

(f) t-Butyl N-[1-[(3-dimethylcarbamoyloxy)phenyl]-3-[(4-trifluoromethyl)phenoxy]propyl]-N-methylcarbamate t-Butyl N-[1-[(3-dimethylcarbamoyloxy)phenyl]-3-hydroxypropyl]-N-methylcarbamate (200 mg, 0.56 mmol) obtained from Example 7e was dissolved in tetrahydrofuran (2 ml) under an atmosphere of nitrogen. Triethylamine (0.14 ml, 1.0 mmol) and methanesulfonyl chloride (0.06 ml, 0.68 mmol) was sequentially added to the solution in an ice bath. The mixture was stirred at room temperature for 30 minutes. The reaction mixture was partitioned between water and ethyl acetate. The organic layer was washed with saturated aqueous sodium chloride solution, dried over magnesium sulfate and concentrated under reduced pressure to give a methanesulfonate. On the other hand N,N-dimethylformamide (2 ml) was added to sodium hydride (30 mg, 0.63 mmol) under an atmosphere of nitrogen. A solution of 4-(trifluoromethyl)phenol (110 mg, 0.63 mmol) in N,N-dimethylformamide was added to the suspension of sodium hydride in an ice bath and the mixture was stirred for 30 minutes. To this reaction mixture was added a solution of the methanesulfonate obtained above in N,N-dimethylformamide and the mixture was stirred at room temperature overnight. The reaction mixture was partitioned between water and ether. The organic layer was washed with saturated aqueous sodium chloride solution, dried over anhydrous magnesium sulfate and concentrated under reduced pressure. The residue was purified by chromatography on a silica gel column using hexane:ethyl acetate=50:50 as the eluent to afford the desired compound (243 mg).

¹H-NMR (400 MHz,CDCl₃) δ ppm: 1.39 (9H,s), 2.34–2.47 (2H,m) 2.62 (3H,s), 3.02 (3H,s), 3.11 (3H,s), 4.07 (2H,brs), 5.57 (1H,brs), 6.95 (2H,d,J=8.6 Hz), 7.05–7.06 (2H,m), 7.14–7.16 (1H,m), 7.34 (1H,t,J=8.1 Hz), 7.54 (2H,d,J=8.6 Hz).

(g) 3-[1-Methylamino-3-[(4-trifluoromethyl)phenoxy]propyl]phenyl dimethylcarbamate hydrochloride t-Butyl N-[1-[(3-dimethylcarbamoyloxy)phenyl]-3-[(4-trifluoromethyl)phenoxy]propyl]-N-methylcarbamate obtained from Example 7f was treated using a similar procedure to that described in Example 6d to afford the title compound as an amorphous solid.

¹H-NMR(400 MHz,CDCl₃) δ ppm: 2.54 (3H,s), 2.58–2.65 (1H,m), 2.98 (3H,s), 2.98–3.07 (1H,m), 3.07 (3H,s), 3.68–3.72 (1H,m), 4.01–4.05 (1H,m), 4.31–4.34 (1H,m), 6.86 (2H,d,J=8.7 Hz), 7.18 (1H,d,J=7.4 Hz), 7.31 (1H,s), 7.42–7.50 (4H,m). MS (FAB) m/z: 397 (M+H)⁺.

EXAMPLE 8

3-[3-(4-Methoxyphenoxy)-1-methylaminopropyl]phenyl dimethylcarbamate hydrochloride (Exemplification compound number 2-86)

4-Methoxyphenol was treated using similar procedures to those described in Example 7f and 7g to afford the title compound as an amorphous solid.

¹H-NMR(400 MHz,CDCl₃) δ ppm: 2.50–2.57 (1H,m), 2.53 (3H,s), 2.93–3.01 (1H,m), 2.99 (3H,s), 3.08 (3H,s), 3.57–3.61 (1H,m), 3.73 (3H,s), 3.91–3.94 (1H,m), 4.32–4.35 (1H,m), 6.73–6.78 (4H,m), 7.18 (1H,d,J=7.8 Hz), 7.34 (1H,s), 7.41–7.49 (2H,m). MS (EI) m/z: 358 (M)⁺.

EXAMPLE 9

3-(1-Methylamino-3-p-toluyloxypropyl)phenyl dimethylcarbamate hydrochloride (Exemplification compound number 2-82)

4-Methylphenol was treated using similar procedures to those described in Example 7f and 7g to afford the title compound as an amorphous solid.

¹H-NMR(400 MHz,CDCl₃) δ ppm: 2.24 (3H,s), 2.53 (3H,s), 2.53–2.58 (1H,m), 2.92–2.99 (1H,m), 2.99 (3H,s), 3.08 (3H,s), 3.56–3.62 (1H,m), 3.91–3.94 (1H,m), 4.32–4.36 (1H,m), 6.69 (2H,d,J=8.4 Hz), 7.02 (2H,d,J=8.4 Hz), 7.18 (1H,d,J=7.9 Hz), 7.34 (1H,s), 7.39–7.47 (2H,m). MS (FAB) m/z: 343 (M+H)⁺.

EXAMPLE 10

3-[3-(4-Chlorophenoxy)-1-methylaminopropyl]phenyl dimethylcarbamate hydrochloride (Exemplification compound number 2-78)

4-Chlorophenol was treated using similar procedures to those described in Example 7f and 7g to afford the title compound as an amorphous solid.

¹H-NMR(400 MHz,CDCl₃) δ ppm: 2.53 (3H,s), 2.53–2.58 (1H,m), 2.94–3.01 (1H,m), 2.99 (3H,s), 3.08 (3H,s), 3.58–3.63 (1H,m), 3.94–3.96 (1H,m), 4.30–4.33 (1H,m), 6.73 (2H,d,J=9.0 Hz), 7.15–7.19 (3H,m), 7.31 (1H,s), 7.31–7.45 (2H,m). MS (FAB) m/z: 363 (M+H)⁺.

EXAMPLE 11

3-[3-(4-Fluorophenoxy)-1-methylaminopropyl]phenyl dimethylcarbamate hydrochloride (Exemplification compound number 2-75)

(a) t-Butyl N-[1-[(3-dimethylcarbamoyloxy)phenyl]-3-(4-fluorophenoxy)propyl]-N-methylcarbamate 4-Fluorophenol was treated using a similar procedure to that described in Example 7f to afford the desired compound.

¹H-NMR 400 MHz,CDCl₃) δ: 1.40 (9H,s), 2.30–2.42 (2H,m), 2.61 (3H,s), 3.02 (3H,s), 3.11 (3H,s), 3.94–3.98 (2H,m), 5.56 (1H,brs), 6.80–6.84 (2H,m), 6.96 (2H,t,J=8.6 Hz), 7.04–7.05 (2H,m), 7.13–7.15 (1H,m), 7.34 (1H,t,J=8.3 Hz).

(b) 3-[3-(4-Fluorophenoxy)-1-methylaminopropyl]phenyl dimethylcarbamate hydrochloride t-Butyl N-[1-[(3-dimethylcarbamoyloxy)phenyl]-3-(4-fluorophenoxy)propyl]-N-methylcarbamate obtained from Example 11a was treated using a similar procedure to that described in Example 6d to afford the title compound as an amorphous solid.

¹H-NMR(400 MHz,CDCl₃) δ ppm: 2.53 (3H,s), 2.53–2.59 (1H,m), 2.94–3.05 (1H,m), 2.99 (3H,s), 3.08 (3H,s), 3.59–3.63 (1H,m), 3.92–3.96 (1H,m), 4.31–4.34 (1H,m), 6.73–6.78 (2H,m), 6.91 (2H,t,J=8.6 Hz), 7.18 (1H,d,J=6.7 Hz), 7.32 (1H,s), 7.42–7.47 (2H,m). MS (FAB) m/z: 347 (M+H)$^+$.

EXAMPLE 12

3-[3-(4-Fluorophenoxy)-1-methylaminopropyl]phenyl ethylcarbamate hydrochloride (Exemplification compound number 2-2)

(a) t-Butyl N-[3-[(4-fluorophenoxy)-[(3-hydroxyphenyl) propyl]-N-methylcarbamate t-Butyl N-[1-[(3-dimethylcarbamoyloxy)phenyl]-3-(4-fluorophenoxy)propyl]-N-methylcarbamate obtained from Example 11a was treated using a similar procedure to that described in Example 6b to afford the desired compound.

$^1$H-NMR(400 MHz,CDCl$_3$) δ ppm: 1.41 (9H,br s), 2.30–2.43 (2H,m), 3.97 (2H,br s), 5.52 (1H,br s), 5.98 (0.5H, br s), 6.40 (0.5H,br s), 6.76–6.86 (5H,m), 6.95 (1H,t,J=8.4 Hz), 7.21 (1H,t,J=7.8 Hz).

(b) 3-[3-(4-Fluorophenoxy)-1-methylaminopropyl]phenyl ethylcarbamate hydrochloride t-Butyl N-[3-[(4-fluorophenoxy)-1-(3-hydroxyphenyl) propyl]-N-methylcarbamate obtained from Example 12a was treated using a similar procedure to that described in Example 6d to afford the title compound as an amorphous solid.

$^1$H-NMR(400 MHz,CDCl$_3$) δ ppm: 0.88 (3H,t,J=7.3 Hz), 2.53 (3H,s), 2.52–2.59 (1H,m), 2.90–3.00 (1H,m), 3.25–3.31 (2H,m), 3.57–3.61 (1H,m), 3.92–3.95 (1H,m), 4.30–4.34 (1H,m), 5.04–5.09 (1H,m), 6.73 (2H,dd,J=9.0 Hz,4.3 Hz), 6.91 (2H,t,J=9.0 Hz), 7.21–7.24 (1H,m), 7.36 (1H,s), 7.41–7.44 (2H,m), 9.88 (1H,br s), 10.22 (1H,br s). MS(FAB) m/z: 347 (M+H)$^{30}$.

EXAMPLE 13

3-[3-(4-Fluorophenoxy)-1-methylaminopropyl]phenyl acetate hydrochloride (Exemplification compound number 2-4)

(a) 3-[1-(N-t-Butoxycarbonyl-N-methylamino)-3-(4-fluorophenoxy)propyl]phenyl acetate t-Butyl N-[3-[(4-fluorophenoxy)-1-(3-hydroxyphenyl) propyl]-N-methylcarbamate (100 mg, 0.27 mmol) obtained from Example 12a was dissolved in dichloromethane (1 ml) under an atmosphere of nitrogen, and triethylamine (0.045 ml, 0.32 mmol) and acetic anhydride (0.030 ml, 0.32 mmol) were added to the solution. The resulting mixture was stirred at room temperature overnight. The reaction mixture was partitioned between water and dichloromethane. The organic layer was washed with water and saturated aqueous sodium chloride solution, dried over magnesium sulfate and concentrated under reduced pressure. The residue was purified by chromatography on a silica gel column using hexane:ethyl acetate=80:20 to 75:25 as the eluent to afford the desired compound (98.7 mg).

$^1$H-NMR(400 MHz,CDCl$_3$) δ ppm: 1.40 (9H,s), 2.40 (3H, s), 2.34–2.57 (2H,m), 2.62 (3H, s), 3.97–3.99 (2H,m), 5.54–5.87 (1H,m), 6.82 (2H,dd,J=9.1 Hz,4.3 Hz), 6.94–6.83 (3H, m), 7.02 (1H,d,J=6.2 Hz), 7.18 (1H,d,J=7.1 Hz), 7.36 (1H,t,J=8.1 Hz).

(b) 3-[3-(4-Fluorophenoxy)-1-methylaminopropyl]phenyl acetate hydrochloride

3-[1-(N-t-Butoxycarbonyl-N-methylamino)-3-(4-fluorophenoxy)propyl]phenyl acetate obtained from Example 13a was treated using a similar procedure to that described in Example 6d to afford the title compound as an amorphous solid.

$^1$H-NMR(400 MHz,CDCl$_3$) δ ppm: 2.28 (3H,s), 2.53 (3H, s), 2.51–2.60 (1H,m), 2.95–3.01 (1H,m), 3.56–3.61 (1H,m), 3.92–3.96 (1H,m), 4.35 (1H,br s), 6.72 (2H,dd,J=8.8 Hz,4.3 Hz), 6.91 (2H,t,J=8.8 Hz), 7.16 (1H,d,J=7.7 Hz), 7.34 (1H,s), 7.43–7.50 (2H,m), 9.97 (1H,br s), 10.30 (1H,br s). MS(FAB) m/z: 318 (M+H)$^+$.

EXAMPLE 14

3-[3-(4-Fluorophenoxy)-1-methylaminopropyl]phenyl 2,2-dimethylpropionate hydrochloride (Exemplification compound number 2-5)

2,2-Dimethylpropionyl chloride was treated using similar procedures to those described in Example 13 to afford the title compound as an amorphous solid.

$^1$H-NMR(400 MHz,CDCl$_3$) δ ppm: 1.33 (s, 9 H), 2.54 (3H,s), 2.48–2.57 (1H,m), 2.96–3.01 (1H,m), 3.55–3.59 (1H, m), 3.91–3.96 (1H,m), 4.32–4.36 (1H,m), 6.73 (2H,dd,J=9.1 Hz,4.3 Hz), 6.91 (2H,t,J=9.1 Hz), 7.11 (1H,d,J=7.1 Hz), 7.30 (1H,s), 7.43–7.50 (2H,m), 9.98 (1H,br s), 10.38 (1H,br s). MS(FAB) m/z: 360 (M+H)$^+$.

EXAMPLE 15

3-[3-(4-Chlorophenyl)-1-methylaminopropyl]phenyl dimethylcarbamate hydrochloride (Exemplification compound number 2-13)

4-Chlorobenzaldehyde was treated using similar procedures to those described in Example 1 to afford the title compound as an amorphous solid.

$^1$H-NMR(400 MHz,CDCl$_3$) δ ppm: 2.39 (3H,s), 2.39–2.56 (3H,m), 2.75 (1H,br s), 3.02 (3H,s), 3.12 (3H,s), 3.83 (1H,br s), 7.05 (2H,d,J=8.3 Hz), 7.20 (2H,d,J=8.3 Hz), 7.17–7.23 (2H,m), 7.40–7.49 (2H,m), 9.85 (1H,br s), 10.25 (1H,br s). MS(FAB) m/z: 347 (M+H)$^+$.

EXAMPLE 16

4-[3-(4-Chlorophenoxy)-1-methylaminopropyl]phenyl dimethylcarbamate hydrochloride (Exemplification compound number 1-78)

(a) Ethyl 3-[N-(t-butoxycarbonyl)-N-methylamino]-3-(4-hydroxyphenyl)propionate

4-Hydroxybenzaldehyde was treated using similar procedures to those described in Example from 7a to 7c to afford the desired compound.

$^1$H-NMR(400 MHz,CDCl$_3$) δ ppm: 1.51 (9H,s), 1.91–1.98 (1H,m) 2.13–2.20 (1H,m), 2.43 (3H,s), 3.02 (3H,s), 3.10 (3H,s), 3.48–3.58 (2H,m), 3.74 (1H,br s), 5.57–5.61 (1H,m), 7.10 (2H,dt,J=8.6,1.9 Hz), 7.28 (2H,d,J=8.6 Hz).

(b) t-Butyl N-[1-[(4-dimethylcarbamoyloxy)phenyl]-3-hydroxypropyl]-N-methylcarbamate Ethyl 3-[N-(t-butoxycarbonyl)-N-methylamino]-3-(4-hydroxyphenyl)propionate obtained from Example 16a was treated using similar procedures to those described in Example 7d and 7e to afford the desired compound.

$^1$H-NMR(400 MHz,CDCl$_3$) δ ppm: 1.40 (9H,s), 2.29–2.44 (2H,m), 2.60 (3H,s), 3.01 (3H,s), 3.10 (3H,s), 3.98 (2H,br s), 5.56 (1H,br s), 6.81 (2H,d,J=8.8 Hz), 7.10 (2H,d,J=8.5 Hz), 7.22 (2H,d,J=8.8 Hz), 7.28–7.30 (2H,m).

(c) 4-[3-(4-Chlorophenoxy)-1-methylaminopropyl]phenyl dimethylcarbamate hydrochloride t-Butyl N-[1-[(4-dimethylcarbamoyloxy)phenyl]-3-hydroxypropyl]-N-methylcarbamate obtained from Example 16b and 4-chlorophenol were treated using similar procedures to those described in Example 7f and 6d to afford the title compound as amorphous solid.

$^1$H-NMR(400 MHz,CDCl$_3$) δ ppm: 2.51 (3H,s), 2.51–2.59 (1H,m), 2.94–3.01 (1H,m), 3.01 (3H,s), 3.09 (3H,s), 3.55–3.59 (1H,m), 3.91–4.13 (1H,m), 4.30–4.34 (1H,m), 6.71 (2H,d,J=9.0 HZ) 7.15–7.19 (4H,m), 7.59 (2H,d,J=8.6 Hz). IR(KBr) ν$_{max}$cm−1: 3430, 2942 2765, 2699, 1725. MS (FAB) m/z: 363 ([M+H]$^+$), 332, 273, 242, 207.

EXAMPLE 17

4-[1-Methylamino-3-[(4-trifluoromethyl)phenoxy]propyl]phenyl dimethylcarbamate hydrochloride (Exemplification compound number 1-85)

t-Butyl N-[1-[(4-dimethylcarbamoyloxy)phenyl]-3-hydroxypropyl]-N-methylcarbamate obtained from Example 16b and 4-trifluoromethylphenol were treated using similar procedures to those described in Example 7f and 7g to afford the title compound as an amorphous solid.

$^1$H-NMR(400 MHz,CDCl$_3$) δ ppm: 2.52 (3H,s), 2.58–2.64 (1H,m), 2.99–3.03 (1H,m), 3.01 (3H,s), 3.09 (3H,s), 3.64–3.68 (1H,m), 3.99–4.03 (1H,m), 4.32–4.35 (1H,m), 6.85 (2H,d,J=8.7 Hz), 7.19 (2H,d,J=8.6 Hz), 7.48 (2H,d, J=8.7 Hz), 7.59 (2H,d,J=8.6 Hz). MS (FAB) m/z: 397 (M+H)$^+$.

EXAMPLE 18

4-[3-[(4-Methoxyphenoxy)-1-methylaminopropyl]phenyl dimethylcarbamate hydrochloride (Exemplification compound number 1-86)

t-Butyl N-[1-(4-dimethylcarbamoyloxy)phenyl-3-hydroxypropyl]-N-methylcarbamate obtained from Example 16b and 4-methoxyphenol were treated using similar procedures to those described in Example 7f and 7g to afford the title compound as an amorphous solid.

$^1$H-NMR(400 MHz,CDCl$_3$) δ ppm: 2.51 (3H,s), 2.51–2.54 (1H,m), 2.92–2.97 (1H,m), 3.01 (3H,s), 3.09 (3H,s), 3.53–3.58 (1H,m), 3.73 (3H,s), 3.90–3.92 (1H,m), 4.34–4.36 (1H,m), 6.72–6.81 (4H,m), 7.18 (2H,d,J=8.4 Hz), 7.60 (2H, d,J=8.4 Hz). MS (FAB) m/z: 359 (M+H)$^+$.

EXAMPLE 19

3-[1-Amino-3-(4-fluorophenoxy)propyl]phenyl dimethylcarbamate hydrochloride (Exemplification compound number 2-65)

(a) t-Butyl[1-[(3-dimethylcarbamoyloxy)phenyl]-3-(4-fluorophenoxy)propyl]carbamate Ammonium acetate was treated using similar procedures to those described in from Example 7a to 7e to afford the desired compound.

$^1$H-NMR(400 MHz,CDCl$_3$) δ ppm: 1.40 (9H,br s) 2.22 (2H,br s), 3.00 (3H,s), 3.09 (3H,s), 3.84–3.96 (2H,m), 4.92 (1H,br s), 5.18 (1H,br s), 6.81 (2H,dd,J=8.8 Hz,4.3 Hz), 6.95 (2H,t,J=8.8 Hz), 7.00–7.05 (2H,m), 7.21 (1H,d,J=7.8 Hz), 7.31 (1H,t,J=7.8 Hz).

(b) 3-[1-Amino-3-(4-fluorophenoxy)propyl]phenyl dimethylcarbamate hydrochloride t-Butyl [1-[(3-dimethylcarbamoyloxy)phenyl]-3-(4-fluorophenoxy)propyl]carbamate obtained from Example 19a was treated using a similar procedure to that described in Example 6d to afford the title compound as an amorphous solid.

$^1$H-NMR(400 MHz,CDCl$_3$) δ ppm: 2.35–2.39 (1H,m), 2.69–2.74 (1H,m), 2.88 (3H,s), 3.04 (3H,s), 3.64–3.71 (1H, m), 3.91–3.96 (1H,m), 4.53 (1H,br s), 6.74 (2H,dd,J=8.9 Hz,4.3 Hz), 6.90 (2H,t,J=8.9 Hz), 7.02 (1H,d,J=8.0 Hz), 7.31–7.39 (3H,m), 8.71 (3H,br s).

EXAMPLE 20

3-[1-Ethylamino-3-(4-fluorophenoxy)propyl]phenyl dimethylcarbamate hydrochloride (Exemplification compound number 2-67)

(a) t-Butyl N-[1-(3-dimethylcarbamoyloxy)phenyl]-3-(4-fluorophenoxy)propyl]-N-ethylcarbamate N,N-Dimethylformamide (2 ml) was added to sodium hydride (12 mg, 0.28 mmol) under an atmosphere of nitrogen, and to the mixture was added a solution of t-butyl [1-[(3-dimethylcarbamoyloxy)phenyl]-3-(4-fluorophenoxy)propyl]carbamate (100 mg, 0.23 mmol) obtained from Example 19a in N,N-dimethylformamide in an ice bath. After stirring the resulting mixture for 20 minutes, ethyl iodide (0.022 ml, 0.28 mmol) was added dropwise thereto and this mixture was stirred at room temperature overnight. The reaction mixture was partitioned between water and ethyl acetate. The organic layer was washed with water and saturated aqueous sodium chloride solution, dried over magnesium sulfate and concentrated under reduced pressure. The residue was purified by chromatography on a silica gel column using hexane:ethyl acetate=90:10 to 70:30 as the eluent to afford the desired compound (63 mg).

$^1$H-NMR(400 MHz,CDCl$_3$) δ ppm: 1.42 (9H,br s), 2.39–2.47 (2H,m), 3.01 (3H,s), 3.02–3.09 (2H,m), 3.10 (3H, s), 3.96–4.05 (2H,m), 5.44 (1H,br s), 6.82 (2H,dd,J=8.9 Hz,4.3 Hz), 6.96 (2H,t,J=8.9 Hz), 7.04 (1H,t,J=7.9 Hz), 7.09 (1H,s), 7.18 (1H,d,J=7.9 Hz), 6.32 (1H,t,J=7.9 Hz).

(b) 3-[1-Ethylamino-3-(4-fluorophenoxy)propyl]phenyl dimethylcarbamate hydrochloride t-Butyl N-[1-(3-dimethylcarbamoyloxy)phenyl]-3-(4-fluorophenoxy)propyl]-N-ethylcarbamate obtained from Example 20a was treated using a similar procedure to that described in Example 6d to afford the title compound as an amorhous solid.

$^1$H-NMR(400 MHz,CDCl$_3$) δ ppm: 1.46 (3H,t,J=7.2 Hz), 2.60–2.65 (1H,m), 2.83–3.00 (2H,m), 2.99 (3H,s), 3.08 (3H, s), 3.06–3.11 (1H,m), 3.52–3.57 (1H,m), 3.86–3.90 (1H,m), 4.40 (1H,br s), 6.71 (2H,dd,J=9.0 Hz,4.3 Hz), 6.90 (2H,t, J=9.0 Hz), 7.18 (1H,d,J=7.8 Hz), 7.37 (1H,s), 7.43 (1H,t, J=7.8 Hz), 7.51 (1H,d,J=7.8 Hz), 9.97 (1H,br s), 10.34 (1H,br s).

EXAMPLE 21

3-[3-(4-Fluorophenoxy)-1-propylaminopropyl]phenyl dimethylcarbamate hydrochloride (Exemplification compound number 2-73)

1-Iodopropane was treated using similar procedures to those described in Example 20 to afford the title compound as an amorphous solid.

$^1$H-NMR(400 MHz,CDCl$_3$) δ ppm: 0.90 (3H,t,J=7.4 Hz), 1.90–2.01 (2H,m), 2.60–2.67 (1H,m), 2.72 (2H,t,J=8.1 Hz), 3.00 (3H,s), 3.08 (3H,s), 3.07–3.15 (1H,m), 3.52–3.57 (1H, m), 3.83–3.89 (1H,m), 4.36–4.40 (1H,m), 6.70 (2H,dd,J=8.9 Hz,4.3 Hz), 6.90 (2H,t,J=8.9 Hz), 7.19 (1H,d,J=7.9 Hz), 7.37 (1H,s), 7.43 (1H,t,J=7.9 Hz), 7.51 (1H,d,J=7.9 Hz), 9.88 (1H, br s), 10.27 (1H,br s)

EXAMPLE 22

3-[4-(4-Fluorophenyl)-1-methylaminobutyl]phenyl dimethylcarbamate hydrochloride (Exemplification compound number 2-25)

(a) t-Butyl N-[1-[(3-dimethylcarbamoyloxy)phenyl]-3-oxopropyl]-N-methylcarbamate t-Butyl N-[1-[(3-dimethylcarbamoyloxy)phenyl]-3-hydroxypropyl]-N-methylcarbamate (200 mg, 0.57 mmol) was dissolved in dichloromethane (3 ml) under an atmosphere of nitrogen and pyridinium dichromate (320 mg, 0.85 mmol) was added to the solution. The resulting mixture was stirred at room temperature overnight. After addition of ether to the reaction mixture, the crystals was collected by filtration and the filtrate was concentrated under reduced pressure. The residue was purified by chromatography on a silica gel column using hexane:ethyl acetate=80:20 to 60:40 as the eluent to afford the desired compound (148 mg).

$^1$H-NMR(400 MHz,CDCl$_3$) δ ppm: 1.48 (9H,s), 2.59 (3H, br s), 2.95–3.01 (2H,m), 3.02 (3H,s), 3.11 (3H,s), 6.02 (1H,br s), 6.99 (1H,s), 7.05–7.08 (2H,m), 7.35 (1H,t,J=7.9 Hz), 9.80 (1H,s).

(b) t-Butyl N-[1-[(3-dimethylcarbamoyloxy)phenyl]-4-(4-fluorophenyl)-3-butenyl]-N-methylcarbamate Tetrahydrofuran (1 ml) was added to sodium hydride (14 mg, 0.31 mmol) under an atmosphere of nitrogen and a solution of (4-fluorobenzyl)triphenylphosphonium bromide (110 mg, 0.27 mmol) in tetrahydrofuran was added to the sodium hydride. The resulting mixture was stirred for 2 hours and then t-butyl N-methy-N-[1-(3-nitrophenyl)-3-oxopropyl]carbamate (72 mg, 0.21 mmol) obtained from Example 22a was added thereto. The resulting mixture was stirred at room temperature for 3 hours. The reaction mixture was partitioned between saturated aqueous sodium chloride solution and ethyl acetate. The organic layer was washed with water and saturated aqueous sodium chloride solution, dried over anhydrous magnesium sulfate and concentrated under reduced pressure. The residue was purified by chromatography on a silica gel column using hexane:ethyl acetate=90:10 to 70:30 to afford the desired compound (80 mg).

$^1$H-NMR(400 MHz,CDCl$_3$) δ ppm: 1.41 (4.5H,s), 1.48 (4.5H,s), 2.47–2.90 (5H,m), 3.01 (1.5H,s), 3.02 (1.5H,s), 3.10 (1.5H,s), 3.11 (1.5H,s), 5.61–6.51 (3H,m), 6.96–7.36 (8H,m).

(c) t-Butyl N-[1-[(3-dimethylcarbamoyloxy)phenyl]-4-(4-fluorophenyl)butyl]-N-methylcarbamate t-Butyl N-[1-[(3-dimethylcarbamoyloxy)phenyl]-4-(4-fluorophenyl)-3-butenyl]-N-methylcarbamate (42 mg, 1.3 mmol) obtained from Example 22b was dissolved in methanol (1 ml) and to the solution was added 5% palladium on charcoal (10 mg). The mixture was stirred under an atmosphere of hydrogen at room temperature for 1 hour and the reaction mixture was filtered in order to remove the catalyst. The filtrate was concentrated under reduced pressure and the residue was purified by chromatography on a silica gel column using hexane:ethyl acetate=90:10 to 75: 25 as the eluent to afford the desired compound (40 mg).

$^1$H-NMR(500 MHz,CDCl$_3$) δ ppm: 1.48 (9H,s), 1.60–1.69 (2H,m), 2.53 (3H,br s), 2.59–2.65 (1H,m), 2.69–2.75 (1H,m), 3.01 (3H,s), 3.10 (3H,s), 5.23 (0.5H,br s), 5.44 (0.5H,br s), 6.94–7.15 (7H,m), 7.30 (1H,t,J=7.9 Hz).

(d) 3-[4-(4-Fluorophenyl)-1-methylaminobutyl]phenyl dimethylcarbamate hydrochloride t-Butyl N-[1-[(3-dimethylcarbamoyloxy)phenyl]-4-(4-fluorophenyl)butyl]-N-methylcarbamate obtained from Example 22c was treated using a similar procedure to that described in Example 6d to afford the title compound as an amorphous solid.

$^1$H-NMR(400 MHz,CDCl$_3$) δ ppm: 1.39–1.47 (1H,m), 1.52–1.60 (1H,m), 2.18–2.27 (1H,m), 2.41 (3H,s), 2.40–2.62 (3H,m), 3.01 (3H,s), 3.11 (3H,s), 3.90 (1H,dd,J=10.5 Hz,4.4 Hz), 6.90 (2H,t,J=8.6 Hz), 7.02 (2H,dd,J=8.6 Hz,5.5 Hz), 7.19 (1H,d,J=7.3 Hz), 7.22 (1H,s), 7.41–7.48 (2H,m), 9.83 (1H,br s), 10.16 (1H,br s).

EXAMPLE 23

3-[3-(4-Fluorophenoxy)-1-methylaminopropyl]phenyl diethylcarbamate hydrochloride (Exemplification compound number 2-6)

(a) t-Butyl N-[1-[(3-diethylcarbamoyloxy)phenyl]-3-(4-fluorophenoxy)propyl]-N-methylcarbamate N,N-Dimethylformamide (1 ml) was added to sodium hydride (14 mg, 0.32 mmol) under an atmosphere of nitrogen and to the sodium hydride was added a solution of t-butyl N-[3-(4-fluorophenoxy)-1-(3-hydroxyphenyl)propyl]-N-methylcarbamate (100 mg, 0.27 mmol) obtained from Example 12a in N,N-dimethylformamide in an ice bath. The mixture was stirred for 30 minutes and to this mixture was added diethylcarbamyl chloride (0.041 ml, 0.32 mmol). The resulting mixture was stirred for 1 hour and the reaction mixture was partitioned between water and ethyl acetate. The organic layer was washed with water and saturated aqueous sodium chloride solution, dried over anhydrous magnesium sulfate and concentrated under reduced pressure. The residue was purified by chromatography on a silica gel column using methylenechloride:ethyl acetate=10:90 as the eluent to afford the desired compound (108 mg).

$^1$H-NMR(400 MHz,CDCl$_3$) (400 MHz,CDCl$_3$) δ ppm: 1.19–1.28 (6H,m), 1.40 (9H,s), 2.31–2.44 (2H,m), 2.62 (3H, s), 3.37–3.47 (4H,m), 3.97–3.99 (2H,m), 5.56 (1H,brs), 6.81–6.84 (2H,m), 6.96 (2H,t,J=8.6 Hz), 7.05–7.11 (2H,m), 7.12–7.16 (1H,m), 7.34 (1H,t,J=8.2 Hz)

(b) 3-[3-(4-Fluorophenoxy)-1-methylaminopropyl]phenyl diethylcarbamate hydrochloride t-Butyl N-[1-[(3-diethylcarbamoyloxy)phenyl]-3-(4-fluorophenoxy)propyl]-N-methylcarbamate obtained from Example 23a was treated using a similar procedure to that described in Example 6d to afford the title compound as an amorphous solid.

$^1$H-NMR(400 MHz,CDCl$_3$) δ ppm: 1.20–1.29 (6H,m), 2.55 (3H,s), 2.55–2.62 (1H,m), 2.98–3.04 (1H,m), 3.36–3.45 (4H,m), 3.59–3.64 (1H,m), 3.94–3.98 (1H,m), 4.33–4.36 (1H,m), 6.74–6.78 (2H,m), 6.92 (2H,t,J=8.6 Hz), 7.21 (1H, d,J=7.5 Hz), 7.34 (1H,s), 7.43–7.50 (2H,m). MS (FAB) m/z: 375 (M+H)$^+$.

EXAMPLE 24

3-[3-(4-Fluorophenoxy)-1-methylaminopropyl]phenyl diisopropylcarbamate hydrochloride (Exemplification compound number 2-9)

Diisopropylcarbamyl chloride was treated using similar procedures to those described in Example 23 to afford the title compound as an amorphous solid.

$^1$H-NMR(400 MHz,CDCl$_3$) δ ppm: 1.28 (12H,brs), 2.54 (3H,s), 2.54–2.59 (1H,m), 2.95–3.02 (1H,m), 3.57–3.62 (1H,m), 3.92–3.99 (2H,m), 4.05 (1H,brs), 4.32–4.35 (1H,m), 6.76–6.78 (2H,m), 6.90 (2H,t,J=8.6 Hz), 7.19 (1H,dd,J=7.9 Hz,1.0 Hz), 7.28 (1H,d,J=1.0 Hz), 7.42 (1H,t,J=7.9 Hz), 7.49 (1H,d,J=7.9 Hz). MS (FAB) m/z: 403 (M+H)$^+$.

EXAMPLE 25

3-[3-(4-Fluorophenoxy)-1-methylaminopropyl]phenyl morpholin-4-carboxylate hydrochloride (Exemplification compound number 2-11)

Morpholin-4-carbonyl chloride was treated using similar procedures to those described in Example 23 to afford the title compound as an amorphous solid.
$^1$H-NMR(400 MHz,CDCl$_3$) δ ppm: 2.53 (3H,s), 2.53–2.59 (1H,m), 2.96–2.99 (1H,m), 3.54–3.64 (5H,m), 3.74 (4H,d, J=4.7 Hz), 3.93–3.95 (1H,m), 4.31–4.35 (1H,m), 6.72–6.75 (2H,m), 6.91 (2H,t,J=8.7 Hz), 7.19 (1H,d,J=6.9 Hz), 7.35 (1H,s), 7.42–7.46 (2H,m). MS (FAB) m/z: 389 (M+H)$^+$.

EXAMPLE 26

O-[3-[3-(4-Fluorophenoxy)-1-methylaminopropyl] phenyl]dimethylthiocarbamate hydrochloride (Exemplification compound number 2-12)

Dimethylthiocarbamyl chloride was treated using similar procedures to those described in Example 23 to afford the title compound as an amorphous solid.
$^1$H-NMR(400 MHz,CDCl$_3$) δ ppm: 2.55 (3H,s), 2.55–2.63 (1H,m), 2.99–3.02 (1H,m), 3.33 (3H,s), 3.43 (3H,s), 3.62–3.68 (1H,m), 3.91–3.95 (1H,m), 4.33–4.37 (1H,m), 6.72–6.75 (2H,m), 6.90 (2H,t,J=8.7 Hz), 7.11 (1H,d,J=7.8 Hz), 7.26 (1H,s), 7.47 (1H,t,J=7.8 Hz), 7.53 (1H,t,J=7.8 Hz). MS (FAB) m/z: 363 (M+H)$^+$.

EXAMPLE 27

3-[1-Dimethylamino-3-[(4-trifluoromethyl)phenoxy] propyl]phenyl dimethylcarbamate hydrochloride (Exemplification compound number 2-142)

3-[1-Methylamino-3-[(4-trifluoromethyl)phenoxy]propyl]phenyl dimethylcarbamate obtained from Example 7g was treated using a similar procedure to that described in Example 3 to afford the title compound as an amorphous solid.
$^1$H-NMR(400 MHz,CDCl$_3$) δ ppm: 2.64 (3H,s), 2.64–2.74 (1H,m), 2.87 (3H,s), 2.95–3.05 (1H,m), 3.00 (3H,s), 3.09 (3H,s), 3.64–3.70 (1H,m), 4.04–4.13 (1H,m), 4.29–4.31 (1H,m), 6.81 (2H,d,J=8.5 Hz), 7.22 (1H,m), 7.30 (1H,s), 7.38 (1H,d,J=7.7 Hz), 7.43–7.50 (3H,m). MS (FAB) m/z: 411 (M+H)$^+$.

EXAMPLE 28

3-[1-Dimethylamino-3-(4-fluorophenoxy)propyl] phenyl dimethylcarbamate hydrochloride (Exemplification compound number 2-132)

3-[3-(4-Fluorophenoxy)-1-methylaminopropyl]phenyl dimethylcarbamate obtained from Example 11b was treated using a similar procedure to that described in Example 3 to afford the title compound as an amorphous solid.

$^1$H-NMR(400 MHz,CDCl$_3$) δ ppm: 2.63–2.68 (4H,m), 2.87 (3H,s), 2.92–3.01 (1H,m), 3.01 (3H,s), 3.10 (3H,s), 3.54–3.60 (1H,m), 3.95–4.13 (1H,m), 4.28–4.30 (1H,m), 6.67–6.70 (2H,m), 6.91 (2H,t,J=8.6 Hz), 7.23 (1H,d,J=7.8 Hz), 7.32 (1H,s), 7.39 (1H,d,J=7.8 Hz), 7.45 (1H,t,J=7.8 Hz). MS (FAB) m/z: 361 (M+H)$^+$.

EXAMPLE 29

4-[1-Dimethylamino-3-[(4-trifluoromethyl)phenoxy] propyl]phenyl dimethylcarbamate hydrochloride (Exemplification compound number 1-142)

4-[1-Methylamino-3-(4-trifluoromethyl)phenoxy]propyl] phenyl dimethylcarbamate obtained from Example 17 was treated using a similar procedure to that described in Example 3 to afford the title compound as an amorphous solid.
$^1$H-NMR(400 MHz,CDCl$_3$) δ ppm: 2.61 (3H,s), 2.72–2.75 (1H,m), 2.91 (3H,s), 2.96–3.02 (1H,m), 3.02 (3H,s), 3.10 (3H,s), 3.58–3.63 (1H,m), 4.03–4.06 (1H,m), 4.27–4.31 (1H,m), 6.81 (2H,d,J=8.5 Hz), 7.23 (2H,d,J=8.2 Hz), 7.49 (2H,d, J=8.5 Hz), 7.57 (2H,d,J=8.2 Hz). MS (FAB) m/z: 411 (M+H)$^+$.

EXAMPLE 30

4-[3-(4-Fluorophenoxy)-1-methylaminopropyl]phenyl dimethylcarbamate hydrochloride (Exemplification compound number 1-75)

t-Butyl N-[1-[(4-dimethylcarbamoyloxy)phenyl]-3-hydroxypropyl]-N-methylcarbamate obtained from Example 16b and 4-fluorophenol were treated using similar procedures to those described in Example 7f and 7g to afford the title compound as an amorphous solid.
$^1$H-NMR(400 MHz,CDCl$_3$) δ ppm: 2.46–2.60 (1H,m), 2.51 (3H,s), 2.92–3.01 (1H,m), 3.01 (3H,s), 3.09 (3H,s), 3.53–3.59 (1H,m), 3.90–3.94 (1H,m), 4.33–4.34 (1H,m), 6.70–6.73 (2H,m), 6.91 (2H,t,J=8.7 Hz), 7.18 (2H,d,J=8.6 Hz), 7.60 (2H,d,J=8.6 Hz). MS (FAB) m/z: 347 (M+H)$^+$.

EXAMPLE 31

4-[1-Dimethylamino-3-(4-fluorophenoxy)propyl] phenyl dimethylcarbamate hydrochloride (Exemplification compound number 1-132)

4-[3-(4-Fluorophenoxy)-1-methylaminopropyl]phenyl dimethylcarbamate obtained from Example 30 was treated using a similar procedure to that described in Example 3 to afford the title compound as an amorphous solid.
$^1$H-NMR(400 MHz,CDCl$_3$) δ ppm: 2.54–2.69 (1H,m), 2.60 (3H,d,J=4.0 Hz), 2.85–2.96 (1H,m), 2.91 (3H,d,J=4.0 Hz), 3.02 (3H,s), 3.11 (3H,s), 3.47–3.52 (1H,m), 3.94–3.96 (1H,m), 4.27–4.30 (1H,m), 6.66–6.70 (2H,m), 6.92 (2H,t, J=8.6 Hz), 7.23 (2H,d,J=8.1 Hz), 7.58 (2H,d,J=8.1 Hz). MS (FAB) m/z: 361 (M+H)$^+$.

EXAMPLE 32

3-[3-(4-Fluorophenyl)-1-methylaminopropyl]phenyl dimethylcarbamate hydrochloride (Exemplification compound number 2-1)

4-Fluorobenzaldehyde was treated using similar procedures to those described in Example 1 to afford the title compound as an amorphous solid.

$^1$H-NMR(400 MHz,CDCl$_3$) δ ppm: 2.39 (3H,s), 2.34–2.54 (3H,m), 2.70–2.78 (1H,m), 3.02 (3H,s), 3.12 (3H,s), 3.80–3.87 (1H,m), 6.91 (2H,t,J=8.4 Hz), 7.07 (2H,dd,J=8.4 Hz,5.6 Hz), 7.17–7.24 (2H,m), 7.40–7.49 (2H,m). MS(EI) m/z: 331 (M+H)$^+$.

EXAMPLE 33

4-[3-(4-Fluorophenyl)-1-methylaminopropyl]phenyl dimethylcarbamate hydrochloride (Exemplification compound number 1-1)

4-Acetylphenol and 4-fluorobenzaldehyde were treated using similar procedures to those described in Example 1 to afford the title compound as an amorphous solid.

$^1$H-NMR(400 MHz,CDCl$_3$) δ ppm: 2.37 (3H,s), 2.33–2.54 (3H,m), 2.69–2.78 (1H,m), 3.03 (3H,s), 3.12 (3H,s), 3.85 (1H,br s), 6.88–6.96 (2H,m), 7.01–7.08 (2H,m), 7.22 (2H,d, J=8.6 Hz), 7.52 (2H,d,J=8.6 Hz), 9.79 (1H,br s), 10.12 (1H,br s). MS(FAB) m/z: 331 (M+H)$^+$.

EXAMPLE 34

3-[4-(4-Chlorophenyl)-1-methylaminobutyl]phenyl dimethylcarbamate hydrochloride (Exemplification compound number 2-26)

t-Butyl N-[1-[(3-dimethylcarbamoyloxy)phenyl]-3-oxopropyl]-N-methylcarbamate obtained from Example 22a and (4-chlorobenzyl)triphenylphosphonium chloride were treated using similar procedures to those described in Example from 22b to 22d to afford the title compound as an amorphous solid.

$^1$H-NMR(400 MHz,CDCl$_3$) δ ppm: 1.40–1.48 (1H,m), 1.58–1.66 (1H,m), 2.20–2.28 (1H,m), 2.42 (3H,s), 2.40–2.57 (3H,m), 3.01 (3H,s), 3.11 (3H,s), 3.94 (1H,br s), 6.99–7.28 (6H,m), 7.44–7.52 (2H,m), 9.77 (1H,br s), 10.15 (1H,br s).

EXAMPLE 35

4-[4-(4-Chlorophenyl)-1-methylaminobutyl]phenyl dimethylcarbamate hydrochloride (Exemplification compound number 1-26)

t-Butyl N-[1-[(4-dimethylcarbamoyloxy)phenyl]-3-hydroxypropyl]-N-methylcarbamate obtained from Example 16b, 3-methoxyphenol and (4-chlorobenzyl)triphenylphosphonium chloride were treated using similar procedures to those described in Example 22 to afford the title compound as an amorphous solid.

$^1$H-NMR(400 MHz,CDCl$_3$) δ ppm: 1.38–1.58 (2H,m), 2.20–2.26 (1H,m), 2.39 (3H,s), 2.38–2.62 (3H,m), 3.01 (3H, s), 3.10 (3H,s), 3.90 (1H,br s), 6.99 (1H,d,J=8.4 Hz), 7.06 (1H,d,J=6.9 Hz), 7.11–7.24 (4H,m), 7.52 (1H,d,J=8.4 Hz), 9.77 (1H,br s), 10.15 (1H,br s).

EXAMPLE 36

4-[3-(3-Methoxyphenoxy)-1-methylaminopropyl]phenyl dimethylcarbamate hydrochloride (Exemplification compound number 1-87)

t-Butyl N-[1-[(4-dimethylcarbamoyloxy)phenyl]-3-hydroxypropyl]-N-methylcarbamate obtained from Example 16b and 3-methoxyphenol were treated using similar procedures to those described in Example 7f and 7g to afford the title compound as an amorphous solid.

$^1$H-NMR(400 MHz,CDCl$_3$) δ ppm: 2.52 (3H,s), 2.52–2.58 (1H,m), 2.92–3.00 (1H,m), 3.00 (3H,s), 3.09 (3H,s), 3.55–3.60 (1H,m), 3.75 (3H,s), 3.91–3.96 (1H,m), 4.32–4.36 (1H,m), 6.36–6.38 (2H,m), 6.47 (1H,dd,J=8.9 Hz,1.9 Hz), 7.11 (1H,t,J=8.9 Hz), 7.18 (2H,d,J=8.6 Hz), 7.60 (2H,d,J=8.6 Hz). MS (FAB) m/z: 359 (M+H)$^+$.

EXAMPLE 37

4-[3-(2-Methoxyphenoxy)-1-methylaminopropyl]phenyl dimethylcarbamate hydrochloride (Exemplification compound number 1-88)

t-Butyl N-[1-[(4-dimethylcarbamoyloxy)phenyl]-3-hydroxypropyl]-N-methylcarbamate obtained from Example 16b and 2-methoxyphenol were treated using similar procedures to those described in Example 7f and 7g to afford the title compound as an amorphous solid.

$^1$H-NMR(400 MHz,CDCl$_3$) δ ppm: 2.56 (3H,s), 2.56–2.62 (1H,m), 2.85–2.89 (1H,m), 3.00 (3H,s), 3.09 (3H,s), 3.86–3.93 (1H,m), 3.90 (3H,s), 4.08–4.11 (1H,m), 4.43–4.46 (1H,m), 6.81 (1H,d,J=7.9 Hz), 6.86–6.91 (2H,m), 6.95–6.98 (1H,m), 7.18 (2H,d,J=8.6 Hz), 7.59 (2H,d,J=8.6 Hz). MS (FAB) m/z: 359 (M+H)$^+$.

EXAMPLE 38

4-[3-(3-Chlorophenoxy)-1-methylaminopropyl]phenyl dimethylcarbamate hydrochloride (Exemplification compound number 1-79)

(a) t-Butyl [3-(3-chlorophenoxy)-1-[(4-dimethylcarbamoyloxy)phenyl]propyl]-N-methylcarbamate t-Butyl N-[1-[(4-dimethylcarbamoyloxy)phenyl]-3-hydroxypropyl]-N-methylcarbamate obtained from Example 16b and 3-chlorophenol were treated using a similar procedure to that described in Example 7f to afford the desired compound.

$^1$H-NMR(400 MHz,CDCl$_3$) δ ppm: 1.41 (9H,s), 2.30–2.41 (2H,m), 2.60 (3H,s), 3.02 (3H,s), 3.10 (3H,s), 4.00 (2H,brs), 5.54 (1H,brs), 6.77 (1H,dd,J=8.2, 2.4 Hz), 6.86–6.93 (2H,m), 7.10 (2H,d,J=8.6 Hz), 7.18 (1H,t,J=8.2 Hz), 7.28–7.30 (2H, m).

(b) 4-[3-(3-Chlorophenoxy)-1-methylaminopropyl]phenyl dimethylcarbamate hydrochloride t-Butyl [3-(3-chlorophenoxy)-1-[(4-dimethylcarbamoyloxy)phenyl]propyl]-N-methylcarbamate obtained from Example 38a was treated using a similar procedure to that described in Example 6d to afford the title compound as an amorphous solid.

$^1$H-NMR(400 MHz,CDCl$_3$) δ ppm: 2.52 (3H,s), 2.52–2.61 (1H,m), 2.93–3.05 (1H,m), 3.00 (3H,s), 3.09 (3H,s), 3.55–3.60 (1H,m), 3.92–3.97 (1H,m), 4.31–4.35 (1H,m), 6.68 (1H,dd,J=8.1 Hz,2.1 Hz), 6.78 (1H,t,J=2.1 Hz), 6.90 (1H,dd,J=8.1 Hz,2.1 Hz), 7.14 (1H,t,J=8.1 Hz), 7.19 (2H,d, J=8.5 Hz), 7.60 (2H,d,J=8.5 Hz). MS (EI) m/z: 363 (M+H)$^+$.

EXAMPLE 39

4-[3-(2-Chlorophenoxy)-1-methylaminopropyl]phenyl dimethylcarbamate hydrochloride (Exemplification compound number 1-80)

t-Butyl N-[1-[(4-dimethylcarbamoyloxy)phenyl]-3-hydroxypropyl]-N-methylcarbamate obtained from Example 16b and 2-chlorophenol were treated using similar procedures to those described in Example 7f and 7g to afford the title compound as an amorphous solid.

$^1$H-NMR(400 MHz,CDCl$_3$) δ ppm: 2.55 (3H,s), 2.58–2.65 (1H,m), 2.98–3.06 (1H,m), 3.00 (3H,s), 3.08 (3H,s), 3.59–3.65 (1H,m), 4.11–4.16 (1H,m), 4.44–4.48 (1H,m), 6.75 (1H,dd,J=8.1 Hz,1.3 Hz), 6.87 (1H,td,J=8.1 Hz,1.3 Hz), 7.13 (1H,td,J=8.1 Hz,1.6 Hz), 7.17 (2H,d,J=8.6 Hz), 7.33 (1H,dd,J=8.1 Hz,1.6 Hz), 7.66 (2H,d,J=8.6 Hz), 9.90 (1H,br s), 10.20 (1H,br s). MS (EI) m/z: 363 (M+H)$^+$.

EXAMPLE 40

4-(1-Methylamino-3-p-toluyloxypropyl)phenyl dimethylcarbamate hydrochloride (Exemplification compound number 1-82)

t-Butyl N-[1-[(4-dimethylcarbamoyloxy)phenyl]-3-hydroxypropyl]-N-methylcarbamate obtained from Example 16b and 2-methylphenol were treated using similar procedures to those described in Example 7f and 7g to afford the title compound as an amorphous solid.

$^1$H-NMR(400 MHz,CDCl$_3$) δ ppm: 2.24 (3H,s), 2.46–2.54 (1H,m), 2.51 (3H,s), 2.95–3.00 (1H,m), 3.00 (3H,s), 3.09 (3H,s), 3.52–3.58 (1H,m), 3.90–3.94 (1H,m), 4.33–4.37 (1H,m), 6.68 (2H,d,J=8.5 Hz), 7.01 (2H,d,J=8.5 Hz), 7.17 (2H,d,J=8.5 Hz), 7.61 (2H,d,J=8.6 Hz). MS (EI) m/z: 342 (M)$^+$.

EXAMPLE 41

4-[3-(4-Chlorophenoxy)-1-dimethylaminopropyl] phenyl dimethylcarbamate hydrochloride (Exemplification compound number 1-135)

4-[3-(4-Chlorophenoxy)-1-methylaminopropyl]phenyl dimethylcarbamate obtained from Example 16d was treated using a similar procedure to that described in Example 3 to afford the title compound as an amorphous solid.

$^1$H-NMR(400 MHz,CDCl$_3$) δ ppm: 2.60 (3H,s), 2.64–2.68 (1H,m), 2.90 (3H,s), 2.90–2.98 (1H,m), 3.02 (3H,s), 3.11 (3H,s), 3.50–3.54 (1H,m), 3.95–3.98 (1H,m), 4.26–4.28 (1H,m), 6.67 (2H,d,J=8.9 Hz), 7.18 (2H,d,J=8.9 Hz), 7.23 (2H,d,J=8.5 Hz), 7.59 (2H,d,J=8.6 Hz). MS (EI) m/z: 376 (M)$^+$.

EXAMPLE 42

4-[3-(4-Chlorophenyl)-1-methylaminopropyl]phenyl dimethylcarbamate hydrochloride (Exemplification compound number 1-13)

4-Acetylphenol and 4-chlorobenzaldehyde were treated using similar procedures to those described in Example 1 to afford the title compound as an amorphous solid.

$^1$H-NMR(400 MHz,CDCl$_3$) δ ppm: 2.37 (3H,s), 2.31–2.53 (3H,m), 2.68–2.79 (1H,m), 3.03 (3H,s), 3.12 (3H,s), 3.84 (1H,br s), 7.03 (2H,d,J=8.2 Hz), 7.20 (2H,d,J=8.2 Hz), 7.22 (2H,d,J=8.1 Hz), 7.52 (2H,d,J=8.1 Hz), 9.85 (1H,br s), 10.15 (1H,br s). MS(EI) m/z: 347 (M+H)$^+$.

EXAMPLE 43

4-[3-(2,4-Difluorophenoxy)-1-methylaminopropyl) phenyl dimethylcarbamate hydrochloride (Exemplification compound number 1-101)

t-Butyl N-[1-[(4-dimethylcarbamoyloxy)phenyl]-3-hydroxypropyl]-N-methylcarbamate obtained from Example 16b and 2,4-difluorophenol were treated using similar procedures to those described in Example 7f and 7g to afford the title compound as an amorphous solid.

$^1$H-NMR(400 MHz,CDCl$_3$) δ ppm: 2.52 (3H,s), 2.50–2.61 (1H,m), 2.92–3.05 (1H,m), 3.01 (3H,s), 3.09 (3H,s), 3.58–3.67 (1H,m), 4.02–4.08 (1H,m), 4.33–4.40 (1H,m), 6.67–6.85 (3H,m), 7.19 (2H,d,J=8.6 Hz), 7.63 (2H,d,J=8.6 Hz). MS(FAB) m/z: 365 (M+H)$^+$.

EXAMPLE 44

4-[3-(2-Chloro-4-fluorophenoxy)-1-methylaminopropyl)phenyl dimethylcarbamate hydrochloride (Exemplification compound number 1-106)

t-Butyl N-[1-[(4-dimethylcarbamoyloxy)phenyl]-3-hydroxypropyl]-N-methylcarbamate obtained from Example 16b and 2-chloro-4-fluorophenol were treated using similar procedures to those described in Example 7f and 7g to afford the title compound as an amorphous solid.

$^1$H-NMR(400 MHz,CDCl$_3$) δ ppm: 2.54 (3H,s), 2.55–2.65 (1H,m), 2.95–3.07 (1H,m), 3.00 (3H,s), 3.09 (3H,s), 3.55–3.65 (1H,m), 4.05–4.12 (1H,m), 4.38–4.45 (1H,m), 6.71 (1H,dd,J=9.1 Hz,4.8 Hz), 6.83–6.89 (1H,m), 7.10 (1H,dd,J=8.0 Hz,3.0 Hz), 7.18 (2H,d,J=8.6 Hz), 7.64 (2H,d,J=8.6 Hz). MS(FAB) m/z: 381 (M+H)$_t$.

EXAMPLE 45

4-[3-(4-Acetylphenoxy)-1-methylaminopropyl)phenyl dimethylcarbamate hydrochloride (Exemplification compound number 1-89)

t-Butyl N-[1-[(4-dimethylcarbamoyloxy)phenyl]-3-hydroxypropyl]-N-methylcarbamate obtained from Example 16b and 4-acetylphenol were treated using similar procedures to those described in Example 7f and 7g to afford the title compound as an amorphous solid.

$^1$H-NMR(400 MHz,CDCl$_3$) δ ppm: 2.52 (6H,s), 2.52–2.66 (1H,m), 2.97–3.07 (1H,m), 3.01 (3H,s), 3.09 (3H,s), 3.63–3.73 (1H,m), 4.00–4.08 (1H,m), 4.30–4.38 (1H,m), 6.82 (2H,d,J=8.9 Hz), 7.19 (2H,d, J=8.6 Hz), 7.59 (2H,d, J=8.6 Hz), 7.87 (2H,d,J=8.9 Hz). MS(FAB) m/z: 371 (M+H)$_{30}$.

EXAMPLE 46

4-[3-(2,4-Dichlorophenoxy)-1-methylaminopropyl) phenyl dimethylcarbamate hydrochloride (Exemplification compound number 1-107)

t-Butyl N-[1-[(4-dimethylcarbamoyloxy)phenyl]-3-hydroxypropyl]-N-methylcarbamate obtained from Example 16b and 2,4-dichlorophenol were treated using similar procedures to those described in Example 7f and 7g to afford the title compound as an amorphous solid.

$^1$H-NMR(400 MHz,CDCl$_3$) δ ppm: 2.53 (3H,s), 2.55–2.66 (1H,m), 2.95–3.07 (1H,m), 3.01 (3H,s), 3.09 (3H,s), 3.55–3.65 (1H,m), 4.07–4.13 (1H,m), 4.36–4.45 (1H,m), 6.67 (1H,d,J=8.8 Hz), 7.10 (1H,dd,J=8.8 Hz,2.5 Hz), 7.18 (2H,d,J=8.6 Hz), 7.33 (1H,d,J=2.5 Hz), 7.64 (2H,d,J=8.6 Hz), 10.05 (2H,br s). MS(FAB) m/z: 397 (M+H)$^+$.

EXAMPLE 47

4-[3-(3,4-Dichlorophenoxy)-1-methylaminopropyl) phenyl dimethylcarbamate hydrochloride (Exemplification compound number 1-110)

t-Butyl N-[1-[(4-dimethylcarbamoyloxy)phenyl]-3-hydroxypropyl]-N-methylcarbamate obtained from Example 16b and 3,4-dichlorophenol were treated using similar procedures to those described in Example 7f and 7g to afford the title compound as an amorphous solid.

$^1$H-NMR(400 MHz,CDCl$_3$) δ ppm: 2.51 (3H,s), 2.57 (1H, br s), 2.98 (1H,br s), 3.01 (3H,s), 3.10 (3H,s), 3.52–3.62 (1H,m), 3.90–3.98 (1H,m), 4.31 (1H,br s), 6.66 (1H,dd,J=8.8 Hz,2.8 Hz), 6.88 (1H,d,J=2.8 Hz), 7.20 (2H,d,J=8.1 Hz), 7.27 (1H,d,J=8.8 Hz), 7.59 (2H,d,J=8.1 Hz), 9.93 (1H,br s), 10.30 (1H,br s). MS(FAB) m/z: 397 (M+H)$^+$.

EXAMPLE 48

4-[1-Methylamino-3-(4-nitrophenoxy)propyl]phenyl dimethylcarbamate hydrochloride (Exemplification compound number 1-92)

(a) t-Butyl N-[1-[(4-dimethylcarbamoyloxy)phenyl]-3-(4-nitrophenoxy)propyl]-N-methylcarbamate Triphenylphosphine (420 mg, 1.6 mmol) was dissolved in tetrahydrofuran (4 ml) under an atmosphere of nitrogen and 40% solution of diethyl azodicarboxylate in toluene (0.72 ml, 1.6 mmol) was added to the solution. After stirring the resulting mixture for 30 minutes at room temperature, 4-nitrophenol (190 mg, 1.4 mmol) was added to the reaction mixture. After stirring this mixture for 30 minutes, t-butyl N-[1-[(4-dimethylcarbamoyloxy)phenyl]-3-hydroxypropyl]-N-methylcarbamate obtained from Example 16b (400 mg, 1.1 mmol) was added and the resulting mixture was stirred for 5 hours. The reaction mixture was partitioned between water and ether. The organic layer was washed with water and saturated aqueous sodium chloride solution, dried over anhydrous magnesium sulfate and concentrated under reduced pressure. The residue was purified by chromatography on a silica gel column using hexane:ethyl acetate=50:50 as the eluent to afford the desired compound (392 mg).

$^1$H-NMR(400 MHz,CDCl$_3$) δ ppm: 1.39 (9H,s), 2.39–2.49 (2H,m), 2.60 (3H,s), 3.02 (3H,s), 3.11 (3H,s), 4.11–4.13 (2H, m), 5.60 (1H,br s), 6.95 (2H,d,J=9.1 Hz), 7.11 (2H,d,J=8.6 Hz), 7.27–7.31 (2H,m), 8.20 (2H,d,J=9.1 Hz).

(b) 4-[1-Methylamino-3-(4-nitrophenoxy)propyl]phenyl dimethylcarbamate hydrochloride t-Butyl N-[1-[(4-dimethylcarbamoyloxy)phenyl]-3-(4-nitrophenoxy)propyl]-N-methylcarbamate obtained from Example 48a was treated using a similar procedure to that described in Example 6d to afford the title compound as an amorphous solid.

$^1$H-NMR(400 MHz,CDCl$_3$) δ ppm: 2.52 (3H,s), 2.62–2.66 (1H,m), 3.01 (3H,s), 3.01–3.10 (1H,m), 3.10 (3H,s), 3.72–3.75 (1H,m), 4.07–4.11 (1H,m), 4.29–4.32 (1H,m), 6.86 (2H,d,J=9.2 Hz), 7.20 (2H,d,J=8.4 Hz), 7.59 (2H,d, J=8.4 Hz), 8.15 (2H,d,J=9.2 Hz). IR(KBr) ν$_{max}$cm−1: 3430, 2941 2756, 2698, 2446, 1724. MS m/z: 374 (M+H)$^+$.

EXAMPLE 49

4-[3-(4-Aminophenoxy)-1-methylaminopropyl]phenyl dimethylcarbamate dihydrochloride (Exemplification compound number 1-95)

(a) t-Butyl N-[3-(4-aminophenoxy)-1-[(4-dimethylcarbamoyloxy)phenyl]propyl]-N-methylcarbamate t-Butyl N-[1-[(4-dimethylcarbamoyloxy)phenyl]-3-(4-nitrophenoxy)propyl]-N-methylcarbamate (1.13 g, 2.4 mmol) obtained from Example 48a was dissolved in methanol (11 ml) and 5% palladium on charcoal (110 mg) was added to the solution. The resulting mixture was stirred at room temperature under an atmosphere of hydrogen for 1 hour. The catalyst was filtered off and the solvent of the filtrate was evaporated under reduced pressure. The residue was recrystallized from a mixture of ethyl acetate and hexane to afford the desired compound (820 mg) as crystals (mp 146–149° C.).

(b) 4-[3-(4-Aminophenoxy)-1-methylaminopropyl]phenyl dimethylcarbamate dihydrochloride t-Butyl N-[3-(4-aminophenoxy)-1-[(4-dimethylcarbamoyloxy)phenyl]propyl]-N-methylcarbamate obtained from Example 49a was treated using a similar procedure to that described in Example 6d to afford the title compound as an amorphous solid.

$^1$H-NMR(400 MHz,DMSO-d$_6$) δ ppm: 2.27–2.36 (1H,m), 2.38 (3H,s), 2.60–2.62 (1H,m), 2.90 (3H,s), 3.03 (3H,s), 3.61–3.63 (1H,m), 3.94–3.96 (1H,m), 4.38–4.41 (1H,m), 6.92 (2H,d,J=8.8 Hz), 7.19–7.25 (4H,m), 7.55 (2H,d,J=8.6 Hz). MS (FAB) m/z: 344 (M+H)$^+$.

EXAMPLE 50

4-[3-(4-Acetylaminophenoxy)-1-methylaminopropyl]phenyl dimethylcarbamate hydrochloride (Exemplification compound number 1-97)

(a) t-Butyl [3-(4-acetylaminophenoxy)-1-[(4-dimethylcarbamoyloxy)phenyl]propyl]methylcarbamate t-Butyl N-[3-(4-aminophenoxy)-1-[(4-dimethylcarbamoyloxy)phenyl]propyl]-N-methylcarbamate (100 mg, 0.23 mmol) obtained from Example 49a was dissolved in pyridine (1 ml) under an atmosphere of nitrogen, and acetic anhydride (0.026 ml, 0.28 mmol) was added to the solution. The resulting mixture was stirred at room temperature for 30 minutes. To the reaction mixture was added 0.5N aqueous hydrochloric acid solution and the mixture was extracted with ethyl acetate. The organic layer was washed with 0.5N aqueous hydrochloric acid solution, water and saturated aqueous sodium chloride solution, dried over anhydrous magnesium sulfate and concentrated under reduced pressure. The residue was purified by chromatography on a silica gel column using ethyl acetate as the eluent to afford the desired compound (106 mg).

$^1$H-NMR (400 MHz,CDCl$_3$) δ: 1.43 (9H,s), 2.32–2.43 (2H,m), 2.61 (3H,s), 3.01 (3H,s), 3.10 (3H,s), 3.97 (2H,brs), 5.52 (1H,brs), 6.22 (1H,s), 6.27–6.31 (2H,m), 7.03 (1H,t, J=8.0HZ), 7.09 (2H,d,J=8.5 Hz), 7.29 (2H,brs).

(b) 4-[3-(4-Acetylaminophenoxy)-1-methylaminopropyl] phenyl dimethylcarbamate hydrochloride t-Butyl [3-(4-Acetylaminophenoxy)-1-[(4-dimethylcarbamoyloxy)phenyl]propyl]methylcarbamate obtained from Example 50a was treated using a similar procedure to that described in Example 6d to afford the title compound as an amorphous solid.

$^1$H-NMR(400 MHz,CDCl$_3$) δ ppm: 2.13 (3H,s), 2.43–2.53 (1H,m), 2.47 (3H,s), 2.88–2.90 (1H,m), 3.01 (3H,s), 3.10 (3H,s), 3.57–3.62 (1H,m), 3.87–3.89 (1H,m), 4.32–4.34 (1H,m), 6.71 (2H,d,J=8.7 Hz), 7.18 (2H,d,J=8.1 Hz), 7.26–7.35 (2H,m), 7.59 (2H,d,J=8.1 Hz), 7.63 (1H,s). MS (FAB) m/z: 386 (M+H)$^+$.

EXAMPLE 51

4-[3-(3-Chlorophenoxy)-1-dimethylaminopropyl) phenyl dimethylcarbamate hydrochloride (Exemplification compound number 1-136)

4-[3-(3-Chlorophenoxy)-1-methylaminopropyl]phenyl dimethylcarbamate obtained from Example 38b was treated using a similar procedure to that described in Example 3 to afford the title compound as an amorphous solid.

$^1$H-NMR(400 MHz,CDCl$_3$) δ ppm: 2.60 (3H,brs), 2.60–2.71 (1H,m), 2.88–2.97 (1H,m), 3.02 (3H,s), 3.11 (3H,s), 3.49–3.55 (1H,m), 3.96–4.00 (1H,m), 4.24–4.29 (1H,m), 6.64 (1H,ddd,J=8.4 Hz,2.2 Hz,0.8 Hz), 6.74 (1H,t,J=2.2 Hz), 6.92 (1H,ddd,J=8.4 Hz,2.2 Hz,0.8 Hz), 7.15 (1H,t,J=8.2 Hz), 7.23 (2H,d,J=8.7 Hz), 7.57 (2H,d,J=8.7 Hz). MS (FAB) m/z: 377 (M+H)$^+$.

EXAMPLE 52

4-[3-(2-Chlorophenoxy-1-dimethylaminopropyl)phenyl dimethylcarbamate hydrochloride (Exemplification compound number 1-137)

4-[3-(2-Chlorophenoxy)-1-methylaminopropyl]phenyl dimethylcarbamate obtained from Example 39 was treated using a similar procedure to that described in Example 3 to afford the title compound as an amorphous solid.

$^1$H-NMR(400 MHZ,CDCl$_3$) δ ppm: 2.58 (3H,s), 2.69–2.77 (1H,m), 2.90–3.00 (4H,m), 3.01 (3H,s), 3.09 (3H,s), 3.47–3.53 (1H,m), 4.13–4.17 (1H,m), 4.32–4.35 (1H,m), 6.73 (1H,dd,J=7.9 Hz,1.3 Hz), 6.89 (1H,td,J=7.9 Hz,1.3 Hz), 7.15 (1H,td,J=7.9 Hz,1.6 Hz), 7.20 (2H,d,J=8.7 Hz), 7.34 (1H,dd,J=7.9 Hz,1.6 Hz), 7.66 (2H,d,J=8.7 Hz) MS (FAB) m/z: 377 (M+H)$^+$.

EXAMPLE 53

4-[1-Methylamino-3-(3-nitrophenoxy)propyl]phenyl dimethylcarbamate hydrochloride (Exemplification compound number 1-94)

(a) t-Butyl N-[1-[(4-dimethylcarbamoyloxy)phenyl]-3-(3-nitrophenoxy)propyl]-N-methylcarbamate t-Butyl N-[1-[(4-dimethylcarbamoyloxy)phenyl]-3-hydroxypropyl]-N-methylcarbamate obtained from Example 16b and 3-nitrophenol were treated using a similar procedure to that described in Example 7f to afford the desired comound.

$^1$H-NMR(400 MHz,CDCl$_3$) δ: 1.40 (9H,s), 2.39–2.48 (2H,m), 2.61 (3H,s), 3.02 (3H,s), 3.11 (3H,s), 4.09–4.15 (2H,m), 5.63 (1H,brs), 7.11 (2H,d,J=8.6 Hz), 7.23 (1H,d,J=8.2 Hz), 7.31 (2H,d,J=8.6 Hz), 7.43 (1H,t,J=8.2 Hz), 7.72 (1H,s), 7.83 (1H,d,J=8.2 Hz).

(b) 4-[1-Methylamino-3-(3-nitrophenoxy)propyl]phenyl dimethylcarbamate hydrochloride t-Butyl N-[1-[(4-dimethylcarbamoyloxy)phenyl]-3-(3-nitrophenoxy)propyl]-N-methylcarbamate obtained from Example 53a was treated using a similar procedure to that described in Example 6d to afford the title compound.

$^1$H-NMR(400 MHz,CDCl$_3$) δ ppm: 2.53 (3H,s), 2.64–2.67 (1H,m), 2.96–3.09 (1H,m), 3.00 (3H,s), 3.09 (3H,s), 3.70–3.74 (1H,m), 4.06–4.10 (1H,m), 4.32–4.36 (1H,m), 7.15 (1H,dd,J=8.2 Hz,2.4 Hz), 7.21 (1H,d,J=8.4 Hz), 7.39 (1H,t,J=8.2 HZ), 7.59 (1H,s), 7.60 (2H,d,J=8.4 Hz), 7.80 (1H,dd,J=8.2 HZ,2.4 Hz). MS (FAB) m/z: 374 (M+H)$^+$.

EXAMPLE 54

4-[3-(3,4-Difluorophenoxy)-1-methylaminopropyl] phenyl dimethylcarbamate hydrochloride (Exemplification compound number 1-102)

t-Butyl N-[1-[(4-dimethylcarbamoyloxy)phenyl]-3-hydroxypropyl]-N-methylcarbamate obtained from Example 16b and 3,4-difluorophenol were treated using similar procedures to those described in Example 7f and 7g to afford the title compound as an amorphous solid.

$^1$H-NMR(400 MHz,CDCl$_3$) δ ppm: 2.52 (3H,br s), 2.55–2.62 (1H,m), 2.92–3.02 (1H,m), 3.01 (3H,s), 3.10 (3H,s), 3.52–3.59 (1H,m), 3.89–3.95 (1H,m), 4.28–4.35 (1H,m), 6.45–6.51 (1H,m), 6.61 (1H,ddd,J=11.9 Hz,6.6 Hz,2.2 Hz), 7.00 (1H,q,J=9.4 Hz), 7.19 (2H,d,J=8.5 Hz), 7.59 (2H,d,J=8.5 Hz) 9.93 (1H,br s), 10.30 (1H,br s). MS(FAB) m/z: 365 (M+H)$^+$.

EXAMPLE 55

4-[3-(4-Chloro-3-fluorophenoxy)-1-methylaminopropyl]phenyl dimethylcarbamate hydrochloride (Exemplification compound number 1-104)

t-Butyl N-[1-[(4-dimethylcarbamoyloxy)phenyl]-3-hydroxypropyl]-N-methylcarbamate obtained from Example 16b and 4-chloro-3-fluorophenol were treated using similar procedures to those described in Example 7f and 7g to afford the title compound as an amorphous solid.

$^1$H-NMR(400 MHz,CDCl$_3$) δ ppm: 2.52 (3H,br s), 2.51–2.62 (1H,m), 2.91–3.04 (1H,m), 3.01 (3H,s), 3.10 (3H,s), 3.53–3.62 (1H,m), 3.90–3.98 (1H,m), 4.27–4.34 (1H,m), 6.52–6.55 (1H,m), 6.60 (1H,dd,J=10.7 Hz,2.7 Hz), 7.18–7.25 (3H,m), 7.59 (2H,d,J=8.3 Hz) ,9.94 (1H,br s), 10.32 (1H,br s). MS(FAB) m/z: 381 (M+H)$^+$.

EXAMPLE 56

4-[3-(4-Cyanophenoxy)-1-methylaminopropyl]phenyl dimethylcarbamate hydrochloride (Exemplification compound number 1-91)

t-Butyl N-[1-[(4-dimethylcarbamoyloxy)phenyl]-3-hydroxypropyl]-N-methylcarbamate obtained from Example 16b and 4-hydroxybenzonitrile were treated using similar procedures to those described in Example 7f and 7g to afford the title compound as an amorphous solid.

$^1$H-NMR(400 MHz,CDCl$_3$) δ ppm: 2.51 (3H,br s), 2.55–2.68 (1H,m), 2.95–3.05 (1H,m), 3.01 (3H,s), 3.10 (3H,s), 3.64–3.72 (1H,m), 3.98–4.07 (1H,m), 4.25–4.35 (1H,m), 6.84 (2H,d,J=8.8 Hz), 7.19 (2H,d,J=8.3 Hz), 7.53 (2H,d,J=8.8 Hz), 7.58 (2H,d,J=8.3 Hz), 9.96 (1H,br s), 10.36 (1H,br s). MS(EI) m/z: 354 (M+H)$^+$.

EXAMPLE 57

4-[3-(4-Bromophenoxy)-1-methylaminopropyl]phenyl dimethylcarbamate hydrochloride (Exemplification compound number 1-81)

t-Butyl N-[1-[(4-dimethylcarbamoyloxy)phenyl]-3-hydroxypropyl]-N-methylcarbamate obtained from Example 16b and 4-bromophenol were treated using similar procedures to those described in Example 7f and 7g to afford the title compound as an amorphous solid.

$^1$H-NMR(400 MHz,CDCl$_3$) δ ppm: 2.51 (3H,br s), 2.52–2.62 (1H,m), 2.92–3.03 (1H,m), 3.01 (3H,s), 3.09 (3H, s), 3.53–3.61 (1H,m), 3.88–3.97 (1H,m), 4.28–4.38 (1H,m), 6.66 (2H,d,J=9.0 Hz), 7.18 (2H,d,J=8.5 Hz), 7.31 (2H,d, J=9.0 Hz), 7.59 (2H,d,J=8.5 Hz), 9.91 (1H,br s), 10.22 (1H,br s). MS(FAB) m/z: 407 (M+H)$^+$.

EXAMPLE 58

4-[3-(4-Fluoro-2-methylphenoxy)-1-methylaminopropyl]phenyl dimethylcarbamate hydrochloride (Exemplification compound number 1-111)

t-Butyl N-[1-[(4-dimethylcarbamoyloxy)phenyl]-3-hydroxypropyl]-N-methylcarbamate obtained from Example 16b and 4-fluoro-2-methylphenol were treated using similar procedures to those described in Example 7f and 7g to afford the title compound as an amorphous solid.

$^1$H-NMR(400 MHz,CDCl$_3$) δ ppm: 2.19 (3H,s), 2.51 (3H, br s), 2.53–2.63 (1H,m), 2.93–3.03 (1H,m), 3.01 (3H,s), 3.09 (3H,s), 3.54–3.62 (1H,m), 3.89–3.97 (1H,m), 4.28–4.37 (1H, m), 6.53 (1H,dd,J=8.7 Hz,4.5 Hz), 6.73 (1H,td,J=8.7 Hz,3.0 Hz), 6.82 (1H,dd,J=8.7 Hz,3.0 Hz), 7.19 (2H,d,J=8.5 Hz), 7.60 (2H,d,J=8.5 Hz) 9.94 (1H,br s), 10.32 (1H,br s). MS(FAB) m/z: 361 (M+H)$^+$.

EXAMPLE 59

4-[1-Methylamino-3-m-toluyloxypropyl]phenyl dimethylcarbamate hydrochloride (Exemplification compound number 1-83)

t-Butyl N-[1-[(4-dimethylcarbamoyloxy)phenyl]-3-hydroxypropyl]-N-methylcarbamate obtained from Example 16b and 3-methylphenol were treated using similar procedures to those described in Example 7f and 7g to afford the title compound as an amorphous solid.

$^1$H-NMR(400 MHz,CDCl$_3$) δ ppm: 2.28 (3H,s) 2.52 (3H, s), 2.48–2.60 (1H,m), 2.90–3.03 (1H,m), 3.00 (3H,s), 3.09 (3H,s), 3.53–3.61 (1H,m), 3.89–3.97 (1H,m), 4.32–4.40 (1H, m), 6.56–6.62 (2H,m), 6.73 (1H,d,J=7.6 Hz), 7.10 (1H,t, J=7.6 Hz), 7.18 (2H,d,J=8.5 Hz),7.61 (2H,d,J=8.5 Hz), 9.93 (1H,br s), 10.25 (1H,br s). MS(EI) m/z: 343 (M+H)$^+$.

EXAMPLE 60

4-[3-(3,4-Dimethylphenoxy)-1-methylaminopropyl] phenyl dimethylcarbamate hydrochloride (Exemplification compound number 1-114)

t-Butyl N-[1-[(4-dimethylcarbamoyloxy)phenyl]-3-hydroxypropyl]-N-methylcarbamate obtained from Example 16b and 3,4-dimethylphenol were treated using similar procedures to those described in Example 7f and 7g to afford the title compound as an amorphous solid.

$^1$H-NMR(400 MHz,CDCl$_3$) δ ppm: 2.15 (3H,s), 2.18 (3H, s), 2.51 (3H,br s), 2.45–2.58 (1H,m), 2.87–3.00 (1H,m), 3.00 (3H,s), 3.08 (3H,s), 3.48–3.57 (1H,m), 3.86–3.94 (1H,m), 4.34 (1H,br s), 6.51 (1H,dd,J=8.2 Hz,2.6 Hz), 6.59 (1H,d, J=2.6 Hz), 6.95 (1H,d,J=8.2 Hz), 7.17 (2H,d,J=8.6 Hz), 7.60 (2H,d,J=8.6 Hz), 9.90 (1H,br s), 10.24 (1H,br s). MS(FAB) m/z: 357 (M+H)$^+$.

EXAMPLE 61

(R)-4-[3-(3-Chlorophenoxy)-1-methylaminopropyl] phenyl dimethylcarbamate hydrochloride (Exemplification compound number 1-79)

(a) Methyl (R)-3-t-butoxycarbonylamino-3-(4-hydroxyphenyl)propionate

Methyl (R)-3-amino-3-(4-hydroxyphenyl)propionate, which was synthesized according to the method described in Tetrahedron: Asymmetry, 2, 183, (1991), was treated using a similar procedure to that described in Example 6a to give the desired compound. The product was recrystallized from a mixture of ethyl acetate and hexane to afford the desired compound (mp 130–132° C.), which had greater than 99% optical purity. The optical purity was determined by HPLC on a Chiralcel OD column (product of Daisel Chemical Industry Co. Ltd.) using hexane:isopropyl alcohol=95:5 as the eluent.

(b) t-Butyl (R)-[1-[(4-dimethylcarbamoyloxy)phenyl]-3-hydroxypropyl]carbamate

Methyl (R)-3-t-butoxycarbonylamino-3-(4-hydroxyphenyl)propionate obtained from Example 61a was treated using similar procedures to those described in Example 7d and 7e to afford the desired product.

$^1$H-NMR(400 MHz,CDCl$_3$) δ ppm: 1.51 (9H,s), 1.92–1.97 (1H,m), 2.14–2.20 (1H,m), 2.43 (1H,br), 3.01 (3H,s), 3.10 (3H,s), 3.51–3.58 (2H,m), 3.73–3.77 (1H,br), 5.57–5.59 (1H, m), 7.10 (2H,d,J=7.7 Hz), 7.28 (2H,d,J=7.7 Hz).

(c) t-Butyl (R)-[3-(3-chlorophenoxy)-1-[(4-dimethylcarbamoyloxy)phenyl]propyl]carbamate t-Butyl (R)-[1-[(4-dimethylcarbamoyloxy)phenyl]-3-hydroxypropyl]carbamate obtained from Example 61b and 3-chlorophenol were treated using a similar procedure to that described in Example 7f to afford the desired compound.

$^1$H-NMR(500 MHz,CDCl$_3$) δ ppm: 1.41 (9H,s), 2.34–2.44 (2H,m), 3.02 (3H,s), 3.11 (3H,s), 4.00 (2H,br s), 5.54 (2H,br s), 6.78 (1H,d,J=8.1 Hz), 6.89 (1H,s), 6.94 (1H,d,J=8.1 Hz), 7.12 (2H,d,J=8.4 Hz), 7.17 (1H,t,J=8.1 Hz), 7.29 (2H,br s).

(d) t-Butyl (R)-N-[3-(3-chlorophenoxy)-1-[(4-dimethylcarbamoyloxy)phenyl]propyl]-N-methylcarbamate N,N-dimethylformamide (30 ml) was added to sodium hydride (1.75 g, 40 mmol) under an atmosphere of nitrogen, and to the sodium hydride was added a solution of t-butyl (R)-[3-(3-chlorophenoxy)-1-[(4-dimethylcarbamoyloxy) phenyl]propyl]carbamate (7.00 g, 16 mmol) obtained from Example 61c in N,N-dimethylformamide in an ice bath. The mixture was stirred for 30 minutes and then methyl iodide (1.9 ml, 30 mmol) was added thereto. The resulting mixture was warmed to room temperature and then stirred overnight. The reaction mixture was partitioned between water and ethyl acetate. The organic layer was washed with water and saturated aqueous sodium chloride solution, dried over anhydrous magnesium sulfate and concentrated under reduced pressure. The residue was purified by chromatography on a silica gel column using hexane:ethyl acetate=95:5 to 85:15 to afford the desired compound (6.14 g).

¹H-NMR(400 MHz,CDCl₃) δ ppm: 1.41 (9H,s), 2.35–2.44 (3H,s), 2.60 (3H,s) 3.02 (3H,s), 3.10 (3H,s), 4.00 (2H,br), 5.54 (1H,br), 6.78 (1H,d,J=8.3 Hz), 7.10 (2H,d,J=8.4 Hz), 7.18 (1H,t,J=8.3 Hz), 7.29 (2H.m).

(e) (R)-4-[3-(3-Chlorophenoxy)-1-methylaminopropyl]phenyl dimethylcarbamate hydrochloride t-Butyl (R)-N-[3-(3-chlorophenoxy)-1-[(4-dimethylcarbamoyloxy)phenyl]propyl]-N-methylcarbamate obtained from Example 61d was treated using a similar procedure to that described in Example 6d to afford the title compound as an amorphous solid.

¹H-NMR(400 MHz,CDCl₃) δ ppm: 2.52 (3H,s), 2.52–2.61 (1H,m), 2.93–3.05 (1H,m), 3.00 (3H,s), 3.09 (3H,s), 3.55–3.60 (1H,m), 3.92–3.97 (1H,m), 4.31–4.35 (1H,m), 6.68 (1H,dd,J=8.1 Hz,2.1 Hz), 6.78 (1H,t,J=2.1 Hz), 6.90 (1H,dd,J=8.1 Hz,2.1 Hz), 7.14 (1H,t,J=8.1 Hz), 7.19 (2H,d, J=8.5 Hz), 7.60 (2H,d,J=8.5 Hz). MS(EI) m/z: 363 (M+H)+

EXAMPLE 62

(R)-4-[3-(4-Chlorophenoxy)-1-methylaminopropyl] phenyl dimethylcarbamate hydrochloride (Exemplification compound number 1-78)

t-Butyl (R)-1-[(4-dimethylcarbamoyloxy)phenyl]-3-hydroxypropyl]carbamate obtained from Example 61b and 4-chlorophenol were treated using similar procedures to those described in Example from 61c to 61e to afford the title compound.

¹H-NMR(400 MHz,CDCl₃) δ ppm: 2.51 (3H,s), 2.51–2.59 (1H,m) 2.94–3.01 (1H,m), 3.01 (3H,s), 3.09 (3H,s), 3.55–3.59 (1H,m), 3.91–4.13 (1H,m), 4.30–4.34 (1H,m), 6.71 (2H,d,J=9.0 Hz), 7.15–7.19 (4H,m), 7.59 (2H,d,J=8.6 Hz). [α]$_D^{22}$ +72 (c 0.37, CHCl₃)

EXAMPLE 63

4-[3-(4-Chlorophenoxy)-1-methylaminopropyl]phenyl diethylcarbamate hydrochloride (Exemplification compound number 1-7)

(a) t-Butyl N-[3-(4-chlorophenoxy)-1-(3-hydroxyphenyl) propyl]-N-methylcarbamate t-Butyl [3-(4-chlorophenoxy)-1-[(4-dimethylcarbamoyloxy)phenyl]propyl]-N-methylcarbamate obtained from Example 16c was treated using a similar procedure to that described in Example 6b to afford the desired compound.

¹H-NMR(400 MHZ,CDCl₃) δ ppm: 1.41 (9H,s), 2.29–2.39 (2H,m), 2.57 (3H,s), 3.97 (2H.br s), 5.21 (1H.br s), 5.51 (1H,br s), 6.79–6.82 (4H,m), 7.17 (2H,d,J=7.4 Hz), 7.22 (2H,d,J=8.9 Hz).

(b) 4-[3-(4-Chlorophenoxy)-1-methylaminopropyl]phenyl diethylcarbamate hydrochloride t-Butyl N-[3-(4-chlorophenoxy)-1-(3-hydroxyphenyl) propyl]-N-methylcarbamate obtained from Example 63a was treated using similar procedures to those described in Example 23 to afford the title compound as an amorphous solid.

¹H-NMR(400 MHz,CDCl₃) δ ppm: 1.18–1.27 (6H,m), 2.50 (3H,s), 2.49–2.58 (1H,m), 2.94–3.01 (1H,m), 3.34–3.45 (4H,m), 3.54–3.59 (1H,m), 3.90–3.96 (1H,m), 4.32 (1H,br s), 6.71 (2H,d,J=9.2 Hz), 7.17 (2H,d,J=8.9 Hz), 7.19 (2H,d, J=9.2 Hz), 7.59 (2H,d,J=8.9 Hz), 9.95 (1H,br s), 10.31 (1H,br s). MS(EI) m/z: 391 (M+H)+

EXAMPLE 64

4-[3-(3-Aminophenoxy)1-methylaminopropyl]phenyl dimethylcarbamate dihydrochloride (Exemplification compound number 1-96)

(a) t-Butyl N-[3-(3-aminophenoxy)-1-[(4-dimethylcarbamoyloxy)phenyl]propyl]-N-methylcarbamate t-Butyl N-[1-[4-dimethylcarbamoyloxy]phenyl-3-(3-nitrophenoxy)propyl]-N-methylcarbamate obtained from Example 53a was treated in a similar procedure to that described in Example 49a to afford the desired compound.

¹H-NMR(400 MHz,CDCl₃) δ ppm: 1.41 (9H,s), 2.16 (3H, s), 2.28–2.33 (1H,m), 2.34–2.47 (1H,m), 2.60 (3H,s), 3.02 (3H,s), 3.11 (3H,s), 3.98–4.06 (2H,m), 5.52 (1H,brs), 6.62 (1H,d,J=6.7 Hz), 6.99 (1H,brs), 7.08–7.12 (3H,m), 7.19 (1H, t,J=8.2 Hz), 7.27–7.33 (2H,m)

(b) 4-[3-(3-Aminophenoxy)1-methylaminopropyl]phenyl dimethylcarbamate dihydrochloride t-Butyl N-[3-(3-aminophenoxy)-1-[(4-dimethylcarbamoyloxy)phenyl]propyl]-N-methylcarbamate obtained from Example 64a was treated using a similar procedure to that described in Example 6d to afford the title compound as an amorphous solid.

¹H-NMR(400 MHz,DMSO-d6) δ ppm: 2.28–2.39 (1H,m), 2.39 (3H,t,J=5.0 Hz), 2.59–2.64 (1H,m), 2.90 (3H,s), 3.03 (3H,s), 3.56–3.63 (1H,m), 3.90–3.95 (1H,m), 4.38–4.42 (1H, m), 6.66–6.75 (3H,m), 7.19–7.27 (3H,m), 7.56 (2H,d,J=8.4 Hz). MS (FAB) m/z: 344 (M+H)⁺.

EXAMPLE 65

4-[3-(3-Acetylaminophenoxy)-1-methylaminopropyl]phenyl dimethylcarbamate hydrochloride (Exemplification compound number 1-98)

(a) t-Butyl [3-(3-acetylaminophenoxy)-1-[(4-dimethylcarbamoyloxy)phenyl]propyl]methylcarbamate t-Butyl N-[3-(3-aminophenoxy)-1-[(4-dimethylcarbamoyloxy)phenyl]propyl]-N-methylcarbamate obtained from Example 64a was treated using a similar procedure to that described in Example 50a to afford the desired compound.

(b) 4-[3-(3-Acetylaminophenoxy)-1-methylaminopropyl] phenyl dimethylcarbamate hydrochloride t-Butyl [3-(3-acetylaminophenoxy)-1-[(4-dimethylcarbamoyloxy)phenyl]propyl]methylcarbamate obtained from Example 65a was treated using a similar procedure to that described in Example 6d to afford the title compound as an amorphous solid.

¹H-NMR(400 MHz,CDCl₃) δ ppm: 2.13 (3H,s), 2.48 (4H, br s), 2.86 (1H,br s), 3.03 (3H,s), 3.12 (3H,s), 3.74 (1H,br s), 3.86 (1H,br s), 4.28 (1H,br s), 6.50 (1H,d,J=5.9 Hz), 6.59 (1H,br s), 7.13–7.16 (3H,m), 7.36–7.37 (1H,m), 7.57 (2H,br s), 8.41 (1H,br s), 9.82 (1H,br s), 10.01 (1H,br s). MS (FAB) m/z: 386 (M+H)⁺.

EXAMPLE 66

4-[1-Methylamino-3-(2-nitrophenoxy)propyl]phenyl dimethylcarbamate hydrochloride (Exemplification compound number 1-93)

t-Butyl N-[1-[(4-dimethylcarbamoyloxy)phenyl]-3-hydroxypropyl]-N-methylcarbamate obtained from Example 16b and 2-nitrophenol were treated using similar procedures to those described in Example 7f and 7g to afford the title compound as an amorphous solid.

$^1$H-NMR(400 MHz,CDCl$_3$) δ ppm: 2.56 (3H,s), 2.62–2.70 (1H,m), 2.95–3.03 (1H,m), 3.00 (3H,s), 3.09 (3H,s), 3.75–3.81 (1H,m), 4.28–4.33 (1H,m), 4.46–4.50 (1H,m), 6.96 (1H,dd,J=8.0 Hz,1.0 Hz), 7.02 (1H,td,J=8.0 Hz,1.0 Hz), 7.17 (2H,d,J=8.6 Hz), 7.48 (1H,td,J=8.0 Hz,1.6 Hz), 7.69 (2H,d,J=8.6 Hz), 7.87 (1H,dd,J=8.0 Hz,1.6 Hz). MS (EI) m/z: 374 (M+H)$^+$.

EXAMPLE 67

4-[1-Methylamino-3-phenoxypropyl]phenyl dimethylcarbamate hydrochloride (Exemplification compound number 1-74)

t-Butyl N-[1-[(4-dimethylcarbamoyloxy)phenyl]-3-hydroxypropyl]-N-methylcarbamate obtained from Example 16b and phenol were treated using similar procedures to those described in Example 7f and 7g to afford the title compound as an amorphous solid.

$^1$H-NMR(400 MHz,CDCl$_3$) δ ppm: 2.48–2.59 (1H,m), 2.52 (3H,s), 2.93–3.00 (1H,m), 3.00 (3H,s), 3.09 (3H,s), 3.56–3.62 (1H,m), 3.94–3.98 (1H,m), 4.34–4.38 (1H,m), 6.79 (2H,d,J=8.5 Hz), 6.91 (1H,t,J=7.3 Hz), 7.17–7.24 (4H, m), 7.61 (2H,d,J=8.5 Hz). MS (EI) m/z: 329 (M+H)$^+$.

EXAMPLE 68

4-[3-(3-Fluorophenoxy)-1-methylaminopropyl]phenyl dimethylcarbamate hydrochloride (Exemplification compound number 1-76)

t-Butyl N-[1-[(4-dimethylcarbamoyloxy)phenyl]-3-hydroxypropyl]-N-methylcarbamate obtained from Example 16b and 3-fluorophenol were treated using similar procedures to those described in Example 7f and 7g to afford the title compound as an amorphous solid.

$^1$H-NMR(400 MHz,CDCl$_3$) δ ppm: 2.52 (3H,s), 2.52–2.61 (1H,m), 2.93–3.00 (1H,m), 3.00 (3H,s), 3.09 (3H,s), 3.55–3.61 (1H,m), 3.93–3.97 (1H,m), 4.32–4.35 (1H,m), 6.50 (1H,dt,J=10.8 Hz,2.3 Hz), 6.57 (1H,dd,J=7.3 Hz,2.3 Hz), 6.62 (1H,td,J=8.3 Hz,2.3 Hz), 7.13–7.20 (3H,m), 7.60 (2H,d,J=8.6 Hz) 9.93 (1H,br s), 10.28 (1H,br s). MS (FAB) m/z: 347 (M+H)$^+$.

EXAMPLE 69

4-[3-(2-Fluorophenoxy)-1-methylaminopropyl]phenyl dimethylcarbamate hydrochloride (Exemplification compound number 1-77)

t-Butyl N-[1-[(4-dimethylcarbamoyloxy)phenyl]-3-hydroxypropyl]-N-methylcarbamate obtained from Example 16b and 2-fluorophenol were treated using similar procedures to those described in Example 7f and 7g to afford the title compound as an amorphous solid.

$^1$H-NMR(400 MHZ,CDCl$_3$) δ ppm: 2.53 (3H,s), 2.53–2.63 (1H,m), 2.97–3.09 (1H,m), 3.00 (3H,s), 3.09 (3H, s), 3.61–3.67 (1H,m), 4.06–4.13 (1H,m), 4.39–4.41 (1H,m), 6.79–6.90 (2H,m), 6.96–7.06 (2H,m), 7.18 (2H,d,J=8.5 Hz), 7.65 (2H,d,J=8.5 Hz), 9.91 (1H,br s), 10.23 (1H,br s). MS (EI) m/z: 347 (M+H)$^+$.

EXAMPLE 70

4-[1-Dimethylamino-3-(3-fluorophenoxy)propyl] phenyl dimethylcarbamate hydrochloride (Exemplification compound number 1-133)

4-[3-(3-Fluorophenoxy)-1-methylaminopropyl]phenyl dimethylcarbamate obtained from Example 68 was treated using a similar procedure to that described in Example 3 to afford the titile compound as an amorphous solid.

$^1$H-NMR(400 MHz,CDCl$_3$) δ ppm: 2.60 (3H,s), 2.60–2.73 (1H,m), 2.91 (3H,s), 2.91–3.02 (1H,m), 3.02 (3H,s), 3.11 (3H,s), 3.49–3.55 (1H,m), 3.96–4.00 (1H,m), 4.26–4.29 (1H, m), 6.46 (1H,dt,J=10.7 Hz,2.3 Hz), 6.53 (1H,dd,J=8.3 Hz,2.3 Hz), 6.64 (1H,td,J=8.3 Hz,2.3 Hz), 7.14–7.24 (3H,m), 7.58 (2H,d,J=8.5 Hz). MS (EI) m/z: 360 (M)$^+$.

EXAMPLE 71

4-[1-Dimethylamino-3-(2-fluorophenoxy)propyl] phenyl dimethylcarbamate hydrochloride (Exemplification compound number 1-134)

4-[3-(2-Fluorophenoxy)-1-methylaminopropyl]phenyl dimethylcarbamate obtained from Example 69 was treated using a similar procedure to that described in Example 3 to afford the titile compound as an amorphous solid.

$^1$H-NMR(400 MHz,CDCl$_3$) δ ppm: 2.58 (3H,s), 2.68–2.73 (1H,m), 2.95 (4H,br s), 3.01 (3H,s), 3.10 (3H,s), 3.49–3.56 (1H,m), 4.09–4.15 (1H,m), 4.31 (1H,br s), 6.78 (1H,t,J=8.3 Hz), 6.87–6.92 (1H,m), 6.97–7.08 (2H,m), 7.21 (2H,d,J=7.9 Hz), 7.64 (2H,d,J=7.9 Hz). MS (EI) m/z: 360 (M)$^+$.

EXAMPLE 72

4-[3-(3-Acetylphenoxy)-1-methylaminopropyl]phenyl dimethylcarbamate hydrochloride (Exemplification compound number 1-90)

t-Butyl N-[1-[(4-dimethylcarbamoyloxy)phenyl]-3-hydroxypropyl]-N-methylcarbamate obtained from Example 16b and 3-acetylphenol were treated using similar procedures to those described in Example 7f and 7g to afford the title compound as an amorphous solid.

$^1$H-NMR(400 MHz,CDCl$_3$) δ ppm: 2.47–2.66 (1H,m), 2.53 (3H,s), 2.56 (3H,s), 2.93–3.06 (1H,m), 3.00 (3H,s), 3.09 (3H,s), 3.61–3.70 (1H,m), 3.98–4.07 (1H,m), 4.32–4.40 (1H, m), 7.02 (1H,dd,J=7.9 Hz,2.5 Hz), 7.18 (2H,d,J=8.5 Hz), 7.32 (1H,t,J=7.9 Hz), 7.34 (1H,br s), 7.51 (1H,d,J=7.9 Hz), 7.60 (2H,d,J=8.5 Hz), 10.10 (2H,br s). MS(EI) m/z: 371 (M+H)$^+$.

EXAMPLE 73

4-[3-(4-Chloro-3-methylphenoxy)-1-methylaminopropyl]phenyl dimethylcarbamate hydrochloride (Exemplification compound number 1-113)

t-Butyl N-[1-[(4-dimethylcarbamoyloxy)phenyl]-3-hydroxypropyl]-N-methylcarbamate obtained from Example 16b and 4-chloro-3-methylphenol were treated using similar procedures to those described in Example 7f and 7g to afford the title compound as an amorphous solid.

$^1$H-NMR(400 MHz,CDCl$_3$) δ ppm: 2.28 (3H,s), 2.50–2.62 (1H,m), 2.51 (3H,br s), 2.89–3.05 (1H,m), 3.01 (3H,s), 3.09 (3H,s), 3.50–3.59 (1H,m), 3.86–3.95 (1H,m), 4.27–4.37 (1H, m), 6.55 (1H,dd,J=8.7 Hz,2.9 Hz), 6.65 (1H,d,J=2.9 Hz), 7.15

(1H,d,J=8.7 Hz), 7.18 (2H,d,J=8.5 Hz), 7.59 (2H,d,J=8.5 Hz), 9.96 (1H,br s), 10.33 (1H,br s). MS(EI) m/z: 377 (M+H)$^+$.

EXAMPLE 74

4-[3-(3-Chloro-4-fluorophenoxy)-1-methylaminopropyl]phenyl dimethylcarbamate hydrochloride (Exemplification compound number 1-109)

t-Butyl N-[1-[(4-dimethylcarbamoyloxy)phenyl]-3-hydroxypropyl]-N-methylcarbamate obtained from Example 16b and 3-chloro-4-fluorophenol were treated using similar procedures to those described in Example 7f and 7g to afford the title compound as an amorphous solid.
$^1$H-NMR(400 MHz,CDCl$_3$) δ ppm: 2.51 (3H,br s), 2.50–2.63 (1H,m), 2.91–3.04 (1H,m), 3.01 (3H,s), 3.10 (3H, s), 3.51–3.60 (1H,m), 3.88–3.97 (1H,m), 4.25–4.36 (1H,m), 6.65 (1H,dt,J=8.9 Hz,3.0 Hz), 6.81 (1H,dd,J=6.0 Hz,3.0 Hz), 6.99 (1H,t,J=8.9 Hz), 7.20 (2H,d,J=8.6 Hz), 7.59 (2H,d,J=8.6 Hz), 9.98 (1H,br s), 10.34 (1H,br s). MS(EI) m/z: 381 (M+H)$^+$.

EXAMPLE 75

4-[3-(4-Acetylphenoxy)-1-dimethylaminopropyl] phenyl dimethylcarbamate hydrochloride (Exemplification compound number 1-146)

4-[3-(4-Acetylphenoxy)-1-methylaminopropyl]phenyl dimethylcarbamate obtained from Example 45 was treated using a similar procedure to that described in Example 3 to afford the title compound an amorphous solid.
$^1$H-NMR(400 MHz,CDCl$_3$) δ ppm: 2.53 (3H,s), 2.62 (3H, br s), 2.67–2.79 (1H,br s), 2.90 (3H,br s), 2.99 (1H,br s), 3.02 (3H,s), 3.10 (3H,s), 3.63 (1H,br s), 4.06 (1H,br s), 4.30 (1H,br s), 6.78 (2H,d,J=8.7 Hz), 7.22 (2H,d,J=8.2 Hz), 7.57 (2H,d, J=8.2 Hz), 7.87 (2H,d,J=8.7 Hz). MS(EI) m/z: 384 (M+H)$^+$.

EXAMPLE 76

4-[3-(3,4-Difluorophenoxy)-1-dimethylaminopropyl] phenyl dimethylcarbamate hydrochloride (Exemplification compound number 1-159)

4-[3-(3,4-Difluorophenoxy)-1-methylaminopropyl]phenyl dimethylcarbamate obtained from Example 54 was treated using a similar procedure to that described in Example 3 to afford the title compound an amorphous solid.
$^1$H-NMR(400 MHz,CDCl$_3$) δ ppm: 2.61 (3H,br s), 2.60–2.75 (1H,m), 2.90 (3H,br s), 2.88–3.00 (1H,m), 3.02 (3H,s), 3.11 (3H,s), 3.45–3.55 (1H,m), 3.88–3.98 (1H,m), 4.22–4.31 (1H,br s), 6.40–6.47 (1H,m), 6.56 (1H,ddd,J=11.7 Hz,6.5 Hz,2.9 Hz,), 7.01 (1H,q,J=9.4 Hz), 7.23 (2H,d,J=8.4 Hz), 7.56 (2H,d,J=8.4 Hz). MS(EI) m/z: 378 (M+H)$^+$.

EXAMPLE 77

4-[3-(3-Chlorophenoxy)-1-methylaminopropyl]phenyl diethylcarbamate hydrochloride (Exemplification compound number 1-8)

t-Butyl [3-(3-chlorophenoxy)-1-[(4-dimethylcarbamoyloxy)phenyl]propyl]-N-methylcarbamate obtained from Example 38a was treated using similar procedures to those described in Example 63 to afford the title compound as an amorphous solid.
$^1$H-NMR(400 MHz,CDCl$_3$) δ ppm: 1.18–1.28 (6H,m), 2.51 (3H,s), 2.50–2.61 (1H,m), 2.94–3.02 (1H,m), 3.36–3.44 (4H,m), 3.54–3.59 (1H,m), 3.91–3.96 (1H,m), 4.34 (1H,br s), 6.68 (1H,d,J=8.5 Hz), 6.77 (1H,s), 6.89 (1H,d,J=8.5 Hz), 7.13 (1H,t,J=8.5 Hz), 7.20 (2H,d,J=8.2 Hz), 7.60 (2H,d,J=8.2 Hz), 9.95 (1H,br s), 10.28 (1H,br s).

EXAMPLE 78

4-[3-(4-Chloro-3-fluorophenoxy)-1-dimethylaminopropyl]phenyl dimethylcarbamate hydrochloride (Exemplification compound number 1-161)

4-[3-(4-Chloro-3-fluorophenoxy)-1-methylaminopropyl] phenyl dimethylcarbamate obtained from Example 55 was treated using a similar procedure to that described in Example 3 to afford the title compound as an amorphous solid.
$^1$H-NMR(400 MHz,CDCl$_3$) δ ppm: 2.61 (3H,br s), 2.62–2.75 (1H,m), 2.90 (3H,br s), 2.96 (1H,br s), 3.02 (3H,s), 3.11 (3H,s), 3.46–3.55 (1H,m), 3.91–4.01 (1H,m), 4.26 (1H, br s), 6.49 (1H,dd,J=8.8 Hz,1.8 Hz), 6.55 (1H,dd,J=10.6 Hz,2.6 Hz,), 7.21 (2H,d,J=8.6 Hz), 7.23 (1H,d,J=8.8 Hz), 7.55 (2H,d,J=8.6 Hz). MS(EI) m/z: 394 (M+H)$^+$.

EXAMPLE 79

4-[3-(3,5-Difluorophenoxy)-1-methylaminopropyl] phenyl dimethylcarbamate hydrochloride (Exemplification compound number 1-103)

t-Butyl N-[1-[(4-dimethylcarbamoyloxy)phenyl]-3-hydroxypropyl]-N-methylcarbamate obtained from Example 16b and 3,5-difluorophenol were treated using similar procedures to those described in Example 7f and 7g to afford the title compound as an amorphous solid.
$^1$H-NMR(400 MHz,CDCl$_3$) δ ppm: 2.52 (3H,br s), 2.52–2.63 (1H,m), 2.91–3.03 (1H,m), 3.01 (3H,s), 3.10 (3H, s), 3.52–3.61 (1H,m), 3.90–3.98 (1H,m), 4.30 (1H,br s), 6.32 (2H,dd,J=8.8 Hz,2.1 Hz), 6.38 (1H,tt,J=9.0 Hz,2.1 Hz), 7.20 (2H,d,J=8.5 Hz), 7.59 (2H,d,J=8.5 Hz), 9.99 (1H,br s), 10.38 (1H,br s). MS(EI) m/z: 365 (M+H)$^+$.

EXAMPLE 80

4-[1-Methylamino -3-(3,4,5-trifluorophenoxy)propyl]phenyl dimethylcarbamate hydrochloride (Exemplification compound number 1-117)

t-Butyl N-[1-[(4-dimethylcarbamoyloxy)phenyl]-3-hydroxypropyl]-N-methylcarbamate obtained from Example 16b and 3,4,5-trifluorophenol were treated using similar procedures to those described in Example 7f and 7g to afford the title compound as an amorphous solid.
$^1$H-NMR(400 MHz,CDCl$_3$) δ ppm: 2.51 (3H,br s), 2.52–2.63 (1H,m), 2.92–3.03 (1H,m), 3.01 (3H,s), 3.10 (3H, s), 3.49–3.58 (1H,m), 3.87–3.95 (1H,m), 4.28 (1H,br s), 6.37–6.47 (2H,m), 7.20 (2H,d,J=8.6 Hz), 7.59 (2H,d,J=8.6 Hz), 9.99 (1H,br s), 10.34 (1H,br s) MS(EI) m/z: 381 (M+H)$^+$.

EXAMPLE 81

(S)-4-[3-(3-Chlorophenoxy)-1-methylaminopropyl] phenyl dimethylcarbamate hydrochloride (Exemplification compound number 1-79)

(a) t-Butyl (S)-[1-[(4-dimethylcarbamoyloxy)phenyl]-3-hydroxypropyl]carbamate
Methyl (S)-3-amino-3-(4-hydroxyphenyl)propionate, which was synthesized according to the method described in Tetrahedron: Asymmetry, 2, 183, (1991), was treated using similar procedures to those described in Example 61a and 61b to afford the desired compound.

$^1$H-NMR(500 MHz,CDCl$_3$) δ ppm: 1.42 (9H,s), 2.78–2.90 (2H,m), 3.00 (3H,s), 3.09.(3H,s), 3.62 (3H,s), 5.09 (1H,br s), 5.42 (1H,br s), 7.07 (2H,d,J=9.0 Hz), 7.28 (2H,d,J=9.0 Hz).

(b) (S)-4-[3-(3-Chlorophenoxy)-1-methylaminopropyl]phenyl dimethylcarbamate hydrochloride t-Butyl (S)-[1-[(4-dimethylcarbamoyloxy)phenyl]-3-hydroxypropyl]carbamate obtained from Example 81a and 3-chlorophenol were treated using similar procedures to those described Example 7f, 61d and 61e to afford the title compound as an amorphous solid.

$^1$H-NMR(400 MHZ,CDCl$_3$) δ ppm: 2.52 (3H,s), 2.52–2.61 (1H,m), 2.93–3.05 (1H,m), 3.00 (3H,s), 3.09 (3H, s), 3.55–3.60 (1H,m), 3.92–3.97 (1H,m), 4.31–4.35 (1H,m), 6.68 (1H,dd,J=8.1 Hz,2.1 Hz), 6.78 (1H,t,J=2.1 Hz), 6.90 (1H,dd,J=8.1 Hz,2.1 Hz), 7.14 (1H,t,J=8.1 Hz), 7.19 (2H,d, J=8.5 Hz), 7.60 (2H,d,J=8.5 Hz).

EXAMPLE 82

(S)-4-[3-(4-Chlorophenoxy)-1-methylaminopropyl] phenyl dimethylcarbamate hydrochloride (Exemplification compound number 1-78)

t-Butyl (S)-[1-([(4-dimethylcarbamoyloxy)phenyl]-3-hydroxypropyl]carbamate obtained from Example 81a and 4-chlorophenol were treated using similar procedures to those described Example 7f, 61d and 61e to afford the title compound as an amorphous solid.

$^1$H-NMR(400 MHz,CDCl$_3$) δ ppm: 2.51 (3H,s), 2.51–2.59 (1H,m), 2.94–3.01 (1H,m), 3.01 (3H,s), 3.09 (3H,s), 3.55–3.59 (1H,m), 3.91–4.13 (1H,m), 4.30–4.34 (1H,m), 6.71 (2H,d,J=9.0 Hz), 7.15–7.19 (4H,m), 7.59 (2H,d,J=8.6 Hz).

EXAMPLE 83

4-[3-(4-Chlorophenoxy)-1-methylaminopropyl]phenyl N-ethyl-N-methylcarbamate hydrochloride (Exemplification compound number 1-10)

(a) t-Butyl N-[3-(4-chlorophenoxy)-1-[4-(N-ethyl-N-methylcarbamoyloxy)phenyl]propyl]-N-methylcarbamate t-Butyl N-[3-(4-chlorophenoxy)-1-(3-hydroxyphenyl) propyl]-N-methylcarbamate (200 mg, 0.51 mmol) obtained from Example 63a was dissolved in dichloromethane (3 ml) and to the solution was added N,N-carbonyldiimidazole (165 mg, 1.0 mmol). The mixture was stirred at room temperature overnight and then ethylamine (0.09 ml, 1.0 mmol) was added thereto. The resulting mixture was stirred for one day. The reaction mixture was partitioned between water and dichloromethane. The organic layer was dried over anhydrous magnesium sulfate and concentrated under reduced pressure. The residue was purified by chromatography on a silica gel column using hexane:ethyl acetate=80: 20 to 60 40 as the eluent to afford the desired compound (96 mg).

$^1$H-NMR(400 MHz,CDCl$_3$) δ ppm: 1.17–1.26 (6H,m), 1.41 (9H,s), 2.33–2.57 (2H,m), 2.59 (3H,s), 2.99 (3H,s), 3.07 (3H,s), 3.41 (2H,q,J=7.1 Hz), 3.46 (2H,q,J=7.1 Hz), 3.98 (2H,br s), 5.56 (1H,br s), 6.81 (2H,d,J=9.0 Hz), 7.10 (2H,d, J=6.4 Hz), 7.22 (2H,d,J=9.0 Hz), 7.29 (2H,d,J=6.4 Hz).

(b) 4-[3-(4-Chlorophenoxy)-1-methylaminopropyl]phenyl N-ethyl-N-methylcarbamate hydrochloride t-Butyl N-[3-(4-chlorophenoxy)-1-[4-(N-ethyl-N-methylcarbamoyloxy)phenyl]propyl]-N-methylcarbamate obtained from Example 83a was treated using a similar procedure to that described in Example 6d to afford the title compound as an amorphous solid.

$^1$H-NMR(400 MHz,CDCl$_3$) δ ppm: 1.19 and 1.23 (3H,t, J=7.1 Hz), 2.50 (3H,s), 2.49–2.60 (1H,m), 2.92–3.00 (1H,m), 2.98 and 3.06 (3H,s), 3.40 and 3.46 (2H,q,J=7.1 Hz), 3.53–3.60 (1H,m), 3.89–3.96 (1H,m), 4.32 (1H,br s), 6.71 (2H,d,J=8.9 Hz), 7.15–7.20 (4H,m), 7.59 (2H,d,J=8.4 Hz), 9.93 (1H,br s), 10.30 (1H,br s).

EXAMPLE 84

4-[3-(3,5-Difluorophenoxy)-1-dimethylaminopropyl] phenyl dimethylcarbamate hydrochloride (Exemplification compound number 1-160)

4-[3-(3,5-Difluorophenoxy)-1-methylaminopropyl]phenyl dimethylcarbamate obtained from Example 79 was treated using a similar procedure to that described in Example 3 to afford the title compound as an amorphous solid.

$^1$H-NMR(400 MHz,CDCl$_3$) δ ppm: 2.60 (3H,br s), 2.63–2.75 (1H,m), 2.90 (3H,br s), 2.92–3.03 (1H,m), 3.02 (3H,s), 3.11 (3H,s), 3.44–3.55 (1H,m), 3.92–4.00 (1H,m), 4.20–4.28 (1H,m), 6.23–6.32 (2H,m), 6.40 (1H,tt,J=8.9 HZ,2.2 HZ), 7.24 (2H,d,J=8.5 Hz), 7.56 (2H,d,J=8.5 Hz). MS(EI) m/z: 378 (M+H$^{30}$.

EXAMPLE 85

4-[3-(2,4-Difluorophenoxy)-1-dimethylaminopropyl] phenyl dimethylcarbamate hydrochloride (Exemplification compound number 1-158)

4-[3-(2,4-Difluorophenoxy)-1-methylaminopropyl]phenyl dimethylcarbamate obtained from Example 43 was treated using a similar procedure to that described in Example 3 to afford the title compound as an amorphous solid.

$^1$H-NMR(400 MHz,CDCl$_3$) δ ppm: 2.59 (3H,br s), 2.63–2.75 (1H,m), 2.94 (3H,br s), 2.90–3.01 (1H,m), 3.02 (3H,s), 3.10 (3H,s), 3.47–3.57 (1H,m), 4.02–4.08 (1H,m), 4.25–4.34 (1H,m), 6.68–6.78 (2H,m), 6.79–6.87 (1H,m), 7.23 (2H,d,J=8.3 Hz), 7.63 (2H,d,J=8.3 Hz). MS(EI) m/z: 378 (M+H)$^+$.

EXAMPLE 86

4-[1-Dimethylamino-3-(3-nitrophenoxy)propyl]phenyl dimethylcarbamate hydrochloride (Exemplification compound number 1-151)

4-[1-Methylamino-3-(3-nitrophenoxy)propyl]phenyl dimethylcarbamate obtained from Example 53 was treated using a similar procedure to that described in Example 3 to afford the title compound as an amorphous solid.

$^1$H-NMR(400 MHz,CDCl$_3$) δ ppm: 2.62 (3H,d,J=4.7 Hz), 2.70–2.78 (1H,m), 2.89 (3H,d,J=4.7 Hz), 2.99–3.09 (1H,m), 3.02 (3H,s), 3.11 (3H,s), 3.63–3.69 (1H,m), 4.06–4.09 (1H, m), 4.29–4.34 (1H,m), 7.10 (1H,dd,J=8.2 Hz,2.3 Hz), 7.24 (2H,d,J=8.7 Hz), 7.40 (1H,t,J=8.2 Hz), 7.55–7.57 (3H,m), 7.81 (1H,dd,J=8.2 Hz,2.3 Hz). MS (EI) m/z: 387 (M)$^+$.

EXAMPLE 87

4-[3-(3-Chlorophenylamino)-1-methylaminopropyl] phenyl dimethylcrbamate dihydrochloride (Exemplification compound number 1-52)

(a) t-Butyl N-[3-[N-t-butoxycarbony-N-methylamino]-3-[(4-dimethylcarbamoyloxy)phenyl]propyl]-N-(3-chlorophenyl)carbamate t-Butyl N-[1-[(4-dimethylcarbamoyloxy)phenyl-3-hydroxypropyl]-N-methylcarbamate (100 mg, 0.28 mmol) obtained from Example 16b was dissolved in tetrahydrofuran (1.5 ml) under an atmosphere of nitrogen. To the solution were added sequentially triethylamine (0.07 ml, 0.50 mmol) and methanesulfonyl chloride (0.03 ml, 0.34 mmol) in an ice bath. The resulting mixture was stirred at room temperature for 45 minutes. The reaction mixture was partitioned between water and ethyl acetate. The organic layer was washed with saturated aqueous sodium chloride solution, dried over anhydrous magnesium sulfate and concentrated under reduced pressure to give the methanesulfonate. On the other hand N,N-dimethylformamide (1.5 ml) was added to sodium hydride (15 mg, 0.33 mmol) and to the sodium hydride was added a solution of t-butyl (3-chlorophenyl)carbamate (75 mg, 0.33 mmol) in N,N-dimethylformamide in an ice bath. This mixture was stirred for 30 minutes and then a solution of the methanesulfonate obtained above in N,N-dimethylformamide was added thereto. The resulting mixture was stirred at room temperature 2 days. The reaction mixture was partitioned between water and ether. The organic layer was washed with saturated aqueous sodium chloride solution, dried over anhydrous sodium sulfate and concentrated under reduced pressure. The residue was purified by chromatography on a silica gel column using hexane:ethyl acetate=60:40 as the eluent to afford the desired compound (106 mg)

$^1$H-NMR(400 MHz,CDCl$_3$) δ ppm: 1.44 (9H,s), 1.47 (9H, s), 2.10–2.18 (2H,m), 2.56 (3H,s), 3.01 (3H,s), 3.09 (3H,s), 3.67 (2H,brs), 5.44 (1H,brs), 7.06 (2H,d,J=8.6 Hz), 7.11 (1H, d,J=8.3 Hz), 7.17–7.29 (5H,m).

(b) 4-[3-(3-Chlorophenylamino)-1-methylaminopropyl]phenyl dimethylcarbamate dihydrochloride t-Butyl N-[3-[N-t-butoxycarbony-N-methylamino]-3-[(4-dimethylcarbamoyloxy)phenyl]propyl]-N-(3-chlorophenyl)carbamate obtained from Example 87a was treated using a similar procedure to that described in Example 6d to afford the title compound.

$^1$H-NMR(400 MHz,CDCl$_3$) δ ppm: 2.46 (3H,s), 2.77–2.82 (1H,m), 3.01 (3H,s), 3.10 (3H,s), 3.21 (1H,t,J=10.7 Hz), 3.36 (2H,br s), 4.08 (1H,br s), 7.25 (2H,d,J=8.0 Hz), 7.33 (2H,d, J=6.7 Hz), 7.46 (1H,br s), 7.56 (1H,s), 7.63 (2H,br s). MS (EI) m/z: 361 (M)$^+$.

EXAMPLE 88

4-[3-(3-Fluoro-4-nitrophenoxy)-1-methylaminopropyl]phenyl dimethylcarbamate hydrochloride (Exemplification compound number 1-195)

3-Fluoro-4-nitrophenol was treated using similar procedures to those described in Example 48 to afford the title compound as an amorphous solid.

$^1$H-NMR(400 MHz,CDCl$_3$) δ ppm: 2.52 (3H,s), 2.62–2.68 (1H,m), 3.01 (3H,s), 3.01–3.07 (1H,m), 3.10 (3H,s), 3,72–3.76 (1H,m), 4.08–4.10 (1H,m), 4.23–4.31 (1H,m), 6.63–6.68 (2H,m), 7.21 (2H,d,J=8.6 Hz), 7.59 (2H,d,J=8.6 Hz), 8.05 (1H,t,J=8.9 Hz). MS (FAB) m/z: 392 (M+H)$^+$.

EXAMPLE 89

4-[1-Dimethylamino-3-(4-nitrophenoxy)propyl]phenyl dimethylcarbamate hydrochloride (Exemplification compound number 1-149)

4-[1-Methylamino-3-(4-nitrophenoxy)propyl]phenyl dimethylcarbamate obtained from Example 48b was treated using a similar procedure to that described in Example 3 to afford the title compound as an amorphous solid.

$^1$H-NMR(400 MHZ,CDCl$_3$) δ ppm: 2.62 (3H,br s), 2.72–2.79 (1H,m), 2.88 (3H,br s), 2.99–3.07 (1H,m), 3.02 (3H,s), 3.11 (3H,s), 3.67–3.73 (1H,m), 4.08–4.13 (1H,m), 4.28–4.31 (1H,m), 6.81 (2H,d,J=9.2 Hz), 7.24 (2H,d,J=8.6 Hz), 7.55 (2H,d,J=8.6 Hz), 8.15 (2H,d,J=9.2 Hz). MS (EI) m/z: 387 (M)$^+$.

EXAMPLE 90

4-[3-(4-Chloro-3-nitrophenoxy)-1-methylaminopropyl]phenyl dimethylcarbamate hydrochloride (Exemplification compound number 1-116)

t-Butyl N-[1-[(4-dimethylcarbamoyloxy)phenyl]-3-hydroxypropyl]-N-methylcarbamate obtained from Example 16b and 4-chloro-3-nitrophenol were treated using similar procedures to those described in Example 7f and 7g to afford the title compound as an amorphous solid.

$^1$H-NMR(400 MHz,CDCl$_3$) δ ppm: 2.51 (3H,s), 2.59–2.67 (1H,m), 2.97–3.10 (1H,m), 3.01 (3H,s), 3.10 (3H,s), 3.67–3.73 (1H,m), 4.02–4.07 (1H,m), 4.28–4.31 (1H,m), 6.98 (1H,dd,J=8.9 Hz,3.0 Hz), 7.21 (2H,d,J=8.5 Hz), 7.28 (1H,d,J=3.0 Hz), 7.39 (1H,d,J=8.9 Hz), 7.59 (2H,d,J=8.5 Hz). MS (FAB) m/z: 408 (M+H)$^+$.

EXAMPLE 91

4-[1-Methylamino-3-(2,3,5-trifluorophenoxy)propyl] phenyl dimethylcarbamate hydrochloride (Exemplification compound number 1-118)

t-Butyl N-[1-[(4-dimethylcarbamoyloxy)phenyl]-3-hydroxypropyl]-N-methylcarbamate obtained from Example 16b and 2,3,5-trifluorophenol were treated using similar procedures to those described in Example 7f and 7g to afford the title compound as an amorphous solid.

$^1$H-NMR(400 MHZ,CDCl$_3$) δ ppm: 2.54 (3H,s), 2.62–2.68 (1H,m), 3.02 (3H,s), 3.02–3.11 (1H,m), 3.11 (3H, s), 3.62–3.66 (1H,m), 4.09–4.12 (1H,m), 4.35–4.38 (1H,m), 6.35–6.39 (1H,m), 6.49–6.54 (1H,m), 7.22 (2H,d,J=8.3 Hz), 7.65 (2H,d,J=8.3 Hz). MS (FAB) m/z: 383 (M+H)$^+$.

EXAMPLE 92

4-[3-(3-Fluorophenylamino)-1-methylaminopropyl] phenyl dimethylcarbamate dihydrochloride (Exemplification compound number 1-51)

t-Butyl (3-fluorophenyl)carbamate was treated using similar procedures to those described in Example 87 to afford the title compound as an amorphous solid.

$^1$H-NMR(400 MHz,CDCl$_3$) δ ppm: 2.46 (3H,s), 2.76–2.82 (1H,m), 3.01 (3H,s), 3.10 (3H,s), 3.20–3.26 (1H,m), 3.34–3.45 (2H,m), 4.07–4.13 (1H,m), 7.06–7.11 (1H,m), 7.24–7.26 (1H,m), 7.30–7.42 (4H,m), 7.64 (2H,br s). MS (FAB) m/z: 346 (M+H)$^+$.

EXAMPLE 93

4-[2-(4-Chlorophenoxy)-1-methylaminoethyl]phenyl dimethylcarbamate hydrochloride (Exemplification compound number 1-34)

(a) 2-(4-Chlorophenoxy)-1-[(4-methoxymethoxy)phenyl]ethanone

1-Iodo-4-methoxymethoxybenzene (1.72 g, 6.5 mmol), which was synthesized according to the method described in Chem. Abstr., 68, 87026, (1968), was dissolved in tetrahydrofuran (40 ml) and 1.5N solution of butyl lithium in hexane (4.3 ml, 6.5 mmol) was added dropwise to the solution at −78° C. The resulting mixture was stirred for 30 minutes and then to the mixture was added a solution of 2-(4-chlorophenoxy)-N-methoxy-N-methylacetamide (1.00 g, 4.4 mmol), which was synthesized according to the method described in Tetrahedron, 54, 15861, (1998), in tetrahydrofuran. The mixture was stirred for 2 hours and the reaction mixture was partitioned between saturated aqueous sodium chloride solution and ether. The organic layer was dried over anhydrous magnesium sulfate and concentrated under reduced pressure. The residue was purified by chromatography on a silica gel column using hexane:ethyl acetate=95:5 to 80:20 as the eluent to afford the desired compound (1.02 g).

$^1$H-NMR(400 MHz,CDCl$_3$) δ ppm: 3.49 (3H,s), 5.20 (2H,s), 5.25 (2H,s), 6.87 (2H,d,J=9.0 Hz), 7.11 (2H,d,J=8.9 Hz), 7.23 (2H,d,J=9.0 Hz), 7.97 (2H,d,J=8.9 Hz).

(b) 2-(4-Chlorophenoxy)-1-(4-hydroxyphenyl)ethanone 2-(4-Chlorophenoxy)-1-[(4-methoxymethoxy)phenyl]ethanone (1.01 g, 3.3 mmol) obtained from Example 93a was dissolved in acetone (10 ml) and to the solution was added 4N aqueous hydrochloric acid solution (10 ml). The resulting mixture was stirred at room temperature overnight and the reaction mixture was neutralized with saturated aqueous sodium hydrogencarbonate solution. The mixture was extracted with ethyl acetate. The organic layer was dried over anhydrous magnesium sulfate and concentrated under reduced pressure to afford the crude desired compound (0.85 g) which was used in next step reaction without further purification.

$^1$H-NMR(400 MHz,CDCl$_3$) δ ppm: 5.34 (2H,s), 6.63 (1H,s), 6.89 (2H,d,J=8.8 Hz), 6.93 (2H,d,J=9.1 Hz), 7.24 (2H,d,J=9.1 Hz), 7.94 (2H,d,J=8.8 Hz).

(c) 4-(2-(4-Chlorophenoxy)-1-methylaminoethyl]phenyl dimethylcarbamate hydrochloride 2-(4-Chlorophenoxy)-1-(4-hydroxyphenyl)ethanone obtained in Example 93b was treated using similar procedures to those described in Example 1a, and 1d to 1f, to afford the title compound as an amorphous solid.

$^1$H-NMR(400 MHz,CDCl$_3$) δ ppm: 2.36 (3H,s), 3.02 (3H,s), 3.11 (3H,s), 4.27–4.36 (2H,m), 4.60 (1H,dd,J=11.3 Hz,9.2 Hz), 6.96 (2H,d,J=8.9 Hz), 7.16 (2H,d,J=8.9 Hz), 7.21 (2H,d,J=8.6 Hz), 7.67 (2H,d,J=8.6 Hz), 10.21 (2H,br s). MS(FAB) m/z: 349 (M+H)$^+$

EXAMPLE 94

3-[3-(3-Fluorophenoxy)-1-methylaminopropyl]phenyl dimethylcarbamate hydrochloride (Exemplification compound number 2-76)

3-Fluorophenol was treated using similar procedures to those described in Example 7f and 7g to afford the title compound as an amorphous solid.

$^1$H-NMR(400 MHz,CDCl$_3$) δ ppm: 2.41–2.61 (1H,m), 2.53 (3H,br s), 2.90–3.02 (1H,m), 2.99 (3H,s), 3.08 (3H,s), 3.59–3.65 (1H,m), 3.94–3.99 (1H,m), 4.32 (1H,br s), 6.51 (1H,dt,J=11.0 Hz,2.2 Hz), 6.57–6.64 (2H,m), 7.13–7.20 (2H, m), 7.33 (1H,s), 7.41–7.47 (2H,m), 9.94 (1H,br s), 10.36 (1H,br s). MS(FAB) m/z: 347 (M+H)$^+$.

EXAMPLE 95

3-[1-Methylamino-3-(4-nitrophenoxy)propyl]phenyl dimethylcarbamate hydrochloride (Exemplification compound number 2-92)

t-Butyl N-[1-[(3-dimethylcarbamoyloxy)phenyl]-3-hydroxypropyl]-N-methylcarbamate obtained from Example 7e was treated using similar procedures to those described in Example 48 to afford the title compound as an amorphous solid.

$^1$H-NMR(400 MHz,CDCl$_3$) δ ppm: 2.54 (3H,s), 2.65–2.70 (1H,m), 2.98 (3H,s), 3.01–3.10 (1H,m), 3.07 (3H,s), 3.75–3.81 (1H,m), 4.08–4.13 (1H,m), 4.30 (1H,dd,J=9.9 Hz,4.1 Hz), 6.87 (2H,d,J=9.3 Hz), 7.17–7.21 (1H,m), 7.31 (1H,s), 7.43–7.48 (2H,m), 8.15 (2H,d,J=9.3 Hz),10.05 (1H,br s), 10.48 (1H,br s). MS(FAB) m/z: 374 (M+H)$^+$.

EXAMPLE 96

4-[3-(2-Fluoro-4-nitrophenoxy)-1-methylaminopropyl]phenyl dimethylcarbamate hydrochloride (Exemplification compound number 1-105)

2-Fluoro-4-nitrophenol was treated using similar procedures to those described in Example 48 to afford the title compound as an amorphous solid.

$^1$H-NMR(400 MHz,CDCl$_3$) δ ppm: 2.53 (3H,s), 2.66–2.74 (1H,m), 3.01 (3H,s), 3.05–3.14 (1H,m), 3.09 (3H,s), 3.76–3.82 (1H,m), 4.21–4.26 (1H,m), 4.34–4.37 (1H,m), 6.88 (1H,t,J=8.7 Hz), 7.21 (2H,d,J=8.6 Hz), 7.63 (2H,d,J=8.6 Hz), 7.95–8.00 (2H,m). MS (FAB) m/z: 392 (M+H)$^+$.

EXAMPLE 97

4-[3-(4-Fluorophenylamino)-1-methylaminopropyl]phenyl dimethylcarbamate dihydrochloride (Exemplification compound number 1-49)

t-Butyl (4-fluorophenyl)carbamate was treated using similar procedures to those described in Example 87 to afford the title compound as an amorphous solid.

$^1$H-NMR(400 MHz,CDCl$_3$) δ ppm: 2.46 (3H,s), 2.72–2.77 (1H,m), 3.01 (3H,s), 3.09 (3H,s), 3.17–3.22 (1H,m), 3.38–3.49 (2H,m), 4.01–4.09 (1H,br s), 7.10 (2H,t,J=8.4 Hz), 7.24–4.26 (2H,m), 7.62–7.65 (4H,m).

EXAMPLE 98

(S)-4-[1-Methylamino-3-(4-nitrophenoxy)propyl]phenyl dimethylcarbamate hydrochloride (Exemplification compound number 1-92)

(a) t-Butyl (S)-[1-[(4-dimethylcarbamoyloxy)phenyl]-3-(4-nitrophenoxy)propyl]carbamate t-Butyl (S)-[1-[(4-dimethylcarbamoyloxy)phenyl]-3-hydroxypropyl]carbamate obtained from Example 81a and 4-nitrophenol were treated using a similar procedure to that described in Example 48a to afford the desired compound.

¹H-NMR(400 MHz,CDCl₃) δ ppm: 1.40 (9H,s), 2.17–2.40 (2H,m), 3.01 (3H,s), 3.10 (3H,s), 3.96–4.10 (2H,m), 4.90–5.01 (2H,br s), 6.91 (2H,d,J=8.8 Hz), 7.09 (2H,d,J=8.8 Hz), 7.27 (2H,d,J=8.8 Hz), 8.19 (2H,d,J=8.8 Hz).

(b) (S)-4-[1-Methylamino-3-(4-nitrophenoxy)propyl]phenyl dimethylcarbamate hydrochloride t-Butyl (S)-[1-[(4-dimethylcarbamoyloxy)phenyl]-3-(4-nitrophenoxy)propyl]carbamate obtained from Example 98a was treated using similar procedures to those described in Example 61d and 61e to afford the title compound.

¹H-NMR(400 MHz,CDCl₃) δ ppm: 2.52 (3H,s), 2.62–2.66 (1H,m), 3.01 (3H,s), 3.01–3.10 (1H,m), 3.10 (3H,s), 3.72–3.75 (1H,m), 4.07–4.11 (1H,m), 4.29–4.32 (1H,m), 6.86 (2H,d,J=9.2 Hz), 7.20 (2H,d,J=8.4 Hz), 7.59 (2H,d,J=8.4 Hz), 8.15 (2H,d,J=9.2 Hz). $[\alpha]_D^{22}$ +143.6 (CHCl₃, C=1.01) MS(FAB) m/z: 374 (M+H)⁺.

EXAMPLE 99

(S)-4-[1-Dimethylamino-3-(4-nitrophenoxy)propyl]phenyl dimethylcarbamate hydrochloride (Exemplification compound number 1-149)

(S)-4-[1-Methylamino-3-(4-nitrophenoxy)propyl]phenyl dimethylcarbamate obtained from Example 98 was treated using a similar procedure to that described in Example 3 to give the desired product, which was recrystallized from a mixture of ethyl acetate and hexane to afford the title compound as crystals (mp 180.5–181.5° C.)

¹H-NMR(400 MHz,CDCl₃) δ ppm: 2.62 (3H,br s), 2.72–2.79 (1H,m), 2.88 (3H,br s), 2.99–3.07 (1H,m), 3.02 (3H,s), 3.11 (3H,s), 3.67–3.73 (1H,m), 4.08–4.13 (1H,m), 4.28–4.31 (1H,m), 6.81 (2H,d,J=9.2 Hz), 7.24 (2H,d,J=8.6 Hz), 7.55 (2H,d,J=8.6 Hz), 8.15 (2H,d,J=9.2 Hz). $[\alpha]_D^{22}$ +116.0 (CHCl₃,C=0.94) MS(EI) m/z: 387 (M)⁺.

EXAMPLE 100

(R)-4-[1-Amino-3-(4-nitrophenoxy)propyl]phenyl dimethylcarbamate hydrochloride (Exemplification compound number 1-66)

(a) t-Butyl (R)-[1-[(4-dimethylcarbamoyloxy)phenyl]-3-(4-nitrophenoxy)propyl]carbamate t-Butyl (R)-[1-[(4-dimethylcarbamoyloxy)phenyl]-3-hydroxypropyl]carbamate obtained from Example 61b and 4-nitrophenol were treated using a similar procedure to that described in Example 48a to afford the desired compound.

¹H NMR(CDCl₃, 400 MHz) δ ppm: 1.40 (9H, s), 2.18–2.40 (2H, m), 3.01 (3H, s), 3.09 (3H, s), 3.99 (1H, dt, J=6.2, 9.6 Hz), 4.08 (1H, dt, J=6.2, 9.6 Hz), 4.85–5.03 (2H, br), 6.91 (2H, d, J=8.8 Hz), 7.09 (2H, d, J=8.8 Hz), 7.27 (2H, d, J=8.8 Hz), 8.18 (2H, d, J=8.8 Hz).

(b) (R)-4-[1-Amino-3-(4-nitrophenoxy)propyl]phenyl dimethylcarbamate hydrochloride t-Butyl (R)-[1-[(4-dimethylcarbamoyloxy)phenyl]-3-(4-nitrophenoxy)propyl]carbamate obtained from Example 100a was treated using a similar procedure to that described in Example 6d to afford the title compound as an amorphous solid.

¹H-NMR(400 MHz,CDCl₃) δ ppm: 2.36–2.46 (1H,m), 2.66–2.75 (1H,m), 2.95 (3H,s), 3.07 (3H,s), 3.81–3.89 (1H,m), 4.06–4.14 (1H,m), 4.46 (1H,dt,J=5.6 Hz,3.2 Hz), 6.87 (2H,d,J=9.6 Hz), 7.06 (2H,d,J=8.8 Hz), 7.52 (2H,d,J=8.8 Hz), 8.14 (2H,d,J=9.6 Hz). $[\alpha]_D^{22}$ −110.5 (CHCl₃,C=1.04) MS(FAB) m/z: 360 (M+H)⁺.

EXAMPLE 101

(R)-4-[1-Methylamino-3-(4-nitrophenoxy)propyl]phenyl dimethylcarbamate hydrochloride (Exemplification compound number 1-92)

t-Butyl (R)-[1-[(4-dimethylcarbamoyloxy)phenyl]-3-(4-nitrophenoxy)propyl]carbamate obtained from Example 100a was treated using similar procedures to those described in Example 61d and 61e to afford the title compound as an amorphous solid.

¹H-NMR(400 MHz,CDCl₃) δ ppm: 2.52 (3H,s), 2.62–2.66 (1H,m), 3.01 (3H,s), 3.01–3.10 (1H,m), 3.10 (3H,s), 3.72–3.75 (1H,m), 4.07–4.11 (1H,m), 4.29–4.32 (1H,m), 6.86 (2H,d,J=9.2 Hz), 7.20 (2H,d,J=8.4 Hz), 7.59 (2H,d,J=8.4 Hz), 8.15 (2H,d,J=9.2 Hz). $[\alpha]_D^{22}$ −142.1 (CHCl₃, C=1.00) MS(FAB) m/z: 374 (M+H)⁺.

EXAMPLE 102

(R)-4-[1-Dimethylamino-3-(4-nitrophenoxy)propyl]phenyl dimethylcarbamate hydrochloride (Exemplification compound number 1-149)

(R)-4-[1-Methylamino-3-(4-nitrophenoxy)propyl]phenyl dimethylcarbamate obtained from Example 101 was treated using a similar procedure to that described in Example 3 to afford the title compound as an amorphous solid.

¹H-NMR(400 MHz,CDCl₃) δ ppm: 2.62 (3H,br s), 2.72–2.79 (1H,m), 2.88 (3H,br s), 2.99–3.07 (1H,m), 3.02 (3H,s), 3.11 (3H,s), 3.67–3.73 (1H,m), 4.08–4.13 (1H,m), 4.28–4.31 (1H,m), 6.81 (2H,d,J=9.2 Hz), 7.24 (2H,d,J=8.6 Hz), 7.55 (2H,d,J=8.6 Hz), 8.15 (2H,d,J=9.2 Hz). $[\alpha]_D^{22}$ −115.2 (CHCl₃,C=0.92) MS(EI) m/z: 387 (M+H)⁺.

EXAMPLE 103

4-[1-Methylamino-3-(pyridin-3-yloxy)propyl]phenyl dimethylcarbamate dihydrochloride (Exemplification compound number 1-119)

t-Butyl N-[1-(4-dimethylcarbamoyloxy)phenyl-3-hydroxypropyl]-N-methylcarbamate obtained from Example 16b and 3-hydroxypyridine were treated using similar procedures to those described in Example 7f and 7g to afford the title compound as an amorphous solid.

¹H-NMR(400 MHz,CDCl₃) δ ppm: 2.45–2.56 (1H,m), 2.58 (3H,s), 2.65–3.73 (1H,m), 3.07 (3H,s), 3.99–4.04 (1H,m), 4.21–4.26 (1H,m), 4.49 (1H,dd,J=10.4 Hz,4.4 Hz), 7.19 (2H,d,J=8.8 Hz), 7.48 (2H,d,J=8.8 Hz), 7.85–7.89 (1H,m), 8.00 (1H,d,J=7.2 Hz), 8.37 (1H,d,J=6.0 Hz), 8.39 (1H,a).

EXAMPLE 104

3-[1-Dimethylamino-3-(4-nitrophenoxy)propyl]phenyl dimethylcarbamate hydrochloride (Exemplification compound number 2-149)

3-[1-Methylamino-3-(4-nitrophenoxy)propyl]phenyl dimethylcarbamate obtained from Example 95 was treated using a similar procedure to that described in Example 3 to afford the title compound as an amorphous solid.

¹H-NMR(400 MHz,CDCl₃) δ ppm: 2.53–2.9 (7H,m), 3.00 (3H,s), 2.98–3.12 (1H,m), 3.09 (3H,s), 3.75–3.81 (1H,m), 4.10–4.15 (1H,m), 4.34 (1H,dd,J=11.0 Hz,3.7 Hz), 6.82 (2H, d,J=8.8 Hz), 7.24 (1H,d,J=7.7 Hz), 7.3 (1H,s), 7.36 (1H,d, J=7.7 Hz), 7.46 (1H,t,J=7.7 Hz), 8.14 (2H,d,J=8.8 Hz). MS(FAB) m/z: 388 (M+H)⁺.

EXAMPLE 105

4-[1-Ethylamino-3-(3-nitrophenoxy)propyl]phenyl dimethylcarbamate hydrochloride (Exemplification compound number 1-70)

(a) t-Butyl N-[1-[(4-dimethylcarbamoyloxy)phenyl]-3-hydroxypropyl]-N-ethylcarbamate 4-Hydroxybenzaldehyde and ethylamine acetate were treated using similar procedures to those described in Example 7a to 7e to afford the desired compound.

(b) 4-[1-Ethylamino-3-(3-nitrophenoxy)propyl]phenyl dimethylcarbamate hydrochloride t-Butyl N-[1-[(4-dimethylcarbamoyloxy)phenyl]-3-hydroxypropyl]-N-ethylcarbamate obtained from Example 105a and 3-nitrophenol were treated similar procedures to those described in Example 7f and 7g to afford the title compound as an amorphous solid.

$^1$H-NMR(400 MHz,CDCl$_3$) δ ppm: 1.46 (3H,t,J=7.3 Hz), 2.67–2.75 (1H,m), 2.82–2.90 (1H,m), 2.93 (3H,s), 3.05–3.19 (1H,m), 3.09 (3H,s), 3.64–3.70 (1H,m), 4.00–4.05 (1H,m), 4.42 (1H,dd,J=10.7 Hz,3.4 Hz), 7.12 (1H,dd,J=8.2 Hz,2.0 Hz), 7.19 (2H,d,J=8.6 Hz), 7.38 (1H,t,J=8.2 Hz), 7.56 (1H,t,J=2.0 Hz), 7.65 (2H,d,J=8.6 Hz), 7.78 (1H,dd,J=8.2 Hz,2.0 Hz), 9.95 (1H,br s), 10.28 (1H,br s). MS(FAB) m/z: 388 (M+H)$^+$.

EXAMPLE 106

4-[1-Ethylamino-3-(4-fluorophenoxy)propyl]phenyl dimethylcarbamate hydrochloride (Exemplification compound number 1-67)

t-Butyl N-[1-[(4-dimethylcarbamoyloxy)phenyl]-3-hydroxypropyl]-N-ethylcarbamate obtained from Example 105a and 4-fluorophenol were treated using similar procedures to those described in Example 7f and 7g to afford the title compound as an amorphous solid.

$^1$H-NMR(400 MHz,CDCl$_3$) δ ppm: 1.46 (3H,t,J=7.0 Hz), 2.56–2.66 (1H,m), 2.79–2.92 (2H,m), 3.01 (3H,s), 3.00–3.10 (1H,m), 3.09 (3H,s), 3.49–3.54 (1H,m), 3.84–3.89 (1H,m), 4.43 (1H, d,J=8.1 Hz), 6.67–6.70 (2H,m), 6.87–6.91 (2H,m), 7.18 (2H,d,J=8.4 HZ), 7.65 (2H,d,J=8.4 Hz), 9.92 (1H,br s), 10.21 (1H,br s). MS(FAB) m/z: 361 (M+H)$^+$.

EXAMPLE 107

4-[1-Ethylamino-3-(3-fluorophenoxy)propyl]phenyl dimethylcarbamate hydrochloride (Exemplification compound number 1-68)

t-Butyl N-[1-[(4-dimethylcarbamoyloxy)phenyl]-3-hydroxypropyl]-N-ethylcarbamate obtained from Example 105a and 3-fluorophenol were treated using similar procedures to those described in Example 7f and 7g to afford the title compound as an amorphous solid.

$^1$H-NMR(400 MHz,CDCl$_3$) δ ppm: 1.45 (3H,t,J=7.3 Hz), 2.60–2.70 (1H,m), 2.83–2.93 (2H,m), 3.01 (3H,s), 3.01–3.13 (1H,m), 3.09 (3H,s), 3.50–3.56 (1H,m), 3.87–3.92 (1H,m), 4.42 (1H, brd,J=8.1 Hz), 6.47 (1H,dt,J=11.0 Hz,2.2 Hz), 6.54 (1H,dd,J=8.1 Hz,2.2 Hz), 6.60 (1H,td,J=8.1 Hz,2.2 Hz), 7.13 (1H,dd,J=8.1 Hz,6.6 Hz), 7.18 (2H,d,J=8.4 Hz), 7.65 (2H,d,J=8.4 Hz), 9.95 (1H,br s), 10.26 (1H,br s) MS(FAB) m/z: 361 (M+H)$^+$.

EXAMPLE 108

3-[1-Methylamino-3-(3-nitrophenoxy)propyl]phenyl dimethylcarbamate hydrochloride (Exemplification compound number 2-94)

t-Butyl N-[1-[(3-dimethylcarbamoyloxy)phenyl]-3-hydroxypropyl]-N-methylcarbamate obtained from Example 7e and 3-nitrophenol were treated using similar procedures to those described in Example 48 to afford the title compound as an amorphous solid.

$^1$H-NMR(400 MHz,CDCl$_3$) δ ppm: 2.25 (3H,s), 2.61–2.69 (1H,m), 2.98 (3H,s), 2.97–3.10 (1H,m), 3.08 (3H,s), 3.73–3.79 (1H,m), 4.07–4.12 (1H,m), 4.35 (1H,dd,J=10.3 Hz,4.4 Hz), 7.14–7.20 (2H,m), 7.35–7.48 (4H,m), 7.60 (1H, t,J=2.0 Hz), 7.79 (1H,dd,J=8.1 Hz,2.2 Hz), 10.10 (2H,br) MS(FAB) m/z: 374 (M+H)$^+$.

EXAMPLE 109

4-[3-(4-Chlorophenylamino)-1-methylaminopropyl]phenyl dimethylcarbamate dihydrochloride (Exemplification compound number 1-50)

t-Butyl (4-chlorophenyl)carbamate was treated using similar procedures to those described in Example 87 to afford the title compound as an amorphous solid.

$^1$H-NMR(400 MHz,CDCl$_3$) δ ppm: 2.46 (3H,s), 2.71–2.76 (1H,m), 3.01 (3H,s), 3.09 (3H,s), 3.16–3.23 (1H,m), 3.38–3.49 (2H,m), 4.05–4.08 (1H,m), 7.23–7.26 (2H,m), 7.39 (2H,d,J=8.8 Hz), 7.58 (2H,d,J=8.8 Hz), 7.63 (2H,br s). MS (FAB) m/z: 362 (M+H)$^+$.

EXAMPLE 110

4-[3-[N-Acetyl-N-(3-chlorophenyl)amino]-1-methylaminopropyl]phenyl dimethylcarbamate hydrochloride (Exemplification compound number 0.1-60)

N-(3-Fluorophenyl)acetamide was treated using similar procedures to those described in Example 87 to afford the title compound as an amorphous solid.

$^1$H-NMR(400 MHz,CDCl$_3$) δ ppm: 1.94 (3H,s), 2.10–2.15 (1H,m), 2.45 (3H,s), 2.71–2.77 (1H,m), 3.02 (3H,s), 3.11 (3H,s), 3.58–3.63 (1H,m), 3.91–3.95 (1H,m), 4.13–4.18 (1H, m), 6.99 (1H,d,J=8.1 Hz), 7.08–7.14 (2H,m), 7.20 (2H,d, J=8.0 Hz), 7.41–7.47 (1H,m), 7.69 (2H,d,J=8.0 Hz). MS (EI) m/z: 387 (M)$^+$.

EXAMPLE 111

4-[1-Methylamino-3-(3-methyl-4-nitrophenoxy)propyl]phenyl dimethylcarbamate hydrochloride (Exemplification compound number 1-115)

3-Methyl-4-nitrophenol was treated using similar procedures to those described in Example 48 to afford the title compound as an amorphous solid.

$^1$H-NMR(400 MHZ,CDCl$_3$) δ ppm: 2.52 (3H,s), 2.58 (3H, s), 2.58–2.66 (1H,m), 3.01 (3H,s), 3.01–3.10 (1H,m), 3.10 (3H,s), 3.67–3.73 (1H,m), 4.03–4.07 (1H,m), 4.29–4.34 (1H, m), 6.68–6.70 (2H,m), 7.20 (2H,d,J=8.3 Hz), 7.59 (2H,d, J=8.3 Hz), 8.01 (1H,d,J=9.1 Hz). MS (FAB) m/z: 388 (M+H)$^+$.

EXAMPLE 112

4-(1-Methylamino-3-o-toluyloxypropyl)phenyl Dimethylcarbamate hydrochloride (Exemplification compound number 1-84)

t-Butyl N-[1-[(4-dimethylcarbamoyloxy)phenyl]-3-hydroxypropyl]-N-methylcarbamate obtained from Example 16b and 2-methylphenol were treated using similar procedures to those described in Example 7f and 7g to afford the title compound as an amorphous solid.

$^1$H-NMR(400 MHz,CDCl$_3$) δ ppm: 2.21 (3H,s), 2.52 (3H, s), 2.57–2.63 (1H,m), 2.95–3.09 (1H,m), 3.00 (3H,s), 3.09 (3H,s), 3.59–3.65 (1H,m), 3.96–4.00 (1H,m), 4.30–4.36 (1H, m), 6.61 (1H,d,J=8.1 Hz), 6.82 (1H,t,J=8.1 Hz), 7.03–7.11 (2H,m), 7.18 (2H,d,J=8.0 Hz), 7.61 (2H,d,J=8.0 Hz). MS (EI) m/z: 342 (M)$^+$.

EXAMPLE 113

4-[(3-(4-Chloro-2-methylphenoxy)-1-methylaminopropyl]phenyl dimethylcarbamate hydrochloride (Exemplification compound number 1-112)

t-Butyl N-[1-[(4-dimethylcarbamoyloxy)phenyl]-3-hydroxypropyl]-N-methylcarbamate obtained from Example 16b and 4-chloro-2-methylphenol were treated using similar procedures to those described in Example 7f and 7g to afford the title compound as an amorphous solid.

$^1$H-NMR(400 MHz,CDCl$_3$) δ ppm: 2.17 (3H,s), 2.51 (3H, t,J=2.7 Hz), 2.56–2.63 (1H,m), 2.94–3.09 (1H,m), 3.01 (3H, s), 3.09 (3H,s), 3.57–3.63 (1H,m), 3.92–3.97 (1H,m), 4.27–4.32 (1H,m), 6.52 (1H,d,J=8.7 Hz), 7.01 (1H,dd,J=8.7 Hz,2.5 Hz), 7.07 (1H,d,J=2.5 Hz), 7.19 (2H,d,J=8.4 Hz), 7.59 (2H,d,J=8.4 Hz). MS (EI) m/z: 376 (M)$^+$.

EXAMPLE 114

4-[1-Dimethylamino-3-(3,4,5-trifluorophenoxy)propyl]phenyl dimethylcarbamate hydrochloride (Exemplification compound number 1-174)

4-[1-Methylamino-3-(3,4,5-trifluorophenoxy)propyl] phenyl dimethylcarbamate obtained from Example 80 was treated using a similar procedure to that described in Example 3 to afford the title compound as an amorphous solid.

$^1$H-NMR (400 MHz,CDCl$_3$) δ ppm: 2.60 (3H,d,J=5.0 Hz) 2.65–2.74 (1H,m), 2.88 (3H,d,J=4.7 Hz), 2.91–3.02 (1H,m), 3.02 (3H,s), 3.11 (3H,s), 3.48 (1H,td,J=9.6 Hz,3.6 Hz), 3.89–3.95 (1H,m), 4.21–4.28 (1H,m), 6.34–6.39 (2H,m), 7.24 (2H,d,J=8.5 Hz), 7.55 (2H,d,J=8.5 Hz). MS(EI) m/z: 396 (M+H)$^+$.

EXAMPLE 115

4-[4-(4-Chlorophenoxy)-1-methylaminobutyl]phenyl dimethylcarbamate hydrochloride (Exemplification compound number 1-193)

(a) Ethyl 3-(4-benzyloxyphenyl)-3-[N-(t-butoxycarbonyl)-N-methylamino]propionate N,N-Dimethylformamide and benzyl bromide (2.3 ml, 19 mmol) were added sequentially to ethyl 3-[N-(t-butoxy carbonyl)-N-methylamino]-3-(4-hydroxyphenyl)propionate (5.10 g, 16 mmol) obtained from Example 16a and potassium carbonate (3.27 g, 24 mmol) and the mixture was stirred at room temperature for 4 hours. The reaction mixture was partitioned between water and ethyl acetate. The organic layer was washed with water and saturated aqueous sodium chloride solution, dried over anhydrous magnesium sulfate and concentrated under reduced pressure. The residue was purified by chromatography on a silica gel column to afford the desired compound (5.57 g).

$^1$H-NMR(400 MHz,CDCl$_3$) δ ppm: 1.23 (3H,t,J=7.2 Hz), 1.48 (9H,s), 2.61 (3H.br s), 2.88–2.92 (2H,m), 4.21 (2H,q, J=7.2 Hz), 5.05 (2H,s), 5.66 (1H,br s), 6.94 (2H,d,J=8.4 Hz), 7.18 (2H,d,J=8.4 Hz), 7.31–7.44 (5H,m).

(b) t-Butyl N-[1-(4-benzyloxyphenyl)-3-hydroxypropyl]-N-methylcarbamate

Tetrahydrofuran (100 ml) was added to lithium aluminum hydride (1.02 g, 27 mmol) under an atmosphere of nitrogen, and a solution of ethyl 3-(4-benzyloxyphenyl)-3-[N-(t-butoxycarbonyl)-N-methylamino]propionate (5.56 g, 13 mmol) obtained from Example 115a in tetrahydrofuran was slowly added thereto at −78° C. After stirring the resulting mixture for 30 minutes, the temperature was gradually raised to 0° C. and then the mixture was stirred for 30 minutes. To the reaction mixture was added sequentially water (1 ml), 15% aqueous sodium hydroxide solution (1 ml) and water (3 ml) and the resulting mixture was stirred at room temperature for 30 minutes. To the mixture was added anhydrous magnesium sulfate and the resulting mixture was filtered. The filtrate was concentrated under reduced pressure. The residue was purified by chromatography on a silica gel column to afford the desired compound (4.78 g).

$^1$H-NMR(400 MHz,CDCl$_3$) δ ppm: 1.51 (9H,s), 1.92–2.15 (2H,m), 2.42 (3H,br s), 3.50–3.74 (3H,m), 5.06 (2H,s), 5.54 (1H,br s), 6.95 (2H,d,J=8.5 Hz), 7.21 (2H,d,J=8.5 Hz), 7.31–7.45 (5H,m).

(c) t-Butyl N-[1-(4-benzyloxyphenyl)-3-cyanopropyl]-N-methylcarbamate t-Butyl N-[1-(4-benzyloxyphenyl)-3-hydroxypropyl]-N-methylcarbamate (1.50 g, 4.0 mmol) obtained from Example 115b was dissolved in tetrahydrofuran (20 ml) under an atmosphere of nitrogen. To the solution was added triethylamine (0.84 ml, 6.0 mmol) and then methanesulfonyl chloride (0.37 ml, 4.8 mmol), in an ice bath. The resulting mixture was stirred at room temperature for 30 minutes. The reaction mixture was partitioned between water and ethyl acetate. The organic layer was washed with saturated aqueous sodium chloride solution, dried over anhydrous magnesium sulfate and concentrated under reduced pressure. The residue was dissolved in N,N-dimethylformamide (20 ml) and to the solution was added 15-crown-5 (1.2 ml, 6.0 mmol) and then sodium cyanide (294 mg, 6.0 mmol). The resulting mixture was stirred at room temperature overnight. The reaction mixture was partitioned between water and ethyl acetate. The organic layer was washed with saturated aqueous sodium chloride solution, dried over anhydrous magnesium sulfate and concentrated under reduced pressure. The residue was purified by chromatography on a silica gel column using hexane:ethyl acetate=80:20 to 70:30 as the eluent to afford the desired compound (1.41 g).

$^1$H-NMR(400 MHz,CDCl$_3$) δ ppm: 1.51 (9H,br s), 2.20–2.28 (1H,m), 2.41 (3H,br s), 5.06 (2H,s), 5.35 (1H,br s), 6.96 (2H,d,J=8.6 Hz), 7.17 (2H,d,J=8.6 Hz), 7.31–7.44 (5H, m).

(d) t-Butyl N-[1-(4-benzyloxyphenyl)-4-hydroxybutyl]-N-methylcarbamate t-Butyl N-(1-(4-benzyloxyphenyl)-3-cyanopropyl]-N-methylcarbamate (1.00 g, 2.6 mmol) obtained from Example 115c was dissolved in dichloromethane (20 ml) under an atmosphere of nitrogen. To the solution was added 0.95 M solution of diisobutylaluminum hydride in hexane (5.5 ml, 5.3 mmol) at −78° C. and the temperature was slowly raised to room temperature and then the mixture was stirred at room temperature for 2 hours. To the resulting mixture was added sodium sulfate (2.6 g) and this mixture was stirred at room temperature for 1 hour. The reaction mixture was filtered and the filtrate was concentrated under reduced pressure. The residue was dissolved in methanol (10 ml) and to the solution was slowly added sodium borohydride (98 mg, 2.6 mmol). The resulting mixture was stirred at room temperature for 1 hour. Water was added to the reaction mixture and the methanol was evaporated under reduced pressure. The aqueous layer was extracted with ethyl acetate. The organic layer was dried over anhydrous magnesium sulfate and concentrated under reduced pressure. The residue was purified by chromatography on a silica gel column using hexane:ethyl acetate=70:30 to 50:50 as the eluent to afford the desired compound (830 mg).

$^1$H-NMR(400 MHz,CDCl$_3$) δ ppm: 1.49 (9H,s), 1.59–1.65 (2H,m), 1.89–2.01 (2H,m), 2.53 (3H,br s), 3.73 (2H,t,J=6.2 Hz), 5.05 (2H,s), 5.20 (0.5H,br s), 5.39 (0.5H,br s), 6.94 (2H,d,J=8.5 Hz), 7.21 (2H,d,J=8.5 Hz), 7.31–7.44 (5H,m).

(e) t-Butyl N-[4-hydroxybutyl-1-(4-hydroxyphenyl)]-N-methylcarbamate t-Butyl N-[1-(4-benzyloxyphenyl)-4-hydroxybutyl]-N-methylcarbamate (278 mg, 0.72 mmol) obtained from Example 126d was dissolved in methanol (5 ml) and to the solution was added 5% palladium on charcoal (30 mg). The mixture was stirred under an atmosphere of hydrogen at room temperature for 2 hours. The catalyst was filtered off and the filtrate was concentrated under reduced pressure to afford the crude desired compound, which was used in the reaction of the next step without further purification.

$^1$H-NMR(400 MHz,CDCl$_3$) δ ppm: 1.49 (9H,s), 1.54–1.67 (2H,m), 1.87–2.06 (2H,m), 2.54 (3H,br s), 3.01 (3H,s), 3.10 (3H,s), 3.73 (2H,t,J=6.2 Hz), 5.22 (0.5H,br s), 5.43 (0.5H,br s), 7.07 (2H,d,J=8.6 Hz), 7.27 (2H,d,J=8.6 Hz).

(f) t-Butyl N-[1-(4-dimethylcarbamoyloxy)phenyl]-4-hydroxybutyl]-N-methylcarbamate The crude product of t-butyl N-(4-hydroxybutyl-1-(4-hydroxyphenyl)]-N-methylcarbamate obtained from Example 126e and potassium carbonate (150 mg, 1.1 mmol) were dissolved in N,N-dimethylformamide (5 ml) under an atmosphere of nitrogen. To the solution was added dimethylcarbamyl chloride (0.079 ml, 0.86 mmol) and the resulting mixture was stirred at room temperature overnight. The reaction mixture was partitioned between water and ethyl acetate. The organic layer was washed with water and saturated aqueous sodium chloride solution, dried over anhydrous magnesium sulfate and concentrated under reduced pressure. The residue was purified by chromatography on a silica gel column to afford the desired compound (220 mg).

$^1$H-NMR(400 MHz,CDCl$_3$) δ ppm: 1.48 (9H,s), 1.80–1.84 (2H,m), 1.99–2.10 (2H,m), 2.56 (3H,br s), 3.01 (3H,s), 3.10 (3H,s), 4.00 (2H,t,J=6.1 Hz), 5.24 (0.5H,br s), 5.45 (0.5H,br s), 6.82 (2H,d,J=8.9 Hz), 7.08 (2H,d,J=8.6 Hz), 7.23 (2H,d, J=8.9 Hz), 7.28 (2H,d,J=8.6 Hz)

(g) 4-[4-(4-Chlorophenoxy)-1-methylaminobutyl]phenyl dimethylcarbamate hydrochloride t-Butyl N-[1-(4-dimethylcarbamoyloxy)phenyl]-4-hydroxybutyl]-N-methylcarbamate obtained from Example 115f and 4-chlorophenol were treated using similar procedures to those described in Example 7f and 7g to afford the title compound as an amorphous solid.

$^1$H-NMR(400 MHz,CDCl$_3$) δ ppm: 1.52–1.76 (2H,m), 2.30–2.42 (1H,m), 2.43 (3H,s), 2.47–2.63 (1H,m), 3.02 (3H, s), 3.11 (3H,s), 3.81 (2H,t,J=6.1 Hz), 4.00 (1H,dd,J=10.5 Hz,4.3 Hz), 6.72 (2H,d,J=9.0 Hz), 7.17 (2H,d,J=9.0 Hz), 7.21 (2H,d,J=8.6 Hz), 7.57 (2H,d,J=8.6 Hz), 9.86 (1H,br s), 10.16 (1H,br s). MS(FAB) m/z: 377 (M+H)+

EXAMPLE 116

4-[1-Methylamino-4-(4-nitrophenoxy)butyl]phenyl dimethylcarbamate hydrochloride (Exemplification compound number 1-194)

t-Butyl N-[1-(4-dimethylcarbamoyloxy)phenyl]-4-hydroxybutyl]-N-methylcarbamate obtained from Example 115f was treated using similar procedures to those described in Example 48 to afford the title compound as an amorphous solid.

$^1$H-NMR(400 MHz,CDCl$_3$) δ ppm: 1.53–1.83 (2H,m), 2.32–2.45 (1H,m), 2.44 (3H,s), 2.55–2.65 (1H,m), 3.02 (3H, s), 3.11 (3H,s), 3.94 (2H,t,J=6.0 Hz), 4.00 (1H,br s), 6.85 (2H,d,J=9.1 Hz), 7.21 (2H,d,J=8.4 Hz), 7.58 (2H,d,J=8.4 Hz), 8.14 (2H,d,J=9.1 Hz), 9.86 (1H,br s), 10.21 (1H,br s). MS(FAB) m/z: 388 (M+H)+

EXAMPLE 117

4-[1-Methylamino-2-(4-nitrophenoxy)ethyl]phenyl dimethylcarbamate hydrochloride (Exemplification compound number 1-39)

N-Methoxy-N-methyl-2-(4-nitrophenoxy)acetamide was treated using similar procedures to those described in Example 93 to afford the title compound as an amorphous solid.

$^1$H-NMR(400 MHZ,CDCl$_3$) δ ppm: 2.34 (3H,s), 3.03 (3H, s), 3.12 (3H,s), 4.37 (1H,br s), 4.48 (1H,dd,J=10.0 Hz,4.2 Hz), 4.74 (1H,dd,J=10.0 Hz,7.9 Hz), 7.13 (2H,d,J=9.2 Hz), 7.23 (2H,d,J=8.5 Hz), 7.67 (2H,d,J=8.5 Hz), 8.13 (2H,d, J=9.2 Hz), 10.33 (2H,br s). MS(FAB) m/z: 360 (M+H)+

EXAMPLE 118

4-[3-[N-Acetyl-N-(4-chlorophenyl)amino]-1-methylaminopropyl]phenyl Dimethylcarbamate hydrochloride (Exemplification compound number 1-59)

N-(4-Chlorophenyl)acetamide was treated using similar procedures to those described in Example 87 to afford the title compound as an amorphous solid.

$^1$H-NMR(400 MHz,CDCl$_3$) δ ppm: 1.90 (3H,s), 2.12–2.18 (1H,m), 2.43 (3H,t,J=2.6 Hz), 2.66–2.73 (1H,m), 3.02 (3H,s), 3.11 (3H,s), 3.61–3.67 (1H,m), 3.95–3.97 (1H,m), 4.02–4.08 (1H,m), 7.19–7.23 (4H,m), 7.42 (2H,d,J=8.6 Hz), 7.67 (2H, d,J=8.5 Hz). MS(FAB) m/z: 404 (M+H)$^+$.

EXAMPLE 119

4-[3-[N-Acetyl-N-(4-nitrophenyl)amino]-1-methylaminopropyl]phenyl dimethylcarbamate hydrochloride (Exemplification compound number 1-61)

N-(4-Nitrophenyl)acetamide was treated using similar procedures to those described in Example 87 to afford the title compound as an amorphous solid.

¹H-NMR(400 MHz,CDCl₃) δ ppm: 1.94 (3H,s), 2.22–2.26 (1H,m), 2.44 (3H,t,J=2.6 Hz), 2.68–2.86 (1H,m), 3.02 (3H,s), 3.11 (3H,s), 3.77–3.83 (1H,m), 3.97–4.05 (2H,m), 7.20 (2H, d,J=8.6 Hz), 7.50 (2H,d,J=8.8 Hz), 7.63 (2H,d,J=8.6 Hz), 8.31 (2H,d,J=8.8 Hz). MS(FAB) m/z: 415 (M+H)⁺.

EXAMPLE 120

4-[1-Methylamino-3-(4-nitrophenylamino)propyl]phenyl dimethylcarbamate dihydrochloride (exemplification compound number 1-53)

t-Butyl (4-nitrophenyl)carbamate was treated using similar procedures to those described in Example 87 to afford the title compound as an amorphous solid.

¹H-NMR(400 MHz,CDCl₃) δ ppm: 2.47 (3H,s), 2.74 (1H, br s), 2.88 (1H,br s), 3.02 (3H,s), 3.11 (3H,s), 3.18 (1H,br s), 4.13 (1H,br s), 6.82 (2H,br s), 7.19–7.24 (2H,m), 7.57 (2H,br s), 8.10 (2H,d,J=6.8 Hz). MS (FAB) m/z: 373 (M+H)⁺.

EXAMPLE 121

(S)-4-[1-Methylamino-3-(4-nitrophenoxy)propyl]phenyl dimethylcarbamate ½ Fumarate (Exemplification compound number 1-92)

(S)-4-[1-Methylamino-3-(4-nitrophenoxy)propyl]phenyl dimethylcarbamate obtained from Example 98 was converted into the ½ fumarate thereof, which was recrystallized from isopropanol to afford the title compopund as crystals (mp 164–166° C.)

¹H-NMR(500 MHz,CD₃OD) δ ppm: 2.32–2.39 (1H,m), 2.48 (3H,s), 2.57–2.64 (1H,m), 2.99 (3H,s), 3.11 (3H,s), 3.88 (1H,dt,J=9.5 Hz,5.0 Hz), 4.13 (1H,dt,J=10.5 Hz,5.0 Hz), 4.30 (1H,dd,J=10.0 Hz,4.0 Hz), 6.68 (1H,s), 6.99 (2H,d,J=9.3 Hz), 7.19 (2H,d,J=8.8 Hz), 7.46 (2H,d,J=8.8 Hz), 8.17 (2H, d,J=9.3 Hz). IR(KBr) ν$_{max}$cm⁻¹: 3423, 3108, 1717, 1591, 1511, 1389, 1341, 1257, 1216, 1175, 1110, 859, 753. Elemental analysis: Calcd for C₂₁H₂₅N₃O₇: C,58.46; H,5.84; N,9.74; 0,25.96. Found: C,58.19; H,5.68; N,9.69; O,26.20. [α]D²² +119.5 (MeOH,C=1.00)

EXAMPLE 122

4-[1-Methylamino-3-(4-nitrophenyl)propyl]phenyl dimethylcarbamate hydrochloride (Exemplification compound number 1-19)

2-Nitrobenzaldehyde was treated using similar procedures to those described in Example 1 to afford the title compound as an amorphous solid.

¹H-NMR(400 MHz,CDCl₃) δ ppm: 2.38 (3H,s), 2.51–2.58 (3H,m), 2.80–2.84 (1H,m), 3.03 (3H,s), 3.12 (3H,s), 3.89 (1H,br s), 7.23 (2H,d,J=8.0 Hz), 7.27 (2H,d,J=8.4 Hz), 7.53 (2H,d,J=8.0 Hz), 8.08 (2H,d,J=8.4 Hz), 9.88 (1H,br s), 10.24 (1H,br s).

EXAMPLE 123

(S)-4-[1-Amino-3-(4-nitrophenoxy)propyl]phenyl dimethylcarbamate hydrochloride (Exemplification compound number 1-66)

t-Butyl (S)-[1-[(4-dimethylcarbamoyloxy)phenyl]-3-(4-nitrophenoxy)propyl]carbamate obtained from Example 98a was treated using a similar procedure to that described in Example 6d to afford the title compound as an amorphous solid.

¹H-NMR(400 MHz,CDCl₃) δ ppm: 2.36–2.46 (1H,m), 2.66–2.75 (1H,m), 2.95 (3H,s), 3.07 (3H,s), 3.81–3.89 (1H, m), 4.06–4.14 (1H,m), 4.46 (1H,dt,J=5.6 Hz,3.2 Hz), 6.87 (2H,d,J=9.6 Hz), 7.06 (2H,d,J=8.8 Hz), 7.52 (2H,d,J=8.8 Hz), 8.14 (2H,d,J=9.6 Hz). [α]$_D$²² +111.3(CHCl₃,C=1.01) MS(FAB) m/z: 360 (M+H)⁺.

EXAMPLE 124

4-[3-(2-Chloro-4-nitrophenoxy)-1-methylaminopropyl]phenyl dimethylcarbamate hydrochloride (Exemplification compound number 1-108)

2-Chloro-4-nitrophenol was treated using similar procedures to those described in Example 48 to afford the title compound as an amorphous solid.

¹H-NMR(400 MHZ,CDCl₃) δ ppm: 2.54 (3H,s), 2.66–2.73 (1H,m), 3.00 (3H,s), 3.06–3.12 (1H,m), 3.09 (3H, s), 3.73–3.79 (1H,m), 4.26–4.30 (1H,m), 4.37–4.41 (1H,m), 6.83 (1H,d,J=9.1 Hz), 7.19 (2H,d,J=8.6 Hz), 7.64 (2H,d, J=8.6 Hz), 8.08 (1H,dd,J=9.1 Hz,2.8 Hz), 8.27 (1H,d,J=2.8 Hz). MS (FAB) m/z: 408 (M+H)⁺.

EXAMPLE 125

(S)-3-[3-(4Nitrophenoxy)-1-methylaminopropyl]phenyl dimethylcarbamate hydrochloride (Exemplification compound number 2-92)

(i) t-Butyl (S)-[1-[(3-dimethylcarbamoyloxy)phenyl]-3-hydroxypropyl]carbamate

Methyl (S)-3-amino-3-(3-hydroxyphenyl)propionate, which was synthesized according to the method described in Tetrahedron: Asymmetry, 2, 183, (1991), was treated using similar procedures to those described in Example 61a and 61b to afford the desired compound.

(b) (S)-3-[3-(4-Nitrophenoxy)-1-methylaminopropyl]phenyl dimethylcarbamate hydrochloride t-Butyl (S)-[1-[(3-dimethylcarbamoyloxy)phenyl]-3-hydroxypropyl]carbamate obtained from Example 125a and 4-nitrophenol were treated using similar procedures to those described in Example 7f, 61d and 61e to afford the title compound as an amorphous solid.

¹H-NMR (400 MHz, CDCl₃) δ ppm: 2.54 (3H, s), 2.67 (1H, m), 2.99 (3H, s), 3.05 (1H, m), 3.07 (3H, s), 3.78 (1H, m), 4.11 (1H, m), 4.30 (1H, m), 6.87 (2H, d, J=9.2 Hz), 7.20 (1H, m), 7.31 (1H, s), 7.45 (2H, m), 8.15 (2H, d, J=9.2 Hz), 9.97 (1H, br s), 10.48 (1H, br s), ms (FAB) m/z: 374 ((M+H)⁺)

EXAMPLE 126

(S)-3-[3-(4-Nitrophenoxy)-1-dimethylaminopropyl]phenyl dimethylcarbamate hydrochloride (Exemplification compound number 2-149)

(S)-3-[3-(4-Nitrophenoxy)-1-methylaminopropyl]phenyl dimethylcarbamate hydrochloride obtained from Example 125b was treated using a similar procedure to that described in Example 3 to afford the title compound as an amorphous solid.

¹H-NMR (400 MHz, CDCl₃) δ ppm: 2.65 (3H, s), 2.74 (1H, m), 2.85 (3H, s), 3.00 (3H, s), 3.07 (1H, m), 3.09 (3H, s), 3.77 (1H, m), 4.12 (1H, m), 4.30 (1H, m), 6.82 (2H, d, J=9.0 Hz), 7.24 (1H, m), 7.30 (1H, m), 7.36 (1H, m), 7.46 (1H, m), 8.15 (2H, d, J=9.0 Hz), ms (FAB) m/z: 388 ((M+H)⁺)

EXAMPLE 127

(S)-4-[3-(2-Chloro-4-nitrophenoxy)-1-methylaminopropyl]phenyl dimethylcarbamate hydrochloride (Exemplification compound number 1-108)

t-Butyl (S)-[1-[(4-dimethylcarbamoyloxy)phenyl]-3-hydroxypropyl]carbamate obtained from Example 81a and 2-chloro-4-nitrophenol were treated using similar procedures to those described in Example 7f, 61d and 61e to afford the title compound as an amorphous solid.

$^1$H-NMR(500 MHz,CDCl$_3$) δ ppm: 2.54 (3H,s), 2.67–2.72 (1H,m), 3.00 (3H,s), 3.05–3.14 (1H,m), 3.09 (3H,s), 3.73–3.77 (1H,m), 4.27–4.30 (1H,m), 4.37–4.41 (1H,m), 6.83 (1H,d,J=9.0 Hz), 7.19 (2H,d,J=9.0 Hz), 7.64 (2H,d, J=9.0 Hz), 8.08 (1H,dd,J=9.0 Hz,3.0 Hz), 8.27 (1H,d,J=3.0 Hz). IR(CHCl$_3$) 2977, 2710, 1587, 1515, 1492, 1392, 1346, 1277, 1176, 1054, 1027, 1019. [α]$_D^{22}$ +135.1(CHCl$_3$, C=0.72)

EXAMPLE 128

(R)-4-[3-(2-Chloro-4-nitrophenoxy)-1-methylaminopropyl]phenyl dimethylcarbamate hydrochloride (Exemplification compound number 1-108)

t-Butyl (R)-[1-[(4-dimethylcarbamoyloxy)phenyl]-3-hydroxypropyl]carbamate obtained from Example 61a and 2-chloro-4-nitrophenol were treated using similar procedures to those described in Example 7f, 61d and 61e to afford the title compound as an amorphous solid.

$^1$H-NMR(500 MHz,CDCl$_3$) δ ppm: 2.54 (3H,s), 2.67–2.72 (1H,m), 3.00 (3H,s), 3.05–3.14 (1H,m), 3.09 (3H,s), 3.73–3.77 (1H,m), 4.27–4.30 (1H,m), 4.37–4.41 (1H,m), 6.83 (1H,d,J=9.0 Hz), 7.19 (2H,d,J=9.0 Hz), 7.64 (2H,d, J=9.0 Hz), 8.08 (1H,dd,J=9.0 Hz,3.0 Hz), 8.27 (1H,d,J=3.0 Hz). IR(CHCl$_3$) 2977, 2710, 1587, 1515, 1492, 1392, 1346, 1277, 1176, 1054, 1027, 1019. [α]$_D^{22}$ −131.0(CHCl$_3$, C=0.86)

EXAMPLE 129

(S)-4-[3-(2-Chloro-4-nitrophenoxy)-1-dimethylaminopropyl]phenyl dimethylcarbamate hydrochloride (Exemplification compound number 1-165)

(S)-4-[3-(2-Chloro-4-nitrophenoxy)-1-methylaminopropyl]phenyl dimethylcarbamate hydrochloride obtained from Example 127 was treated using a similar procedure to that described in Example 3 to afford the title compound as an amorphous solid.

$^1$H-NMR(500 MHz,CDCl$_3$) δ ppm: 2.61 (3H,d,J=5.0 Hz), 2.80–2.89 (1H,m), 2.95 (3H,d,J=5.0 Hz), 3.01 (3H,s), 3.02–3.10 (1H,m), 3.10 (3H,s), 3.66–3.74 (1H,m), 4.23–4.30 (1H,m), 4.31–4.37 (1H,m), 6.82 (1H,d,J=9.0 Hz), 7.22 (2H, d,J=9.0 Hz), 7.62 (2H,d,J=9.0 Hz), 8.09 (1H,dd,J=9.0 Hz,2.5 Hz), 8.27 (1H,d,J=2.5 Hz). IR(CHCl$_3$) 2970, 2317, 1725, 1587, 1517, 1492, 1467, 1392, 1346, 1277, 1176, 1054, 1029, 1018. [α]$_D^{22}$ +142.0(CHCl$_3$,C=0.96)

EXAMPLE 130

(R)-4-[3-(2-Chloro-4-nitrophenoxy)-1-dimethylaminopropyl]phenyl dimethylcarbamate hydrochloride (Exemplification compound number 1-165)

(R)-4-[3-(2-Chloro-4-nitrophenoxy)-1-methylaminopropyl]phenyl dimethylcarbamate hydrochloride obtained from Example 128 was treated using a similar procedure to that described in Example 3 to afford the title compound as an amorphous solid.

$^1$H-NMR(500 MHz,CDCl$_3$) δ ppm: 2.61 (3H,d,J=5.0 Hz), 2.80–2.89 (1H,m), 2.95 (3H,d,J=5.0 Hz), 3.01 (3H,s), 3.02–3.10 (1H,m), 3.10 (3H,s), 3.66–3.74 (1H,m), 4.23–4.30 (1H,m), 4.31–4.37 (1H,m), 6.82 (1H,d,J=9.0 Hz), 7.22 (2H, d,J=9.0 Hz), 7.62 (2H,d,J=9.0 Hz), 8.09 (1H,dd,J=9.0 Hz,2.5 Hz), 8.27 (1H,d,J=2.5 Hz). IR(CHCl$_3$) 2970, 2317, 1725, 1587, 1517, 1492, 1467, 1392, 1346, 1277, 1176, 1054, 1029, 1018. [α]$_D^{22}$ −141.6(CHCl$_3$,C=1.16)

EXAMPLE 131

4-[3-(2-Chloro-4-nitrophenoxy)-1-dimethylaminopropyl]phenyl dimethylcarbamate hydrochloride (Exemplification compound number 1-165)

4-[3-(2-Chloro-4-nitrophenoxy)-1-methylaminopropyl]phenyl dimethylcarbamate hydrochloride obtained from Example 124 was treated using a similar procedure to that described in Example 3 to afford the title compound as an amorphous solid.

$^1$H-NMR(400 MHz,CDCl$_3$) δ ppm: 2.61(3H,d,J=5.1 Hz), 2.81–2.89(1H,m), 2.95(3H,d.J=5.1 Hz), 3.01(3H,s), 3.01–3.10(1H,m), 3.10(3H,s), 3.67–3.72(1H,m), 4.26–4.33 (2H,m), 6.81(1H,d,J=9.0 Hz), 7.22(2H,d,J=8.4 Hz), 7.61(2H, d,J=8.4 Hz), 8.09(1H,dd,J=9.0,2.7 Hz), 8.28(1H,d,J=2.7 Hz). IR(KBr) ν$_{max}$cm$^{-1}$: 3427, 2934, 2555, 2457, 1726, 1516. MS m/z: 422([M+H]$^+$), 406, 377, 221, 204.

EXAMPLE 132

4-[1-Methylamino-3-(5-chloropyridin-3-yloxy)propyl]phenyl dimethylcarbamate hydrochloride (Exemplification compound number 1-120)

t-Butyl N-[1-(4-dimethylcarbamoyloxy)phenyl]-3-hydroxypropyl]-N-methylcarbamate obtained from Example 16b and 5-chloropyridin-3-ol were treated using similar procedures to those described in Example 7f and 7g to afford the title compound as an amorphous solid.

$^1$H-NMR(400 MHz,CDCl$_3$) δ ppm: 2.49(3H,brs), 2.62(1H,brs), 3.02(3H,s), 3.12(3H,s), 4.39(2H,br s), 4.83(1H,br s), 7.22(2H,br s), 7.67(2H,br s), 7.84(1H,br s), 8.41(1H,br s), 9.05(1H,br s), 10.14(1H,br s), 10.39(1H,br s). IR(KBr) ν$_{max}$cm$^{-1}$: 2941, 2738, 2473, 2023, 1732, 1549. MS m/z: 364([M+H]$^+$), 333, 273, 259, 242, 207.

EXAMPLE 133

4-[1-Methylamino-3-(6-methylpyridin-3-yloxy)propyl]phenyl dimethylcarbamate hydrochloride (Exemplification compound number 1-122)

t-Butyl N-[1-(4-dimethylcarbamoyloxy)phenyl]-3-hydroxypropyl]-N-methylcarbamate obtained from Example 16b and 6-methylpyridin-3-ol were treated using similar procedures to those described in Example 7f and 7g to afford the title compound as an amorphous solid.

$^1$H-NMR(400 MHz,CDCl$_3$) δ ppm: 2.47(3H,t,J=5.2 Hz), 2.58(3H,s), 2.58–2.66(1H,m), 2.83(3H,s), 3.02(3H,s), 3.02–3.11(1H,m), 3.11(3H,s), 4.31–4.36(1H,m), 4.41–4.43 (1H,m), 4.56–4.61(1H,m), 7.19(2H,d,J=8.5 Hz), 7.53(1H,d, J=8.9 Hz), 7.68(2H,d,J=8.5 Hz), 7.80(1H,dd,J=8.9,2.0 Hz), 8.57(1H,d,J=2.0 Hz), 10.23(2H,br s). IR(KBr) ν$_{max}$cm$^{-1}$: 3427, 2937, 2682, 1739, 1555. MS m/z: 344([M+H]$^+$), 313, 273, 242, 207.

EXAMPLE 134

4-[1-Methylamino-3-(2-methylpyridin-3-yloxy)propyl]phenyl dimethylcarbamate hydrochloride (Exemplification compound number 1-121)

t-Butyl N-[1-(4-dimethylcarbamoyloxy)phenyl]-3-hydroxypropyl]-N-methylcarbamate obtained from Example 16b and 2-methylpyridin-3-ol were treated using similar procedures to those described in Example 7f and 7g to afford the title compound as an amorphous solid.

$^1$H-NMR(400 MHz,CDCl$_3$) δ ppm: 2.47(3H,s), 2.68(1H, brs), 2.80(3H,s), 3.01(3H,s), 3.01–3.09(1H,m), 3.11(3H,s), 4.21(1H,br s), 4.38(1H,br s), 4.41(1H,br s), 7.22(2H,d,J=8.0 Hz), 7.68–7.69(3H,m), 7.84(1H,br s), 8.25(1H,br s), 10.19 (1H,br s), 10.26(1H,br s). IR(KBr) ν$_{max}$cm$^{-1}$: 3423, 2938, 2759, 2690, 1722, 1550. MS m/z: 344([M+H]$^+$), 313, 273, 242, 207.

EXAMPLE 135

(R)-3-[3-(4-Nitrophenoxy)-1-methylaminopropyl] phenyl dimethylcarbamate hydrochloride (Exemplification compound number 2-194)

(a) t-Butyl (R)-[1-[(3-dimethylcarbamoyloxy)phenyl]-3-hydroxypropyl]carbamate

Methyl (R)-3-amino-3-(3-hydroxyphenyl)propionate, which was synthesized according to the method described in Tetrahedron: Asymmetry, 2, 183, (1991), was treated using similar procedures to those described in Example 61a and 61b to afford the desired compound.

(b) (R)-3-[3-(4-Nitrophenoxy)-1-methylaminopropyl]phenyl dimethylcarbamate hydrochloride t-Butyl (R)-[1-[(3-dimethylcarbamoyloxy)phenyl]-3-hydroxypropyl]carbamate obtained from Example 135a and 4-nitrophenol were treated using similar procedures to those described in Example 7f, 61d and 61e to afford the title compound as an amorphous solid.

$^1$H-NMR (400 MHz, CDCl$_3$) δ ppm: 2.54 (3H, s), 2.66 (1H, m), 2.99 (3H, s), 3.05 (1H, m), 3.07 (3H, s), 3.79 (1H, m), 4.11 (1H, m), 4.31 (1H, m), 6.87 (2H, d, J=9.2 Hz), 7.19 (1H, m), 7.32 (1H, s), 7.45 (2H, m), 8.16 (2H, d, J=9.2 Hz), ms (FAB) m/z: 374 ((M+H)$^+$)

EXAMPLE 136

(R)-3-[3-(4-Nitrophenoxy)-1-dimethylaminopropyl] phenyl dimethylcarbamate hydrochloride (Exemplification compound number 2-149)

(R)-3-[3-(4-Nitrophenoxy)-1-methylaminopropyl]phenyl dimethylcarbamate hydrochloride obtained from Example 135 was treated using a similar procedure to that described in Example 3 to afford the title compound as an amorphous solid.

$^1$H-NMR (400 MHz, CDCl$_3$) δ ppm: 2.66 (3H, m), 2.73 (1H, m), 2.86 (3H, m), 3.00 (3H, s), 3.07 (1H, m), 3.09 (3H, m), 3.78 (1H, m), 4.13 (1H, m), 4.34 (1H, m), 6.82 (2H, J=9.2 Hz), 7.24 (1H, dd, J=8.1 Hz, 1.5 Hz), 7.31 (1H, s), 7.37 (1H, d, J=8.1), 7.46 (1H, t, J=8.1), 8.14 (2H, J=9.2), ms (FAB) m/z: 388 ((M+H)$^+$)

EXAMPLE 137

4-[1-Ethylamino-3-(4-nitrophenoxy)propyl]phenyl dimethylcarbamate hydrochloride (Exemplification compound number 1-71)

t-Butyl N-[1-[(4-dimethylcarbamoyloxy)phenyl]-3-hydroxypropyl]-N-ethylcarbamate obtained from Example 105a and 4-nitrophenol were treated using similar procedures to those described in Example 48a and 48b to afford the title compound as an amorphous solid.

$^1$H-NMR (400 MHz, CDCl$_3$) δ ppm: 1.46 (3H, t, J=7.3 Hz), 2.71 (1H, m), 2.88 (2H, m), 3.01 (3H, s), 3.10 (3H, s), 3.14 (1H, m), 3.70 (1H, m), 4.04 (1H, m), 4.40 (1H, m), 6.83 (2H, d, J=9.5 Hz), 7.19 (2H, d, J=8.8 Hz), 7.63 (2H, d, J=8.8 Hz), 8.14 (2H, d, J=9.5 Hz), ms (FAB) m/z: 388 ((M+H)$^+$)

EXAMPLE 138

4-[1-Ethylamino 3-(4-nitrophenoxy)propyl]phenyl dimethylcarbamate hydrochloride (Exemplification compound number 1-189)

4-[1-Ethylamino-3-(4-nitrophenoxy)propyl]phenyl dimethylcarbamate hydrochloride obtained from Example 143 was treated using a similar procedure to that described in Example 3 to afford the title compound as an amorphous solid.

$^1$H-NMR (500 MHz, CDCl$_3$) δ ppm: 1.37 (1.5H, t, J=6.8 Hz), 1.52 (1.5H, t, J=6.8 Hz), 2.63 (3H, d, J=3.4 Hz), 2.76 (2H, m), 2.93 (3H, d, J=3.4 Hz), 3.02 (3H, s), 3.04 (1H, m), 3.11 (3H, s), 3.27 (0.5H, m), 3.39 (0.5H, m), 3.77 (0.5H, m), 3.78 (0.5H, m), 4.11 (1H, m), 4.40 (0.5H, m), 4.54 (0.5H, m), 6.81 (2H, d, J=8.8 Hz), 7.22 (2H, m), 7.56 (1H, dd, J=8.8 Hz), 7.64 (1H, dd, J=7.8 Hz), 8.13 (2H, d, J=8.8 Hz), ms (FAB) m/z: 402 ((M+H)$^+$)

EXAMPLE 139

4-[1-Ethylamino-3-(4-chlorophenoxy)propyl]phenyl dimethylcarbamate hydrochloride (Exemplification compound number 1-69)

t-Butyl N-[1-[(4-dimethylcarbamoyloxy)phenyl]-3-hydroxypropyl]-N-ethylcarbamate obtained from Example 105a and 4-chlorophenol were treated using similar procedures to those described in Example 48a and 48b to afford the title compound as an amorphous solid.

$^1$H-NMR (400 MHz, CDCl$_3$) δ ppm: 1.44 (3H, t, J=7.3 Hz), 2.63 (1H, m), 2.89 (2H, m), 3.01 (3H, s), 3.08 (1H, m), 3.09 (3H, s), 3.52 (1H, m), 3.88 (1H, m), 4.43 (1H, m), 6.69 (2H, m), 7.17 (4H, m), 7.63 (2H, m), ms (FAB) m/z: 377 ((M+H)$^+$)

EXAMPLE 140

4-[1-Ethylamino-3-(4-chlorophenoxy)propyl]phenyl dimethylcarbamate hydrochloride (Exemplification compound number 1-190)

4-[1-Ethylamino-3-(4-chlorophenoxy)propyl]phenyl dimethylcarbamate hydrochloride obtained from Example 139 was treated using a similar procedure to that described in Example 3 to afford the title compound as an amorphous solid.

¹H-NMR (400 MHz, CDCl₃) δ ppm: 1.51 (1.5H, m), 1.34 (1.5H, m), 2.58 (3H, br s), 2.93 (3H, br s), 3.02 (3H, s), 3.11 (3H, s), 3.23–2.62 (4H, m), 3.42 (0.5H, m), 3.53 (0.5H, m), 3.86 (0.5H, m), 3.95 (0.5H, m), 4.31 (0.5H, m), 4.44 (0.5H, m), 6.67 (2H, m), 7.18 (4H, m), 7.57 (1H, d, J=7.8 Hz), 7.64 (1H, d, J=7.8 Hz) ms (FAB) m/z: 391 ((M+H)⁺)

EXAMPLE 141

4-[1-Ethylamino-3-(3,4-difluorophenoxy)propyl] phenyl dimethylcarbamate hydrochloride (Exemplification compound number 1-72)

t-Butyl N-[1-(4-dimethylcarbamoyloxy)phenyl]-3-hydroxypropyl]-N-ethylcarbamate obtained from Example 105a and 3,4-difluorophenol were treated using similar procedures to those described in Example 7f and 7g to afford the title compound as an amorphous solid.

¹H-NMR (400 MHz, CDCl₃) δ ppm: 1.45 (3H, t, J=7.3 Hz), 2.62 (1H, m), 2.87 (2H, m), 3.01 (3H, s), 3.08 (1H, m) 3.10 (3H, s), 3.52 (1H, m), 3.87 (1H, m), 4.39 (1H, m) 6.45 (1H, m), 6.58 (1H, m), 6.99 (1H, m), 7.19 (2H, d, J=8.4 Hz), 7.63 (2H, d, J=8.4 Hz), ms (FAB) m/z: 379 ((M+H)⁺)

EXAMPLE 142

4-[1-Ethylmethylamino-3-(3,4-difluorophenoxy) propyl]phenyl dimethylcarbamate hydrochloride (Exemplification compound number 1-191)

4-[1-Ethylamino-3-(3,4-difluorophenoxy)propyl]phenyl dimethylcarbamate hydrochloride obtained from Example 141 was treated using a similar procedure to that described in Example 3 to afford the title compound as an amorphous solid.

¹H-NMR (500 MHz, CDCl₃) δ ppm: 1.34 (1.5H, t, J=7.3 Hz), 1.52 (1.5H, t, J=7.3 Hz), 2.57 (1.5H, d, J=4.9 Hz), 2.91 (1.5H, d, J=4.9 Hz), 3.02 (3H, d, J=2.0 Hz), 3.11 (3H, d, J=2.0 Hz), 3.56–2.65 (5H, m), 3.92 (1H, m), 4.26 (0.5H, m), 4.39 (0.5H, m), 6.43 (1H, m), 6.56 (1H, m), 7.00 (1H, m), 7.21 (1H, d, J=8.8 Hz), 7.23 (1H, d, J=8.8 Hz), 7.56 (1H, d, J=8.8 Hz), 7.64 (1H, d, J=8.8 Hz), ms (FAB) m/z: 393 ((M+H)⁺)

EXAMPLE 143

4-[1-Ethylmethylamino-3-(4-fluorophenoxy)propyl] phenyl dimethylcarbamate hydrochloride (Exemplification compound number 1-188)

4-[1-Ethylamino-3-(4-fluorophenoxy)propyl]phenyl dimethylcarbamate hydrochloride obtained from Example 106 was treated using a similar procedure to that described in Example 3 to afford the title compound as an amorphous solid.

¹H-NMR (500 MHz, CDCl₃) δ ppm: 1.33 (1.5H, m), 1.51 (1.5H, m), 2.09 (1.5H, s), 2.91 (1.5H, s), 3.02 (3H, s), 3.10 (3H, s), 3.53–2.66 (5H, m), 3.93 (1H, m), 4.27 (0.5H, m), 4.39 (0.5H, m), 6.68 (2H, dd, J=3.9 Hz, 8.8 Hz), 6.91 (2H, t, J=8.8 Hz), 7.21 (2H, m), 7.56 (1H, d, J=7.8 Hz), 7.66 (1H, d, J=7.8 Hz), ms (FAB) m/z: 375 ((M+H)⁺)

EXAMPLE 144

3-[3-(3-Chlorophenoxy)-1-methylaminopropyl]phenyl dimethylcarbamate hydrochloride (Exemplification compound number 2-79)

t-Butyl N-[1-[(3-dimethylcarbamoyloxy)phenyl]-3-hydroxypropyl]-N-methylcarbamate obtained from Example 7e and 3-chlorophenol were treated using similar procedures to those described in Example 48a and 48b to afford the title compound as an amorphous solid.

¹H-NMR(400 MHz,CDCl₃) δ ppm: 2.54 (3H,s), 2.56–2.62 (1H,m), 2.93–2.99 (1H,m), 2.99 (3H,s), 3.08 (3H,s), 3.60–3.66 (1H,m), 3.94–3.99 (1H,m), 4.29–4.33 (1H,m), 6.70 (1H,d,J=8.1 Hz), 6.79 (1H,s), 6.90 (1H,d,J=8.1 Hz), 7.14 (1H,tri,J=8.1 Hz), 7.17–7.20 (1H,m), 7.33 (1H,s), 7.43–7.44 (2H,m). ms(FAB)m/z:(FAB+): 363((M+H)⁺)

EXAMPLE 145

3-[3-(4-Chlorophenoxy)-1-dimethylmethylaminopropyl]phenyl dimethylcarbamate hydrochloride (Exemplification compound number 2-135)

3-[3-(4-Chlorophenoxy)-1-methylaminopropyl]phenyl dimethylcarbamate hydrochloride obtained from Example 10 was treated using a similar procedure to that described in Example 3 to afford the title compound as an amorphous solid.

¹H-NMR(400 MHz,CDCl₃) δ ppm: 2.60–2.73 (1H,m), 2.73 (6H,br), 2.91–2.99 (1H,m), 3.01 (3H,s), 3.10 (3H,s), 3.55–3.61 (1H,m), 3.96–4.00 (1H,m), 4.27–4.31 (1H,m), 6.67 (2H,d,J=9.0 Hz), 7.18 (2H,d,J=9.0 Hz), 7.22 (1H,dt, J=7.9 Hz,1.8 Hz), 7.30 (1H,tri,J=1.8 Hz), 7.38 (1H,d,J=7.9 Hz), 7.45 (1H,tri,J=7.9 Hz) ms(FAB)m/z: 377((M+H)⁺)

EXAMPLE 146

3-[3-(3-Chloro-4-fluorophenoxy)-1-methylaminopropyl]phenyl dimethylcarbamate hydrochloride (Exemplification compound number 2-109)

t-Butyl N-[1-[(3-dimethylcarbamoyloxy)phenyl]-3-hydroxypropyl]-N-methylcarbamate obtained from Example 7e and 3-chloro-4-fluorophenol were treated using similar procedures to those described in Example 48a and 48b to afford the title compound as an amorphous solid.

¹H-NMR(400 MHz,CDCl₃) δ ppm: 2.54 (3H,s), 2.56–2.62 (1H,m), 2.92–2.98 (1H,m), 3.00 (3H,s), 3.09 (3H,s), 3.56–3.64 (1H,m), 3.92–3.97 (1H,m), 4.28–4.32 (1H,m), 6.65–6.68 (1H,m), 6.82–6.84 (1H,m), 6.99 (1H,tri,J=8.8 Hz), 7.17–7.20 (1H,m), 7.31 (1H,s), 7.44 (2H,d,J=5.1 Hz). ms(FAB)m/z: 381((M+H)⁺)

EXAMPLE 147

3-[3-(4-Chloro-3-fluorophenoxy)-1-methylaminopropyl]phenyl dimethylcarbamate hydrochloride (Exemplification compound number 2-104)

t-Butyl N-[1-[(3-dimethylcarbamoyloxy)phenyl]-3-hydroxypropyl]-N-methylcarbamate obtained from Example 7e and 4-chloro-3-fluorophenol were treated using similar procedures to those described in Example 48a and 48b to afford the title compound as an amorphous solid.

¹H-NMR(400 MHZ,CDCl₃) δ ppm: 2.54 (3H,s), 2.56–2.62 (1H,m), 2.93–2.98 (1H,m), 2.99 (3H,s), 3.08 (3H, s), 3.60–3.65 (1H,m), 3.94–3.99 (1H,m), 4.29–4.31 (1H,m), 6.56 (1H,dd,J=2.9 Hz,1.5 Hz), 6.62 (1H,dd,J=2.9 Hz,1.5 Hz), 7.17–7.23 (2H,m), 7.31 (1H,m), 7.44 (2H,d,J=5.1 Hz) ms(FAB)m/z: 381((M+H)⁺)

EXAMPLE 148

3-[3-(3-Chlorophenoxy)-1-dimethylaminopropyl] phenyl dimethylcarbamate hydrochloride (Exemplification compound number 2-136)

3-[3-(3-Chlorophenoxy)-1-methylaminopropyl]phenyl dimethylcarbamate hydrochloride obtained from Example 144 was treated using a similar procedure to that described in Example 3 to afford the title compound as an amorphous solid.

¹H-NMR(400 MHZ,CDCl₃) 6:2.64 (3H,d,J=4.8 Hz), 2.60–2.71 (1H,m), 2.88 (3H,d,J=4.8 Hz), 2.93–3.00 (1H,m), 3.01 (3H,s), 3.10 (3H,s), 3.56–3.62 (1H,m), 3.97–4.02 (1H, m), 4.28–4.34 (1H,m), 6.64 (1H,dd,J=8.0 Hz,2.0 Hz), 6.74 (1H,tri,J=2.0 Hz), 6.91 (1H,dd,J=8.0 Hz,2.0 Hz), 7.14 (1H, tri,J=8.1 Hz), 7.23 (1H,dJ=8.0), 7.32 (1H,s), 7.38 (1H,d, J=8.0 Hz), 7.46 (1H,tri,J=8.1 Hz) ms(FAB)m/z: 377((M+H)⁺)

EXAMPLE 149

3-[3-(3-Chloro-4-fluorophenoxy)-1-dimethylaminopropyl]phenyl dimethylcarbamate hydrochloride (Exemplification compound number 2-166)

3-[3-(3-Chloro-4-fluorophenoxy)-1-methylaminopropyl] phenyl dimethylcarbamate hydrochloride obtained from Example 146 was treated using a similar procedure to that described in Example 3 to afford the title compound as an amorphous solid.

¹H-NMR(400 MHz,CDCl₃) δ ppm: 2.60–2.70 (1H,m), 2.73 (6H,br), 2.90–3.00 (1H,m), 3.01 (3H,s), 3.10 (3H,s), 3.54–3.60 (1H,m), 3.94–3.99 (1H,m), 4.26–4.29 (1H,m), 6.59–6.63 (1H,m), 6.76–6.78 (1H,m), 6.99 (1H,tri,J=8.8 Hz), 7.26 (1H,dd,J=8.1 Hz,2.2 Hz), 7.30 (1H,d,J=2.2 Hz), 7.37 (1H,dd,J=8.1 Hz,2.2 Hz), 7.46 (1H,tri,J=7.7 Hz). ms(FAB) m/z: 395((M+H)⁺)

EXAMPLE 150

3-[3-(4-Chloro-3-fluorophenoxy)-1-dimethylaminopropyl]phenyl dimethylcarbamate hydrochloride (Exemplification compound number 2-161)

3-[3-(4-Chloro-3-fluorophenoxy)-1-methylaminopropyl] phenyl dimethylcarbamate hydrochloride obtained from Example 147 was treated using a similar procedure to that described in Example 3 to afford the title compound as an amorphous solid.

¹H-NMR(400 MHz,CDCl₃) δ ppm: 2.63–2.70 (1H,m), 2.75 (6H,br), 2.93–2.99 (1H,m), 3.01 (3H,s), 3.10 (3H,s), 3.56–3.62 (1H,m), 3.96–4.01 (1H,m), 4.27–4.31 (1H,m), 6.48–6.57 (2H,m), 7.20 (1H,d,J=8.1 Hz), 7.23 (1H,d,J=6.6 Hz), 7.30 (1H,s), 7.37 (1H,d,J=8.1 Hz), 7.46 (1H,tri,J=8.1 Hz). ms(FAB)m/z: 395((M+H)⁺)

EXAMPLE 151

(R)-4-[3-(3,4-Difluorophenoxy)-1-methylaminopropyl]phenyl dimethylcarbamate hydrochloride (Exemplification compound number 1-102)

t-Butyl (R)-N-[1-(4-dimethylcarbamoyloxy)phenyl]-3-hydroxypropyl]carbamate obtained from Example 61b and 3,4-difluorophenol were treated using similar procedures to those described in Example 7f and 7g to afford the title compound as an amorphous solid.

¹H-NMR(400 MHz,CDCl₃) δ ppm: 2.51(3H,s), 2.45–2.64 (1H,m), 2.90–3.05(1H,m), 3.01(3H,s), 3.10(3H,s), 3.50–3.60 (1H,m), 3.87–3.97(1H,m), 4.27–4.36(1H,m), 6.44–6.52(1H, m), 6.61(1H,ddd,J=11.7 Hz,6.6 Hz,2.9 Hz), 7.00(1H,q,J=9.5 Hz), 7.19(2H,d,J=8.8 Hz), 7.59(2H,d,J=8.8 Hz) 9.5–10.6(br). MS (FAB⁺): 365(M+H)⁺. [α]$_D^{22}$ −94.8(CHCl₃, C=0.92)

EXAMPLE 152

(R)-4-[3-(3,4-Difluorophenoxy)-1-dimethylaminopropyl]phenyl dimethylcarbamate hydrochloride (Exemplification compound number 1-159)

(R)-4-[3-(3-Difluorophenoxy)-1-methylaminopropyl] phenyl dimethylcarbamate hydrochloride obtained from Example 151 was treated using a similar procedure to that described in Example 3 to afford the title compound as an amorphous solid.

¹H-NMR(400 MHz,CDCl₃) δ ppm: 2.60(3H,brs), 2.55–2.73(1H,br), 2.89(3H,brs), 2.82–2.98(1H,br), 3.02(3H, s), 3.11(3H,s), 3.45–3.56(1H,br), 3.90–4.00(1H,br), 4.22–4.34(1H,br), 6.40–6.49(1H,m), 6.51–6.62(1H,m), 7.01 (1H,q,J=9.5 Hz), 7.23(2H,d,J=6.6 Hz), 7.56(2H,d,J=6.6 Hz). MS (FAB+): 379(M+H)+[α]$_D^{22}$ −88.9(CHCl₃,C=0.98)

EXAMPLE 153

4-[3-(4-Nitrophenylsulfanyl)-1-methylaminopropyl] phenyl dimethylcarbamate hydrochloride (Exemplification compound number 1-43)

t-Butyl N-[1-(4-dimethylcarbamoyloxy)phenyl]-3-hydroxypropyl]-N-methylcarbamate obtained from Example 16b and 4-nitrothiophenol were treated using similar procedures to those described in Example 7f and 7g to afford the title compound as an amorphous solid.

¹H-NMR (400 MHz, CDCl₃) δ ppm: 2.43 (3H, s), 2.56 (1H, m), 2.82 (2H, m), 3.01 (1H, m), 3.02 (3H, s), 3.12 (3H, s), 4.13 (1H, m), 7.23 (4H, m), 7.58 (2H, d, J=8.1 Hz), 8.09 (2H, d, J=8.8 Hz) ms (FAB) m/z: 390 ((M+H)⁺)

EXAMPLE 154

4-[3-(4-Nitrophenylsulfanyl)-1-dimethylaminopropyl]phenyl dimethylcarbamate hydrochloride (Exemplification compound number 1-47)

4-[3-(4-Nitrophenylsulfanyl)-1-methylaminopropyl]phenyl dimethylcarbamate hydrochloride obtained from Example 153 was treated using a similar procedure to that described in Example 3 to afford the title compound as an amorphous solid.

¹H-NMR (400 MHz, CDCl₃) δ ppm: 2.59 (3H, m), 2.67 (1H, m), 2.76 (3H, m), 2.80 (1H, m), 3.01 (1H, m), 3.04 (3H, s), 3.10 (1H, m), 3.13 (3H, s), 4.25 (1H, m), 7.25 (4H, m), 7.53 (2H, d, J=8.1 Hz), 8.12 (2H, d, J=8.8 Hz), ms (FAB) m/z: 404 ((M+H)⁺)

EXAMPLE 155

4-[3-(4-Chlorophenylsulfanyl)-1-methylaminopropyl]phenyl dimethylcarbamate hydrochloride (Exemplification compound number 1-42)

t-Butyl N-[1-(4-dimethylcarbamoyloxy)phenyl]-3-hydroxypropyl]-N-methylcarbamate obtained from Example 16b and 4-chlorothiophenol were treated using similar procedures to those described in Example 7f and 7g to afford the title compound as an amorphous solid.

¹H-NMR (400 MHz, CDCl₃) δ ppm: 2.40 (3H, s), 2.46 (1H, m), 2.63 (2H, m), 2.86 (1H, m), 3.02 (3H, s), 3,11 (3H, s) 4.17 (1H, m), 7.22 (6H, m), 7.54 (2H, d, J=8.8 Hz), ms (FAB) m/z: 379 ((M+H)⁺)

EXAMPLE 156

4-[3-(4-Chlorophenylsulfanyl)-1-dimethylaminopropyl]phenyl dimethylcarbamate hydrochloride (Exemplification compound number 1-46)

4-[3-(4-Chlorophenylsulfanyl)-1-methylaminopropyl]phenyl dimethylcarbamate hydrochloride obtained from Example 155 was treated using a similar procedure to that described in Example 3 to afford the title compound as an amorphous solid.

¹H-NMR (400 MHz, CDCl₃) δ ppm: 2.54 (3H, d, J=4.8 Hz), 2.60–2.50 (3H, m), 2.73 (3H, d, J=4.8 Hz), 2.90 (1H, m), 3.03 (3H, s), 3.12 (3H, s), 4.21 (1H, m), 7.24 (6H, m), 7.51 (2H, d, J=8.8 Hz), ms (FAB) m/z: 393 ((M+H)⁺)

EXAMPLE 157

4-[3-(4-Fluorophenylsulfanyl)-1-methylaminopropyl]phenyl dimethylcarbamate hydrochloride (Exemplification compound number 1-41)

t-Butyl N-[1-(4-dimethylcarbamoyloxy)phenyl]-3-hydroxypropyl]-N-methylcarbamate obtained from Example 16b and 4-fluorothiophenol were treated using similar procedures to those described in Example 7f and 7g to afford the title compound as an amorphous solid.

¹H-NMR (500 MHz, CDCl₃) δ ppm: 2.40 (3H, s), 2.43 (1H, m), 2.60 (2H, m), 2.84 (1H, m), 3.02 (3H, s), 3.11 (3H, s), 4.19 (1H, m), 6.98 (2H, t, J=8.8 Hz), 7.19 (2H, d, J=8.8 Hz), 7.30 (2H, dd, J=8.8 Hz, 5.9 Hz), 7.54 (2H, d, J=8.8 Hz), ms (FAB) m/z: 363 ((M+H)⁺)

EXAMPLE 158

4-[3-(4-Fluorophenylsulfanyl)-1-dimethylaminopropyl]phenyl dimethylcarbamate hydrochloride (Exemplification compound number 1-45)

4-[3-(4-Fluorophenylsulfanyl)-1-methylaminopropyl] phenyl dimethylcarbamate hydrochloride obtained from Example 157 was treated using a similar procedure to that described in Example 3 to afford the title compound as an amorphous solid.

¹H-NMR (400 MHz, CDCl₃) δ ppm: 2.63–2.42 (3H, m), 2.54 (3H, br s), 2.73 (3H, br s), 2.86 (1H, m), 3.03 (3H, s), 3.12 (3H, s), 4.21 (1H, m), 7.01 (2H, t, J=8.8 Hz), 7.24 (2H, d, J=7.7 Hz), 7.32 (2H, dd, J=8.8 Hz, 5.1 Hz), 7.50 (2H, d, J=7.7 Hz), ms (FAB) m/z: 377 ((M+H)⁺)

EXAMPLE 159

4-[3-(Pyridin-2-yloxy)-1-dimethylaminopropyl]phenyl dimethylcarbamate hydrochloride (Exemplification compound number 1-180)

t-Butyl N-[1-[(4-dimethylcarbamoyloxy)phenyl]-3-hydroxypropyl]-N-methylcarbamate obtained from Example 16b and pyridin-2-ol were treated using similar procedures to those described in Example 48a, 48b and 3 to afford the title compound as an amorphous solid.

¹H-NMR (500 MHz, CDCl₃) δ ppm: 2.60 (3H, d, J=4.4 Hz), 2.95 (2H, m), 3.01 (3H, s), 3.05 (3H, d, J=4.4 Hz), 3.10 (3H, s), 4.17 (1H, br s), 4.63 (1H, br s), 4.99 (1H, br s), 7.13 (1H, br d), 7.19 (2H, d, J=7.7 Hz), 7.37 (1H, br t), 7.82 (2H, d, J=7.7 Hz), 8.21 (1H, br t), 8.31 (1H, d, J=5.4 Hz), ms (FAB) m/z: 344 ((M+H)⁺)

EXAMPLE 160

4-[3-(6-Chloropyridin-2-yloxy)-1-methylaminopropyl]phenyl dimethylcarbamate hydrochloride (Exemplification compound number 1-124)

The title compound was obtained as an amorphous solid using t-butyl N-[1-[(4-dimethylcarbamoyloxy)phenyl]-3-hydroxypropyl]-N-methylcarbamate obtained in step (b) of Example 16 and 6-chloropyridine-2-ol by conducting successively reactions similar to those mentioned in steps (a) and (b) of Example 48.

¹H-NMR (500 MHz, CDCl₃) δ ppm: 2.49 (1H, m), 2.98 (1H, m), 3.01 (3H, s), 3.10 (3H, s), 4.41 (1H, br s), 4.47 (1H, br s), 4.61 (1H, br s), 7.05 (1H, m), 7.19 (2H, d, J=6.9 Hz), 7.54 (2H, br d), 7.86 (1H, br s), 8.14 (1H, br s), ms (FAB) m/z: 364 ((M+H)⁺)

EXAMPLE 161

4-[3-(6-Chloropyridin-2-yloxy)-1-dimethylaminopropyl]phenyl dimethylcarbamate hydrochloride (Exemplification compound number 1-181)

The title compound was obtained as an amorphous solid using 4-[3-(6-chloropyridin-2-yloxy)-1-methylaminopropyl]phenyl dimethylcarbamate hydrochloride obtained in Example 160 in a similar manner to that mentioned in Example 3.

¹H-NMR (500 MHz, CDCl₃) δ ppm: 2.60 (3H, d, J=3.2 Hz), 2.70 (1H, m), 2.84 (3H, d, J=3.2 Hz), 2.97 (1H, m), 3.02 (3H, s), 3.11(3H, s), 3.94 (1H, m), 4.32 (2H, br s), 6.65 (1H, br d, J=8.6 Hz), 7.22 (2H, d, J=7.9 Hz), 7.55 (3H, m), 8.02 (1H, br s), ms (FAB) m/z: 378 ((M+H)⁺)

EXAMPLE 162

(S)-4-[3-(3,4-Difluorophenoxy)-1-methylaminopropyl]phenyl dimethylcarbamate hydrochloride (Exemplification compound number 1-102)

The title compound was obtained as an amorphous solid using t-butyl (S)-[1-[(4-dimethylcarbamoyloxy)phenyl]-3- hydroxypropyl]carbamate obtained in step (b) of Example 81 and 3,4-difluorophenol by conducting successively reactions similar to those mentioned in steps (f) and (g) of Example 7.

$^1$H-NMR(400 MHz,CDCl$_3$) δ ppm: 2.51(3H,s), 2.48–2.62 (1H,m), 2.90–3.05(1H,m), 3.01(3H,s), 3.10(3H,s), 3.50–3.61 (1H,m), 3.88–3.97(1H,m), 4.27–4.37(1H,m), 6.45–6.55(1H, m), 6.61(1H,ddd,J=11.9 Hz,6.5 Hz,3.0 Hz), 7.00(1H,q,J=9.4 Hz), 7.19(2H,d,J=8.5 Hz), 7.59(2H,d,J=8.5 Hz) 9.4–10.7(br). MS (FAB$^+$): 365(M+H)$^+$. [α]$_D^{22}$ +94.6(CHCl$_3$, C=1.05)

EXAMPLE 163

(S)-4-[3-(3,4-Difluorophenoxy)-1-dimethylaminopropyl]phenyl dimethylcarbamate hydrochloride (Exemplification compound number 1-159)

The title compound was obtained as an amorphous solid using (S)-4-[3-(3,4-difluorophenoxy)-1-methylaminopropyl]phenyl dimethylcarbamate hydrochloride obtained in Example 162 in a similar manner to that mentioned in Example 3.

$^1$H-NMR(400 MHz,CDCl$_3$) δ ppm: 2.61(3H,brs), 2.60–2.74(1H,br), 2.90(3H,brs), 2.84–3.00(1H,br), 3.02(3H, s), 3.11(3H,s), 3.42–3.58(1H,br), 3.88–4.00(1H,br), 4.20–4.34(1H,br), 6.40–6.48(1H,m), 6.52–6.62(1H,m), 7.01 (1H,q,J=9.5 Hz), 7.23(2H,d,J=6.4 Hz), 7.56(2H,d,J=6.4 Hz). MS (FAB+): 379(M+H)$^+$[α]$_D^{22}$ +86.5(CHCl$_3$,C=1.06)

EXAMPLE 164

(S)-4-[3-(4-Chlorophenoxy)-1-methylaminopropyl] phenyl dimethylcarbamate ½ Fumarate Salt (Exemplification compound number 1-78)

The title compound was obtained as crystals using (S)-4-[3-(4-chlorophenoxy)-1-methylaminopropyl]phenyl dimethylcarbamate obtained in Example 82 in a similar manner to that mentioned in Example 121.

Melting point: 173–174° C. $^1$H-NMR(400 MHz,CDCl$_3$) δ ppm: 2.16–2.29(1H,m), 2.39(3H,s), 2.46–2.59(1H,m), 2.99 (3H,s), 3.08(3H,s), 3.61–3.71(1H,m), 3.84–3.94(1H,m), 4.03–4.12(1H,m), 6.71(2H,d,J=8.8 Hz), 6.78(1H,s), 7.13 (2H,d,J=8.8 Hz), 7.16(2H,d,J=8.8 Hz), 7.39(2H,d,J=8.8 Hz). MS (FAB+): 363(M+H)$^+$[α]$_D^{22}$ +78.4(CHCl$_3$,C=1.03)

EXAMPLE 165

4-[3-(4-dimethylcarbamoyloxy)phenyl-3-methylaminopropyloxy]benzoic acid (Exemplification compound number 1-99)

(a) Benzyl 4-[3-(4-dimethylcarbamoyloxy)phenyl-3-methylaminopropyloxy]benzoate

The title compound was obtained as an amorphous solid using t-butyl N-[1-[(4-dimethylcarbamoyloxy)phenyl]-3-hydroxypropyl]-N-methylcarbamate obtained in step (b) of Example 16 and benzyl 4-hydroxybenzoate by conducting successively reactions similar to those mentioned in steps (a) and (b) of Example 48.

$^1$H-NMR(500 MHz,CDCl$_3$) δ ppm: 2.00–2.07 (1H,m), 2.22–2.29 (1H,m), 2.29 (3H,s), 3.01 (3H,s), 3.09 (3H,s), 3.76 (1H,t,J=7.5 Hz), 3.84–3.89 (1H,m), 4.00 (1H,dt,J=5.5 Hz,10.0 Hz), 5.33 (2H,s), 6.85 (2H,d,J=9.0 Hz), 7.07 (2H,d, J=8.5 Hz), 7.27 (2H,d,J=8.5 Hz), 7.32–7.34 (3H,m), 7.44 (2H,d,J=8.0 Hz), 8.00 (2H,d,J=9.0 Hz).

(b) 4-[3-(4-dimethylcarbamoyloxy)phenyl-3-methylaminopropyloxy]benzoic acid.

The crude title compound was synthesized using benzyl 4-[3-t-butoxycarbonylamino-3-(4-dimethylcarbamoyloxy) phenylpropyloxy]benzoate obtained in step (a) of Example 165 by conducting a reaction similar to that mentioned in step (c) of Example 1, from which the title compound was obtained as an amorphous solid by washing with ether.

$^1$H-NMR(400 MHz,CDCl$_3$) δ ppm: 2.18–2.28 (1H,m), 2.38 (3H,s), 2.52–2.62 (1H,m), 3.02 (3H,s), 3.11 (3H,s), 3.90–3.98 (1H,m), 4.13–4.22 (2H,m), 6.77 (2H,d,J=8.8 Hz), 7.17 (2H,d,J=8.8 Hz), 7.47 (2H,d,J=8.8 Hz), 7.74 (2H,d, J=8.8 Hz). IR(CHCl$_3$) 2952, 2470, 1716, 1605, 1511, 1389, 1250, 1169, 1036, 1018, 851.

EXAMPLE 166

4-[3-(4-dimethylcarbamoyloxy)phenyl-3-dimethylaminopropyloxy]benzoic Acid (Exemplification compound number 1-156)

The title compound was obtained as an amorphous solid using benzyl 4-[3-t-butoxycarbonylamino-3-(4-dimethylcarmoyloxy)phenylpropyloxy]benzoate obtained in step (a) of Example 165 by conducting successively reactions similar to those mentioned in Example 6 (b), 3 and 165 (b).

$^1$H-NMR(400 MHz,CDCl$_3$) δ ppm: 2.23–2.36 (1H,m), 2.41 (6H,s), 2.65–2.74 (1H,m), 3.03 (3H,s), 3.12 (3H,s), 3.88–3.94 (1H,m), 4.08–4.14 (1H,m), 4.27 (1H,dd,J=9.4 Hz,5.0 Hz), 6.79 (2H,d,J=8.8 Hz), 7.20 (2H,d,J=8.8 Hz), 7.38 (2H,d,J=8.8 Hz), 7.71 (2H,d,J=8.8 Hz). IR(CHCl$_3$) 2962, 1719, 1605, 1510, 1470, 1391, 1251, 1168, 1037, 1017, 851.

EXAMPLE 167

4-[3-(6-Nitropyridin-2-yloxy)-1-methylaminopropyl] phenyl dimethylcarbamate hydrochloride (Exemplification compound number 1-126)

The title compound was obtained as an amorphous solid using t-butyl N-[1-[(4-dimethylcarbamoyloxy)phenyl]-3-hydroxypropyl]-N-methylcarbamate obtained in step (b) of Example 16 and 6-nitropyridine-2-ol by conducting successively reactions similar to those mentioned in steps (a) and (b) of Example 48.

$^1$H-NMR (500 MHz, CDCl$_3$) δ ppm: 2.50 (3H, s), 2.68 (1H, m), 3.01 (3H, s), 3.05 (1H, m), 3.10 (3H, s), 4.14 (1H, m), 4.25 (1H, m), 4.47 (1H, m), 6.78 (1H, d, J=8.6 Hz), 7.19 (2H, d, J=7.8 Hz), 7.58 (2H, d, J=7.8 Hz), 8.33 (1H, dd, J=8.6 Hz, 2.9 Hz), 8.96 (1H, d, J=2.9 Hz), 9.95 (1H, br s), 10.30 (1H, br s), ms (FAB) m/z: 375 ((M+H)$^+$)

EXAMPLE 168

4-[3-(6-Nitropyridin-2-yloxy)-1-dimethylaminopropyl]phenyl dimethylcarbamate hydrochloride (Exemplification compound number 1-183)

The title compound was obtained as an amorphous solid using 4-[3-(6-nitropyridin-2-yloxy)-1-methylaminopropyl] phenyl dimethylcarbamate hydrochloride obtained in Example 167 in a similar manner to that mentioned in Example 3.

$^1$H-NMR (500 MHz, CDCl$_3$) δ ppm: 2.63 (3H, d, J=4.7 Hz), 2.75 (1H, m), 2.82 (3H, d, J=4.7 Hz), 3.01 (1H, m), 3.02 (3H, s), 3.11 (3H, s), 4.13 (1H, m), 4.33 (1H, m), 4.45 (1H, m), 6.73 (1H, d, J=9.0 Hz), 7.23 (2H, d, J=8.4 Hz), 7.51 (2H, d, J=8.4 Hz), 8.32 (1H, dd, J=9.0 Hz, 2.8 Hz), 8.96 (1H, d, J=2.8 Hz), ms (FAB) m/z: 389 ((M+H)$^+$)

EXAMPLE 169

4-[3-(6-Trifluoromethylpyridin-2-yloxy)-1-methylaminopropyl]phenyl dimethylcarbamate hydrochloride (Exemplification compound number 1-125)

The title compound was obtained as an amorphous solid using t-butyl N-[1-[(4-dimethylcarbamoyloxy)phenyl]-3-hydroxypropyl]-N-methylcarbamate obtained in step (b) of Example 16 and 6-trifluoromethylpyridine-2-ol by conducting successively reactions similar to those mentioned in steps (a) and (b) of Example 48.

$^1$H-NMR (500 MHz, CDCl$_3$) δ ppm: 2.50 (3H, m), 2.64 (1H, m), 2.99 (1H, m), 3.01 (3H, s), 3.10 (3H, s), 4.06 (1H, m), 4.19 (1H, m), 4.40 (1H, m), 6.78 (1H, d, J=8.8 Hz), 7.19 (2H, d, J=8.5 Hz), 7.59 (2H, d, J=8.5 Hz), 7.75 (1H, dd, J=8.8 Hz, 2.0 Hz), 8.83 (1H, s), 9.97 (1H, br s), 10.26 (1H, br s), IR (KBr) cm$^{-1}$: 2950, 2770, 2700, 1730, 1610, 1390, 1330, 1290, 1220, 1180, 1160, 1130

EXAMPLE 170

4-[3-(6-Trifluoromethylpyridin-2-yloxy)-1-dimethylaminopropyl]phenyl dimethylcarbamate hydrochloride (Exemplification compound number 1-182)

The title compound was obtained as an amorphous solid using 4-[3-(6-trifluoromethylyridin-2-yloXY)-1-methylaminopropyl]phenyl dimethylcarbamate hydrochloride obtained in Example 169 in a similar manner to that mentioned in Example 3.

$^1$H-NMR (500 MHz, CDCl$_3$) δ ppm: 2.88–2.63 (7H, m), 3.00 (1H, m), 3.02 (3H, s), 3.11 (3H, s), 4.02 (1H, m), 4.30 (1H, m), 4.38 (1H, m), 5.73 (1H, d, J=7.8 Hz), 7.22 (2H, d, J=8.8 Hz), 7.52 (2H, d, J=8.8 Hz), 7.74 (1H, m), 8.33 (1H, s), IR (KBr) cm$^{-1}$: 2930, 2630, 2580, 2510, 2460, 1730, 1610, 1390, 1330, 1290, 1220, 1180, 1160, 1130

EXAMPLE 171

Methyl 3-[3-(4-dimethylcarbamoyloxy)phenyl-3-methylaminopropyloxy]-thiophenecarboxylate (Exemplification compound number 1-130)

The title compound was obtained as an amorphous solid using t-butyl N-[1-[(4-dimethylcarbamoyloxy)phenyl]-3-hydroxypropyl]-N-methylcarbamate obtained in step (b) of Example 16 and methyl 3-hydroxythiophenecarboxylate by conducting successively reactions similar to those mentioned in steps (a) and (b) of Example 48.

$^1$H-NMR (500 MHz, CDCl$_3$) δ ppm: 2.55 (1H, m), 2.64 (3H, m) 3.01 (3H, s), 3.08 (1H, m), 3.09 (3H, s), 3.87 (3H, s), 4.04 (1H, m), 4.30 (1H, m), 4.53 (1H, m), 6.78 (1H, d, J=4.9 Hz), 7.18 (2H, d, J=7.8 Hz), 7.48 (3H, m), 9.84 (1H, br s), 10.65 (1H, br s), ms (FAB) m/z: 393 ((M+H)$^+$)

EXAMPLE 172

Methyl 3-[3-(4-dimethylcarbamoyloxy)phenyl-3-dimethylaminopropyloxy]-thiophenecarboxylate (Exemplification compound number 1-187)

The title compound was obtained as an amorphous solid using methyl 3-[3-(4-dimethylcarbamoyloxy)phenyl-3-methylaminopropyloxy]-thiophenecarboxylate obtained in Example 171 in a similar manner to that mentioned in Example 3.

$^1$H-NMR (500 MHz, CDCl$_3$) δ ppm: 2.58 (3H, d, J=4.9 Hz), 2.68 (1H, m), 2.93 (1H, m), 3.00 (3H, m), 3.01 (3H, s), 3.10 (3H, s), 3.56 (1H, m), 3.86 (3H, s), 4.24 (1H, m) 4.55 (1H, m), 6.67 (1H, d, J=5.4 Hz), 7.19 (2H, d, J=8.8 Hz), 7.36 (1H, d, J=5.4 Hz), 7.69 (2H, d, J=8.8 HZ), IR (film) cm$^{-1}$: 3420, 3100, 3020, 2950, 2660, 2580, 2510, 2460, 1720, 1540, 1440, 1390, 1220, 1070

EXAMPLE 173

4-[3-(2-Nitropyridin-4-yloxy)-1-methylaminopropyl]phenyl dimethylcarbamate hydrochloride (Exemplification compound number 1-128)

The title compound was obtained as an amorphous solid using t-butyl N-[1-[(4-dimethylcarbamoyloxy)phenyl]-3-hydroxypropyl]-N-methylcarbamate obtained in step (b) of Example 16 and 2-nitropyridine-4-ol by conducting successively reactions similar to those mentioned in steps (a) and (b) of Example 48.

$^1$H-NMR (500 MHz, DMSO-d$_6$) δ ppm: 2.39 (1H, m), 2.50 (3H, d, J=2.0 Hz), 2.64 (1H, m), 2.88 (3H, s), 3.01 (3H, s), 3.94 (1H, m), 4.32 (2H, m), 7.18 (2H, d, J=8.8 Hz), 7.32 (1H, d, J=5.9 Hz), 7.51 (2H, d, J=8.8 Hz), 8.70 (1H, m), 9.01 (1H, s), ms (FAB) m/z: 375 ((M+H)$^+$)

EXAMPLE 174

4-[3-(4-Methylthiophenoxy)-1-methylaminopropyl]phenyl dimethylcarbamate hydrochloride (Exemplification compound number 1-199)

The title compound was obtained as an amorphous solid using t-butyl N-[1-[(4-dimethylcarbamoyloxy)phenyl]-3-hydroxypropyl]-N-methylcarbamate obtained in step (b) of Example 16 and 4-methylthiophenol by conducting successively reactions similar to those mentioned in steps (a) and (b) of Example 48.

$^1$H-NMR(400 MHz,CDCl$_3$) δ ppm: 2.41 (3H,s), 2.45–2.64 (2H,m), 2.51 (3H,s), 2.90–3.09 (2H,m), 3.00 (3H,s), 3.09 (3H,s), 3.51–3.62 (1H,m), 3.88–3.98 (1H,m), 4.28–4.42 (1H, m), 6.72 (2H,d,J=8.8 Hz), 7.18 (2H,d,J=8.4 HZ) 7.19 (2H,d, J=8.8Hz), 7.60 (2H,d,J=8.4 Hz), 9.7–10.2 (1H,br), 10.2–10.5 (1H,br). MS (FAB): 375 (M+H)$^+$.

EXAMPLE 175

4-[3-(4-Methylthiophenoxy)-1-dimethylaminopropyl]phenyl dimethylcarbamate hydrochloride (Exemplification compound number 1-200)

The title compound was obtained as an amorphous solid using 4-[3-(4-methylthiophenoxy)-1-methylaminopropyl] phenyl dimethylcarbamate obtained in Example 174 in a similar manner to that mentioned in Example 3.

$^1$H-NMR(400 MHz,CDCl$_3$) δ ppm: 2.42 (3H,s), 2.54–2.74 (1H,m), 2.59 (3H,brs), 2.85–2.99 (1H,m), 2.85–2.99 (1H,m), 2.91 (3H,brs), 3.02 (3H,s), 3.10 (3H,s), 3.46–3.56 (1H,m), 3.92–4.01 (1H,m), 4.23–4.33 (1H,m), 6.69 (2H,d,J=8.7 Hz), 7.16–7.25 (4H,m) 7.58 (2H,d,J=8.4 Hz), 12.8 (1H,brs). MS (FAB): 389(M+H)$^+$.

EXAMPLE 176

(S)-4-[3-(4-Methylthiophenoxy)-1-methylaminopropyl]phenyl dimethylcarbamate hydrochloride (Exemplification compound number 1-199)

The title compound was obtained as an amorphous solid using t-butyl (S)-[1-[(4-dimethylcarbamoyloxy)phenyl]-3-hydroxypropyl]carbamate obtained in step (a) of Example 81 and 4-methylthiophenol by conducting successively reactions similar to those mentioned in step (a) of Example 48 and steps (d) and (e) of Example 61.

$^1$H-NMR(400 MHz,CDCl$_3$) δ ppm: 2.41 (3H,s), 2.45–2.63 (1H,m), 2.51 (3H,s), 2.89–3.07 (1H,m), 3.00 (3H,s), 3.09 (3H,s), 3.50–3.62 (1H,m), 3.86–4.00 (1H,m), 4.35 (1H,brs), 6.72 (2H,d,J=8.8 Hz), 7.18 (2H,d,J=8.6 Hz), 7.19 (2H,d, J=8.8 Hz), 7.60 (2H,d,J=8.6 Hz), 9.75–10.05 (1H,br), 10.10–10.45 (1H,br). MS (FAB): 375(M+H)$^+$.

EXAMPLE 177

(R)-4-[3-(4-Methylthiophenoxy)-1-methylaminopropyl]phenyl dimethylcarbamate hydrochloride (Exemplification compound number 1-199)

The title compound was obtained using t-butyl (R)-[1-[(4-dimethylcarbamoyloxy)phenyl]-3-hydroxypropyl]carbamate obtained in step (b) of Example 61 and 4-methylthiophenol by conducting successively reactions similar to those mentioned in steps (c), (d) and (e) of Example 61.

$^1$H-NMR(400 MHz, CDCl$_3$) δ ppm: 2.41 (3H,s), 2.45–2.63 (1H,m), 2.51 (3H,s), 2.89–3.07 (1H,m), 3.00 (3H, s), 3.09 (3H,s), 3.50–3.62 (1H,m), 3.86–4.00 (1H,m), 4.35 (1H,brs), 6.72 (2H,d,J=8.8 Hz), 7.18 (2H,d,J=8.6 Hz), 7.19 (2H,d,J=8.8 Hz), 7.60 (2H,d,J=8.6 Hz), 9.75–10.05 (1H,br), 10.10–10.45 (1H,br). MS (FAB): 375(M+H)$^+$.

EXAMPLE 178

4-[3-(Pentafluorophenoxy)-1-methylaminopropyl] phenyl dimethylcarbamate hydrochloride (Exemplification compound number 1-203)

The title compound was obtained as an amorphous solid using t-butyl N-[1-[(4-dimethylcarbamoyloxy)phenyl]-3-hydroxypropyl]-N-methylcarbamate obtained in step (b) of Example 16 and pentafluorophenol by conducting successively reactions similar to those mentioned in steps (a) and (b) of Example 48.

$^1$H-NMR(400 MHz,CDCl$_3$) δ ppm: 2.52 (3H,s), 2.40–2.63 (1H,m), 2.90–3.15 (1H,m), 3.02 (3H,s), 3.11 (3H,s), 3.69–3.85 (1H,m), 4.20–4.31 (1H,m), 4.38 (1H,brs), 7.23 (2H,d,J=8.4 Hz), 7.66 (2H,d,J=8.4 Hz), 9.95 (1H,brs),10.34 (1H,brs). MS (FAB): 419(M+H)$^+$.

EXAMPLE 179

4-[3-(Naphthalen-1-yloxy)-1-methylaminopropyl] phenyl dimethylcarbamate hydrochloride (Exemplification compound number 1-205)

The title compound was obtained as an amorphous solid using t-butyl N-[1-[(4-dimethylcarbamoyloxy)phenyl]-3-hydroxypropyl]-N-methylcarbamate obtained in step (b) of Example 16 and 1-naphthylphenol by conducting successively reactions similar to those mentioned in steps (a) and (b) of Example 48.

$^1$H-NMR(400 MHz,CDCl$_3$) δ ppm: 2.56 (3H,s), 2.65–2.79 (1H,m), 2.99 (3H,s), 3.06 (3H,s), 3.12–3.25 (1H,m), 3.70–3.82 (1H,m), 4.06–4.14 (1H,m), 4.41–4.53 (1H,br), 6.56 (1H,d,J=7.5 Hz), 7.15 (2H,d,J=8.5 Hz), 7.22–7.29 (1H, m), 7.37 (1H,d,J=8.3 Hz), 7.44–7.51 (2H,m), 7.62 (2H,d, J=8.5 Hz), 7.73–7.80 (1H,m), 8.16–8.24 (1H,m), 10.03 (1H, brs),10.41 (1H,brs). MS (FAB): 379(M+H)$^+$.

EXAMPLE 180

4-[3-(Quinolin-6-yloxy)-1-methylaminopropyl]phenyl dimethylcarbamate hydrochloride (Exemplification compound number 1-206)

The title compound was obtained as an amorphous solid using t-butyl N-[1-[(4-dimethylcarbamoyloxy)phenyl]-3-hydroxypropyl]-N-methylcarbamate obtained in step (b) of Example 16 and 6-hydroxyquinoline by conducting successively reactions similar to those mentioned in steps (a) and (b) of Example 48.

$^1$H-NMR(400 MHz,CDCl$_3$) δ ppm: 2.54 (3H,s), 2.57–2.73 (1H,m), 2.90–3.14 (1H,m), 2.99 (3H,s), 3.07 (3H,s), 3.67–3.78 (1H,m), 4.00–4.10 (1H,m), 4.35–4.45 (1H,m), 6.89 (1H,d,J=2.9 Hz), 7.18 (2H,d,J=8.1 Hz), 7.26–7.34 (2H, m), 7.63 (2H, d,J=8.1 Hz), 7.96 (2H,d,J=8.8 Hz), 8.73 (1H, dd,J=4.4 Hz,1.5 Hz). MS (FAB): 380(M+H)$^+$.

EXAMPLE 181

4-[3-(Pentafluorophenoxy)-1-dimethylaminopropyl] phenyl dimethylcarbamate hydrochloride (Exemplification compound number 1-204)

The title compound was obtained as an amorphous solid using 4-[3-(pentafluorophenoxy)-1-methylaminopropyl] phenyl dimethylcarbamate obtained in Example 178 in a similar manner to that mentioned in Example 3.

$^1$H-NMR(400 MHZ,CDCl$_3$) δ ppm: 2.59 (3H,s), 2.60–2.76 (1H,m), 2.88–3.05 (1H,m), 2.93 (3H,s), 3.03 (3H, s), 3.12 (3H,s), 3.62–3.73 (1H,m), 4.18–4.29 (1H,m), 4.29–4.40 (1H,m), 7.27 (2H,d,J=8.4 Hz), 7.64 (2H,d,J=8.4 Hz). MS (FAB): 433(M+H)$^+$.

EXAMPLE 182

4-[3-(4-Nitrophenoxy)-1-dimethylaminopropyl]-2-methylphenyl dimethylcarbamate hydrochloride (Exemplification compound number 4-12)

(a) t-Butyl N-[1-[(4-dimethylcarbamoyloxy)-2-methylphenyl]-3-hydroxypropyl]-N-methylcarbamate The title compound was obtained using 2-methyl-4-hydroxybenzaldehyde by conducting successively reactions similar to those mentioned in steps (a)–(e) of Example 7.

$^1$H-NMR(400 MHz,CDCl$_3$) δ ppm: 1.51 (9H,s), 1.90–2.04 (1H,m), 2.07–2.21 (1H,m), 2.21 (3H,s), 2.44 (3H,s), 3.02 (3H,s), 3.11 (3H,s), 3.50–3.60 (2H,m), 3.75 (1H,brs), 5.53–5.60 (1H,m), 7.05 (1H,d,J=7.8 Hz), 7.11–7.13 (2H,m).

(b) 4-[3-(4-Nitrophenoxy)-1-dimethylaminopropyl]-2-methylphenyl dimethylcarbamate hydrochloride The title compound was obtained as an amorphous solid using t-butyl N-[1-[(4-dimethylcarbamoyloxy)-2-methylphenyl]-3-hydroxypropyl]-N-methylcarbamate obtained in step (a) of Example 182 and 4-nitrophenol by conducting successively reactions similar to those mentioned in steps (a) and (b) of Example 48.

¹H-NMR(400 MHz,CDCl₃) δ ppm: 2.21 (3H,s), 2.51 (3H, s), 2.62–2.67 (1H,m), 3.02 (3H,s), 2.98–3.09 (1H,m), 3.12 (3H,s), 3.75–3.78 (1H,m), 4.08–4.12 (1H,m), 4.26 (1H,d, J=6.6 Hz), 6.86 (2H,d,J=9.1 Hz), 7.14 (1H,d,J=8.1 Hz), 7.39 (1H,d,J=8.1 Hz), 7.46 (1H,s), 8.15(2H,d,J=9.1 Hz). MS (FAB) m/z: 388 (M+H)⁺.

EXAMPLE 183

(S)-4-[3-(4-Nitrophenoxy)-1-methylaminopropyl]-2-methylphenyl dimethylcarbamate hydrochloride (Exemplification compound number 4-12)

(a) t-Butyl (S)-[1-[(4-dimethylcarbamoyloxy)-3-methylphenyl]-3-hydroxypropyl]carbamate The title compound was obtained using methyl (S)-3-amino-3-(4-hydroxy-2-methylphenyl)propionate, which was synthesized using 4-hydroxy-2-methylbenzaldehyde as a starting material by the procedure described in Tetrahedron: Asymmetry, 2, 183 (1991), by conducting successively reactions similar to those mentioned in steps (a) and (b) of Example 61.

¹H NMR(CDCl₃, 400 MHz) δ ppm: 1.44 (9H, s), 1.71–1.82 (2H, m), 2.16 (1H, br), 2.20 (3H, s), 3.02 (3H, s), 3.12 (3H, s), 3.67 (2H, br), 4.84 (1H, br), 5.00 (1H, br), 7.03 (1H, d, J=8.2 Hz), 7.10–7.13 (2H, m). $[\alpha]_D^{22}$ −46 (c 0.90, CHCl₃).

(b) (S)-4-[3-(4-Nitrophenoxy)-1-methylaminopropyl]-2-methylphenyl dimethylcarbamate hydrochloride The title compound was obtained as an amorphous solid using t-butyl (S)-[1-[(4-dimethylcarbamoyloxy)-2-methylphenyl]-3-hydroxypropyl]carbamate obtained in step (a) of Example 183 and 4-nitrophenol by conducting successively reactions similar to those mentioned in step (a) of Example 48 and steps (d) and (e) of Example 61.

¹H NMR(CDCl₃, 400 MHz) δ ppm: 2.49 (3H, s), 2.54–2.60 (1H, m), 2.93–2.96 (1H, m), 3.02 (3H, s), 3.12 (3H, s), 3.77–3.80 (1H, m), 4.07–4.10 (1H, m), 4.20–4.23 (1H, m), 7.86 (2H, d, J=9.2 Hz), 7.13 (1H, d, J=8.5 Hz), 7.37 (1H, d, J=8.5 Hz), 7.43 (1H, s), 8.15 (2H, d, J=9.2 Hz). MS(FAB) m/z: 388 (M+H)⁺. $[\alpha]_D^{22}$ +189 (c 0.95, CHCl₃).

EXAMPLE 184

(R)-4-[3-(4-Nitrophenoxy)-1-methylaminopropyl]-2-methylphenyl dimethylcarbamate hydrochloride (Exemplification compound number 4-12)

(a) t-Butyl (R)-[1-[(4-dimethylcarbamoyloxy)-3-methylphenyl]-3-hydroxypropyl]carbamate The title compound was obtained using methyl (R)-3-amino-3-(4-hydroxy-2-methylphenyl)propionate, which was synthesized using 4-hydroxy-2-methylbenzaldehyde as a starting material by the procedure described in Tetrahedron: Asymmetry, 2, 183 (1991), by conducting successively reactions similar to those mentioned in steps (a) and (b) of Example 61.

¹H NMR(CDCl₃, 400 MHz) δ ppm: 1.44 (9H,s), 1.76–1.83 (1H,m), 2.00–2.09 (1H,m), 2.21 (3H,s), 3.02 (3H,s), 3.12 (3H,s), 3.69 (2H,brs), 4.83–4.93 (2H,m), 7.04 (1H,d,J=8.2 Hz), 7.11–7.13 (2H,m). $[\alpha]_D$ +52.9 (c 0.90, CHCl₃)

(b) (R)-4-[3-(4-Nitrophenoxy)-1-methylaminopropyl]-2-methylphenyl dimethylcarbamate hydrochloride The title compound was obtained as an amorphous solid using t-butyl (R)-[1-[(4-dimethylcarbamoyloxy)-2-methylphenyl]-3-hydroxypropyl]carbamate obtained in step (a) of Example 184 and 4-nitrophenol by conducting successively reactions similar to those mentioned in step (a) of Example 48 and steps (d) and (e) of Example 61.

¹H NMR(CDCl₃, 400 MHz) δ ppm: 2.21 (3H,s), 2.52 (3H,s), 2.61–2.67 (1H,m), 3.01 (3H,s), 3.01–3.12 (1H,m), 3.12 (3H,s), 3.73–3.78 (1H,m), 4.08–4.13 (1H,m), 4.26 (1H, brs), 6.86 (2H,d,J=9.1 Hz), 7.13 (1H,d,J=8.2 Hz), 7.39 (1H, d,J=8.2 Hz), 7.47 (1H,s), 8.15 (2H,d,J=9.1 Hz), 9.94 (1H, brs), 10.36 (1H,brs). $[\alpha]_D$ −123.4 (c 0.95, CHCl₃). MS (FAB) m/z: 388(M+H)⁺.

EXAMPLE 185

4-[3-(4-Chlorophenoxy)-1-dimethylaminopropyl]-2-methylphenyl dimethylcarbamate hydrochloride (Exemplification compound number 4-13)

The title compound was obtained as an amorphous solid using t-butyl N-[1-[(4-dimethylcarbamoyloxy)-2-methylphenyl]-3-hydroxypropyl]-N-methylcarbamate obtained in step (a) of Example 182 and 4-chlorophenol by conducting successively reactions similar to those mentioned in steps (a) and (b) of Example 48.

¹H-NMR(400 MHz,CDCl₃) δ ppm: 2.21 (3H,s), 2.50 (3H, s), 2.50–2.59 (1H,m), 2.92–3.02 (1H,m), 3.02 (3H,s), 3.12 (3H,s), 3.59 (1H,td,J=9.6, 4.1 Hz), 3.90–3.95 (1H,m), 4.25–4.28 (1H,m), 6.72 (2H,d,J=9.0 Hz), 7.12 (1H,d,J=8.3 Hz), 7.17 (2H,d,J=9.0 Hz), 7.39 (1H,dd,J=8.3, 1.9 Hz), 7.46 (1H,s). MS (FAB) m/z: 377(M+H)⁺.

EXAMPLE 186

4-[3-(4-Methylthiophenoxy)-1-dimethylaminopropyl]-2-methylphenyl dimethylcarbamate hydrochloride (Exemplification compound number 4-16)

The title compound was obtained as an amorphous solid using t-butyl N-[1-[(4-dimethylcarbamoyloxy)-2-methylphenyl]-3-hydroxypropyl]-N-methylcarbamate obtained in step (a) of Example 182 and 4-methylthiohenol by conducting successively reactions similar to those mentioned in steps (a) and (b) of Example 48.

¹H-NMR(400 MHz,CDCl₃) δ ppm: 2.21 (3H,s), 2.41 (3H, s), 2.50 (3H,s), 2.50–2.59 (1H,m), 2.91–3.01 (1H,m), 3.01 (3H,s), 3.12 (3H,s), 3.59 (1H,td,J=9.6, 4.0 Hz), 3.91–3.96 (1H,m), 4.28 (1H,dd,J=10.3, 3.9 Hz), 6.74 (2H,d,J=8.8 Hz), 7.12 (1H,d,J=8.3 Hz), 7.19 (2H,d,J=8.8 Hz), 7.39 (1H,d, J=8.3 Hz), 7.47 (1H,s). MS (FAB) m/z: 389(M+H)⁺.

EXAMPLE 187

2-Methyl-1-[2-(4-nitrophenoxy)-ethyl]-1,2,3,4-tetrahydroisoquinolin-6-yl dimethylcarbamate hydrochloride (Exemplification compound number 4-52)

(a) Ethyl N-[2-(3-methoxyphenyl)-ethyl]-malonate

To a solution of 2-(3-methoxy-phenyl)-ethylamine (1.0 g, 6.6 mmol) in dichloromethane (10 ml) were added potassium carbonate (1.1 g, 8.0 mmol) and ethyl malonyl chloride (0.92 ml, 7.2 mmol) at 0° C., and resulting mixture was stirred for 30 minutes at 0° C. under a nitrogen atmosphere. After stirring, water (50 ml) was added, and the resulting mixture was extracted with dichloromethane (30 ml×2). The organic layer was washed successively with water (30 ml×1) and saturated aqueous sodium chloride solution (30 ml×1), dried over anhydrous sodium sulfate, filtered, and evaporated in vacuo to afford the crude product. The obtained crude product was purified by chromatography on a silica gel column using a mixed solvent of hexane and ethyl acetate (50:50-33:67) as the eluent to afford the title compound (1.1 g, yield: 63%) as a colorless oil.

$^1$H-NMR(500 MHz,CDCl$_3$) δ ppm: 1.26 (3H, t, J=7.5 Hz), 2.81 (2H, t, J=7.0 Hz), 3.27 (2H, s), 3.55 (2H, q, J=7.0 Hz), 3.80 (3H, s), 4.17 (2H, q, J=7.5 Hz), 6.78–6.80 (3H, m), 7.08 (1H, br s), 7.22 (1H, t, J=8.0 Hz)

(b) Ethyl (6-methoxy-3,4-dihydro-2H-isoquinolin-1-yliden)-acetate

Ethyl N-[2-(3-methoxy-phenyl)-ethyl]-malonate (20.8 g, 78.4 mmol) synthesized in step (a) of Example 187 was dissolved in phosphorus oxychloride (60 ml), and the resulting mixture was stirred for 4 hours at 80° C. under a nitrogen atmosphere. After stirring, the reaction mixture was poured into ice-cold water (300 ml), neutralized with potassium carbonate, and extracted with ethyl acetate (300 ml×2). The organic layer was washed with saturated aqueous sodium chloride solution (300 ml×1), dried over anhydrous sodium sulfate, filtered, and evaporated in vacuo to afford the crude product. The obtained crude product was purified by chromatography on a silica gel column using a mixed solvent of hexane and ethyl acetate (1:1) as the eluent to afford a yellow oily product (7.56 g) containing the title compound as the major product.

$^1$H NMR(CDCl$_3$, 500 MHz) δ ppm: 1.30 (3H, t, J=7.5 Hz), 2.88 (2H, t, J=7.0 Hz), 3.43 (2H, dt, J=3.0, 7.0 Hz), 3.84 (3H, s), 4.16 (2H, q, J=7.5 Hz), 5.08 (1H, s), 6.70 (1H, d, J=2.5 Hz), 6.80 (1H, dd, J=2.5, 9.0 Hz), 7.62 (1H, d, J=9.0 Hz), 9.04 (1H, br s)

(c) Ethyl (6-methoxy-1,2,3,4-tetrahydroisoquinolin-1-yl)-acetate

To a solution of ethyl (6-methoxy-3,4-dihydro-2H-isoquinolin-1-yliden)-acetate (7.56 g) obtained in step (b) of Example 187 in acetic acid (50 ml) was added platinum oxide (400 mg), and the resulting mixture was stirred for 3 hours at room temperature under a hydrogen atmosphere. After stirring, the reaction mixture was filtered through celite and evaporated in vacuo. The residue obtained was neutralized with 1N aqueous sodium hydroxide solution and potassium carbonate, and extracted with ethyl acetate (300 ml×2). The organic layer was washed with saturated aqueous sodium chloride solution (300 ml×1), dried over anhydrous sodium sulfate, filtered, and evaporated in vacuo to afford the crude product. The crude product was purified by chromatography on a silica gel column using a mixed solvent of ethyl acetate and methanol (1:0-5:1) as the eluent to afford the title compound (4.88 g) as a yellow oil.

$^1$H NMR(CDCl$_3$, 400 MHz) δ ppm: 1.26 (3H, t, J=7.2 Hz), 2.67–2.76 (2H, m), 2.80–2.87 (2H, m), 3.01 (1H, ddd, J=5.2, 7.6, 12.4 Hz), 3.19 (1H, dt, J=5.2, 12.4 Hz), 4.17 (2H, q, J=7.2 Hz), 4.41 (1H, dd, J=3.2, 9.6 Hz), 6.63 (1H, d, J=2.8 Hz), 6.72 (1H, dd, J=2.8, 8.8 Hz), 7.01 (1H, d, J=8.8 Hz).

(d) t-Butyl 1-ethoxycarbonylmethyl-6-hydroxy-3,4-dihydro-1H-isoquinoline-2-carboxylate To a solution of ethyl (6-methoxy-1,2,3,4-tetrahydroisoquinolin-1-yl)-acetate (4.88 g, 19.6 mmol) synthesized in step (c) of Example 187 in dichloromethane (30 ml) was added 1M solution of boron tribromide in dichloromethane (30 ml) at −78° C. with stirring, and the resulting mixture was stirred for 3 hours at room temperature under a nitrogen atmosphere. After stirring, water (10 ml) was added, and the resulting mixture was neutralized with saturated aqueous sodium hydrogen carbonate solution and extracted with dichloromethane (40 ml×2). The organic layer was dried over anhydrous sodium sulfate, filtered, and evaporated in vacuo to afford the crude product (2.10 g). To a solution of the crude product (2.10 g) in tetrahydrofuran (20 ml) was added di-t-butyl dicarbonate (2.84 g, 13.0 mmol), and the resulting mixture was stirred for 1 hour at room temperature under a nitrogen atmosphere. After stirring, the reaction mixture was evaporated in vacuo and purified by chromatography on a silica gel column using a mixed solvent of hexane and ethyl acetate (90:10-50:50) as the eluent to afford the title compound (1.72 g, yield: 26%) as a colorless oil.

$^1$H NMR(CDCl$_3$, 500 MHz) δ ppm: 1.25 (3H, t, J=8.0 Hz), 1.48 (9H, s), 2.59–2.90 (4H, m), 3.23–3.30 (0.5H, m), 3.32–3.42 (0.5H, m), 3.84–3.92 (0.5H, m), 4.02–4.10 (0.5H, m), 4.08–4.18 (2H, m), 5.26 (1H, br s), 5.46 (0.5H, t, J=7.0 Hz), 5.56 (0.5H, t, J=7.0 Hz), 6.60 (1H, s), 6.62–6.68 (1H, m), 7.02 (1H, d, J=8.0 Hz).

(e) t-Butyl 6-dimethylcarbamoyloxy-1-ethoxycarbonylmethyl-6-hydroxy-3,4-dihydro-1H-isoquinoline-2-carboxylate To a solution of t-butyl 1-ethoxycarbonylmethyl-6-hydroxy-3,4-dihydro-1H-isoquinoline-2-carboxylate (1.70 g, 5.07 mmol) synthesized in step (d) of Example 187 in dimethylformamide (5 ml) were added potassium carbonate (1.03 g, 7.50 mmol) and N,N-dimethylcarbamoyl chloride (0.69 ml, 7.5 mmol), and the resulting mixture was stirred for 2.5 hours at room temperature under a nitrogen atmosphere. After stirring, water (20 ml) was added, and the resulting mixture was extracted with ethyl acetate (20 ml×2). The organic layer was washed with saturated aqueous sodium chloride solution (30 ml×1), dried over anhydrous sodium sulfate, filtered, and evaporated in vacuo to afford the crude product. The crude product was purified by chromatography on a silica gel column using a mixed solvent of hexane and ethyl acetate (2:1-1:1) as the eluent to afford the title compound (1.97 g, yield: 95%) as a colorless oil.

$^1$H NMR(CDCl$_3$, 500 MHz) δ ppm: 1.25 (3H, t, J=7.0 Hz), 1.47 (9H, s), 2.62–2.98 (4H, m), 3.00 (3H, s), 3.08 (3H, s), 3.18–3.26 (0.5H, m), 3.32–3.40 (0.5H, m), 3.90–3.92 (0.5H, m), 4.10–4.18 (2.5H, m), 5.53 (0.5H, t, J=7.0 Hz), 5.64 (0.5H, t, J=7.0 Hz), 6.89 (1H, s), 6.89–6.97 (1H, m), 7.14–7.19 (1H, m).

(f) t-Butyl 6-dimethylcarbamoyloxy-1-(2-hydroxyethyl)-3,4-dihydro-1H-isoquinoline-2-carboxylate To a solution of t-butyl 6-dimethylcarbamoyloxy-1-ethoxycarbonylmethyl-6-hydroxy-3,4-dihydro-1H-isoquinoline-2-carboxylate (1.97 g, 4.84 mmol) synthesized in step (e) of Example 187 in tetrahydrofuran (30 ml) was added lithium aluminum hydride (270 mg, 7.2 mmol) at −78° C., and the resulting mixture was stirred for 20 minutes at −78° C. and for 20 minutes at 0° C. successively under a nitrogen atmosphere. After stirring, to the reaction mixture were added water (0.3 ml), 15% aqueous sodium hydroxide solution (0.3 ml) and water (0.9 ml) in this order with stirring, and the resulting mixture was dried over anhydrous sodium sulfate, filtered, and evaporated in vacuo to afford the crude product. The crude product was purified by chromatography on a silica gel column using a mixed solvent of hexane and ethyl acetate (1:1-0:1) as the eluent to afford the title compound (1.38 g, yield: 78%) as a colorless oil.

$^1$H NMR(CDCl$_3$, 400 MHz) δ ppm: 1.49 (9H, s), 1.74 (1H, t, J=12.4 Hz), 2.00–2.10 (1H, m), 2.71 (1H, dt, J=4.4, 16.0 Hz), 2.86–2.94 (1H, m), 3.00 (3H, s), 3.09 (3H, s), 3.54 (1H, t, J=11.0 Hz), 3.65 (1H, br), 4.02 (1H, dt, J=4.4, 12.4 Hz), 4.12 (0.8H, br), 4.23 (0.2H, br), 5.30 (1H, d, J=12.0 Hz), 6.89 (1H, d, J=2.0 Hz), 6.93 (1H, dd, J=2.0, 8.0 Hz), 7.15 (1H, d, J=8.0 Hz).

(g) 2-Methyl-1-[2-(4-nitrophenoxy)-ethyl]-1,2,3,4-tetrahydroisoquinolin-6-yl dimethylcarbamate hydrochloride The title compound was obtained as an amorphous solid using t-butyl 6-dimethylcarbamoyloxy-1-(2-hydroxyethyl)-3,4-dihydro-1H-isoquinoline-2-carboxylate obtained in step (f) of Example 187 and 4-nitrophenol by conducting successively reactions similar to those mentioned in steps (a) and (b) of Example 48 and Example 3.

$^1$H NMR(CDCl$_3$, 400 MHz): δ 2.19–2.27 (1H, m), 2.89 (3H, d, J=5.2 Hz), 3.02 (3H, s), 3.04–3.20 (3H, m), 3.10 (3H, s), 3.32–3.40 (1H, m), 3.71–3.80 (1H, m), 4.14–4.20 (1H, m), 4.50 (1H, t, J=6.4 Hz), 4.60–4.65 (1H, m), 7.02–7.10 (5H, m), 8.23 (2H, d, J=8.8 Hz). MS(FAB) m/z: 400 (M+H)$^+$.

EXAMPLE 188

2-Methyl-1-[2-(4-chloro-3-methylphenoxy)-ethyl]-1,2,3,4-tetrahydroisoquinolin-6-yl dimethylcarbamate hydrochloride (Exemplification compound number 4-60)

The title compound was obtained as an amorphous solid using t-butyl 6-dimethylcarbamoyloxy-1-(2-hydroxyethyl)-3,4-dihydro-1H-isoquinoline-2-carboxylate obtained in step (f) of Example 187 and 4-chloro-3-methylphenol by conducting successively reactions similar to those mentioned in steps (a) and (b) of Example 48 and Example 3.

$^1$H-NMR (400 MHz, CDCl$_3$) δ ppm: 7.24 (1H, d, J=8.8), 7.10 (1H, m), 7.03 (2H, m), 6.83 (1H, s), 6.72 (1H, d, J=7.6), 4.53 (1H, br s), 4.35 (1H, br s), 3.98 (1H, br s), 3.75 (1H, br s), 3.35 (1H, br s), 3.15 (1H, m), 3.10 (3H, s), 3.02 (3H, s), 2.89 (3H, s), 2.35 (3H, s), 2.16 (1H, br s), 1.72 (2H, br s) MS(FAB) m/z: 403 (M+H)$^+$.

EXAMPLE 189

2-Methyl-1-[2-(2-chloro-4-nitrophenoxy)-ethyl]-1,2,3,4-tetrahydroisoquinolin-6-yl dimethylcarbamate hydrochloride (Exemplification compound number 4-58)

The title compound was obtained as an amorphous solid using t-butyl 6-dimethylcarbamoyloxy-1-(2-hydroxyethyl)-3,4-dihydro-1H-isoquinoline-2-carboxylate obtained in step (f) of Example 187 and 2-chloro-4-nitrophenol by conducting successively reactions similar to those mentioned in steps (a) and (b) of Example 48 and Example 3.

$^1$H NMR(CDCl$_3$, 400 MHz): δ 2.32–2.44 (1H, m), 2.90 (3H, s), 2.92–3.02 (1H, m), 3.02 (3H, s), 3.08–3.22 (2H, m), 3.10 (3H, s), 3.34–3.42 (1H, m), 3.68–3.78 (1H, m), 4.26–4.34 (1H, m), 4.56–4.62 (1H, m), 4.92–5.00 (1H, m), 7.05 (1H, d, J=2.4 Hz), 7.09 (1H, dd, J=2.4, 9.0 Hz), 7.16 (1H, d, J=9.0 Hz), 7.28 (1H, d, J=9.0 Hz), 8.19 (1H, dd, J=2.4, 9.0 Hz), 8.32 (1H, d, J=2.4 Hz) MS(FAB) m/z: 433 (M+H)$^+$.

EXAMPLE 190

2-Methyl-1-(R)-[2-(2-chloro-4-nitrophenoxy)-ethyl]-1,2,3,4-tetrahydroisoquinolin-6-yl dimethylcarbamate hydrochloride (Exemplification compound number 4-60)

(a) 6-Methoxy-1-(R)-(2-t-butyldimethylsilyloxyethyl)-3,4-dihydro-1H-isoquinoline-trifluoroacetamide To a solution of 6-methoxy-1-(R)-(2-t-butyldimethylsilyloxyethyl)-3,4-dihydro-1H-isoquinoline (1.30 g, 4.05 mmol), synthesized according to the procedure described in J. Org. Chem. 57, 4732 (1992), and pyridine (0.65 ml, 8.10 mmol) in dichloromethane (20 ml) was added dropwise trifluoroacetic anhydride (0.69 ml, 4.86 mmol) under cooling in an ice bath, and the resulting mixture was stirred at room temperature. After confirming the disappearance of the starting material by thin layer chromatography, saturated aqueous sodium hydrogen carbonate solution was added with stirring, and the resulting mixture was extracted with ethyl acetate. The extract was washed successively with dilute hydrochloric acid and saturated aqueous sodium chloride solution, dried over anhydrous sodium sulfate, and evaporated in vacuo. The residue obtained was purified by chromatography on a silica gel column using a mixed solvent of hexane and ethyl acetate (2:1) as the eluent to afford the title compound (1.50 g, yield: 88%) as a pale yellow oil.

$^1$H-NMR (500 MHz, CDCl$_3$) δ ppm: 7.08 (1H, m), 6.79 (1H, m), 6.68 (0.25H, d, J=2.5), 6.64 (0.75H, d, J=2.5), 5.62 (0.75H, dd, J=9.0, 5.5), 5.19 (0.25H, m), 4.41 (0.25H, ddd, J=13.5, 6.5, 4.5), 4.01 (0.75H, br d), 3.79 (3H, s), 3.59 (3H, m), 3.01(1H, m), 2.85 (1H, m), 2.13 (1H, m), 2.04 (0.75H, m), 1.92 (0.25H, m), 0.93 (2.25H , s), 0.90 (6.75H, s), 0.03 (0.25H, s), 0.06(2.63H, s), 0.05 (2.63H, s) [α]$_D^{25}$ −45.4° (c 1.06 CH$_2$Cl$_2$)

(b) 6-Methoxy-1-(R)-(2-hydroxyethyl)-3,4-dihydro-1H-isoquinoline-trifluoroacetamide To a solution of 6-methoxy-1-(R)-(2-t-butyldimethylsilyloxyethyl)-3,4-dihydro-1H-isoquinoline-trifluoroacetamide (1.14 g, 2.73 mmol) obtained in step (a) of Example 190 in acetonitrile (10 ml) was added dropwise 48% solution of hydrofluoric acid in water (0.5 ml, 13.67 mmol) gradually with stirring under cooling in a water bath. The resulting mixture was further stirred at room temperature, and after confirming the disappearance of the starting material by thin layer chromatography, saturated aqueous sodium hydrogen carbonate solution was added with stirring, and the resulting mixture was extracted with ethyl acetate. The extract was washed with saturated aqueous sodium chloride solution, dried over anhydrous sodium sulfate and evaporated in vacuo. The residue obtained was purified by chromatography on a silica gel column using a mixed solvent of hexane and ethyl acetate (2:1) as the eluent to afford the title compound (0.65 g, yield: 79%) as a colorless oil.

$^1$H-NMR (500 MHz, CDCl$_3$) δ ppm: 7.11 (1H, d, J=8.5), 6.82 (1H, dd, J=8.5, 2.5), 6.65 (1H, d, J=2.5), 5.60 (1H, dd, J=10.8, 3.0), 4.09 (1H, br d), 3.79 (3H, s), 3.68 (1H, m), 3.50 (2H, m), 3.04 (1H, m), 2.84 (1H, m), 2.16 (1H, m), 1.93 (1H, m) [α]$_D^{25}$ −30.0° (c 0.98 CH$_2$Cl$_2$)

(c) 6-Methoxy-1-(R)-(2-bromoethyl)-3,4-dihydro-1H-isoquinoline-trifluorooacetamide To a solution of 6-methoxy-1-(R)-(2-hydroxyethyl)-3,4-dihydro-1H-isoquinoline-trifluoroacetamide (330 mg, 1.09 mmol) obtained in step (b) of Example 190 and carbon tetrabromide (542 mg, 1.63 mmol) in dichloromethane (5 ml) was added gradually triphenyl phosphine (343 mg, 1.31 mmol) with stirring under cooling in a water bath. The resulting mixture was further stirred at room temperature, and after confirming the disappearance of the starting material by thin layer chromatography, the reaction mixture was evaporated in vacuo. The residue obtained was purified by chromatography on a silica gel column using a mixed solvent of hexane and ethyl acetate (80:20) as the eluent to afford the title compound (390 mg, yield: 98%) as a colorless oil.

$^1$H-NMR (500 MHz, CDCl$_3$) δ ppm: 7.10 (1H, m), 6.80 (1H, m), 6.70 (0.15H, d, J=2.5), 6.66 (0.85H, d, J=2.5), 5.63 (0.85H, dd, J=9.3, 5.0), 5.10 (0.15H, t, J=7.5), 4.41 (0.85H, ddd, J=13.5, 6.5, 4.5), 4.03 (0.85H, br d), 3.79 (3H, s), 3.64

(1H, m), 3.44 (1H, m), 3.30 (1H, m), 3.02 (1H, m), 2.86 (1H, m), 2.45 (1H, m), 2.36 (1H, m) $[\alpha]_D^{25}$ −45.1° (c 1.05 CH$_2$Cl$_2$)

(d) 6-hydroxy-1-(R)-(2-bromoethyl)-3,4-dihydro-1H-isoquinoline-trifluoroacetamide To a solution of 6-methoxy-1-(R)-(2-bromoethyl)-3,4-dihydro-1H-isoquinoline-trifluoroacetamide (390 mg, 1.07 mmol) obtained in step (c) of Example 190 in dichloromethane (5 ml) was added 1M solution of boron tribromide in dichloromethane (2.14 ml, 2.14 mmol) gradually at −78° C. with stirring. The resulting mixture was further stirred at −78° C., and after confirming the disappearance of the starting material by thin layer chromatography, saturated aqueous sodium hydrogen carbonate solution was added to the reaction mixture, and after raising the temperature to ambient temperature, the resulting mixture was extracted with ethyl acetate. The extract was washed successively with dilute hydrochloric acid and saturated aqueous sodium chloride solution, dried over anhydrous sodium sulfate, and evaporated in vacuo. The residue obtained was purified by chromatography on a silica gel column using a mixed solvent of hexane and ethyl acetate (2:1) as the eluent to afford the title compound (280 mg, yield: 75%) as a colorless oil.

$^1$H-NMR (500 MHz, CDCl$_3$) δ ppm: 7.04 (1H, m), 6.72 (1H, m), 6.65 (0.15H, d, J=2.0), 6.62 (0.85H, d, J=2.0), 5.61 (0.85H, dd, J=9.3, 5.0), 5.10 (0.15H, t, J=7.5), 4.37 (0.15H, m), 4.02 (0.85H, br d), 3.63 (1H, m), 3.45 (1H, m), 3.33 (1H, m), 2.97 (1H, m), 2.84 (1H, m), 2.45 (1H, m), 2.35 (1H, m) $[\alpha]_D^{25}$ −60.10 (c 0.94 CH$_2$Cl$_2$)

(e) 6-dimethylcarbamoyloxy-1-(R)-(2-bromoethyl)-3,4-dihydro-1H-isoquinoline-trifluoroacetamide To a solution of 6-hydroxy-1-(R)-(2-bromoethyl)-3,4-dihydro-1H-isoquinoline-trifluoroacetamide (270 mg, 0.77 mmol) obtained in step (d) of Example 190 and potassium carbonate (268 mg, 1.94 mmol) in dimethylformamide (3 ml) was added dimethylcarbamyl chloride (0.2 ml, 1.55 mmol) gradually with stirring under cooling in an ice bath. Subsequently, the resulting mixture was stirred at 40° C., and after confirming the disappearance of the starting material by thin layer chromatography, water was added to the reaction mixture, and the resulting mixture was extracted with ethyl acetate. The extract was washed with saturated aqueous sodium chloride solution, dried over anhydrous sodium sulfate and evaporated in vacuo. The residue obtained was purified by chromatography on a silica gel column using a mixed solvent of hexane and ethyl acetate (80:20) as the eluent to afford the title compound (170 mg, yield: 52%) as a colorless oil.

$^1$H-NMR (500 MHz, CDCl$_3$) δ ppm: 7.16 (m, 1H), 6.99 (1H, d, J=8.5), 6.97 (0.15H, s), 6.93 (0.85H, s), 5.70 (0.85H, m), 5.16 (0.15H, m), 4.44 (0.15H, m), 4.04 (0.85H, br d), 3.62 (1H, m), 3.41 (2H, m), 3.09 (3H, s), 3.05 (1H, m), 3.01 (3H, s), 2.85 (1H, m), 2.37 (2H, m) $[\alpha]_D^{25}$ −49.0° (c 0.86 CH$_2$Cl$_2$)

(f) 6-dimethylcarbamoyloxy-1-(R)-(2-(4-chloro-3-methylphenoxy)ethyl)-3,4-dihydro-1H-isoquinoline trifluoroacetamide To a solution of potassium carbonate (115 mg, 0.83 mmol), potassium iodide (catalytic amount) and 4-chloro-m-cresol (65 mg, 0.46 mmol) in dimethylformamide (2 ml) was added a solution of 6-dimethylcarbamoyloxy-1-(R)-(2-bromoethyl)-3,4-dihydro-1H-isoquinoline-trifluoroacetamide (160 mg, 0.38 mmol) obtained in step (e) of Example 190 in dimethylformamide (2 ml) gradually with stirring under cooling in an ice bath. Subsequently, the resulting mixture was stirred at 100° C., and after confirming the disappearance of the starting material by thin layer chromatography, the reaction temperature was cooled to ambient temperature and water was added to the reaction mixture with stirring. The resulting mixture was extracted with ethyl acetate, and the extract was washed with saturated aqueous sodium chloride solution, dried over anhydrous sodium sulfate and evaporated in vacuo. The residue obtained was purified by chromatography on a silica gel column using a mixed solvent of hexane and ethyl acetate (80:20) as the eluent to afford the title compound (154 mg, yield: 84%) as a pale yellow oil.

$^1$H-NMR (500 MHz, CDCl$_3$) δ ppm: 7.23 (0.2H, d, J=13.5), 7.20 (0.8H, d, J=9.0), 7.15 (0.8H, d, J=8.5), 7.05 (0.2H, d, J=8.0), 6.96 (2H, m), 6.74 (1H, m), 6.64 (1H, m), 5.78 (0.8H, dd, J=9.5, 5.0), 5.29 (0.2H, t, J=7.0), 4.49 (0.2H, m), 4.02 (3H, m), 3.43 (0.2H, m), 3.09 (3H, s), 3.05 (1H, m), 3.01 (3H, s), 2.88 (1H, td, J=16.0, 3.5), 2.33 (3H, s), 2.30 (2H, m) $[\alpha]_D^{25}$ −63.3° (c 0.25 CH$_2$Cl$_2$)

(g) 1-(R)-(2-(4-Chloro-3-methylphenoxy)-ethyl)-1,2,3,4-tetrahydroisoquinolin-6-yl dimethylcarbamate To a solution of 6-dimethylcarbamoyloxy-1-(R)-(2-(4-chloro-3-methylphenoxy)ethyl)-3,4-dihydro-1H-isoquinoline-trifluoroacetamide (154 mg, 0.54 mmol) obtained in step (f) of Example 190 in methanol (1 ml) was added gradually 1M aqueous solution of potassium carbonate (1 ml) with stirring under cooling in a water-bath. The resulting mixture was stirred at 40° C., and after confirming the disappearance of the starting material by thin layer chromatography, the reaction temperature was cooled to ambient temperature, and saturated aqueous sodium hydrogen carbonate solution was added to the reaction mixture with stirring. The resulting mixture was extracted with ethyl acetate, and the extract was washed with saturated aqueous sodium chloride solution, dried over anhydrous sodium sulfate and evaporated in vacuo. The residue obtained was purified by chromatography on a silica gel column using a mixed solvent of ethyl acetate and methanol (2:1) as the eluent to afford the title compound (90 mg, yield: 73%) as a pale yellow oil.

$^1$H-NMR (400 MHz, CDCl$_3$) δ ppm: 7.21(1H, d, J=8.8), 7.12 (1H, d, J=8.8), 6.90 (1H, dd, J=8.4, 2.4), 6.86 (1H, d, J=2.4), 6.80 (1H, d, J=2.8), 6.69 (1H, dd, J=8.8, 2.8), 4.18 (2H, m), 4.06 (1H, m), 3.18 (1H, m), 3.09 (3H, s), 3.01 (3H, s), 3.00 (1H, m), 2.77 (2H, m), 2.33 (3H, s), 2.28 (1H, m), 2.14 (1H, m) $[\alpha]_D^{25}$ +4.3° (c 0.65 CH$_2$Cl$_2$)

(h) 2-Methyl-1-(R)-[2-(4-chloro-3-methylphenoxy)-ethyl]-1,2,3,4-tetrahydroisoquinolin-6-yl dimethylcarbamate hydrochloride The title compound was obtained as an amorphous solid using 1-(R)-(2-(4-chloro-3-methylphenoxy)-ethyl)-1,2,3,4-tetrahydroisoquinolin-6-yl dimethylcarbamate obtained in step (g) of Example 190 by conducting a reaction similar to that mentioned in Example 3.

$^1$H-NMR (400 MHz, CDCl$_3$) δ ppm: 7.24 (1H, d, J=8.8), 7.10 (1H, m), 7.03 (2H, m), 6.83 (1H, s), 6.72 (1H, d, J=7.6), 4.53 (1H, br s), 4.35 (1H, br s), 3.98 (1H, br s), 3.75 (1H, br s), 3.35 (1H, br s), 3.15 (1H, m), 3.10 (3H, s), 3.02 (3H, s), 2.89 (3H, s), 2.35 (3H, s), 2.16 (1H, br s), 1.72 (2H, br s) $[\alpha]_D^{25}$ −54.9° (c 0.67 CH$_2$Cl$_2$)

EXAMPLE 191

2-Methyl-1-[2-(4-chlorophenoxy)-ethyl]-1,2,3,4-tetrahydroisoquinolin-7-yl dimethylcarbamate hydrochloride (Exemplification compound number 5-73)

(a) t-Butyl 7-dimethylcarbamoyloxy-1-(2-hydroxyethyl)-3,4-dihydro-1H-isoquinoline-2-carboxylate The title compound was obtained as an oily material using 2-(4-methoxyphenyl)-ethylamine as the starting material by conducting successively reactions similar to those mentioned in steps (a)–(f) of Example 187.

$^1$H NMR(CDCl$_3$, 500 MHz) δ ppm: 1.49 (9H, s), 1.77 (1H, t, J=13.5 Hz), 2.02–2.11 (1H, m), 2.71 (1H, dt, J=4.0, 15.5 Hz), 2.85–2.92 (1H, m), 3.00 (3H, s), 3.09 (3H, s), 3.09–3.16 (1H, m), 3.54 (1H, t, J=12.0 Hz), 3.64 (1H, br s), 4.03 (1H, dt, J=4.0, 12.5 Hz), 4.07 (0.8H, br s), 4.25 (0.2H, br s), 5.29 (1H, d, J=10.0 Hz), 6.92 (1H, s), 6.93 (1H, d, J=8.0 Hz), 7.09 (1H, d, J=8.0 Hz).

(b) 2-Methyl-1-[2-(4-chlorophenoxy)-ethyl]-1,2,3,4-tetrahydroisoquinolin-7-yl dimethylcarbamate hydrochloride The title compound was obtained as an amorphous solid using t-butyl 7-dimethylcarbamoyloxy-1-(2-hydroxyethyl)-3,4-dihydro-1H-isoquinoline-2-carboxylate obtained in step (f) of Example 187 and 4-chlorophenol by conducting successively reactions similar to those mentioned in steps (a) and (b) of Example 48 and Example 3.

$^1$H NMR(CDCl$_3$, 500 MHz): δ 2.14–2.22 (1H, m), 2.89 (3H, d, J=4.5 Hz), 2.97 (3H, s), 3.02 (3H, s), 3.02–3.13 (2H, m), 3.21 (1H, br d, J=15.5 Hz), 3.31–3.38 (1H, m), 3.71–3.78 (1H, m), 4.03–4.09 (1H, m), 4.37–4.42 (1H, m), 4.50 (1H, t, J=6.5 Hz), 6.86 (1H, d, J=2.0 Hz), 6.91 (2H, d, J=8.5 Hz), 7.09 (1H, dd, J=2.0, 8.5 Hz), 7.24 (1H, d, J=8.5 Hz), 7.25 (2H, d, J=8.5 Hz). MS(FAB) m/z: 388 (M+H)$^+$.

EXAMPLE 192

2-Methyl-1-[2-(4-nitrophenoxy)-ethyl]-2,3-dihydro-1H-benzo[c]azepin-7-yl dimethylcarbamate hydrochloride (Exemplification compound number 4-132)

(a) 4-Formyl-3-hydroxy-phenyl dimethylcarbamate

To a suspension of sodium hydride (5.74 g, 239 mmol), which was prepared free from mineral oil by washing with hexane, in dimethylformamide (100 ml) was added 2,4-dihydroxybenzaldehyde (15.0 g, 109 mmol) at 0° C. with stirring, and the resulting mixture was stirred for 30 minutes at 0° C. under a nitrogen atmosphere. Subsequently, N,N-dimethylcarbamoyl chloride (10.1 ml, 110 mmol) was added at 0° C., and the resulting mixture was stirred for 2 hours at room temperature under a nitrogen atmosphere. After stirring, water (300 ml) was added to the reaction mixture, and the resulting mixture was washed with ethyl acetate (200 ml×1). The aqueous layer was acidified to pH 1 with concentrated hydrochloric acid and extracted with ethyl acetate (200 ml×3). The extract was washed successively with water (300 ml×3) and saturated aqueous sodium chloride solution (200 ml×2), dried over anhydrous sodium sulfate, filtered, and evaporated in vacuo to afford the crude product. The crude product was purified by chromatography on a silica gel column using a mixed solvent of hexane and ethyl acetate (5:1-1:2) as the eluent to afford the title compound (6.78 g, yield: 30%) as a colorless solid.

Mp 58–60° C. $^1$H NMR(CDCl$_3$, 400 MHz) δ ppm: 3.02 (3H s), 3.10 (3H, s), 6.77 (1H, d, J=2.0 Hz), 6.82 (1H, dd, J=2.0, 8.0 Hz), 7.53 (1H, d, J=8.0 Hz), 9.84 (1H, s), 11.21 (1H, s).

(b) 5-dimethylcarbamoyloxy-2-formyl-phenyl trifluoromethanesulfonate

To a solution of 4-formyl-3-hydroxy-phenyl dimethylcarbamate (2.60 g, 12.4 mmol) synthesized in step (a) of Example 192 in dichloromethane (30 ml) were added pyridine (1.61 ml, 20.0 mmol) and trifluoromethanesulfonic anhydride (2.35 ml, 14.0 mmol) at 0° C. with stirring, and the resulting mixture was stirred for 1 hour at room temperature under a nitrogen atmosphere. After stirring, water (20 ml) was added to the reaction mixture, and the resulting mixture was extracted with dichloromethane (20 ml×2). The organic layer was washed successively with 1N hydrochloric acid (20 ml×1) and saturated aqueous sodium chloride solution (20 ml×1), dried over anhydrous sodium sulfate, filtered, and evaporated in vacuo to afford the crude product (4.14 g). The crude product was used for the following reaction without further purification.

$^1$H NMR(CDCl$_3$, 500 MHz) δ ppm: 3.04 (3H, s), 3.12 (3H, s), 7.31 (1H, d, J=2.0 Hz), 7.35 (1H, dd, J=2.0, 9.0 Hz), 8.00 (1H, d, J=9.0 Hz), 10.21 (1H, s).

(c) 4-Formyl-3-vinyl-phenyl dimethylcarbamate

To a solution of 5-dimethylcarbamoyloxy-2-formyl-phenyl trifluoromethanesulfonate (4.13 g, 12.1 mmol) obtained in step (b) of Example 192 in 1,4-dioxane (15 ml) were added tetrakis(triphenylphosphine)palladium (693 mg, 0.600 mmol), 2,6-di-t-butylphenol (5 mg), lithium chloride (1.54 g, 36.4 mmol) and tributyl(vinyl)tin (4.23 ml, 14.5 mmol) with stirring, and the resulting mixture was stirred for 3 hours at 100° C. under a nitrogen atmosphere. Subsequently, saturated aqueous potassium fluoride solution (5 ml) was added to the reaction mixture, and the resulting mixture was stirred for 2 hours at room temperature, filtered, and evaporated in vacuo. To the residue was added water (40 ml), and the resulting mixture was extracted with ethyl acetate (50 ml×2). The organic layer was washed successively with 1N hydrochloric acid (40 ml×1) and saturated aqueous sodium chloride solution (40 ml×1), dried over anhydrous sodium sulfate, filtered, and evaporated in vacuo to afford the crude product. The crude product was purified by chromatography on a silica gel column using a mixed solvent of hexane and ethyl acetate (10:1-1:1) as the eluent to afford the title compound (2.11 g, yield: 79%) as a colorless oil.

$^1$H NMR(CDCl$_3$, 400 MHz) δ ppm: 3.04 (3H, s), 3.12 (3H, s), 5.53 (1H, dd, J=1.6, 11.2 Hz), 5.72 (1H, d, J=18.0 Hz), 7.21 (1H, dd, J=2.4, 8.0 Hz), 7.33 (1H, d, J=2.4 Hz), 7.53 (1H, dd, J=11.2, 18.0 Hz), 7.84 (1H, d, J=8.0 Hz), 10.24 (1H, s).

(d) Ethyl 3-(4-dimethylcarbamoyloxy-2-vinyl-phenyl)-3-hydroxy-propionate

To a solution of diisopropylamine (1.26 g, 12.5 mmol) in tetrahydrofuran (30 ml) was added 1.6M solution of n-butyllithium in hexane (7.20 ml, 11.5 mmol) at −20° C. with stirring, and the resulting mixture was stirred for 20 minutes at −20° C. under a nitrogen atmosphere. Subsequently, ethyl acetate (1.07 ml, 11.0 mmol) was added at −78° C., and the resulting mixture was stirred for 20 minutes at −78° C. under a nitrogen atmosphere. Subsequently, to the reaction mixture was added a solution of 4-formyl-3-vinyl-phenyl dimethylcarbamate (2.11 g, 9.62 mmol) obtained in step (c) of Example 192 in tetrahydrofuran at −78° C., and the resulting mixture was stirred for 30 minutes at −78° C. under a nitrogen atmosphere. After stirring, to the reaction mixture was added saturated aqueous ammonium chloride solution (40 ml), and the resulting mixture was extracted with ethyl acetate (40 ml×2). The organic layer was washed successively with water (40 ml×1) and saturated aqueous sodium chloride solution (40 ml×1), dried over anhydrous sodium sulfate, filtered, and evaporated in vacuo to afford the crude product. The crude product was purified by chromatography on a silica gel column using a mixed solvent of hexane and ethyl acetate (1:1-1:2) as the eluent to afford the title compound (2.95 g, yield: 99%) as a colorless oil.

$^1$H NMR(CDCl$_3$, 500 MHz) δ ppm: 1.28 (3H, t, J=7.5 Hz), 2.65 (2H, d, J=6.0 Hz), 3.01 (3H, s), 3.10 (3H, s), 3.23–3.25 (1H, m), 4.19 (2H, q, J=7.5 Hz), 5.35 (1H, d, J=11.0 Hz), 5.38–5.43 (1H, m), 5.63 (1H, d, J=17.0 Hz), 6.99 (1H, dd, J=11.0, 17.0 Hz), 7.05 (1H, d, J=8.5 Hz), 7.20 (1H, s), 7.52 (1H, d, J=8.5 Hz).

(e) 4-(1,3-Dihydroxy-propyl)-3-vinyl-phenyl dimethylcarbamate

To a solution of ethyl 3-(4-dimethylcarbamoyloxy-2-vinyl-phenyl)-3-hydroxy-propionate (5.28 g, 17.2 mmol) obtained in step (d) of Example 192 in tetrahydrofuran (50 ml) was added lithium tetrahydroborate (544 mg, 25.0 mmol) at −20° C. with stirring, and the reaction temperature was raised gradually to ambient temperature over one hour under a nitrogen atmosphere. To the reaction mixture were added successively water (20 ml) and 1N hydrochloric acid (20 ml), and the resulting mixture was extracted with ethyl acetate (40 ml×2). The organic layer was dried over anhydrous sodium sulfate, filtered, and evaporated in vacuo to afford the crude product. The crude product was purified by chromatography on a silica gel column using mixed solvents of hexane and ethyl acetate (1:1-0:1) and ethyl acetate and methanol (5:1) successively as the eluents to afford the title compound (4.44 g, yield: 97%) as a colorless oil.

$^1$H NMR(CDCl$_3$, 500 MHz) δ ppm: 1.78–1.90 (2H, m), 2.88 (1H, s), 3.00 (3H, s), 3.10 (3H, s), 3.44 (1H, s), 3.77 (2H, br s), 5.14–5.19 (1H, m), 5.32 (1H, d, J=11.0 Hz), 5.60 (1H, d, J=17.5 Hz), 6.96 (1H, dd, J=11.0, 17.5 Hz), 7.03 (1H, dd, J=2.5, 8.5 Hz), 7.17 (1H, d, J=2.5 Hz), 7.51 (1H, d, J=8.5 Hz).

(f) 4-[3-(t-Butyl-diphenyl-silanyloxy)-1-hydroxy-propyl]-3-vinyl-phenyl dimethylcarbamate To a solution of 4-(1,3-dihydroxy-propyl)-3-vinyl-phenyl dimethylcarbamate (4.44 g, 16.7 mmol) synthesized in step (e) of Example 192 in dichloromethane (40 ml) were added triethylamine (4.18 ml, 30.0 mmol), t-butyldimethylchlorosilane (4.67 g, 17.0 mmol) and a catalytic amount of 4-dimethylaminopyridine at −0° C. with stirring, and the resulting mixture was stirred for 5 hours at room temperature under a nitrogen atmosphere. After stirring, water (30 ml) was added to the reaction mixture, and the resulting mixture was extracted with dichloromethane (40 ml×2). The organic layer was washed successively with 1N hydrochloric acid (50 ml×1) and saturated aqueous sodium chloride solution (50 ml×1), dried over anhydrous sodium sulfate, filtered, and evaporated in vacuo to afford the crude product. The crude product was purified by chromatography on a silica gel column using a mixed solvent of hexane and ethyl acetate (2:1-1:1) as the eluent to afford the title compound (5.87 g, yield: 70%) as a colorless oil.

$^1$H NMR(CDCl$_3$, 500 MHz) δ ppm: 1.09 (9H, s), 1.85–1.90 (2H, m), 3.01 (3H, s), 3.10 (3H, s), 3.32 (1H, s), 3.84–3.93 (2H, m), 5.27 (1H, d, J=10.5 Hz), 5.28–5.33 (1H, br m), 5.60 (1H, d, J=17.0 Hz), 6.97 (1H, dd, J=10.5, 17.0 Hz), 7.05 (1H, dd, J=2.5, 9.0 Hz), 7.19 (1H, d, J=2.5 Hz), 7.38–7.45 (5H, m), 7.51 (1H, d, J=9.0 Hz), 7.69 (4H, d, J=7.0 Hz).

(g) 4-[1-Bromo-3-(t-butyl-diphenyl-silanyloxy)-1-hydroxy-propyl]-3-vinyl-phenyl dimethylcarbamate To a solution of 4-[3-(t-butyl-diphenyl-silanyloxy)-1-hydroxy-propyl]-3-vinyl-phenyl dimethylcarbamate (3.00 g, 5.95 mmol) synthesized in step (f) of Example 192 and carbon tetrabromide (3.98 g, 12.0 mmol) in dichloromethane (20 ml) was added triphenyl phosphine (3.14 g, 12.0 mmol) at room temperature, and the resulting mixture was stirred for 1 hour at room temperature under a nitrogen atmosphere. After stirring, the reaction mixture was evaporated in vacuo, and the residue was purified by chromatography on a silica gel column using a mixed solvent of hexane and ethyl acetate (5:1-2:1) as the eluent to afford the title compound (2.62 g, yield: 78%) as a colorless oil.

$^1$H NMR(CDCl$_3$, 500 MHz) δ ppm: 1.05 (9H, s), 2.26–2.33 (1H, m), 2.41–2.48 (1H, m), 3.02 (3H, s), 3.10 (3H, s), 3.74 (1H, dt, J=5.0, 9.0 Hz), 3.86–3.90 (1H, m), 5.40 (1H, d, J=10.5 Hz), 5.66 (1H, d, J=17.0 Hz), 5.70 (1H, dd, J=5.0, 9.0 Hz), 7.04 (1H, dd, J=2.0, 9.0 Hz), 7.10 (1H, dd, J=10.5, 17.0 Hz), 7.19 (1H, d, J=2.0 Hz), 7.33–7.43 (5H, m), 7.46 (1H, d, J=9.0 Hz), 7.60 (2H, d, J=7.5 Hz), 7.69 (2H, d, J=7.5 Hz).

(i) 4-[1-Allylamino-3-(t-butyl-diphenyl-silanyloxy)-1-hydroxy-propyl]-3-vinyl-phenyl dimethylcarbamate To a solution of 4-[1-bromo-3-(t-butyl-diphenyl-silanyloxy)-1-hydroxy-propyl]-3-vinyl-phenyl dimethylcarbamate (2.62 g, 4.62 mmol) synthesized in step (g) of Example 192 in acetonitrile (20 ml) was added allylamine (1.87 ml, 25.0 mmol) at room temperature, and the resulting mixture was stirred at room temperature overnight under a nitrogen atmosphere. After stirring, the reaction mixture was evaporated in vacuo, and the residue was purified by chromatography on a silica gel column using a mixed solvent of hexane and ethyl acetate (2:1-0:1) as the eluent to afford the title compound (1.82 g, yield: 72%) as a colorless oil.

$^1$H NMR(CDCl$_3$, 500 MHz) δ ppm: 1.06 (9H, s), 1.79–1.84 (2H, m), 3.00 (1H, dd, J=7.0, 16.0 Hz), 3.02 (3H, s), 3.07–3.12 (1H, m), 3.10 (3H, s), 3.65 (1H, dt, J=5.0, 11.0 Hz), 3.76 (1H, dt, J=5.0, 11.0 Hz), 4.32 (1H, t, J=6.0 Hz), 5.04 (1H, d, J=11.0 Hz), 5.11 (1H, d, J=17.5 Hz), 5.24 (1H, d, J=11.0 Hz), 5.56 (1H, d, J=17.5 Hz), 5.81–5.89 (1H, m), 7.02 (1H, dd, J=3.0, 9.0 Hz), 7.15 (1H, dd, J=11.0, 17.5 Hz), 7.19 (1H, d, J=3.0 Hz), 7.26–7.44 (6H, m), 7.63–7.68 (4H, m).

(j) t-Butyl allyl-[3-(t-butyl-diphenyl-silanyloxy)-1-(4-dimethylcarbamoyloxy-2-vinyl-phenyl)-propyl]-carbamate To a solution of 4-[1-allylamino-3-(t-butyl-diphenyl-silanyloxy)-1-hydroxy-propyl]-3-vinyl-phenyl dimethylcarbamate (1.80 g, 3.31 mmol) synthesized in step (i) of Example 192 in tetrahydrofuran (20 ml) were added triethylamine (1.12 ml, 8.00 mmol) and di-t-butyl dicarbonate (870 mg, 4.00 mmol), and the resulting mixture was stirred for 3 hours at 50° C. under a nitrogen atmosphere. After stirring, the reaction mixture was evaporated in vacuo, and the residue was purified by chromatography on a silica gel column using a mixed solvent of hexane and ethyl acetate (5:1-1:1) as the eluent to afford the title compound (1.90 g, yield: 89%) as a colorless oil.

$^1$H NMR(CDCl$_3$, 400 MHz) δ ppm: 1.04 (9H, s), 1.38 (9H, s), 2.10–2.30 (2H, m), 3.02 (3H, s), 3.11 (3H, s), 3.24–3.60 (2H, br), 3.67 (1H, q, J=8.0 Hz), 3.72–3.82 (1H, m), 4.72–4.79 (0.4H, m), 4.79 (0.6H, d, J=9.6 Hz), 5.24 (1H, d, J=11.2 Hz), 5.37 (1H, br), 5.51 (1H, br), 5.55 (1H, d, J=17.6 Hz), 6.98 (1H, d, J=8.0 Hz), 7.01 (1H, dd, J=11.2, 17.6 Hz), 7.19 (1H, d, J=8.0 Hz), 7.22 (1H, d, J=2.4 Hz), 7.32–7.43 (5H, m), 7.60 (1.6H, br s), 7.66 (2.4H, d, J=7.2 Hz).

(k) t-Butyl 1-[2-(t-butyl-diphenyl-silanyloxy)-ethyl]-7-dimethylcarbamoyloxy-1,3-dihydro-benzo[c]azepine-2-carboxylate To a solution of t-butyl allyl-[3-(t-butyl-diphenyl-silanyloxy)-1-(4-dimethylcarbamoyloxy-2-vinyl-phenyl)-propyl]-carbamate (360 mg, 0.56 mmol) synthesized in step (j) of Example 192 in dichloromethane (40 ml) was added tricyclohexylphosphine [1,3-bis(2,4,6-trimethylphenyl)-4,5-dihydroimidazol-2-ylidene] [benzylidene] ruthenium(IV) dichloride (47.5 mg, 0.0560 mmol), and the resulting mixture was stirred for 3 hours at 45° C. under a nitrogen atmosphere.

After stirring, the reaction mixture was evaporated in vacuo, and the residue was purified by chromatography on a silica gel column using a mixed solvent of hexane and ethyl acetate (5:1-2:1) as the eluent to afford the title compound (330 mg, yield: 96%) as a colorless oil $^1$H NMR(CDCl$_3$, 400 MHz) δ ppm: 1.04 (9H, s), 1.38 (9H, s), 2.10–2.30 (2H, m), 3.02 (3H, s), 3.11 (3H, s), 3.24–3.60 (2H, br), 3.67 (1H, q, J=8.0 Hz), 3.72–3.82 (1H, m), 4.72–4.79 (0.4H, m), 4.79 (0.6H, d, J=9.6 Hz), 5.24 (1H, d, J=11.2 Hz), 5.37 (1H, br), 5.51 (1H, br), 5.55 (1H, d, J=17.6 Hz), 6.98 (1H, d, J=8.0 Hz), 7.01 (1H, dd, J=11.2, 17.6 Hz), 7.19 (1H, d, J=8.0 Hz), 7.22 (1H, d, J=2.4 Hz), 7.32–7.43 (5H, m), 7.60 (1.6H, br s), 7.66 (2.4H, d, J=7.2 Hz).

(l) t-Butyl 7-dimethylcarbamoyloxy-1-(2-hydroxyethyl)-1,3-dihydro-benzo[c]azepine-2-carboxylate To a solution of t-butyl 1-[2-(t-butyl-diphenyl-silanyloxy)-ethyl]-7-dimethylcarbamoyloxy-1,3-dihydro-benzo[c]azepine-2-carboxylate (1.82 g, 2.96 mmol) synthesized in step (k) of Example 192 in tetrahydrofuran (10 ml) was added 1M solution of tetrabutylammonium fluoride in tetrahydrofuran (6.0 ml, 6.0 mmol) at room temperature, and the resulting mixture was stirred for 1 hour at room temperature under a nitrogen atmosphere. After stirring, water (30 ml) was added to the reaction mixture, and the resulting mixture was extracted with ethyl acetate (40 ml×2). The organic layer was washed successively with water (40 ml×1) and saturated aqueous sodium chloride solution (40 ml×1), dried over anhydrous sodium sulfate, filtered, and evaporated in vacuo to afford the crude product. The crude product was purified by chromatography on a silica gel column using a mixed solvent of hexane and ethyl acetate (1:1-0:1) as the eluent to afford the title compound (1.07 g, yield: 96%) as a colorless oil.

$^1$H NMR(CDCl$_3$, 500 MHz) δ ppm: 1.30 (5H, s), 1.40 (4H, s), 1.90–2.08 (1H, m), 2.07–2.24 (1H, br), 3.00 (3H, s), 3.09 (3H, s), 3.59 (1H, br s), 3.65 (1H, br s), 3.76–3.88 (0.4H, br), 3.98 (0.6H, d, J=19.0 Hz), 4.58 (0.6H, d, J=19.0 Hz), 4.78–5.10 (0.4H, br), 4.92–5.20 (0.4H, br), 5.31 (0.6H, br t, J=7.5 Hz), 5.77–5.83 (1H, m), 6.32 (0.6H, d, J=11.5 Hz), 6.39 (0.4H, d, J=13.0 Hz), 6.92 (1H, dd, J=2.0, 8.0 Hz), 6.95 (1H, s), 7.13 (0.6H, d, J=8.0 Hz), 7.25, (0.4H, d, J=8.9 Hz).

(m) 2-Methyl-1-[2-(4-nitrophenoxy)-ethyl]-2,3-dihydro-1H-benzo[c]azepin-7-yl dimethylcarbamate hydrochloride The title compound was obtained as an amorphous solid using t-butyl 7-dimethylcarbamoyloxy-1-(2-hydroxyethyl)-1,3-dihydro-benzo[c]azepine-2-carboxylate obtained in step (1) of Example 192 and 4-nitrophenol by conducting successively reactions similar to those mentioned in steps (a) and (b) of Example 48 and Example 3.

$^1$H NMR(CDCl$_3$, 400 MHz) δ ppm: 2.12–2.21 (1H, m), 2.60 (3H, s), 2.85–2.93 (1H, m), 3.02 (3H, s), 3.10 (3H, s), 3.81 (1H, dd, J=4.4, 19.6 Hz), 3.85–3.90 (1H, m), 4.06 (1H, dt, J=5.2, 9.6 Hz), 4.39 (1H, d, J=19.6 Hz), 4.77 (1H, d, J=11.6 Hz), 5.85 (1H, ddd, J=3.2, 4.4, 12.4 Hz), 6.36 (1H, d, J=12.4 Hz), 6.86 (2H, d, J=8.8 Hz), 7.04 (1H, dd, J=2.4, 8.8 Hz), 7.14 (1H, d, J=8.8 Hz), 7.21 (1H, d, J=2.4 Hz), 8.16 (2H, d, J=8.8 Hz). MS(FAB) m/z: 412 (M+H)$^+$.

EXAMPLE 193

2-Methyl-1-[2-(2-chloro-4-nitrophenoxy)-ethyl]-1,3,4,5-tetrahydro-1H-benzo[c]azepin-7-yl dimethylcarbamate hydrochloride (Exemplification compound number 4-137)

(a) t-Butyl 7-dimethylcarbamoyloxy-1-(2-hydroxyethyl)-1,3,4,5-tetrahydro-benzo[c]azepine-2-carboxylate To a solution of t-butyl 7-dimethylcarbamoyloxy-1-(2-hydroxyethyl)-1,3-dihydro-benzo[c]azepine-2-carboxylate (207 mg, 0.550 mmol) synthesized in step (k) of Example 192 in methanol (10 ml) was added 10% palladium carbon (27 mg), and the resulting mixture was stirred for 1 hour at room temperature. After stirring, the reaction mixture was filtered through celite and evaporated in vacuo to afford the crude product. The crude product was purified by chromatography on a silica gel column using a mixed solvent of ethyl acetate and methanol (1:1-0:1) as the eluent to afford the title compound (189 mg, yield: 91%) as a colorless oil.

$^1$H NMR(CDCl$_3$, 400 MHz) δ ppm: 1.36 (5.4H, s), 1.45 (3.6H, s), 1.68–1.84 (1H, br), 1.86–2.00 (1H, br), 1.88–2.06 (0.4H, br), 2.06–2.18 (0.6H, br), 2.22–2.44 (1H, br), 2.83 (2H, br s), 3.00 (3H, s), 3.08 (3H, s), 3.55–3.68 (1H, br), 3.67 (2H, br s), 3.75–3.90 (1H, br), 5.03–5.18 (0.4H, br), 5.38–5.52 (0.6H, br), 6.88 (2H, s), 7.15 (0.4H, br s), 7.24 (0.6H, br s).

(b) 2-Methyl-1-[2-(2-chloro-4-nitrophenoxy)-ethyl]-1,3,4,5-tetrahydro-1H-benzo[c]azepin-7-yl dimethylcarbamate hydrochloride $^1$H NMR(CDCl$_3$, 400 MHz) δ ppm: 1.88–2.32 (2H, m), 2.42 (1H, br s), 2.60–2.80 (0.4H, br), 2.70 (3H, d, J=4.4 Hz), 2.91 (0.6H, dd, J=5.6, 15.6 Hz), 3.01 (1.8H, s), 3.02 (1.2H, s), 3.09 (1.8H, s), 3.10 (1.2H, s), 3.15–3.40 (4H, m), 3.62 (0.4H, t, J=13.6 Hz), 3.82 (0.6H, t, J=13.6 Hz), 4.07–4.16 (0.6H, m), 4.30 (1H, dt, J=5.6, 9.2 Hz), 4.53–4.59 (0.4H, m), 4.80 (0.4H, br s), 5.18 (0.6H, br s), 6.93–7.14 (3H, m), 7.17 (0.6H, d, J=8.8 Hz), 7.37 (0.4H, d, J=8.8 Hz), 8.10–8.16 (1H, m), 8.25 (1H, s). MS(FAB) m/z: 448 (M+H)$^+$.

EXAMPLE 194

2-Methyl-1-[2-(4-chloro-3-methylphenoxy)-ethyl]-2,3-dihydro-1H-benzo[c]azepin-7-yl dimethylcarbamate hydrochloride (Exemplification compound number 4-140)

The title compound was obtained as an amorphous solid using t-butyl 7-dimethylcarbamoyloxy-1-(2-hydroxyethyl)-1,3-dihydro-benzo[c]azepine-2-carboxylate obtained in step (1) of Example 192 and 4-chloro-3-methylphenol by conducting successively reactions similar to those mentioned in steps (a) and (b) of Example 48 and Example 3.

$^1$H NMR(CDCl$_3$, 400 MHz) δ ppm: 2.03–2.12 (1H, m), 2.30 (3H, s), 2.60 (3H, d, J=5.2 Hz), 2.77–2.85 (1H, m), 3.02 (3H, s), 3.10 (3H, s), 3.65 (1H, dt, J=4.4, 9.6 Hz), 3.78 (1H, dd, J=4.4, 20.0 Hz), 3.85–3.90 (1H, m), 4.37 (1H, d, J=17.2 Hz), 4.79 (1H, dt, J=3.6, 12.4 Hz), 5.82 (1H, ddd, J=2.8, 4.4, 12.4 Hz), 6.55 (1H, dd, J=2.8, 8.8 Hz), 6.64 (1H, d, J=12.4 Hz), 6.68 (1H, d, J=2.8 Hz), 7.03 (1H, dd, J=2.8, 8.8 Hz), 7.13–7.19 (3H, m). MS(FAB) m/z: 415 (M+H)$^+$.

EXAMPLE 195

2-Methyl-1-[2-(2-chloro-4-fluorophenoxy)-ethyl]-2,3-dihydro-1H-benzo[c]azepin-7-yl dimethylcarbamate hydrochloride (Exemplification compound number 4-139)

The title compound was obtained as an amorphous solid using t-butyl 7-dimethylcarbamoyloxy-1-(2-hydroxyethyl)-1,3-dihydro-benzo[c]azepine-2-carboxylate obtained in step (1) of Example 192 and 2-chloro-4-fluorophenol by conducting successively reactions similar to those mentioned in steps (a) and (b) of Example 48 and Example 3.

$^1$H NMR(CDCl$_3$, 400 MHz) δ ppm: 2.07–2.09 (1H,m), 2.61 (3H,s), 2.83–2.92 (1H,m), 3.03 (3H,s), 3.11 (3H,s), 3.74–3.82 (2H,m), 4.02–4.07 (1H,m), 4.38 (1H,d,J=19.1 Hz), 4.77–4.82 (1H,m), 5.82–5.87 (1H,m), 6.69 (1H,d,J=12.7 Hz), 6.82–6.92 (2H,m), 7.06–7.12 (2H,m), 7.18 (1H,d,J=2.3 Hz), 7.28 (1H,t,J=8.2 Hz). MS (FAB) m/z: 419(M+H)$^+$.

EXAMPLE 196

2-Methyl-1-[2-(4-methylthiophenoxy)-ethyl]-2,3-dihydro-1H-benzo[c]azepin-7-yl dimethylcarbamate hydrochloride (Exemplification compound number 4-136)

The title compound was obtained as an amorphous solid using t-butyl 7-dimethylcarbamoyloxy-1-(2-hydroxyethyl)-1,3-dihydro-benzo[c]azepine-2-carboxylate obtained in step (1) of Example 192 and 4-methylthiophenol by conducting successively reactions similar to those mentioned in steps (a) and (b) of Example 48 and Example 3.

$^1$H NMR(CDCl$_3$, 400 MHz) δ ppm: 2.03–2.11 (1H,m), 2.44 (3H,s), 2.60 (3H,s), 2.83 (1H,brs), 3.03 (3H,s), 3.11 (3H,s), 3.65–3.70 (1H,m), 3.78 (1H,d,J=18.9 Hz), 3.89–3.92 (1H,m), 4.38 (1H,d,J=18.9 Hz), 4.79 (1H,d,J=10.4 Hz), 5.82 (1H,d,J=12.6 Hz), 6.65 (1H,d,J=12.6 Hz), 6.74 (2H,d,J=8.7 Hz), 7.03 (1H,d,J=7.2, 1.1 Hz), 7.16 (1H,d,J=8.3 Hz), 7.19–7.22 (3H,m). MS (FAB) m/z: 413(M+H)$^+$.

EXAMPLE 197

2-Methyl-(1R)-[2-(4-methylthiophenoxy)-ethyl]-2,3-dihydro-1H-benzo[c]azepin-7-yl dimethylcarbamate hydrochloride (Exemplification compound number 4-136)

(a) 4-Benzyloxy-2-hydoxy-benzaldehyde

To a solution of 2,4-dihydroxybenzaldehyde (50.0 g, 362 mmol) in acetonitrile (350 ml) were added sodium hydrogen carbonate (34.6 g, 412 mmol), potassium iodide (6.0 g, 36 mmol), and benzyl chloride (54.0 ml, 470 mmol), and the resulting mixture was refluxed for 24 hours under a nitrogen atmosphere. At the end of the reaction, 1N hydrochloric acid (400 ml) was added, and the resulting mixture was extracted with ethyl acetate (400 ml×2). The organic layer was washed successively with 3% aqueous potassium carbonate solution (300 ml×2), water (300 ml×1), 1N hydrochloric acid (300 ml×1) and saturated aqueous sodium chloride solution (300 ml×1), dried over anhydrous sodium sulfate, filtered, and evaporated in vacuo to afford the crude product. The crude product was recrystallized from a mixture of t-butyl methyl ether and hexane to afford the title compound (45.9 g, yield: 56%) as pale orange crystals.

Mp 71–72° C. $^1$H NMR(CDCl$_3$, 500 MHz) δ ppm: 5.11 (2H, s), 6.51 (1H, d, J=2.0 Hz), 6.62 (1H, dd, J=2.0, 8.5 Hz), 7.35–7.45 (6H, m), 9.72 (1H, s), 11.46 (1H, s).

(b) 4-Benzyloxy-2-methoxymethoxy-benzaldehyde

To a solution of 4-benzyloxy-2-hydoxy-benzaldehyde (44.9 g, 197 mmol) synthesized in step (a) of Example 197 in dichloromethane (200 ml) were added diisopropylethylamine (52.0 ml, 300 mmol) and methoxymethyl chloride (20.5 ml, 270 mmol) at 0° C. with stirring, and the resulting mixture was stirred overnight at room temperature under a nitrogen atmosphere. After stirring, water (200 ml) was added, and the resulting mixture was extracted with dichloromethane (200 ml×2). The organic layer was washed successively with water (300 ml×1) and saturated aqueous sodium chloride solution (300 ml×1), dried over anhydrous sodium sulfate, filtered, and evaporated in vacuo to afford the crude product. The crude product was purified by chromatography on a silica gel column using a mixed solvent of hexane and ethyl acetate (5:1-1:1) as the eluent to afford the title compound (42.2 g, yield: 79%) as a colorless oil.

$^1$H NMR(CDCl$_3$, 500 MHz) δ ppm: 3.51 (3H, s), 5.11(2H, s), 5.26 (2H, s), 6.68 (1H, dd, J=2.0, 9.0 Hz), 6.80 (1H, d, J=9.0 Hz), 7.34–7.43 (5H, m), 7.81 (1H, d, J=9.0 Hz), 9.72 (1H, s), 11.46 (1H, s).

(c) Ethyl 3-(4-benzyloxy-2-methoxymethoxy-phenyl)-acrylate

To a suspension of 55% sodium hydride dispersion in mineral oil (1.57 g, 36.0 mmol) in tetrahydrofuran (100 ml) was added ethyl diethylphosphonoacetate (7.17 g, 32.0 mmol) at 0° C. with stirring, and the resulting mixture was stirred for 30 minutes at 0° C. under a nitrogen atmosphere. Subsequently, a solution of 4-benzyloxy-2-methoxymethoxy-benzaldehyde (7.46 g, 27.4 mmol) obtained in step (b) of Example 197 in tetrahydrofuran was added at 0° C. with stirring, and the resulting mixture was stirred for 2 hours at 0° C. under a nitrogen atmosphere. After stirring, water (200 ml) was added, and the resulting mixture was extracted with ethyl acetate (200 ml×2). The organic layer was washed successively with water (100 ml×1) and saturated aqueous sodium chloride solution (100 ml×1), dried over anhydrous sodium sulfate, filtered, and evaporated in vacuo to afford the crude product. The crude product was purified by chromatography on a silica gel column using a mixed solvent of hexane and ethyl acetate (5:1-1:1) as the eluent to afford the title compound (9.32 g, yield: 99%) as a colorless oil.

$^1$H NMR(CDCl$_3$, 400 MHz) δ ppm: 1.32 (3H, t, J=7.2 Hz), 3.47 (3H, s), 4.24 (2H, q, J=7.2 Hz), 5.05 (2H s), 5.21 (2H, s), 6.39 (1H, d, J=16.0 Hz), 6.62 (1H, dd, J=2.0, 8.8 Hz), 6.81 (1H, d, J=2.0 Hz), 7.30–7.43 (5H, m), 7.45 (1H, d, J=8.8 Hz), 7.95 (1H, d, J=16.0 Hz).

(d) Ethyl (3R)-amino-(3R)-(4-hydroxy-2-methoxymethoxy-phenyl)-propionate acetate To a solution of (S)-N-benzyl-1-phenylethylamine (4.24 g, 20.1 mmol) in tetrahydrofuran (40 ml) was added 1.6 M solution of n-butyllithium in hexane (12.4 ml, 18.9 mmol) at −78° C. with stirring, and the resulting mixture was stirred for 20 minutes at −78° C. under a nitrogen atmosphere. Subsequently, a solution of ethyl 3-(4-benzyloxy-2-methoxymethoxy-phenyl)-acrylate (4.32 g, 12.6 mmol) synthesized in Example 3 in tetrahydrofuran was added dropwise at −78° C. with stirring, and the resulting mixture was stirred for 30 minutes at −78° C. under a nitrogen atmosphere. After stirring, a saturated aqueous ammonium chloride solution (40 ml) was added at −78° C. with stirring, and the resulting mixture was extracted with ethyl acetate (50 ml×2). The organic layer was washed with saturated aqueous sodium chloride solution (50 ml×1), dried over anhydrous sodium sulfate, filtered, and evaporated in vacuo to afford the crude product. The crude product was purified by chromatography on a silica gel column using a mixed solvent of hexane and ethyl acetate (10:1-5:1) as the eluent to afford ethyl 3-(4-benzyloxy-2-methoxymethoxy-phenyl)-(3R)-[benzyl-((1S)-phenyl-ethyl)-amino]-propionate (7.21 g) containing a small amount of (S)-N-benzyl-1-phenylethylamine.

$^1$H NMR(CDCl$_3$, 500 MHz) δ ppm: 0.98 (3H, t, J=7.0 Hz), 1.23 (3H, d, J=7.0 Hz), 2.60 (1H, dd, J=9.0, 13.5 Hz), 2.73 (1H, dd, J=7.0, 15.0 Hz), 3.47 (3H, s), 3.73 (2H, dd, J=14.5, 22.5 Hz), 3.79–3.92 (2H, m), 4.08 (1H, q, J=7.0 Hz), 4.80 (1H, dd, J=6.0, 8.0 Hz), 5.03 (2H, s), 5.15 (2H, dd, J=7.0, 17.0 Hz), 6.61 (1H, dd, J=2.5, 8.5 Hz), 6.83 (1H, d, J=2.5 Hz), 7.13–7.44 (16H, m).

Subsequently, to a solution of ethyl 3-(4-benzyloxy-2-methoxymethoxy-phenyl)-(3R)-[benzyl-((1S)-phenyl-ethyl)-amino]-propionate (7.21 g) obtained above as a yellow oil in a mixture of methanol/water/acetic acid (80 ml/8 ml/4 ml) was added 20% palladium hydroxide (1.8 g), and the resulting mixture was stirred for 4 hours at room temperature under an atmosphere of hydrogen. After stirring, the reaction mixture was filtered through celite and evaporated in vacuo to afford the crude product. The crude product was purified by chromatography on a silica gel column using a mixed solvent of ethyl acetate and methanol (1:0-3:1) as the eluent to afford the title compound (2.77 g, yield: 67%) as an amorphous solid.

$[\alpha]_D^{23}$ −8.0 (c 0.82, MeOH). $^1$H NMR(CD$_3$OD, 400 MHz) δ ppm: 1.20 (3H, t, J=7.6 Hz), 1.90 (3H, s), 2.93 (1H, dd, J=6.0, 16.4 Hz), 2.98 (1H, dd, J=8.8, 16.4 Hz), 3.49 (3H, s), 4.13 (2H, q, J=7.6 Hz), 4.71 (1H, t, J=7.4 Hz), 5.24 (2H, s), 6.45 (1H, dd, J=2.4, 8.8 Hz), 6.69 (1H, d, J=2.8 Hz), 7.12 (1H, d, J=8.8 Hz).

(e) Ethyl (3R)-t-butoxycarbonylamino-(3R)-(4-hydroxy-2-methoxymethoxy-phenyl)-propionate To a solution of ethyl (3R)-amino-(3R)-(4-hydroxy-2-methoxymethoxy-phenyl)-propionate acetate (4.26 g, 12.9 mmol) obtained in step (d) of Example 197 in methanol (20 ml) were added triethylamine (3.62 ml, 26.0 mmol) and di-t-butyl dicarbonate (3.27 g, 15.0 mmol) with stirring, and the resulting mixture was stirred for 30 minutes at room temperature under a nitrogen atmosphere. After stirring, the reaction mixture was evaporated in vacuo, and the residue obtained was purified by chromatography on a silica gel column using a mixed solvent of hexane and ethyl acetate (2:1-1:2) as the eluent to afford the title compound (4.64 g, yield: 97%) as a colorless solid. The optical purity of the title compound obtained was determined to be 98.8% ee by chiral liquid chromatography (Dicel Chiral cel Oj, hexane:isopropanol=95:5, 1 ml/min, R-isomer: 20.48 min and S-isomer: 23.68 min).

Mp 82–86° C. $[\alpha]_D^{23}$ +42.3 (c 0.86, CHCl$_3$). $^1$H NMR (CDCl$_3$, 500 MHz) δ ppm: 1.16 (3H, t, J=7.0 Hz), 1.43 (9H, s), 2.79 (1H, dd, J=7.0, 14.5 Hz), 2.86 (1H, dd, J=6.0, 14.5 Hz), 3.45 (3H, s), 4.05 (2H, q, J=7.0 Hz), 4.85–5.20 (3H, m), 5.43 (0.2H, br s), 5.81 (0.8H, d, J=8.0 Hz), 6.28 (1H, d, J=8.0 Hz), 6.50 (1H, br s), 6.57 (1H, br s), 6.98 (1H, d, J=8.0 Hz).

(f) Ethyl (3R)-t-butoxycarbonylamino-(3R)-(4-dimethylcarbamoyloxy-2-methoxymethoxy-phenyl)-propionate To a solution of ethyl (3R)-t-butoxycarbonylamino-(3R)-(4-hydroxy-2-methoxymethoxy-phenyl)-propionate (2.35 g, 6.36 mmol) synthesized in step (e) of Example 197 in dimethylformamide (10 ml) were added potassium carbonate (1.80 g, 13.0 mmol) and N,N-dimethylcarbamoyl chloride (0.65 ml, 7.0 mmol) with stirring, and the resulting mixture was stirred for 3 hours at room temperature under a nitrogen atmosphere. After stirring, water (30 ml) was added to the reaction mixture, and the resulting mixture was extracted with ethyl acetate (40 ml×2). The organic layer was washed with saturated aqueous sodium chloride solution (40 ml×1), dried over anhydrous sodium sulfate, filtered, and evaporated in vacuo to afford the crude product. The crude product was purified by chromatography on a silica gel column using a mixed solvent of hexane and ethyl acetate (2:1-1:2) as the eluent to afford the title compound (2.73 g, yield: 97%) as a colorless oil.

$[\alpha]_D^{23}$ +25.3 (c 1.09, CHCl$_3$). $^1$H NMR(CDCl$_3$, 500 MHz) δ ppm: 1.17 (3H, t, J=7.0 Hz), 1.41 (9H, s), 2.77–2.89 (2H, m), 2.99 (3H, s), 3.07 (3H, s), 3.49 (3H, s), 4.01–4.10 (2H, m), 5.24 (2H, dd, J=7.0, 10.0 Hz), 5.30 (1H, br s), 5.74 (1H, br d, J=9.0 Hz), 6.73 (1H, dd, J=2.0, 9.0 Hz), 6.89 (1H, d, J=2.0 Hz), 7.23 (1H, d, J=9.0 Hz).

(g) t-Butyl [(1R)-(4-dimethylcarbamoyloxy-2-methoxymethoxy-phenyl)-3-hydroxypropyl]-carbamate To a solution of ethyl (3R)-t-butoxycarbonylamino-(3R)-(4-dimethylcarbamoyloxy-2-methoxymethoxy-phenyl)-propionate (4.68 g, 10.6 mmol) synthesized in step (f) of Example 197 in tetrahydrofuran (30 ml) was added lithium aluminum hydride (524 mg, 13.8 mmol) at −5° C. with stirring, and the resulting mixture was stirred successively for 10 minutes at −50° C. and for 15 minutes at 0° C. under a nitrogen atmosphere. After stirring, to the reaction mixture were added water (0.5 ml), 15% aqueous sodium hydroxide solution (0.5 ml) and water (1.5 ml) at 0° C. in this order, and the resulting mixture was dried over anhydrous sodium sulfate, filtered, and evaporated in vacuo to afford the crude product. The crude product was purified by chromatography on a silica gel column using a mixed solvent of hexane and ethyl acetate (2:1-0:1) as the eluent to afford the title compound (3.48 g, yield: 82%) as a colorless oil.

$[\alpha]_D^{23}$ +48.0 (c 1.09, CHCl$_3$) $^1$H NMR(CDCl$_3$, 400 MHz) δ ppm: 1.43 (9H, s), 1.94 (2H, dt, J=4.8, 6.0 Hz), 3.00 (3H, s), 3.08 (3H, s), 3.30 (1H, br s), 3.49 (3H, s), 3.61–3.74 (2H, m), 5.06 (1H, q, J=5.6 Hz), 5.23 (2H, dd, J=6.4, 10.8 Hz), 5.47 (1H, d, J=9.6 Hz), 6.74 (1H, dd, J=2.4, 8.8 Hz), 6.90 (1H, d, J=2.4 Hz), 7.19 (1H, d, J=8.8 Hz).

(h) 4-[(1R)-Amino-3-(4-methylthiophenoxy)-propyl]-3-hydroxy-phenyl dimethylcarbamate To a solution of t-butyl [(1R)-(4-dimethylcarbamoyloxy-2-methoxymethoxy-phenyl)-3-hydroxypropyl]-carbamate (1.63 g, 4.08 mmol) synthesized in step (g) of Example 197, 4-methylthiophenol (660 mg, 4.50 mmol) and triphenylphosphine (1.60 g, 6.12 mmol) in tetrahydrofuran (15 ml), was added dropwise 40 wt % solution of diethyl azodicarboxylate in toluene (2.66 g, 6.12 mmol) at 0° C. with stirring, and the resulting mixture was stirred for 1 hour at room temperature under a nitrogen atmosphere. After stirring, the reaction mixture was evaporated in vacuo, and the residue obtained was purified by chromatography on a silica gel column using a mixed solvent of hexane and ethyl acetate (2:1-1:2) as the eluent to afford the crude product (2.74 g) containing hydrazine dicarboxylate. Subsequently, to a solution of the crude product (2.74 g) in methanol (18 ml) was added concentrated hydrochloric acid (6 ml), and the resulting mixture was stirred overnight at room temperature. After stirring, the reaction mixture was neutralized with 15% aqueous sodium hydroxide solution and adjusted to pH 10 with saturated aqueous sodium hydrogen carbonate solution and then extracted with ethyl acetate (50 ml×2). The organic layer was dried over anhydrous sodium sulfate, filtered, and evaporated in vacuo to afford the crude product. The crude product was purified by chromatography on a silica gel column using a mixed solvent of ethyl acetate and methanol (1:0-5:1) as the eluent to afford the title compound (1.05 g, yield: 69%) as a colorless oil.

$[\alpha]_D^{23}$ −66.5 (c 0.77, CHCl$_3$). $^1$H NMR(CDCl$_3$, 500 MHz) δ ppm: 2.12–2.18 (1H, m), 2.21–2.28 (1H, m), 2.44 (3H, s), 2.99 (3H, s), 3.07 (3H, s), 3.89 (1H, dt, J=4.0, 10.0 Hz), 4.00 (1H, dt, =5.0, 10.0 Hz), 4.43 (1H, t, J=7.5 Hz), 6.51 (1H, dd, J=2.5, 8.0 Hz), 6.60 (1H, d, J=2.5 Hz), 6.82 (2H, d, J=8.5 Hz), 6.86 (1H, d, J=8.0 Hz), 7.25 (2H, d, J=8.5 Hz)

(i) t-Butyl [(1R)-(4-dimethylcarbamoyloxy-2-hydroxy-phenyl)-3-(4-methylthiophenoxy)-propyl]-carbamate To a solution of 4-[(1R)-amino-3-(4-methylthiophenoxy)-propyl]-3-hydroxy-phenyl dimethylcarbamate (1.05 g, 2.80 mmol) synthesized in step (h) of Example 197 in methanol (10 ml) were added triethylamine (0.83 ml, 6.00 mmol) and di-t-butyl dicarbonate (650 mg, 3.00 mmol), and the resulting mixture was stirred for 1 hour at room temperature under a nitrogen atmosphere. After stirring, the reaction mixture was evaporated in vacuo, and the residue obtained was purified by chromatography on a silica gel column using a mixed solvent of hexane and ethyl acetate (2:1-0:1) as the eluent to afford the title compound (1.34 g, yield: 100%) as a colorless solid.

$[\alpha]_D^{23}$ +14.3 (c 0.52, CHCl$_3$). $^1$H NMR(CDCl$_3$, 400 MHz) δ ppm: 1.40 (9H, s), 2.26–2.37 (2H, m), 2.44 (3H, s), 3.00 (3H, s), 3.07 (3H, s), 3.89–3.95 (1H, m), 3.98–4.03 (1H, m), 5.00 (1H, dd, J=8.0, 15.2 Hz), 5.25 (1H, br s), 6.63 (1H, dd, J=3.2, 8.0 Hz), 6.66 (1H, d, J=3.2 Hz), 6.81 (2H, d, J=8.8 Hz), 7.10 (1H, d, J=8.0 Hz), 7.24 (2H, d, J=8.8 Hz).

(j) t-Butyl [(1R)-(4-dimethylcarbamoyloxy-2-vinyl-phenyl)-3-(4-methylthiophenoxy)-propyl]-carbamate To a solution of t-butyl [(1R)-(4-dimethylcarbamoyloxy-2-hydroxy-phenyl)-3-(4-methylthiophenoxy)-propyl]-carbamate (1.34 g, 2.80 mmol) synthesized in step (i) of Example 197 in dichloromethane (10 ml) were added pyridine (0.48 ml, 6.0 mmol) and trifluoromethanesulfonic anhydride (0.50 ml, 3.0 mmol) at 0° C. with stirring, and the resulting mixture was stirred for 1 hour at room temperature under a nitrogen atmosphere. After stirring, water (20 ml) was added to the reaction mixture, and the resulting mixture was extracted with dichloromethane (20 ml×2). The organic layer was washed successively with 0.5N hydrochloric acid (20 ml×1) and saturated aqueous sodium chloride solution (20 ml×1), dried over anhydrous sodium sulfate, filtered, and evaporated in vacuo to afford the crude triflate derivative (1.48 g).

$^1$H NMR(CDCl$_3$, 500 MHz) δ ppm: 1.38 (9H, br s), 2.17–2.34 (2H, m), 2.44 (3H, s), 3.01 (3H, s), 3.09 (3H, s), 3.97 (2H, t, J=6.0 Hz), 5.13 (1H, dd, J=8.0, 12.5 Hz), 5.44 (1H, br s), 6.82 (2H, d, J=8.5 Hz), 7.14 (1H, d, J=8.5 Hz), 7.15 (1H, s), 7.25 (2H, d, J=8.5 Hz), 7.43 (1H, d, J=8.5 Hz).

Subsequently, to a solution of the crude triflate derivative (1.48 g) obtained above in 1,4-dioxane (20 ml) were added tetrakis(triphenylphosphine)palladium (647 mg, 0.560 mmol), 2,6-di-t-butylphenol (5 mg), lithium chloride (356 mg, 8.40 mmol) and tributyl(vinyl)tin (0.88 ml, 3.0 mmol), and the resulting mixture was stirred for 3 hours at 100° C. under a nitrogen atmosphere. Subsequently, saturated aqueous potassium fluoride solution (10 ml) was added, and the resulting mixture was stirred for 2 hours at room temperature and then filtered and evaporated in vacuo. To the residue obtained was added water (40 ml), and the resulting mixture was extracted with ethyl acetate (50 ml×2). The organic layer was washed successively with 1N hydrochloric acid (40 ml×1) and saturated aqueous sodium chloride solution (40 ml×1), dried over anhydrous sodium sulfate, filtered, and evaporated in vacuo to afford the crude product. The crude product was purified by chromatography on a silica gel column using a mixed solvent of hexane and ethyl acetate (5:1-1:1) as the eluent to afford the title compound (1.08 g, yield: 79%) as a colorless oil.

$[\alpha]_D^{23}$ –7.7 (c 0.58, CHCl$_3$). $^1$H NMR(CDCl$_3$, 400 MHz) δ ppm: 1.40 (9H, s), 2.18 (2H, br m), 2.44 (3H, s), 3.01 (3H, s), 3.09 (3H, s), 3.84–3.96 (2H, m), 5.23 (1H, br s), 5.31 (1H, d, J=10.8 Hz), 5.58 (1H, dd, J=1.2, 16.8 Hz), 6.80 (2H, d, J=8.0 Hz), 7.00–7.16 (1H, br m), 7.02 (1H, dd, J=2.8, 8.8 Hz), 7.19–7.28 (4H, m).

(k) t-Butyl allyl-[(1R)-(4-dimethylcarbamoyloxy-2-vinyl-phenyl)-3-(4-methylthiophenoxy)-propyl]-carbamate To a solution of t-butyl [(1R)-(4-dimethylcarbamoyloxy-2-vinyl-phenyl)-3-(4-methylthiophenoxy)-propyl]-carbamate (1.08 g, 2.22 mmol) synthesized in step (j) of Example 197 in dimethylformamide (10 ml) was added sodium hydride (160 mg, 6.66 mmol), being prepared free from mineral oil by washing with hexane, at 0° C., and the resulting mixture was stirred for 30 minutes at 0° C. under a nitrogen atmosphere. Subsequently, allyl bromide (0.57 ml, 6.7 mmol) was added at 0° C., and the resulting mixture was stirred for 2 hours at room temperature under a nitrogen atmosphere. After stirring, water (30 ml) was added, and the resulting mixture was extracted with ethyl acetate (30 ml×2). The organic layer was washed successively with water (30 ml×1) and saturated aqueous sodium chloride solution (30 ml×1), dried over anhydrous sodium sulfate, filtered, and evaporated in vacuo to afford the crude product. The crude product was purified by chromatography on a silica gel column using a mixed solvent of hexane and ethyl acetate (2:1-1:1) as the eluent to afford the title compound (932 mg, yield: 80%) as a colorless oil.

$[\alpha]_D^{23}$ +76.1 (c 0.63, CHCl$_3$). $^1$H NMR(CDCl$_3$, 500 MHz) δ ppm: 1.43 (9H, s), 2.29–2.42 (1H, br m), 2.40–2.52 (1H, br m), 2.43 (3H, s), 3.02 (3H, s), 3.11 (3H, s), 3.47 (2H, br s), 3.97 (1H, dt, J=6.0, 8.0 Hz), 4.06 (1H, br q, J=8.0 Hz), 4.82 (1H, d, J=17.0 Hz), 4.84 (1H, d, J=9.5 Hz), 5.28 (1H, d, J=10.5 Hz), 5.48 (1H, br s), 5.58 (1H, d, J=16.5 Hz), 5.67 (1H, br s), 6.82 (2H, d, J=8.5 Hz), 7.02 (1H, dd, J=10.5, 16.5 Hz), 7.04–7.06 (1H, m), 7.24–7.26 (3H, m), 7.34 (1H, d, J=7.5 Hz).

(l) t-Butyl 7-dimethylcarbamoyloxy-(1R)-[2-(4-methylthiophenoxy)-ethyl]-1,3-dihydro-benzo[c]azepine-2-carboxylate To a solution of t-butyl allyl-[(1R)-(4-dimethylcarbamoyloxy-2-vinyl-phenyl)-3-(4-methylthiophenoxy)-propyl]-carbamate (907 mg, 1.72 mmol) synthesized in step (k) of Example 197 in dichlorometane (100 ml) was added tricyclohexylphosphine [1,3-bis(2,4,6-trimethylphenyl)-4,5-dihydroimidazol-2-ylidene] [benzylidene] ruthenium(IV) dichloride (146 mg, 0.172 mmol), and the resulting mixture was stirred for 3 hours at 45° C. under a nitrogen atmosphere. After stirring, the reaction mixture was evaporated in vacuo, and the residue was purified by chromatography on a silica gel column using a mixed solvent of hexane and ethyl acetate (2:1-1:1) as the eluent to afford the title compound (796 mg, yield: 93%) as a colorless oil.

$[\alpha]_D^{23}$ –43.8 (c 0.71, CHCl$_3$). $^1$H NMR(CDCl$_3$, 500 MHz) δ ppm: 1.29 (6H, s), 1.38 (3H, s), 2.27 (1H, br s), 2.36 (1H, br s), 2.44 (3H, s), 3.00 (3H, s), 3.09 (3H, s), 3.77–4.18 (3H, br m), 4.74 (0.34H, d, J=16.0 Hz), 4.99 (0.66H, br s), 5.23 (0.66H, br s), 5.35 (0.34H, br s), 5.78 (0.34H, d, J=11.5 Hz), 5.84 (0.66H, d, J=11.5 Hz), 6.35 (1H, d, J=11.5 Hz), 6.80 (0.68H, d, J=7.5 Hz), 6.82 (1.32H, d, J=7.5 Hz), 6.88 (1H, br s), 6.96 (1H, s), 7.08 (1H, br s), 7.20–7.26 (2H, m).

(m) 2-Methyl-(1R)-[2-(4-methylthiophenoxy)-ethyl]-2,3-dihydro-1H-benzo[c]azepin-7-yl dimethylcarbamate hydrochloride The title compound was obtained as an amorphous solid using t-butyl 7-dimethylcarbamoyloxy-(1R)-[2-(4-methylthiophenoxy)-ethyl]-1,3-dihydro-benzo[c]azepine-2-carboxylate obtained in step (1) of Example 197 by conducting successively reactions similar to those mentioned in step (d) of Example 6 and Example 3.

$[\alpha]_D^{23}$ –24.2 (c 0.73, CHCl$_3$) $^1$H NMR(CDCl$_3$, 400 MHz) δ ppm: 2.03–2.15 (1H, m), 2.43 (3H, s), 2.53 (3H, s), 2.64–2.76 (1H, m), 3.02 (3H, s), 3.10 (3H, s), 3.76–3.79 (2H, m), 3.92 (1H, quintet, J=5.2 Hz), 4.19 (1H, br s), 4.63 (1H, d, J=7.6 Hz), 5.84 (1H, d, J=12.4 Hz), 6.60 (1H, d, J=12.4 Hz), 6.76 (2H, d, J=8.8 Hz), 7.00 (1H, dd, J=2.0, 8.0 Hz), 7.14 (1H, d, J=2.0 Hz), 7.15 (1H, d, J=8.0 Hz), 7.21 (2H, d, J=8.8 Hz).

EXAMPLE 198

2-Methyl-(1S)-[2-(4-methylthiophenoxy)-ethyl]-2,3-dihydro-1H-benzo[c]azepin-7-yl dimethylcarbamate hydrochloride (Exemplification compound number 4-136)

The title compound was obtained as an amorphous solid using (R)-N-benzyl-1-phenylethylamine as the starting material instead of (S)-N-benzyl-1-phenylethylamine, by conducting successively reactions similar to those mentioned in Example 197.

$[\alpha]_D^{23}$ +19.9 (c 0.87, CHCl$_3$). $^1$H NMR(CDCl$_3$, 400 MHz) δ ppm: 2.03–2.15 (1H, m), 2.43 (3H, s), 2.53 (3H, s), 2.64–2.76 (1H, m), 3.02 (3H, s), 3.10 (3H, s), 3.76–3.79 (2H, m), 3.92 (1H, quintet, J=5.2 Hz), 4.19 (1H, br s), 4.63 (1H, d, J=7.6 Hz), 5.84 (1H, d, J=12.4 Hz), 6.60 (1H, d, J=12.4 Hz), 6.76 (2H, d, J=8.8 Hz), 7.00 (1H, dd, J=2.0, 8.0 Hz), 7.14 (1H, d, J=2.0 Hz), 7.15 (1H, d, J=8.0 Hz), 7.21 (2H, d, J=8.8 Hz).

EXAMPLE 199

2-Methyl-(1S)-[2-(4-nitrophenoxy)-ethyl]-2,3-dihydro-1H-benzo[c]azepin-7-yl dimethylcarbamate hydrochloride (Exemplification compound number 4-132)

The title compound was obtained as an amorphous solid using 4-nitrophenol as the starting material instead of 4-methylthiophenol by conducting successively reactions similar to those mentioned in Example 197.

$[\alpha]_D^{23}$ +30.9 (c 0.67, CHCl$_3$) $^1$H NMR(CDCl$_3$, 400 MHz) δ ppm: 2.12–2.21 (1H, m), 2.60 (3H, s), 2.85–2.93 (1H, m), 3.02 (3H, s), 3.10 (3H, s), 3.81 (1H, dd, J=4.4, 19.6 Hz), 3.85–3.90 (1H, m), 4.06 (1H, dt, J=5.2, 9.6 Hz), 4.39 (1H, d, J=19.6 Hz), 4.77 (1H, d, J=11.6 Hz), 5.85 (1H, ddd, J=3.2, 4.4, 12.4 Hz), 6.36 (1H, d, J=12.4 Hz), 6.86 (2H, d, J=8.8 Hz), 7.04 (1H, dd, J=2.4, 8.8 Hz), 7.14 (1H, d, J=8.8 Hz), 7.21 (1H, d, J=2.4 Hz), 8.16 (2H, d, J=8.8 Hz)

EXAMPLE 200

2-Methyl-(1S)-[2-(4-nitrophenoxy)-ethyl]-2,3-dihydro-1H-benzo[c]azepin-7-yl dimethylcarbamate hydrochloride (Exemplification compound number 4-132)

The title compound was obtained as an amorphous solid using 4-nitrophenol as the starting material instead of 4-methylthiophenol by conducting successively reactions similar to those mentioned in Example 198.

$[\alpha]_D^{23}$ −25.0 (c 0.70, CHCl$_3$). $^1$H NMR(CDCl$_3$, 400 MHz) δ ppm: 2.12–2.21 (1H, m), 2.60 (3H, s), 2.85–2.93 (1H, m), 3.02 (3H, s), 3.10 (3H, s), 3.81 (1H, dd, J=4.4, 19.6 Hz), 3.85–3.90 (1H, m), 4.06 (1H, dt, J=5.2, 9.6 Hz), 4.39 (1H, d, J=19.6 Hz), 4.77 (1H, d, J=11.6 Hz), 5.85 (1H, ddd, J=3.2, 4.4, 12.4 Hz), 6.36 (1H, d, J=12.4 Hz), 6.86 (2H, d, J=8.8 Hz), 7.04 (1H, dd, J=2.4, 8.8 Hz), 7.14 (1H, d, J=8.8 Hz), 7.21 (1H, d, J=2.4 Hz), 8.16 (2H, d, J=8.8 Hz).

EXAMPLE 201

2-Methyl-[2-(4-chloro-3-methylphenoxy)-ethyl]-2,3-dihydro-1H-benzo[c]azepin-8-yl dimethylcarbamate hydrochloride (Exemplification compound number 5-160)

(a) t-Butyl 8-dimethylcarbamoyloxy-1-(2-hydroxyethyl)-1,3-dihydro-benzo[c]azepin-2-carboxylate The title compound was obtained as an amorphous solid using 2,5-dihydroxybenzaldehyde as the starting material by conducting successively reactions similar to those mentioned in steps (a)–(l) of Example 192.

$^1$H NMR(CDCl$_3$, 400 MHZ) δ ppm: 1.29 (9H, s), 1.90–1.98 (1H, m), 2.13–2.14 (1H, m), 2.99 (3H, s), 3.12 (3H, s), 3.48–3.56 (2H, m), 3.90–4.04 (1H, m), 4.74–4.83 (1H, m), 5.11–5.19 (1H, m), 5.80 (1H, d, J=12.0 Hz), 6.43 (1H, d, J=12.0 Hz), 6.96–7.01 (2H, m), 7.24 (1H, d, J=8.9 Hz).

(b) 2-Methyl-[2-(4-chloro-3-methylphenoxy)-ethyl]-2,3-dihydro-1H-benzo[c]azepin-8-yl dimethylcarbamate hydrochloride The title compound was obtained as an amorphous solid using t-butyl 8-dimethylcarbamoyloxy-1-(2-hydroxyethyl)-1,3-dihydro-benzo[c]azepin-2-carboxylate obtained in step (a) of Example 201 and 4-chloro-3-methylphenol by conducting successively reactions similar to those mentioned in steps (a) and (b) of Example 48 and Example 3.

$^1$H NMR(CD$_3$OD, 400 MHz) δ ppm: 2.19–2.27 (1H, m), 2.31 (3H, s), 2.47–2.56 (1H, m), 2.89 (3H, s), 2.95 (3H, s), 3.02 (3H, s), 3.66–3.72 (1H, m), 4.01–4.12 (2H, m), 4.25–4.29 (1H, m), 4.80–4.84 (1H, m), 5.82–5.87 (1H, m), 6.70 (1H, dd, J=2.9, 8.7 Hz), 6.78 (1H, d, J=12.7 Hz), 6.82 (1H, d, J=2.9 Hz), 7.02 (1H, d, J=2.4 Hz), 7.20–7.22 (2H, m), 7.47 (1H, d, J=8.4 Hz). MS(FAB) m/z: 415 (M+H)$^+$.

EXAMPLE 202

2-Methyl-[2-(4-chloro-3-methylphenoxy)-ethyl]-2,3-dihydro-1H-benzo[c]azepin-6-yl dimethylcarbamate hydrochloride (Exemplification compound number 5-300)

(a) t-Butyl 6-dimethylcarbamoyloxy-1-(2-hydroxyethyl)-1,3-dihydro-benzo[c]azepin-2-carboxylate The title compound was obtained as an amorphous solid using 2,3-dihydroxybenzaldehyde as the starting material by conducting successively reactions similar to those mentioned in steps (a)–(l) of Example 192.

$^1$H NMR(CDCl$_3$, 400 MHz) δ ppm: 1.31 (5.4H, s), 1.42 (3.2H, s), 1.88–2.28 (2H, m), 3.02 (3H, s), 3.13 (3H, s), 3.59 (1H, br s), 3.66 (1H, br s), 3.85–4.05 (0.4H, br), 3.98 (0.6H, d, J=15.6 Hz), 4.41 (0.6H, d, J=15.6 Hz), 4.60–5.00 (0.4H, br), 5.00–5.20 (0.4H, br), 5.35 (0.6H, br t, J=7.2 Hz), 5.86–5.91 (1H, m), 6.56 (0.6H, d, J=12.4 Hz), 6.64 (0.4H, d, J=12.4 Hz), 6.99–7.26 (3H, m)

(b) 2-Methyl-[2-(4-chloro-3-methylphenoxy)-ethyl]-2,3-dihydro-1H-benzo[c]azepin-6-yl dimethylcarbamate hydrochloride The title compound was obtained as an amorphous solid using t-butyl 6-dimethylcarbamoyloxy-1-(2-hydroxyethyl)-1,3-dihydro-benzo[c]azepin-2-carboxylate obtained in step (a) of Example 201 and 4-chloro-3-methylphenol by conducting successively reactions similar to those mentioned in steps (a) and (b) of Example 48 and Example 3.

$^1$H NMR(CDCl$_3$, 400 MHz) δ ppm: 2.14–2.21 (1H, m), 2.30 (3H, s), 2.64 (3H, d, J=4.8 Hz), 2.78–2.89 (1H, m), 3.04 (3H, s), 3.18 (3H, s), 3.65 (1H, dt, J=4.4, 9.6 Hz), 3.78 (1H, d, J=19.2 Hz), 3.89 (1H, dt, J=5.2, 10.4 Hz), 4.34 (1H, dd, J=3.6, 19.2 Hz), 4.79 (1H, d, J=3.6, 11.2 Hz), 5.91 (1H, dt, J=3.6, 12.4 Hz), 6.52 (1H, dd, J=2.8, 8.8 Hz), 6.67 (1H, d, J=2.8 Hz), 6.88 (1H, d, J=12.4 Hz), 7.04 (1H, d, J=7.2 Hz), 7.15–7.32 (3H, m). MS(FAB) m/z: 415 (M+H)$^+$.

EXAMPLE 203

3-[3-(4-Chloro-3-nitrophenoxy)-1-methylaminopropyl]phenyl dimethylcarbamate hydrochloride (Exemplification compound number 2-116)

The title compound was obtained using t-butyl N-[1-[(3-dimethylcarbamoyloxy)phenyl]-3-hydroxypropyl]-N-methylcarbamate obtained in step (e) of Example 7 and 4-chloro-3-nitrophenol by conducting successively reactions similar to those mentioned in steps (a) and (b) of Example 48.

$^1$H-NMR (400 MHz, CDCl$_3$) δ: 7.46 (2H,m), 7.38 (1H, d, J=9.2), 7.30 (2H, d, J=2.8), 7.19 (1H, td, J=7.2, 2.0), 6.99 (1H, dd, J=9.2, 2.4), 4.30 (1H, dd, J=10.4, 4.8), 4.06 (1H, m), 3.73 (1H, td, J=10.9, 4.4), 3.09 (s, 3H), 3.03 (m, 1H), 2.98 (s, 3H), 2.63 (1H, m), 2.53 (3H, m) ms (FAB) m/z: 408 (M+H)$^+$.

TEST EXAMPLE

Test Example 1

In vitro study

Test Example 1a

Acetylcholinesterase Inhibitory Activity Test

Whole brains of mice were used as a source of acetylcholinesterase. Acetylcholinesterase activity was determined according to a previously described method (Biochem Pharmacol 7: 88, 1961). Briefly, 10 μl of dimethylsulfoxide (DMSO)-dissolved test substance was added to 3 ml of phosphate buffer solution containing the brain homogenate [2990 μl of 100 mM phosphate buffer solution (100 mM of Na$_2$HPO$_4$ and 100 mM of NaH$_2$PO$_4$, pH=7.4)+10 μl of brain homogenate] and preincubated for 10 min at room temperature. Then 50 μl of dithiobisnitrobenzoate (DTNB) solution (395 mg of DTNB and 150.5 mg of NaHCO$_3$ dissolved in 100 ml of 100 mM phosphate buffer solution) was added to the solution which was again preincubated for 20 min at room temperature. Fifty microliters of acetylthiocholine iodide (ATC) solution (8.676 mg of ATC dissolved in 1 ml of distilled water) were added to the solution to initiate the response. Immediately and 8 min after the response was started, absorbance (412 nm) was determined and the inhibition rate (%) caused by the test substance was calculated. Furthermore, the concentration of the test substance needed to inhibit acetylcholinesterase activity by 50% (IC$_{50}$) was calculated.

Test Example 1b

Serotonin Re-Uptake Inhibitory Activity

Serotonin re-uptake inhibitory activity was determined using synaptosome prepared from rat whole brains except the cerebellums. Briefly, 10 μl of DMSO solution-dissolved test substance (control group; DMSO solution alone) was added to 1 ml of synaptosome and incubated for 5 min at 37° C. (in the control, DMSO alone was added to the synaptosome and incubated at 4° C.). Furthermore, 10 μl of [$^3$H]5-HT solution (final concentration: 10 μM as a total concentration of 5-HT, 100 nM as [$^3$H]5-HT) was added and incubated for 5 min at 37° C. Then 4 ml of ice-cold saline was added to stop the response. The response solution was filtered, 4 ml of saline was added, and the solution was once again filtered. Furthermore, 5 ml of Pico-Fluor was added, then $^3$H levels on filter papers were counted by a liquid scintillation counter. Concentrations of test compounds to inhibit serotonin re-uptake by 50% (IC$_{50}$) were calculated.

The results are summarized in Table 6.

TABLE 6

| | IC$_{50}$ (nM) | |
| --- | --- | --- |
| Test Compound No. | Acetylcholinesterase inhibitory activity | Serotonin re-uptake inhibitory activity |
| Test Compound 16 | 210 | 493 |
| Test Compound 30 | 790 | 594 |
| Test Compound 31 | 440 | 323 |
| Test Compound 38 | 175 | 199 |
| Test Compound 41 | 79 | 507 |
| Test Compound 54 | 670 | 166 |
| Test Compound 55 | 280 | 60 |
| Test Compound 61 | 230 | 182 |
| Test Compound 62 | 270 | 343 |
| Test Compound 68 | 580 | 145 |
| Test Compound 70 | 90 | 86 |
| Test Compound 76 | 300 | 124 |
| Test Compound 81 | 320 | 228 |
| Test Compound 82 | 83 | 377 |
| Test Compound 89 | 87 | 319 |
| Test Compound 95 | 52 | 221 |
| Test Compound 102 | 170 | 167 |
| Test Compound 104 | 53 | 176 |
| Test Compound 124 | 64 | 110 |
| Test Compound 125 | 19 | 841 |
| Test Compound 127 | 40 | 856 |
| Test Compound 128 | 15 | 70 |
| Test Compound 129 | 64 | 650 |
| Test Compound 130 | 42 | 88 |
| Test Compound 131 | 57 | 129 |
| Test Compound 136 | 980 | 236 |
| Test Compound 152 | 310 | 67 |
| Test Compound 162 | 790 | 594 |
| Test Compound 174 | 93 | 85 |
| Test Compound 175 | 291 | 380 |
| Test Compound 176 | 88 | 56 |
| Test Compound 177 | 201 | 120 |
| Test Compound 179 | 372 | 86 |
| Test Compound 180 | 111 | 104 |
| Test Compound 181 | 198 | 44 |
| Test Compound 182 | 50 | 44 |
| Test Compound 183 | 26 | 67 |
| Test Compound 184 | 56 | 49 |
| Test Compound 185 | 156 | 170 |
| Test Compound 186 | 106 | 62 |
| Test Compound 187 | 11 | 940 |
| Test Compound 188 | 53 | 150 |
| Test Compound 189 | 6 | 300 |
| Test Compound 190 | 12 | 460 |
| Test Compound 191 | 265 | 520 |
| Test Compound 192 | 66 | 63 |
| Test Compound 193 | 24 | 680 |
| Test Compound 194 | 103 | 61 |
| Test Compound 195 | 50 | 44 |
| Test Compound 196 | 48 | 18 |
| Test Compound 197 | 19 | 6 |
| Test Compound 199 | 14 | 6 |
| Test Compound 200 | 609 | 930 |
| Test Compound 202 | 146 | 900 |
| Test Compound 203 | 49 | 40 |

As clearly shown in Table 4, the tested compounds of the present invention exert remarkable inhibitory activities toward both acetylcholinesterase activity and serotonin reuptake activity. Thus the compounds of the present invention are useful as safe and effective remedies.

Test Example 2

Ex vivo activity test

Test Example 2a

Acetylcholinesterase Inhibiting Activity

Sixty min after oral administration of the test compound to a mouse, the whole brain except the cerebellum was removed. The removed brain was homogenized in phosphate buffer solution (pH: 8.0) with the volume of buffer corresponding to 1.6 times the brain tissue weight. The homogenised solution (100 µL) was mixed with acetylthiocholine solution (60 mM, 10 µL) and incubated for 60 sec at 26° C. After centrifugation at 10,000 rpm for 10 min, the supernatant (10 µL) was mixed with dithionitrobenzoic acid solution (10 mM, 200 µL) and left for 20 min at room temperature for the color to develop. Then the absorbance (415 nm) was determined with a microplate-reader. Relative inhibitory activity (%) of the test compound against the production level of thiocholine in the brain homogenate of the control group (100%), in which the test compound was not administered, was calculated.

Test Example 2b

Serotonin Transporter Binding Inhibition Test

Sixty min after oral administration of the test compound to a mouse, the whole brain except the cerebellum was removed. The removed brain was homogenized in 50 mM Tris HCl buffer solution (pH: 7.7) with the volume of buffer corresponding to 3 times the brain tissue weight. The homogenised solution (250 µL) was mixed with [$^3$H]citalopram (NEN Life Science Products: final concentration 0.77 nM) (1) in the presence of fluvoxamine (final concentration: 1 mM) or (2) in the absence of fluvoxamine, and incubated for 60 sec at 25° C. After Tris HCl buffer solution (2.5 ml) was added, the solution was centrifuged at 3,000 rpm for 6 min. The sediment was recovered. After this process was repeated twice, the sediment was suspended in 1 mL of the buffer solution and Pico-Fluor-40 (4 mL) added. Then the radioactivity was determined with a liquid scintillation counter (ALOKA, LSC-3500). Serotonin transporter protein binding level was calculated by subtraction of the radioactivity in the presence of citalopram (2) from that in the absence of citalopram (1).

Compounds of the present invention showed potent inhibitory activities against both acetylcholinesterase activity and serotonin transporter protein binding in the brains of mice following oral administration. Thus compounds of the present invention are useful as safe and effective remedies.

FORMULATION EXAMPLE

Formulation Example 1

Hard Capsules

Each capsule is manufactured by addition of 100 mg of powder of test compound 1, 100 mg of lactose, 50 mg of cellulose, and 6 mg of magnesium stearate into a hard gelatin capsule. After washing, the capsule is dried.

Formulation Example 2

Soft Capsules

Test compound 2 is added into a digestable oily substance, for example soybean oil, cottonseed oil, or olive oil, and well mixed. The mixture is placed into a gelatin capsule with a plunger pump and a soft capsule containing 100 mg of active compound obtained. After washing, the soft capsule is dried.

Formulation Example 3

Tablets

According to conventional methods, the tablet is manufactured using 100 mg of test compound 3, 0.2 mg of colloidal silicon dioxide, 5 mg of magnesium stearate, 275 mg of crystalline cellulose, 11 mg of starch, and 98.8 mg of lactose.

If desired, the tablet is coated.

Formulation Example 4

Suspension

A suspension is manufactured containing 100 mg of finely powdered test compound 4, 10 mg of sodium carboxymethylcellulose, 5 mg of sodium benzoate, 1.0 g of sorbitol solution (Japanese Pharmacopoeia), and 0.025 ml of vanillin, in 5 ml.

Formulation Example 5

Cream

A cream formulation is manufactured by addition of 100 mg of finely powdered test compound 5 into 5 g of cream containing 40% of white petrolatum, 3% fine crystallized wax, 10% lanolin, 5% span 20, 0.3% Tween 20, and 41.7% water.

Compounds of the present invention exert inhibitory activities towards both acetylcholinesterase activity and selective serotonin re-uptake, and are useful as preventative and/or therapeutic agents for Alzheimer's disease, depression, Huntington's chorea, Pick disease, tardive dyskinesia, obsessive-compulsive disorder, or panic disorder.

What is claimed is:

1. A compound of formula (I):

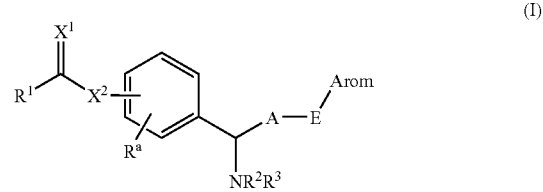

wherein $R^1$ represents a $C_1$–$C_6$ alkyl group, an amino group, a ($C_1$–$C_6$ alkyl) amino group, a di($C_1$–$C_6$ alkyl) amino group or a nitrogen-containing saturated heterocyclic group;

$R^2$ and $R^3$ are the same or different and represent a hydrogen atom or a $C_1$–$C_6$ alkyl group;

Arom represents an unsubstituted phenyl group or a phenyl group substituted at from 1 to 5 positions by one or more substituents which are the same or different and are from the substituent group α;

A represents a $C_1$–$C_6$ alkylene group;

$R^a$ represents a hydrogen atom, a $C_1$–$C_6$ alkyl group or a $C_2$–$C_6$ alkenyl group;

E represents an oxygen atom, a sulfur atom or a group of the formula —$NR^4$—, wherein $R^4$ represents a hydrogen atom or a $C_1$–$C_7$ alkanoyl group;

$X^1$ represents an oxygen atom or a sulfur atom;

$X^2$ is oxygen and is attached at position C4 of the phenyl ring;

the substituent group a being selected from the group consisting of a halogen atom, $C_1$–$C_6$ alkyl group, halogeno $C_1$–$C_6$ alkyl group, $C_1$–$C_6$ alkoxy group, $C_1$–$C_6$ alkylthio group, $C_1$–$C_3$ alkylenedioxy group, $C_1$–$C_7$ alkanoyl group, $C_2$–$C_7$ alkyloxycarbonyl group, amino group, $C_1$–$C_7$ alkanoylamino group, hydroxyl group, mercapto group, cyano group, nitro group and carboxyl group;

or a pharmacologically acceptable salt or ester thereof.

2. A compound of formula (I):

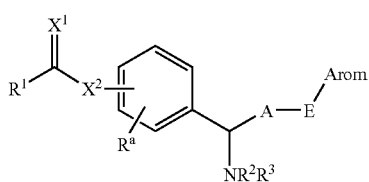

(I)

wherein $R^1$ represents a $C_1$–$C_6$ alkyl group, an amino group, a ($C_1$–$C_6$ alkyl) amino group, a di($C_1$–$C_6$ alkyl) amino group or a nitrogen-containing saturated heterocyclic group;

$R^2$ and $R^3$ are the same or different and represent a hydrogen atom or a $C_1$–$C_6$ alkyl group;

Arom represents an unsubstituted phenyl group or a phenyl group substituted at from 1 to 5 positions by one or more substituents which are the same or different and are from the substituent group α;

A represents a $C_1$–$C_6$ alkylene group;

$R^a$ represents a hydrogen atom, a $C_1$–$C_6$ alkyl group or a $C_2$–$C_6$ alkenyl group;

E represents an oxygen atom, a sulfur atom or a group of the formula —$NR^4$—, wherein $R^4$ represents a hydrogen atom or a $C_1$–$C_7$ alkanoyl group;

$X^1$ represents an oxygen atom or a sulfur atom;

$X^2$ is oxygen and is attached at position C4 of the phenyl ring;

wherein the group of formula $R^1$—C(=$X^1$)— is a ($C_1$–$C_4$ alkyl) carbamoyl group or a di($C_1$–$C_4$ alkyl) carbamoyl group;

the substituent group a being selected from the group consisting of a halogen atom, $C_1$–$C_6$ alkyl group, halogeno $C_1$–$C_6$ alkyl group, $C_1$–$C_6$ alkoxy group, $C_1$–$C_6$ alkylthio group, $C_1$–$C_3$ alkylenedioxy group, $C_1$–$C_7$ alkanoyl group, $C_2$–$C_7$ alkyloxycarbonyl group, amino group, $C_1$–$C_7$ alkanoylamino group, hydroxyl group, mercapto group, cyano group, nitro group and carboxyl group;

or a pharmacologically acceptable salt or ester thereof.

3. A compound of formula (I):

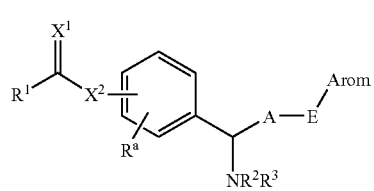

(I)

wherein
$R^2$ and $R^3$ are the same or different and represent a hydrogen atom or a $C_1$–$C_6$ alkyl group;

Arom represents an unsubstituted phenyl group or a phenyl group substituted at from 1 to 5 positions by one or more substituents which are the same or different and are from the substituent group α;

A represents a $C_1$–$C_6$ alkylene group;

$R^a$ represents a hydrogen atom, a $C_1$–$C_6$ alkyl group or a $C_2$–$C_6$ alkenyl group;

E represents an oxygen atom, a sulfur atom or a group of the formula —$NR^4$—, wherein $R^4$ represents a hydrogen atom or a $C_1$–$C_7$ alkanoyl group;

$X^2$ is oxygen and is attached at position C4 of the phenyl ring;

wherein the group of formula $R^1$—C(=$X^1$)— is a dimethylcarbamoyl group or an ethylmethylcarbamoyl group;

the substituent group α being selected from the group consisting of a halogen atom, $C_1$–$C_6$ alkyl group, halogeno $C_1$–$C_6$ alkyl group, $C_1$–$C_6$ alkoxy group, $C_1$–$C_6$ alkylthio group, $C_1$–$C_3$ alkylenedioxy group, $C_1$–$C_7$ alkanoyl group, $C_2$–$C_7$ alkyloxycarbonyl group, amino group, $C_1$–$C_7$ alkanoylamino group, hydroxyl group, mercapto group, cyano group, nitro group and carboxyl group;

or a pharmacologically acceptable salt or ester thereof.

4. A compound of formula (I):

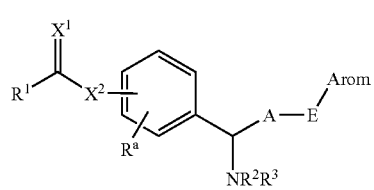

(I)

wherein $R^1$ represents a $C_1$–$C_6$ alkyl group, an amino group, a ($C_1$–$C_6$ alkyl) amino group, a di($C_1$–$C_6$ alkyl) amino group or a nitrogen-containing saturated heterocyclic group;

$R^2$ and $R^3$ are the same or different and represent a hydrogen atom or a $C_1$–$C_6$ alkyl group;

Arom is a phenyl group substituted at one or two positions by one or more substituents which are the same or different and are from a substituent group α1, or a phenyl group substituted at three positions by halogen atoms;

A represents a $C_{1-6}$ alkylene group;

$R^a$ represents a hydrogen atom, a $C_1$–$C_6$ alkyl group or a $C_2$–$C_6$ alkenyl group;

E represents an oxygen atom, a sulfur atom or a group of the formula —$NR^4$—, wherein $R^4$ represents a hydrogen atom or a $C_1$–$C_7$ alkanoyl group;

$X^1$ represents an oxygen atom or a sulfur atom;

$X^2$ is oxygen and is attached at position C4 of the phenyl ring;

the substituent group α1 being selected from the group consisting of a halogen atom, unsubstituted $C_1$–$C_4$ alkyl group, $C_1$–$C_4$ alkyl group substituted by from 1 to 3 fluorine atoms, $C_1$–$C_4$ alkoxy group, $C_1$–$C_4$ alkylthio group, methylenedioxy group, ethylenedioxy group, $C_1$–$C_4$ alkanoyl group, cyano group and nitro group;

or a pharmacologically acceptable salt thereof.

5. A compound of formula (I):

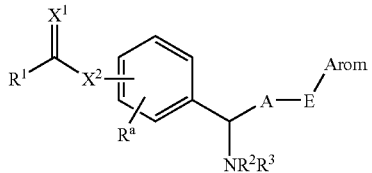

(I)

wherein $R^1$ represents a $C_1$–$C_6$ alkyl group, an amino group, a ($C_1$–$C_6$ alkyl) amino group, a di($C_1$–$C_6$ alkyl) amino group or a nitrogen-containing saturated heterocyclic group;

$R^2$ and $R^3$ are the same or different and represent a hydrogen atom or a $C_1$–$C_6$ alkyl group;

Arom is a phenyl group substituted at one or two positions by one or more substituents which are the same or different and are from a substituent group α3, or a phenyl group substituted at three positions by fluorine atoms;

A represents a $C_1$–$C_6$ alkylene group;

$R^a$ represents a hydrogen atom, a $C_1$–$C_6$ alkyl group or a $C_2$–$C_6$ alkenyl group;

E represents an oxygen atom, a sulfur atom or a group of the formula —$NR^4$—, wherein $R^4$ represents a hydrogen atom or a $C_1$–$C_7$ alkanoyl group;

$X^1$ represents an oxygen atom or a sulfur atom;

$X^2$ is oxygen and is attached at position C4 of the phenyl ring;

the substituent group α3 being selected from the group consisting of a fluorine atom, chlorine atom, methylthio group, acetyl group, cyano group and nitro group;

or a pharmacologically acceptable salt thereof.

6. A compound of formula (I):

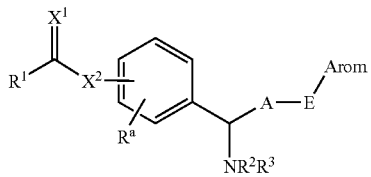

(I)

wherein $R^1$ represents a $C_1$–$C_6$ alkyl group, an amino group, a ($C_1$–$C_6$ alkyl) amino group, a di($C_1$–$C_6$ alkyl) amino group or a nitrogen-containing saturated heterocyclic group;

$R^2$ and $R^3$ are the same or different and represent a hydrogen atom or a $C_1$–$C_6$ alkyl group;

Arom is a phenyl group substituted at one position by a fluorine atom, a chlorine atom or a nitro group, or a phenyl group substituted at two positions by fluorine atoms;

A represents a $C_1$–$C_6$ alkylene group;

$R^a$ represents a hydrogen atom, a $C_1$–$C_6$ alkyl group or a $C_2$–$C_6$ alkenyl group;

E represents an oxygen atom, a sulfur atom or a group of the formula —$NR^4$—, wherein $R^4$ represents a hydrogen atom or a $C_1$–$C_7$ alkanoyl group;

$X^1$ represents an oxygen atom or a sulfur atom;

$X^2$ is oxygen and is attached at position C4 of the phenyl ring;

or a pharmacologically acceptable salt thereof.

7. A compound of formula (I):

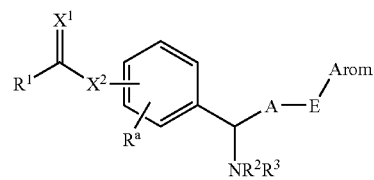

(I)

wherein $R^1$ represents a $C_1$–$C_6$ alkyl group, an amino group, a ($C_1$–$C_6$ alkyl) amino group, a di($C_1$–$C_6$ alkyl) amino group or a nitrogen-containing saturated heterocyclic group;

$R^2$ and $R^3$ are the same or different and represent a hydrogen atom or a $C_1$–$C_6$ alkyl group;

Arom is a 4-fluorophenyl group, a 4-chlorophenyl group, a 4-nitrophenyl group or a 3,4-difluorophenyl group;

A represents a $C_1$–$C_6$ alkylene group;

$R^a$ represents a hydrogen atom, a $C_1$–$C_6$ alkyl group or a $C_2$–$C_6$ alkenyl group E represents an oxygen atom, a sulfur atom or a group of the formula —$NR^4$—, wherein $R^4$ represents a hydrogen atom or a $C_1$–$C_7$ alkanoyl group;

$X^1$ represents an oxygen atom or a sulfur atom;

$X^2$ is oxygen and is attached at position C4 of the phenyl ring;

or a pharmacologically acceptable salt thereof.

8. The compound or pharmacologically acceptable salt or ester thereof according to any one of claims 1, 4, 5, 6 or 7, wherein the group of formula: $R^1$—C (=$X^1$)— is a carbamoyl group, a ($C_1$–$C_4$ alkyl) carbamoyl group, a di($C_1$–$C_4$ alkyl)carbamoyl group, a thiocarbamoyl group, a ($C_1$–$C_4$ alkyl) thiocarbamoyl group or a di($C_1$–$C_4$ alkyl) thiocarbamoyl group.

9. The compound or pharmacologically acceptable salt or ester thereof according to any one of claims 1, 4, 5, 6 or 7, wherein the group of formula $R^1$—C(=$X^1$)— is a ($C_1$–$C_4$ alkyl) carbamoyl group, a di($C_1$–$C_4$ alkyl)carbamoyl group, a ($C_1$–$C_4$ alkyl) thiocarbamoyl group or a di($C_1$–$C_4$ alkyl) thiocarbamoyl group.

10. The compound or pharmacologically acceptable salt or ester thereof according to any one of claims 1, 4, 5, 6 or 7, wherein the group of formula $R^1$—C(=$X^1$)— is a di($C_1$–$C_4$ alkyl)carbamoyl group.

11. The compound or pharmacologically acceptable salt or ester thereof according to any one of claims 1, 4, 5, 6 or 7, wherein the group of formula $R^1$—C(=$X^1$) is a dimethylcarbamoyl group.

12. The compound or pharmacologically acceptable salt or ester thereof according to any one of claims 1, 2, 3, 4, 5, 6 or 7, wherein $R^3$ is a $C_1$–$C_6$ alkyl group.

13. The compound or pharmacologically acceptable salt or ester thereof according to any one of claims 1, 2, 3, 4, 5, 6 or 7, wherein $R^3$ is a methyl group or an ethyl group.

14. The compound or pharmacologically acceptable salt or ester thereof according to any one of claims 1, 2, 3, 4, 5, 6 or 7, wherein $R^3$ is a methyl group.

15. The compound or pharmacologically acceptable salt or ester thereof according to any one of claims 1, 2, 3, 4, 5, 6 or 7, wherein $R^2$ is a hydrogen atom or a $C_1$–$C_6$ alkyl group.

16. The compound or pharmacologically acceptable salt or ester thereof according to any one of claims 1, 2, 3, 4, 5, 6 or 7, wherein $R^2$ is a hydrogen atom, a methyl group or an ethyl group.

17. The compound or pharmacologically acceptable salt or ester thereof according to any one of claims 1, 2, 3, 4, 5, 6 or 7, wherein $R^2$ is a hydrogen atom or a methyl group.

18. The compound or pharmacologically acceptable salt or ester thereof according to any one of claims 1, 2, 3, 4, 5, 6 or 7, wherein $R^a$ is a hydrogen atom or a methyl group.

19. The compound or pharmacologically acceptable salt or ester thereof according to any one of claims 1, 2, 3, 4, 5, 6 or 7, wherein $R^a$ is a hydrogen atom.

20. The compound or pharmacologically acceptable salt or ester thereof according to claims 1 or 2, wherein Arom is a phenyl group substituted at from 1 to 3 positions by one or more substituents which are the same or different and are from the substituent group α, the substituent group α being selected from the group consisting of a halogen atom, $C_1$–$C_6$ alkyl group, halogeno $C_1$–$C_6$ alkyl group, $C_1$–$C_6$ alkoxy group, $C_1$–$C_6$ alkylthio group, $C_1$–$C_3$ alkylenedioxy group, $C_1$–$C_7$ alkanoyl group, $C_2$–$C_7$ alkyloxycarbonyl group, amino group, $C_1$–$C_7$ alkanoylamino group, hydroxyl group, mercapto group, cyano group, nitro group and carboxyl group.

21. The compound or pharmacologically acceptable salt thereof according to claims 1 or 2, wherein Arom is a phenyl group substituted at one or two positions by substituent(s) which are the same or different and are from a substituent group α2, or a phenyl group substituted at three positions by fluorine atoms or chlorine atoms;

substituent group α2 being selected from the group consisting of a fluorine atom, chlorine atom, methyl group, trifluoromethyl group, methoxy group, methylthio group, acetyl group, cyano group and nitro group.

22. The compound or pharmacologically acceptable salt thereof according to claims 1 or 2, wherein Arom is a phenyl group substituted at one or two positions by one or more substituents which are the same or different and are from a substituent group α4, or a phenyl group substituted at three positions by fluorine atoms;

substituent group α4 being selected from the group consisting of a fluorine atom, chlorine atom, methylthio group and nitro group.

23. The compound or pharmacologically acceptable salt or ester thereof according to any one of claims 1, 2, 3, 4, 5, 6 or 7, wherein A is a $C_1$–$C_4$ alkylene group.

24. The compound or pharmacologically acceptable salt or ester thereof according to any one of claims 1, 2, 3, 4, 5, 6 or 7, wherein A is a methylene group or an ethylene group.

25. The compound or pharmacologically acceptable salt or ester thereof according to any one of claims 1, 2, 3, 4, 5, 6 or 7, wherein A is an ethylene group.

26. The compound or pharmacologically acceptable salt or ester thereof according to any one of claims 1, 2, 3, 4, 5, 6 or 7, wherein E is an oxygen atom.

27. The compound or pharmacologically acceptable salt or ester thereof according to any one of claims 1, 4, 5, 6 or 7, wherein $R^1$ is an amino group, a ($C_1$–$C_6$ alkyl)amino group or a di($C_1$–$C_6$ alkyl)amino group.

28. The compound or pharmacologically acceptable salt or ester thereof according to any one of claims 1, 4, 5, 6 or 7, wherein $R^1$ is an amino group, a ($C_1$–$C_4$ alkyl)amino group or a di($C_1$–$C_4$ alkyl)amino group.

29. The compound or pharmacologically acceptable salt or ester thereof according to any one of claims 1, 4, 5, 6 or 7, wherein $R^1$ is a ($C_1$–$C_4$ alkyl)amino group or a di($C_1$–$C_4$ alkyl)amino group.

30. The compound or pharmacologically acceptable salt or ester thereof according to any one of claims 1, 4, 5, 6 or 7, wherein $X^1$ is an oxygen atom.

31. The compound or pharmacologically acceptable salt thereof according to claim 1, wherein the compound is 4-[3-(4-nitrophenoxy)-1-methylaminopropyl]phenyl dimethylcarbamate.

32. A compound of the formula (I):

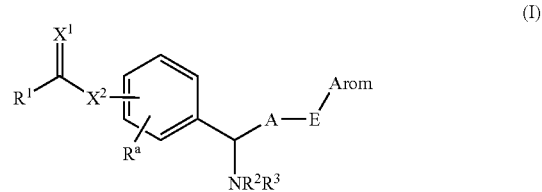

(I)

wherein $R^1$ represents a $C_1$–$C_6$ alkyl group, an amino group, a ($C_1$–$C_6$ alkyl)amino group, a di($C_1$–$C_6$ alkyl)amino group or a nitrogen-containing saturated heterocyclic group;

$R^2$ and $R^3$ are the same or different and represent a hydrogen atom or a $C_1$–$C_6$ alkyl group;

Arom represents an unsubstituted phenyl group or a phenyl group substituted at from 1 to 3 positions by substituents, which are the same or different and are from a substituent group α;

A represents a $C_1$–$C_6$ alkylene group;

E represents an oxygen atom, a sulfur atom or a group of the formula —$NR^4$—, wherein $R^4$ represents a hydrogen atom or a $C_1$–$C_7$ alkanoyl group;

$X^1$ represents an oxygen atom or a sulfur atom;

$X^2$ is oxygen and is attached at position C4 of the phenyl ring;

the substituent group α being selected from the group consisting of a halogen atom, $C_1$–$C_6$ alkyl group, halogeno $C_1$–$C_6$ alkyl group, $C_1$–$C_6$ alkoxy group, $C_1$–$C_6$ alkylthio group, $C_1$–$C_3$ alkylenedioxy group, $C_1$–$C_7$ alkanoyl group, $C_2$–$C_7$ alkyloxycarbonyl group, amino group, $C_1$–$C_7$ alkanoylamino group, hydroxyl group, mercapto group, cyano group, nitro group and carboxyl group;

or a pharmacologically acceptable salt or ester thereof.

33. A pharmaceutical composition comprising a pharmaceutically effective amount of a compound or pharmacologically acceptable salt or ester thereof according to claim 1, in combination with a pharmaceutically acceptable carrier.

34. A pharmaceutical composition comprising a pharmaceutically effective amount of a compound or pharmacologically acceptable salt or ester thereof according to claim 2, in combination with a pharmaceutically acceptable carrier.

35. A pharmaceutical composition comprising a pharmaceutically effective amount of a compound or pharmacologically acceptable salt or ester thereof according to claim 3, in combination with a pharmaceutically acceptable carrier.

36. A pharmaceutical composition comprising a pharmaceutically effective amount of a compound or pharmacologically acceptable salt thereof according to claim 4, in combination with a pharmaceutically acceptable carrier.

37. A pharmaceutical composition comprising a pharmaceutically effective amount of a compound or pharmacologically acceptable salt thereof according to claim 5, in combination with a pharmaceutically acceptable carrier.

38. A pharmaceutical composition comprising a pharmaceutically effective amount of a compound or pharmacologically acceptable salt thereof according to claim 6, in combination with a pharmaceutically acceptable carrier.

39. A pharmaceutical composition comprising a pharmaceutically effective amount of a compound or pharmacologically acceptable salt thereof according to claim 7, in combination with a pharmaceutically acceptable carrier.

40. A pharmaceutical composition comprising a pharmaceutically effective amount of a compound or pharmacologically acceptable salt thereof according to claim 31, in combination with a pharmaceutically acceptable carrier.

41. A method for treating depression, Huntington's chorea, Pick's disease, tardive dyskinesia, a compulsive disorder or a panic disorder in a mammal comprising administering to a mammal a pharmaceutically effective amount of a compound or a pharmacologically acceptable salt or ester thereof according to claim 1.

42. A method for treating depression, Huntington's chorea, Pick's disease, tardive dyskinesia, a compulsive disorder or a panic disorder in a human comprising administering to said human a pharmaceutically effective amount of a compound or pharmacologically acceptable salt or ester thereof according to claim 1.

43. A method for treating depression, Huntington's chorea, Pick's disease, tardive dyskinesia, a compulsive disorder or a panic disorder in a human comprising administering to said human a pharmaceutically effective amount of a compound or pharmacologically acceptable salt or ester thereof according to claim 2.

44. A method for treating depression, Huntington's chorea, Pick's disease, tardive dyskinesia, a compulsive disorder or a panic disorder in a human comprising administering to said human a pharmaceutically effective amount of a compound or pharmacologically acceptable salt or ester thereof according to claim 3.

45. A method for treating depression, Huntington's chorea, Pick's disease, tardive dyskinesia, a compulsive disorder or a panic disorder in a human comprising administering to said human a pharmaceutically effective amount of a compound or pharmacologically acceptable salt thereof according to claim 4.

46. A method for treating depression, Huntington's chorea, Pick's disease, tardive dyskinesia, a compulsive disorder or a panic disorder in a human comprising administering to said human a pharmaceutically effective amount of a compound or pharmacologically acceptable salt thereof according to claim 5.

47. A method for treating depression, Huntington's chorea, Pick's disease, tardive dyskinesia, a compulsive disorder or a panic disorder in a human comprising administering to said human a pharmaceutically effective amount of a compound or pharmacologically acceptable salt thereof according to claim 6.

48. A method for treating depression, Huntington's chorea, Pick's disease, tardive dyskinesia, a compulsive disorder or a panic disorder in a human comprising administering to said human a pharmaceutically effective amount of a compound or pharmacologically acceptable salt thereof according to claim 7.

49. A method for treating Alzheimer's disease in a human comprising administering to said human a pharmaceutically effective amount of a compound or pharmacologically acceptable salt or ester thereof according to claim 1.

50. A method for treating Alzheimer's disease in a human comprising administering to said human a pharmaceutically effective amount of a compound or pharmacologically acceptable salt or ester thereof according to claim 2.

51. A method for treating Alzheimer's disease in a human comprising administering to said human a pharmaceutically effective amount of a compound or pharmacologically acceptable salt thereof according to claim 3.

52. A method for treating Alzheimer's disease in a human comprising administering to said human a pharmaceutically effective amount of a compound or pharmacologically acceptable salt thereof according to claim 4.

53. A method for treating Alzheimer's disease in a human comprising administering to said human a pharmaceutically effective amount of a compound or pharmacologically acceptable salt thereof according to claim 5.

54. A method for treating Alzheimer's disease in a human comprising administering to said human a pharmaceutically effective amount of a compound or pharmacologically acceptable salt thereof according to claim 6.

55. A method for treating Alzheimer's disease in a human comprising administering to said human a pharmaceutically effective amount of a compound or pharmacologically acceptable salt thereof according to claim 7.

56. The compound or pharmacologically acceptable salt thereof according to claim 1, wherein $R^1$ is a dimethylamino group, $X^1$ and $X^2$ are both oxygen, Ra is H, $R^2$ is hydrogen, $R^3$ is methyl, A is —$C_2H_4$, E is oxygen and Arom is a phenyl group substituted in the 4-position by a $NO_2$ group.

57. The compound according to claim 1, wherein the compound is selected from the group consisting of
  4-[3-(4-fluorophenoxy)-1-methylaminopropyl]phenyl dimethylcarbamate,
  4-[3-(3-fluorophenoxy)-1-methylaminopropyl]phenyl dimethylcarbamate,
  4-[3-(4-chlorophenoxy)-1-methylaminopropyl]phenyl dimethylcarbamate,
  4-[3-(3-chlorophenoxy)-1-methylaminopropyl]phenyl dimethylcarbamate,
  4-[3-(4-nitrophenoxy)-1-methylaminopropyl]phenyl dimethylcarbamate,
  4-[3-(3,4-difluorophenoxy)-1-methylaminopropyl]phenyl dimethylcarbamate,
  4-[3-(4-chloro-3-fluorophenoxy)-1-methylaminopropyl]phenyl dimethylcarbamate,
  4-[3-(2-chloro-4-nitrophenoxy)-1-methylaminopropyl]phenyl dimethylcarbamate,
  4-[1-dimethylamino-3-(4-fluorophenoxy)propyl]phenyl dimethylcarbamate,
  4-[1-dimethylamino-3-(3-fluorophenoxy)propyl]phenyl dimethylcarbamate,
  4-[3-(4-chlorophenoxy)-1-dimethylaminopropyl]phenyl dimethylcarbamate,
  4-[3-(3-chlorophenoxy)-1-dimethylaminopropyl]phenyl dimethylcarbamate,
  4-[3-(4-cyanophenoxy)-1-dimethylaminopropyl]phenyl dimethylcarbamate,
  4-[1-dimethylamino-3-(4-nitrophenoxy)propyl]phenyl dimethylcarbamate,
  4-[3-(3,4-difluorophenoxy)-1-dimethylaminopropyl]phenyl dimethylcarbamate,
  4-[3-(2-chloro-4-nitrophenoxy)-1-dimethylaminopropyl]phenyl dimethylcarbamate,
  4-[3-(4-nitrophenylsulfanyl)-1-methylaminopropyl]phenyl dimethylcarbamate, 4-[1-methylamino-3-[(4-trifluoromethyl)phenoxy]propyl]phenyl dimethylcarbamate, 4-[3-(4-cyanophenoxy)-1-methylaminopropyl]phenyl dimethylcarbamate and 4-[1-methylamino-3-(3-nitrophenoxy)propyl]phenyl dimethylcarbamate or a pharmacologically acceptable salt thereof, or 4-(1-methylamino-3-p-toluyloxypropyl)phenyl dimethylcarbamate hydrochloride.

58. The compound according to claim 1, wherein the compound is 4-[3-(4-chlorophenoxy)-1-methylaminopropyl]phenyl dimethylcarbamate or a pharmacologically acceptable salt thereof.

59. The compound according to claim 1, wherein the compound is (S)-4-[3-(4-nitrophenoxy)-1-methylaminopropyl]phenyl dimethylcarbamate or a pharmacologically acceptable salt thereof.

60. The compound according to claim 1, wherein the compound is (S)-4-[3-(4-chlorophenoxy)-1-methylaminopropyl]phenyl dimethylcarbamate or a pharmacologically acceptable salt thereof.

61. The compound according to claim 1, wherein the compound is (S)-4-[3-(4-nitrophenoxy)-1-methylaminopropyl]phenyl dimethylcarbamate hydrochloride.

62. The compound according to claim 1, wherein the compound is (S)-4-[3-(4-chlorophenoxy)-1-methylaminopropyl]phenyl dimethylcarbamate hydrochloride.

63. The compound according to claim 1, wherein the compound is (S)-4-[3-(4-nitrophenoxy)-1-methylaminopropyl]phenyl dimethylcarbamate hemifumarate.

64. The compound according to claim 1, wherein the compound is (S)-4-[3-(4-chlorophenoxy)-1-methylaminopropyl]phenyl dimethylcarbamate hemifumarate.

65. A method of treating depression, Huntington's chorea, Pick's disease, tardive dyskinesia, a compulsive disorder or a panic disorder in a human comprising administering to said human a pharmaceutically effective amount of a compound or a pharmaceutically acceptable salt thereof according to any one of claims 31, 58, 59 or 60.

66. A method of treating depression, Huntington's chorea, Pick's disease, tardive dyskinesia, a compulsive disorder or a panic disorder in a human comprising administering to said human a pharmaceutically effective amount of a compound according to any one of claims 61, 62, 63 or 64.

67. A method of treating depression, Huntington's chorea, Pick's disease, tardive dyskinesia, a compulsive disorder or a panic disorder in a human comprising administering to said human a pharmaceutically effective of a compound according to claim 63.

68. A method of treating Alzheimer's disease in a human comprising administering to said human a pharmaceutically effective amount of a compound or pharmaceutically acceptable salt thereof according to any one of claims 31, 58, 59 or 60.

69. A method of treating Alzheimer's disease in a human comprising administering to said human a pharmaceutically effective amount of a compound according to any one of claims 61, 62, 63 or 64.

70. A method of treating Alzheimer's disease in a human comprising administering to said human a pharmaceutically effective amount of a compound according to claim 63.

* * * * *

UNITED STATES PATENT AND TRADEMARK OFFICE
CERTIFICATE OF CORRECTION

PATENT NO.        : 7,504,437 B2                                         Page 1 of 1
APPLICATION NO.   : 10/629108
DATED             : March 17, 2009
INVENTOR(S)       : Koyama et al.

It is certified that error appears in the above-identified patent and that said Letters Patent is hereby corrected as shown below:

On the Title page,

[*] Notice:  Subject to any disclaimer, the term of this patent is extended or adjusted under 35 USC 154(b) by (58) days Delete the phrase "by 58 days" and insert -- by 81 days --

Signed and Sealed this

Eighth Day of September, 2009

David J. Kappos
*Director of the United States Patent and Trademark Office*